United States Patent
Huber et al.

(10) Patent No.: US 9,446,039 B2
(45) Date of Patent: Sep. 20, 2016

(54) AMINOHETEROARYL COMPOUNDS AS MTH1 INHIBITORS

(71) Applicant: CEMM—FORSCHUNGSZENTRUM FÜR MOLEKULARE MEDIZIN GMBH, Vienna (AT)

(72) Inventors: Kilian Huber, Vienna (AT); Giulio Superti-Furga, Vienna (AT)

(73) Assignee: CeMM Forschungszentrum für Molekulare Medizin GmbH, Vienna (AT)

( * ) Notice: Subject to any disclaimer, the term of this patent is extended or adjusted under 35 U.S.C. 154(b) by 0 days.

(21) Appl. No.: 14/424,595

(22) PCT Filed: Aug. 27, 2013

(86) PCT No.: PCT/EP2013/067744
§ 371 (c)(1),
(2) Date: Feb. 27, 2015

(87) PCT Pub. No.: WO2014/033136
PCT Pub. Date: Mar. 6, 2014

(65) Prior Publication Data
US 2016/0015702 A1    Jan. 21, 2016

(30) Foreign Application Priority Data

Aug. 27, 2012  (EP) .................... 12181920
Apr. 3, 2013   (EP) .................... 13162175

(51) Int. Cl.
| | | |
|---|---|---|
| A61K 31/44 | (2006.01) | |
| A61K 31/4545 | (2006.01) | |
| A61K 45/06 | (2006.01) | |
| G01N 33/573 | (2006.01) | |
| G01N 33/50 | (2006.01) | |
| G01N 33/94 | (2006.01) | |

(52) U.S. Cl.
CPC .......... *A61K 31/4545* (2013.01); *A61K 45/06* (2013.01); *G01N 33/5011* (2013.01); *G01N 33/573* (2013.01); *G01N 33/94* (2013.01); *G01N 2333/4704* (2013.01); *G01N 2333/914* (2013.01); *G01N 2430/00* (2013.01); *G01N 2500/04* (2013.01); *G01N 2800/52* (2013.01)

(58) Field of Classification Search
None
See application file for complete search history.

(56) References Cited

FOREIGN PATENT DOCUMENTS

WO    WO 2006-021881    3/2006

OTHER PUBLICATIONS

Cho et al., "MiR-145 inhibits cell proliferation of human lung adenocarcinoma by targeting EGFR and NUDT1," *RNA Biology*, 8(1):125-131, 2011.
Cui et al., "Structure based drug design of crizotinib (PF-02341066), a potent and selective dual inhibitor of mesenchymal-epithelial transition factor (c-MET) kinase and anaplastic lymphoma kinase (ALK)," *Journal of Medicinal Chemistry*, 54(18):6342-6363, 2011.
Database Registry, Chemical Abstracts Service, Database Accession No. 1374356-45-2, 2012.
PCT International Search Report and Written Opinion issued in International Application No. PCT/EP2013/067744, mailed Nov. 19, 2013.
Rai, "Human Mut T homolog 1 (MTH1): a roadblock for the tumor-suppressive effects of oncogenic RAS-induced ROS," *Small GTPases*, 3(2):120-125, 2012.
Tian et al., "Biological fingerprinting analysis of the interactome of a kinase inhibitor in human plasma by a chemiproteomic approach," *Journal of Chromatography*, 1134(1-2):134-142, 2006.
Yang et al., "Chemical-protein interactome and its application in off-target identification," *Interdisciplinary Sciences, Computational Life Sciences*, 3(1):22-30, 2011.

*Primary Examiner* — Heidi Reese
(74) *Attorney, Agent, or Firm* — Parker Highlander PLLC

(57) ABSTRACT

The present invention relates to an (S)-enantiomer of an aminoheteroaryl compound for use in treating and/or preventing cancer in a subject. The invention further relates to a pharmaceutical composition comprising said compound. Another aspect of the invention is directed to an in vitro method for determining the effectiveness of said (S)-enantiomer of an aminoheteroaryl compound, or said pharmaceutical composition, the method comprising the steps of: (a) obtaining a cell or tissue sample from a subject; and (b) determining the subject's NUDT1/MTH1-status; wherein a NUDT1/MTH1-positive cell or tissue sample is indicative of an effective treatment and/or prevention of cancer. In addition, provided herein is a screening method for identifying a target of an (S)-enantiomer of an aminoheteroaryl compound. Furthermore, in context of this invention, the herein described compounds inhibit the biological activity of MTH1.

34 Claims, 30 Drawing Sheets

Figure 1:
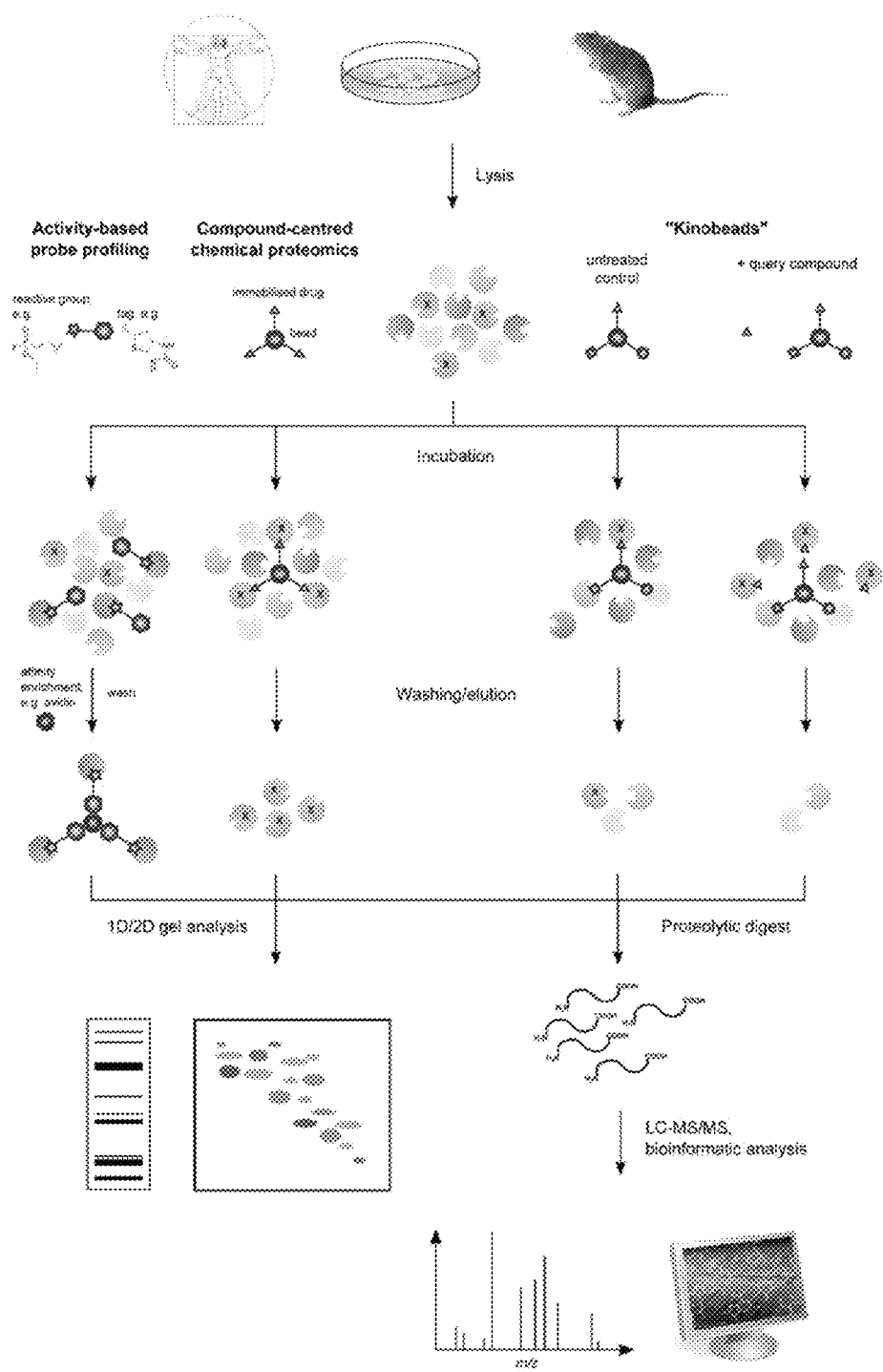

| | (R)-crizotinib | (S)-crizotinib | (RS)-crizotinib [racemate] |
|---|---|---|---|
| IC50 | 5.236e-006 | 4.845e-008 | 3.150e-007 |

(S)-3-(1-(2,6-dichloro-3-fluorophenyl)ethoxy)-
5-(1-(piperidin-4-yl)-1H-pyrazol-4-yl)pyridin-2-amine FIG. 17B
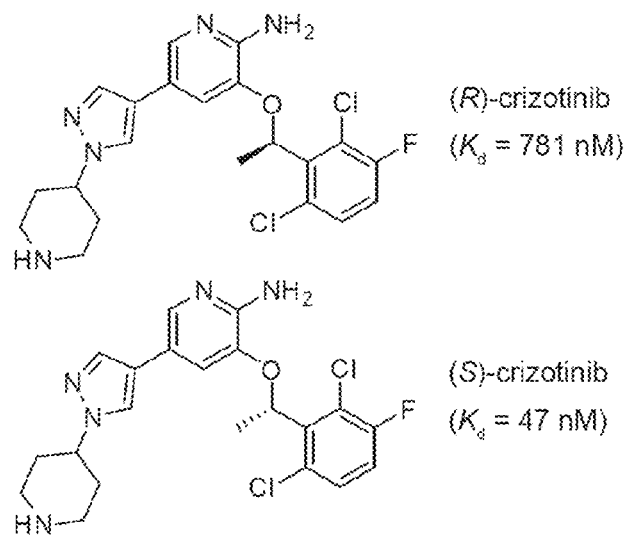
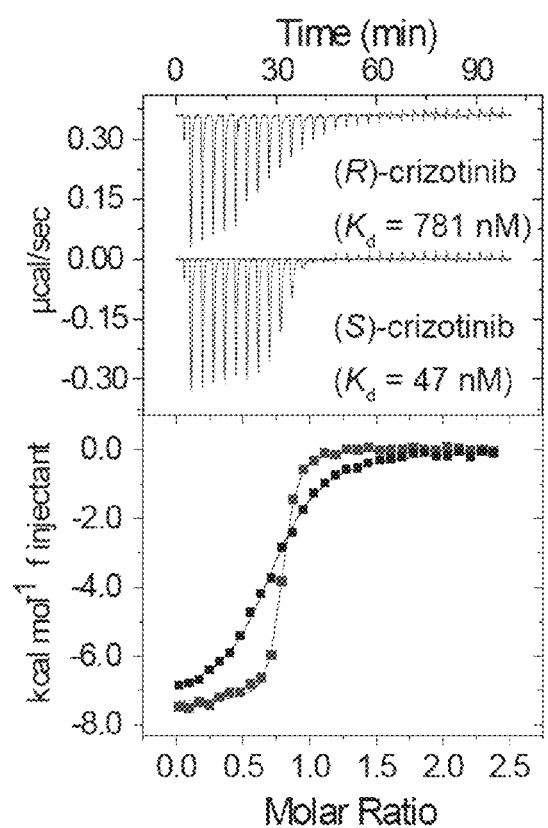

FIGs. 18A-B
A
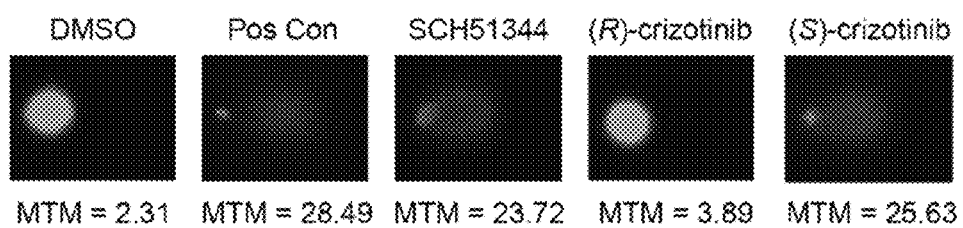
B
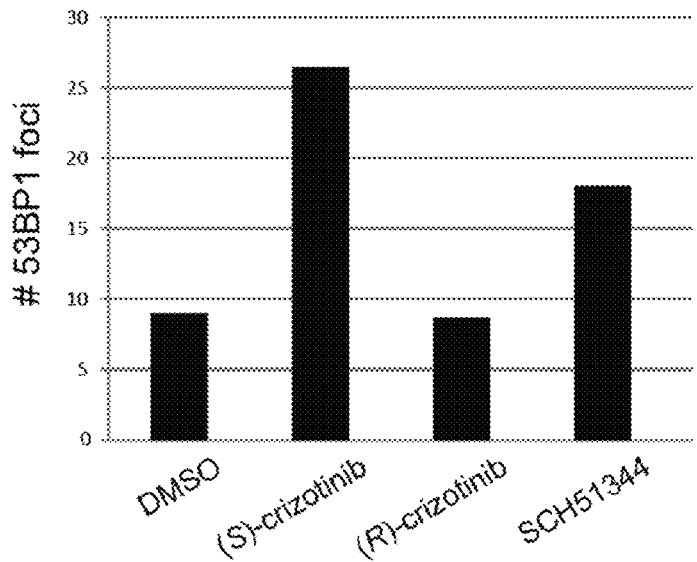

FIGs. 18C-D
C
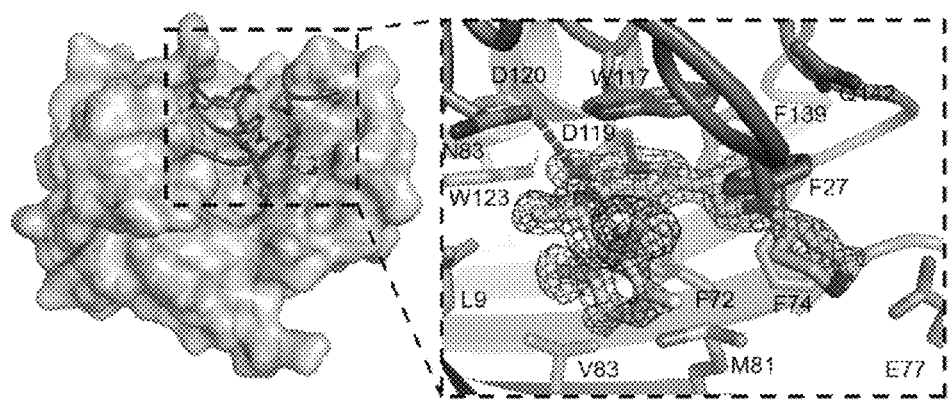
D
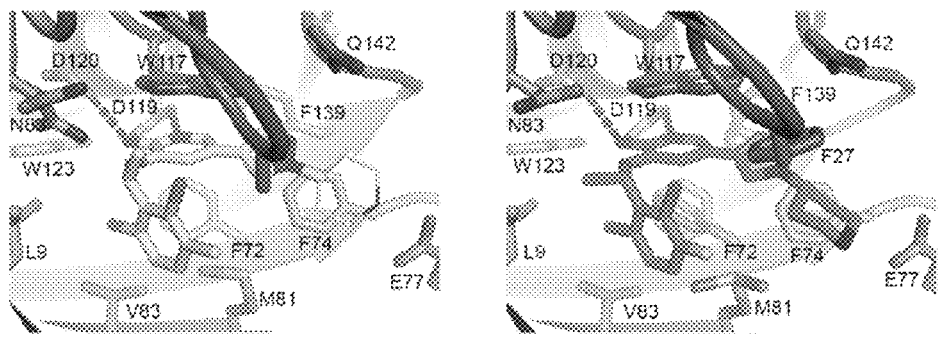

FIGs. 21A-B
A
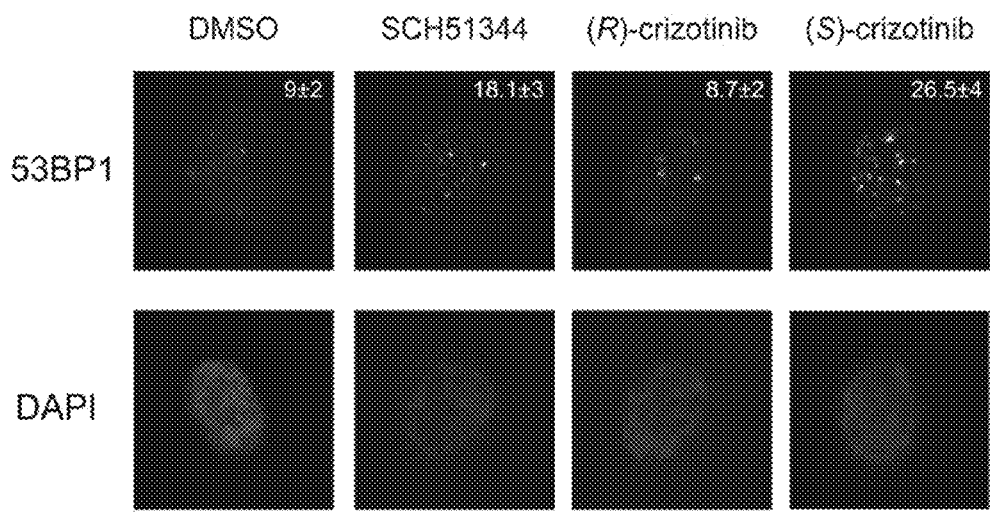
B
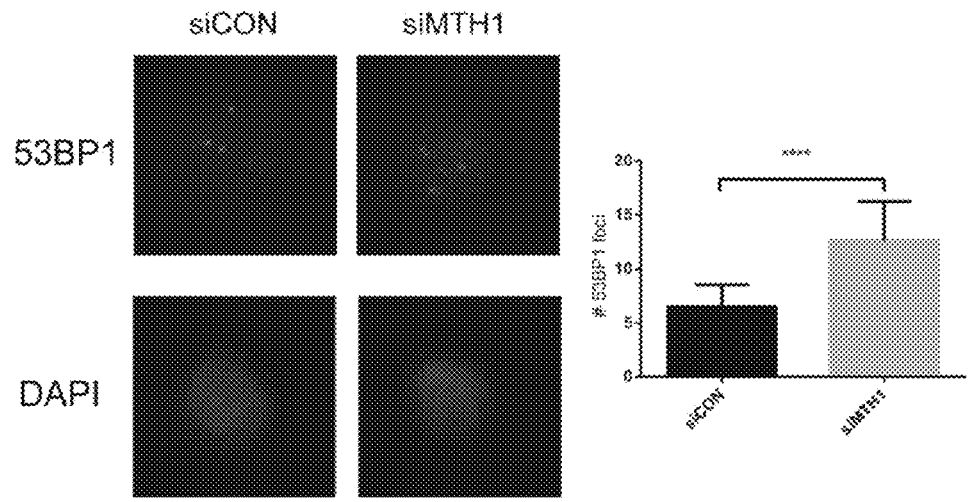

FIGs. 22A-B
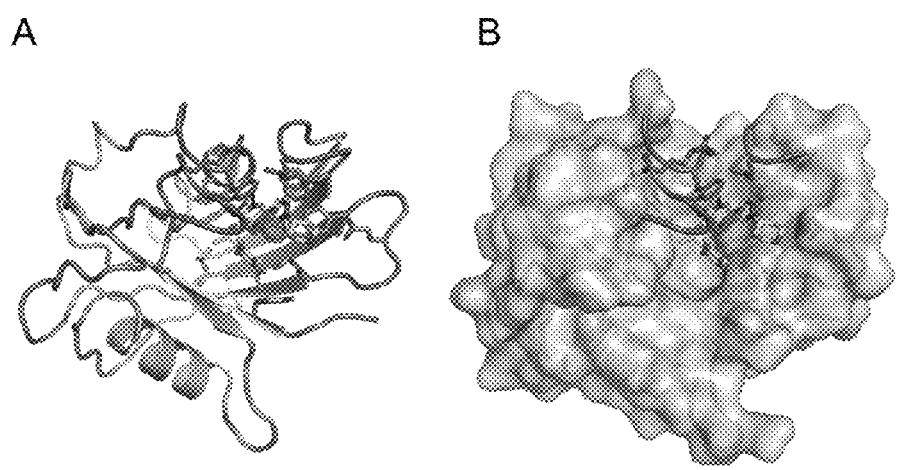
FIGs. 23A-B
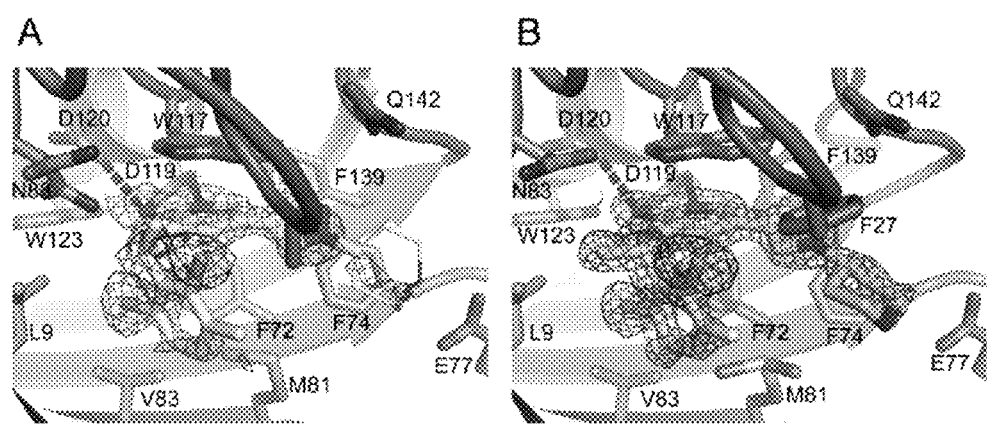

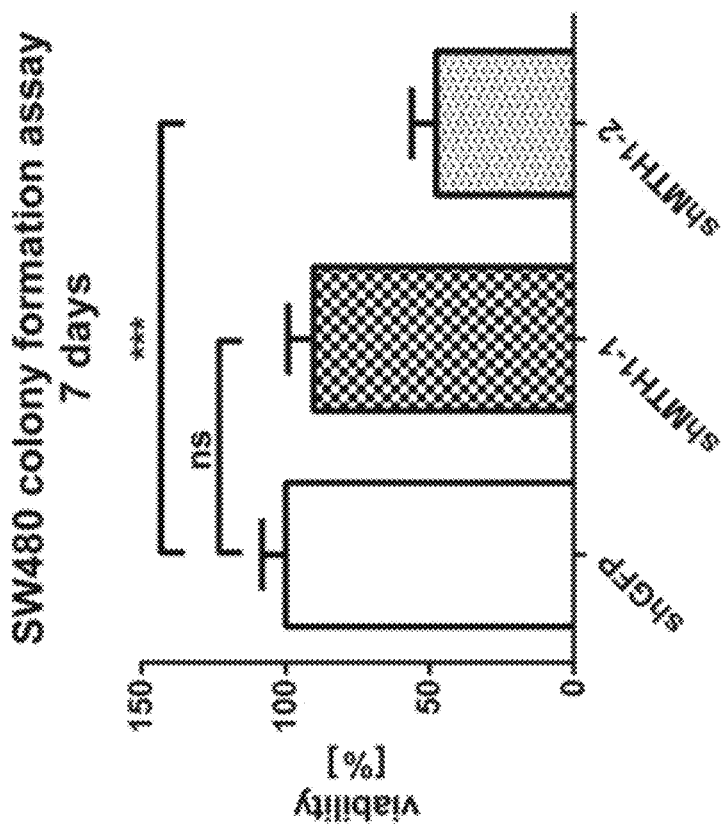
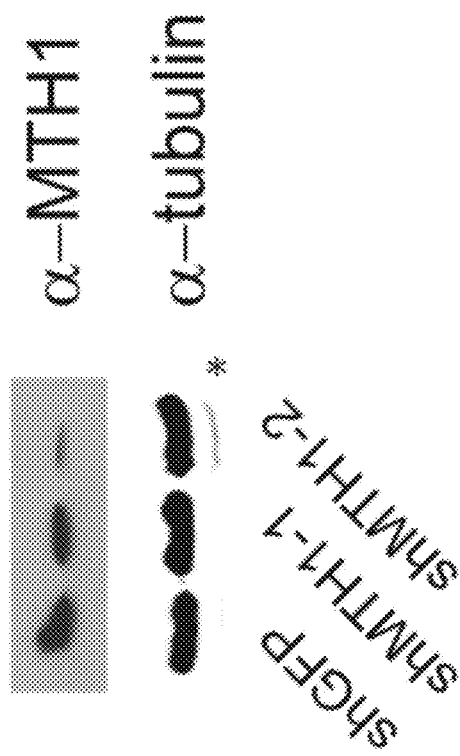
FIG. 26

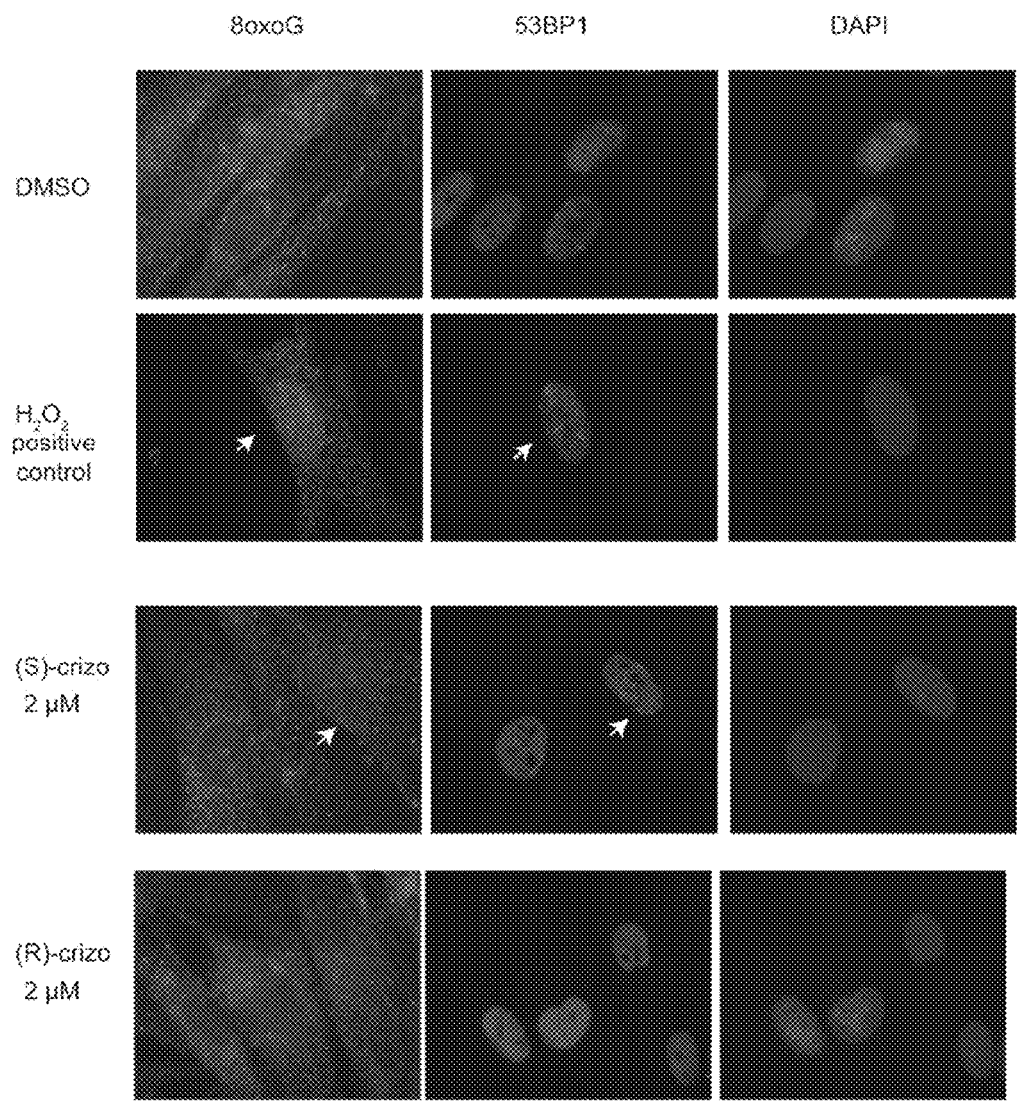

US 9,446,039 B2

AMINOHETEROARYL COMPOUNDS AS MTH1 INHIBITORS

This application is a national phase application under 35 U.S.C. §371 of International Application No. PCT/EP2013/067744, filed Aug. 27, 2013, which claims benefit of European Application No. 12181920.5, filed Aug. 27, 2012 and European Application No. 13162175.7, filed Apr. 3, 2013. The entire text of each of the above referenced disclosures is specifically incorporated herein by reference.

The present invention relates to an (S)-enantiomer of an aminoheteroaryl compound for use in treating and/or preventing cancer in a subject. The invention further relates to a pharmaceutical composition comprising said compound. Another aspect of the invention is directed to an in vitro method for determining the effectiveness of said (S)-enantiomer of an aminoheteroaryl compound, or said pharmaceutical composition, the method comprising the steps of: (a) obtaining a cell or tissue sample from a subject; and (b) determining the subject's NUDT1/MTH1-status; wherein a NUDT1/MTH1-positive cell or tissue sample is indicative of an effective treatment and/or prevention of cancer. In addition, provided herein is a screening method for identifying a target of an (S)-enantiomer of an aminoheteroaryl compound. Furthermore, in context of this invention, the herein described compounds inhibit the biological activity of MTH1.

Drugs intended for human use require extensive toxicologic studies before they can finally be applied to patients in order to ensure that the beneficial effects outweigh potential side effects. However, certain off-target effects may only become visible after long-term use and once broader patient cohorts have been exposed to the compound. Those conditions obviously cannot be assessed completely in standard clinical trials. A chemical proteomic analysis of the BCR-Abl kinase inhibitor dasatinib for instance revealed that this compound can lead to atypical infections in chronic myelogenous leukaemia (CML) patients due to inhibition of BTK and TEC kinases.[1] Apart from potentially negative consequences for patients, certain drugs may exhibit so-called "polypharmacology", which means that their clinical efficacy is due to simultaneous interference with several cellular proteins and respective signalling pathways which all are relevant for disease.[2] Thus these off-target activities can also be beneficial and may not be of concern to the patient. However, comprehensive knowledge about a drug's molecular target profile (i.e. the gene-drug interactome) may further enhance therapeutic efficacy by specific selection of patients based on defined molecular lesions and improve the prevention of side effects ("patient stratification"). Furthermore, new and distinct patient groups may selectively benefit from the off-target effect, independently of the originally established target. Finally, knowledge about this particularly relevant off-target may also provide lead structures that enable development of more specific modulators for novel targeted therapeutics within the same or different clinical settings. If a second medical use can be discovered for a clinically established drug by such an approach both patients and pharmaceutical companies can benefit from this "drug repurposing" as the approval process with authorities can be greatly accelerated. Among target deconvolution strategies, chemical proteomics is the most powerful technique to decipher a molecule's cellular interactome which outmatches any in vitro screening strategy. First and foremost, in vitro assays are limited to certain subproteomes such as kinases, whilst in a chemical proteomics experiment the compound of interest is exposed to a complete proteome covering all classes of enzymes including kinases, histone deacetylases but also transcription factors and many more. Notably, only chemical proteomics allows assessment of proteins in their natural abundance and state of posttranslational modification (PTM) such as phosphorylation and acetylation. Crizotinib (PF-02341066, Xalkori®) is a novel dual inhibitor of anaplastic lymphoma kinase (ALK) and hepatocyte growth factor receptor kinase (c-Met) developed by Pfizer.[3] Crizotinib is the first Food and Drug Administration (FDA) approved ALK kinase inhibitor and is used to treat patients which have been diagnosed with ALK-positive tumours. Aberrant ALK signalling induces transformation, proliferation and antagonizes cell cycle arrest and apoptosis. The molecular lesions behind oncogenic ALK activity can be associated with either ALK gene amplification, mutation or chromosomal translocations such as EML4-ALK.[4] EML4-ALK is an oncogenic fusion protein consisting of the echinoderm microtubule-associated protein-like[4] and ALK genes (EML4-ALK).[5] This translocation occurs in approximately 3-13% of adenocarcinomas in non-small cell lung cancer (NSCLC) and is, apart from one reported case, considered to be mutually exclusive with mutations in EGFR or KRAS.[6] Patients are selected for treatment with crizotinib based on a prerequisite fluorescence in situ hybridisation (FISH) analysis which detects EML4-ALK. Crizotinib also shows high clinical benefit in other ALK-positive tumours such as anaplastic large cell lymphomas (ALCL), neuroblastoma (NB) and inflammatory myofibroblastic tumours (IMT), ranging from controlled disease to significant progression-free survival and remission.[7] It has been shown that the (R)-enantiomer of crizotinib is slightly more potent than racemic crizotinib and significantly more potent than the (S)-enantiomer of crizotinib (herein also called "(S)-crizotinib") in inhibiting c-Met activity.[9] The different ability of (R)-crizotinib and the (S)-enantiomer of crizotinib in inhibiting c-Met activity is consistent with specific binding as revealed in a cocrystal structure of crizotinib bound to c-Met.[9] Indeed, clinically, only (R)-crizotinib is used. In addition, as indicated above, it is the general understanding that crizotinib potentially inhibits cell proliferation in ALK-positive and c-Met-dependent cells.[3,23]

Cancer is the leading cause of death in economically developed countries and the second leading cause of death in developing countries (World Health Organization. The Global Burden of Disease: 2004 Update. Geneva: World Health Organization; 2008; Jemal (2011) CA Cancer J Clin. 61: 69-90). In addition, novel therapies that target cancer and which are not restricted to selected cancer cells or tissue, such as those being ALK-positive and/or c-Met-dependent, but which are for example RAS-, e.g. KRAS-dependent cancers/cancer cells, are desired. Therefore, the technical problem underlying the present invention is the provision of means and methods for the medical intervention of proliferative diseases, in particular cancerous diseases/cancer.

This technical problem is solved by the embodiments provided herein and as characterized in the claims.

Accordingly, the present invention relates to an (S)-enantiomer of an aminoheteroaryl compound for use in treating and/or preventing cancer in a subject, wherein the compound has the following chemical structure represented by Formula (1)

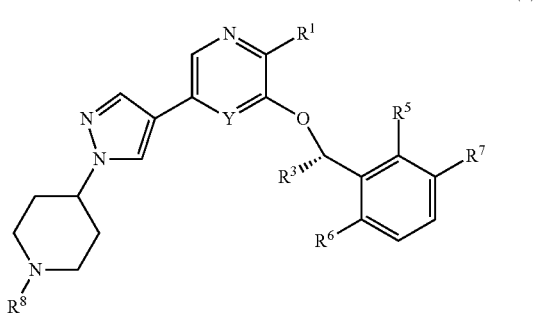

Formula (1)

wherein:
$R^1$ is —$NH_2$, —$NR^2H$, —OH or —SH;
$R^2$ is $C_{1-6}$ alkyl, $C_{2-6}$ alkenyl or $C_{2-6}$ alkynyl;
$R^3$ is $C_{1-3}$ alkyl, $C_{2-3}$ alkenyl, $C_{2-3}$ alkynyl or cyclopropyl;
Y is N or $CR^4$;
$R^4$ is hydrogen, halogen, $C_{1-6}$ alkyl, $C_{2-6}$ alkenyl, $C_{2-6}$ alkynyl or $C_{3-6}$ cycloalkyl;
each $R^5$, $R^6$ and $R^7$ is independently fluorine, chlorine, bromine or iodine;
$R^8$ is hydrogen or -A-$B_n$-X, wherein
   A is a single bond, —C(=O)— or —C(=O)$CH_2$—;
   B is $C_{1-4}$ alkylene, $C_{2-4}$ alkenylene or —($OCH_2CH_2$)—;
   n is 0, 1, 2, 3, 4 or 5, and
   X is —$NHR^2$; —$NH_2$; —SH; —OH or O-alkyl;
or a pharmaceutically acceptable salt, solvate or prodrug thereof.

In context of the present invention, it has been surprisingly found that an (S)-enantiomer of an aminoheteroaryl compound (e.g. (S)-3-[1-(2,6-dichloro-3-fluoro-phenyl)-ethoxy]-5-(1-piperidin-4-yl-1H-pyrazol-4-yl)-pyridin-2-ylamine; herein also referred to as "(S)-enantiomer of crizotinib") can be used to treat or prevent RAS-dependent cancer.

It is the established scientific view that the (S)-enantiomer of crizotinib has no use as an anti-cancer drug since it is not a good inhibitor of the oncogenic kinase c-Met. In particular, Cui (2011) J. Med. Chem. 54: 6342-6363 discloses using crizotinib (i.e. (R)-crizotinib) for treating cancer. This prior art study concludes that crizotinib has antitumor efficacy in cells that express activated c-Met or ALK fusion proteins. Significantly, Cui, op. cit., further discloses that in contrast to crizotinib (i.e. (R)-crizotinib), the (S)-enantiomer of crizotinib does not, or hardly (if at all) inhibit c-Met. The finding in the prior art that crizotinib effectively inhibits c-Met (whereas the (S)-enantiomer does not have c-Met inhibiting activity) was attributed to the fact that specifically (R)-crizotinib binds to the c-Met binding pocket (Cui, op. cit.). Since inhibition of c-Met is required to treat cancer, Cui, op. cit., teaches that the (S)-enantiomer of crizotinib cannot treat cancer. In addition, WO 2006/021881 (A2) discloses that the pure (R)-enantiomer of the substance 3-[1-(2,6-dichloro-3-fluoro-phenyl)-ethoxy]-5-(1-piperidin-4-yl-1H-pyrazol-4-yl)-pyridin-2-ylamine (i.e. crizotinib) inhibits c-Met considerably better than the racemate of crizotinib. Thus, the common understanding in the prior art is that an (S)-enantiomer of an aminoheteroaryl compound (such as the (S)-enantiomer of crizotinib) does not substantially or effectively inhibit c-Met and is, thus, not suited as an anti-cancer drug. In agreement with this, in the prior art only crizotinib (i.e. (R)-crizotinib) and not the (S)-enantiomer of crizotinib has been used to inhibit growth of cancer cells.

Thus, the skilled person is taught in the prior art that these two enantiomeric compounds have disparate biological behaviours. The skilled person can therefore not draw any expectation of activity of an (S)-enantiomer of an aminoheteroaryl compound (e.g. the (S)-enantiomer of crizotinib) from the biological activity of the (R)-enantiomer of crizotinib.

Further, the prior art directly and unambiguously teaches that crizotinib (i.e. (R)-crizotinib) is not suited for treating RAS (like, e.g. KRAS)-dependent cancers since activating ALK rearrangements have been found to be mutually exclusive with mutations of RAS (Gainor (2013) Clinical Cancer Research 19, 4273-4281). In agreement with this, the appended illustrative examples show that c-Met inhibition does not suppress growth of KRAS mutated SW480 cells. However, the inventors show herein, as documented in the appended illustrative examples, that an (S)-enantiomer of an aminoheteroaryl compound (such as the (S)-enantiomer of crizotinib) is highly potent in inhibiting RAS (e.g. KRAS) mutated cancer cells in vitro and in vivo. Accordingly, the inventive finding that the (S)-enantiomer of crizotinib is useful in the treatment or prevention of RAS-dependent cancers could not have been predicted based on the scientific evidence available.

In other words, the prior art teaches that only the (R)- and not the (S)-enantiomer of crizotinib is useful for the treatment of cancer and that the (R)-enantiomer is not suited for the treatment of RAS-dependent cancers. This is in strong contrast to the finding of the present invention that an (S)-enantiomer of an aminoheteroaryl compound, like the pure (S)-enantiomer of crizotinib, is highly potent in inhibiting cancer, in particular RAS-dependent cancers.

Again, as in cancer activated ALK is mutually exclusive with activated RAS, crizotinib (i.e. (R)-crizotinib) is not suited for the treatment of RAS-dependent cancers. Surprisingly, the herein provided (S)-enantiomer of an aminoheteroaryl compound (e.g. the (S)-enantiomer of crizotinib) is effective in the treatment of cancer, in particular of cancers with activating RAS mutations (e.g. activating mutations of K-RAS).

Furthermore, as is evident from the following and appended examples and figures, it was surprisingly found in context of this invention that (a) cancer cell(s) or (a) cancer tissue can successfully be treated with kinase inhibitors, even if the corresponding kinase is not active/not functional in said cell(s) and/or tissue(s). An example of such a kinase is the herein described anaplastic lymphoma kinase (ALK). It was found and documented herein that anti-ALK kinase inhibitors as disclosed herein are functional and can be used as anti-cancer agents in cells wherein said kinase is not even present or is not even active or wherein said kinase has merely reduced activity. As shown and illustrated herein, it was additionally found that ALK inhibitors have a surprising target different from the anaplastic lymphoma kinase, namely the (human) mutT homologue 1/NUDT1/MTH1, i.e. a triphosphatase (here: 7,8-dihydro-8-oxoguanine-triphophatase). This is insofar very surprising that here kinase inhibitors are successfully be used in the inhibition of the activity of an enzyme with converse catalytic activity.

In context of this invention, "NUDT1" relates to the gene and "MTH1" to the expressed protein of the above described triphosphatase.

The invention relates to the above described compound of Formula (1), wherein $R^1$ is —$NH_2$, —OH or —SH; $R^3$ is methyl; Y is $CR^4$; $R^4$ is hydrogen or halogen; each $R^5$, $R^6$ and $R^7$ is independently fluorine or chlorine; $R^8$ is hydrogen or wherein B is $C_{1-4}$ alkylene or —($OCH_2CH_2$)—; n is 1, 2 or 3, and X is —$NH_2$; or a pharmaceutically acceptable salt, solvate or prodrug thereof. In a more preferred embodiment, the invention relates to the above described compound, wherein $R^8$ is hydrogen; —C(=O)$CH_2CH_2CH_2CH_2CH_2$—$NH_2$; —C(=O)$CH_2$—O—$CH_2CH_2$—O—$CH_2CH_2$—$NH_2$;

or —CH$_2$CH$_2$CH$_2$—NH$_2$; or a pharmaceutically acceptable salt, solvate or prodrug thereof. In a most preferred embodiment, the invention relates to the above described compound, wherein the compound has one of the following chemical structures represented by Formulae (2) to (5):

Formula (2)

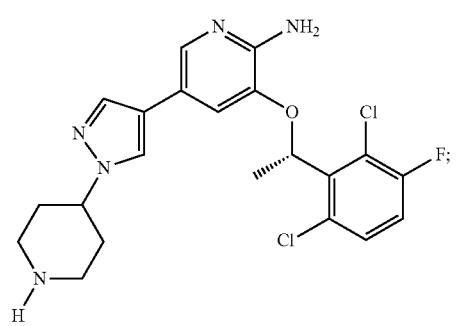

Formula (3)

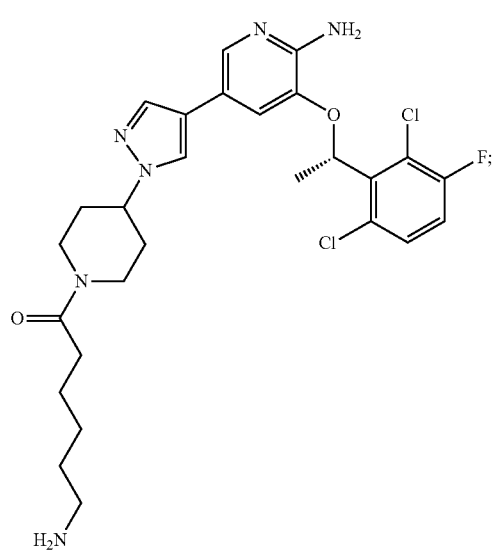

Formula (4)

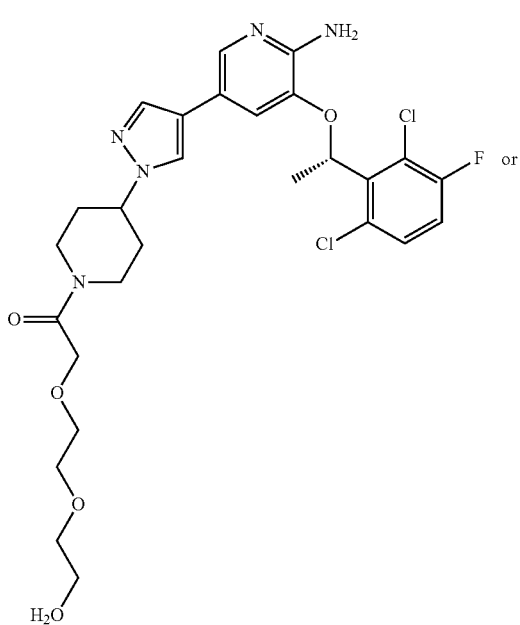

or

Formula (5)

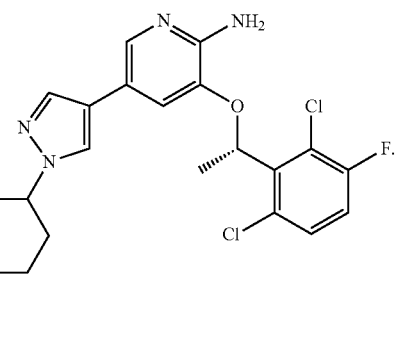

The invention relates to the herein defined aminoheteroaryl compound for use in treating and/or preventing cancer in a subject, wherein said aminoheteroaryl compound is in its (S)-enantiomer configuration.

Accordingly, the invention relates to a method of treatment and/or prevention of cancer in a subject in need of such a treatment, comprising administering to said subject a therapeutically effective amount of the herein defined (S)-enantiomer of an aminoheteroaryl compound. Accordingly, the present invention provides for means and methods for the treatment of subjects in need of such a treatment (either curative or preventive) which suffer from cancer. It is noted that the treatment and/or prevention is independent of the ALK-status and/or the c-Met-status of the cancer. Accordingly, the cancer to be treated and/or prevented may be an ALK-negative cancer (i.e. a cancer which does not have an activating ALK aberration) and/or a c-Met-negative cancer.

Thus, one aspect of the invention relates to the above described (S)-enantiomer of an aminoheteroaryl compound for use in treating and/or preventing cancer in a subject, wherein the treatment and/or prevention is independent of the ALK-status and/or the c-Met-status of the cancer cell or tissue of said subject. The ALK-status may be the level of ALK biological activity and/or the level of ALK expression. The level of ALK biological activity may be determined, e.g. by measuring the ALK kinase activity. To measure the ALK kinase activity in a patient, cancer cells or tissues of said patient may be isolated and the phosphorylation of downstream targets of ALK may be determined by Western blot using phosphospecific antibodies. The level of ALK expression may be determined, e.g., by polymerase chain reaction (PCR), real-time PCR (RT-PCT) or Western blot. The ALK-status of a cancer cell or tissue is positive, if the ALK biological activity and/or the ALK expression is increased in said cancer cell or tissue as compared to a sample of a healthy control person. It is commonly known in the art that the ALK-status (i.e. the level of ALK biological activity and/or the level of ALK expression) depends on the existence of an activating aberration (e.g. a chromosomal translocation) within the ALK gene. For example, an ALK-positive cancer cell or tissue relates to a cancer cell or tissue, wherein the ALK gene has an activating aberration (such as EML4-ALK or kinase domain activating mutations, e.g. ALK F1174L). In line with this, an ALK-negative cancer cell or tissue relates to a cancer cell or tissue wherein the ALK gene has not an activating aberration (such as EML4-ALK or kinase domain activating mutation). The existence of an activating ALK aberration may be determined, e.g., by sequencing, fluorescence-in-situ hybridization (FISH), by polymerase chain reaction (PCR), real-time PCR (RT-PCT) or Western blot.

As described above, the herein provided (S)-enantiomer of an aminoheteroaryl compound is useful in the treatment of cancer independent of the cancer's c-Met status. In accordance with the present invention, the c-Met-status may be the level of c-Met biological activity and/or the level of c-Met expression. The level of c-Met biological activity may be determined by measuring the kinase activity of c-Met. To measure the c-Met kinase activity in a patient, cancer cells or tissues of said patient may be isolated and the phosphorylation of downstream targets of c-Met may be determined by Western blot using phosphospecific antibodies. The level of c-Met expression may be determined, e.g., by PCR, RT-PCT or Western blot. The c-Met-status of a cancer cell or tissue is positive, if the c-Met biological activity and/or the c-Met expression is increased in said cancer cell or tissue as compared to a sample of a healthy control person. For example, the c-Met status may be positive as a result of activating mutations in c-Met. Such activating mutations may result in an increased biological activity of c-Met in a cancer cell or tissue as compared to the biological activity of c-Met in a cell or tissue of a healthy control subject.

Surprisingly, an (S)-enantiomer of an aminoheteroaryl compound (like the (S)-enantiomer of crizotinib) as provided herein is suitable for the treatment of a cancer independent of the ALK- or c-Met-status of the cancer (i.e. independent of the level of the biological activity or the level of the expression of ALK or c-Met in the cancer cell or tissue) as documented in the appended examples in in vitro and in vivo experiments. Thus, said cancer cell or tissue may be ALK-negative (i.e. may not have an activating ALK aberration) and/or c-Met-negative (i.e. may not have an increased expression of c-Met or kinase activating mutations as compared to a cell or tissue of a healthy control subject). This is surprising because crizotinib (i.e. (R)-crizotinib) is only described to be effective in ALK positive and c-Met positive cancer cells.

As described herein and illustrated in the appended examples, it was surprisingly found that the dual inhibitor of anaplastic lymphoma kinase (ALK) and hepatocyte growth factor receptor kinase (c-Met), crizotinib, is a highly potent inhibitor of the human MutT homologue 1 (MTH1) 7,8-dihydro-8-oxoguanine-triphosphatase which has been linked to oncogene-induced malignant transformation and cancer cell escape from senescence. Furthermore, it has astonishingly been found that the (S)-enantiomer of crizotinib is a particularly good MTH1 inhibitor, since this enantiomer showed considerably better MTH1 inhibitory activity than racemic or (R)-crizotinib.

These findings are highly surprising, since, at present, it is the general understanding that crizotinib effectively inhibits cell proliferation only in ALK-positive and c-Met-dependent cells.[3,23] Furthermore, considering that clinically, only (R)-crizotinib is used as this enantiomer has been shown to be considerably more potent than the (S)-enantiomer in inhibiting c-Met kinase activity,[9] the herein described invention is even more surprising.

Comprehensive knowledge about a drug's cellular target profile is a key prerequisite for patient stratification, thereby maximising treatment efficacy whilst minimizing side effects. On top of that, drugs which have proven to be particularly active in the treatment of devastating diseases such as cancer may still have an additional or even completely unknown mode of action which if revealed could lead to the development of novel therapeutics. Crizotinib abrogates malignant ALK signalling by binding to the adenosine triphosphate (ATP) binding pocket within the kinase active site and therefore acts as an (ATP) competitive kinase inhibitor. The inventors of the present invention hypothesised that crizotinib's high efficacy could at least partially be due to interference with several targets other than ALK which are relevant for cancer cell survival and set out to profile crizotinib by chemical proteomics. In particular, as shown in the appended examples, to investigate potentially relevant on- or off-targets of the clinically highly efficient and first-in-class dual ALK/c-Met kinase inhibitor crizotinib (Xalkori®), the inventors of the present invention applied a chemical proteomics approach interrogating several tumour cell lines with different genetic lesions. Investigating several human tumour cell lines the inventors of the present invention have surprisingly identified several unknown off-targets of crizotinib including the unexpected non-kinase target human MTH1 which has been linked to malignant transformation induced by mutant RAS and which has been shown to enable tumours to overcome the oncogene-induced senescence (OIS) barrier.

In particular, as demonstrated in the appended illustrative examples, inhibition of MTH1 catalytic activity by racemic crizotinib could be confirmed in an in vitro luminescence-based enzymatic assay indicating low nanomolar potency. Racemic crizotinib also induced DNA damage in MRC-5 lung fibroblasts as demonstrated by the comet assay. In addition, (S)-crizotinib but not (R)-crizotinib yielded a significant tail moment in the comet assay. At the same time, staining for 53BP1, a specific marker for DNA damage, was increased when cells were treated with the (S)-enantiomer of crizotinib, which was in line with the effect observed for anti-MTH1 siRNA. Considering the strong link between MTH1 and the expression of oncogenic RAS, reactive oxygen species (ROS), oxidative damage and tumour development, the data provided herein surprisingly suggests that small-molecule MTH1 inhibitors such as crizotinib, preferably racemic crizotinib, or more preferably the (S)-enantiomer of crizotinib, could also be applied to the treatment of several diverse ALK-negative cancers.

It is noted that the term "crizotinib" is also known as "PF-2341066" and relates to the (R)-enantiomer of the chemical substance 3-[1-(2,6-dichloro-3-fluoro-phenyl)-ethoxy]-5-(1-piperidin-4-yl-1H-pyrazol-4-yl)-pyridin-2-ylamine (see, e.g., Zou (2007) Cancer Res. 67: 4408-4417[3]; Cui (2011) J. Med. Chem. 54: 6342-6363[9]; and Christensen (2007) Mol Cancer Ther. 6: 3314-3322[23]). The terms "crizotinib", "(R)-crizotinib", and "(R)-enantiomer of crizotinib" are used interchangeably herein. To simplify matters, as used herein, the terms "racemic crizotinib" or "racemate of crizotinib" relate to the racemic form of the chemical substance 3-[1-(2,6-dichloro-3-fluoro-phenyl)-ethoxy]-5-(1-piperidin-4-yl-1H-pyrazol-4-yl)-pyridin-2-ylamine. In line with this, as used herein, the terms "(S)-crizotinib" and "(S)-enantiomer of crizotinib" relate to the (S)-enantiomer of the chemical substance 3-[1-(2,6-dichloro-3-fluoro-phenyl)-ethoxy]-5-(1-piperidin-4-yl-1H-pyrazol-4-yl)-pyridin-2-ylamine.

As demonstrated in the illustrative appended examples, the potency to inhibit MTH1 catalytic activity of racemic crizotinib, (R)-crizotinib and the (S)-enantiomer of crizotinib is considerably different. In particular, in an assay to determine inhibition of MTH1 catalytic activity, the $IC_{50}$ value determined for racemic crizotinib was about 10 times higher than the one observed for the enantiomerically pure (R)-crizotinib. Furthermore, the (S)-enantiomer of crizotinib indicated more than 100-fold higher inhibitory potency than (R)-crizotinib. Apparently, the (S)-conformation leads to an increased affinity of an aminoheteroaryl compound to MTH1. Accordingly, in context of the present invention it has been surprisingly demonstrated that crizotinib, more preferably racemic crizotinib, and even more preferably the pure (S)-enantiomer of crizotinib are highly potent inhibitors of MTH1, an enzyme which has been linked to the development, progression and maintenance of RAS-driven cancer.

Therefore, the present invention provides for the surprising finding, that the (S)-enantiomer of an aminoheteroaryl compound of the invention (such as the (S)-enantiomer of crizotinib) effectively inhibits the biological activity (in particular the catalytic activity) of MTH1. Considering that MTH1 has been linked to malignant transformation induced by mutant RAS, it is one aspect of the present invention that the (S)-enantiomer of an aminoheteroaryl compound of the invention (such as the (S)-enantiomer of crizotinib) can be used in treating and/or preventing cancer. In addition, since inhibition of MTH1 is independent of the cancer's ALK- and/or c-Met-status, it is a further aspect of the present invention that the (S)-enantiomer of an aminoheteroaryl compound of the invention (such as the (S)-enantiomer of crizotinib) can be used in treating and/or preventing ALK-negative and/or c-Met-negative cancer.

As described herein, the invention relates to an (S)-enantiomer of an aminoheteroaryl compound or Formula (1) (such as the (S)-enantiomer of crizotinib) or a pharmaceutically acceptable salt, solvate or prodrug thereof, for use in treating and/or preventing cancer. According to the present invention, the treatment and/or prevention is independent of the ALK-status and/or the c-Met-status of the cancer to be treated.

One embodiment of the invention relates to the compound for the use of the invention, wherein $R^1$ is —$NH_2$, —OH or SH;

$R^3$ is methyl;

Y is $CR^4$;

$R^4$ is hydrogen or halogen;

each $R^5$, $R^6$ and $R^7$ is independently fluorine or chlorine;

$R^8$ is hydrogen or -A-$B_n$-X, wherein

B is $C_{1-4}$ alkylene or —($OCH_2CH_2$)—;

n is 1, 2 or 3, and

X is —$NH_2$;

or a pharmaceutically acceptable salt, solvate or prodrug thereof.

A further embodiment of the invention relates to the compound for the use of the invention, wherein $R^8$ is hydrogen;

—C(=O) $CH_2CH_2CH_2CH_2CH_2$—$NH_2$;

—C(=O)$CH_2$—O—$CH_2CH_2$—O—$CH_2CH_2$—$NH_2$; or

—$CH_2CH_2CH_2$—$NH_2$;

or a pharmaceutically acceptable salt, solvate or prodrug thereof.

Another embodiment of the invention relates to the compound for the use of the invention, wherein the compound has one of the following chemical structures represented by Formulae (2) to (5):

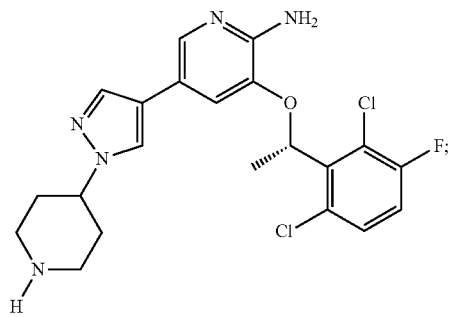

Formula (2)

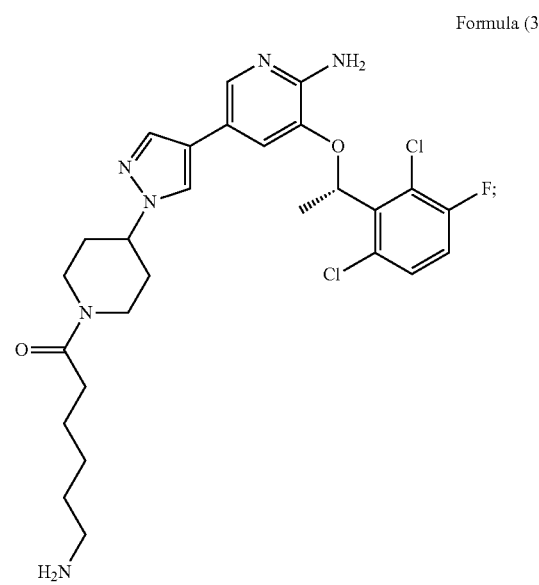

Formula (3)

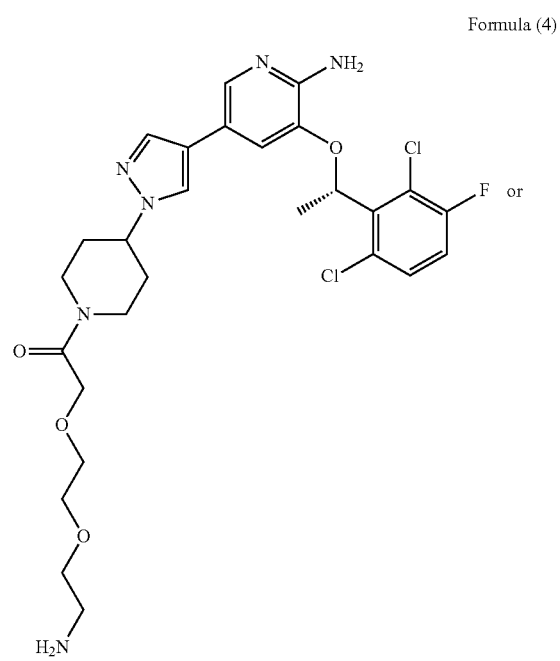

Formula (4)

-continued

Formula (5)

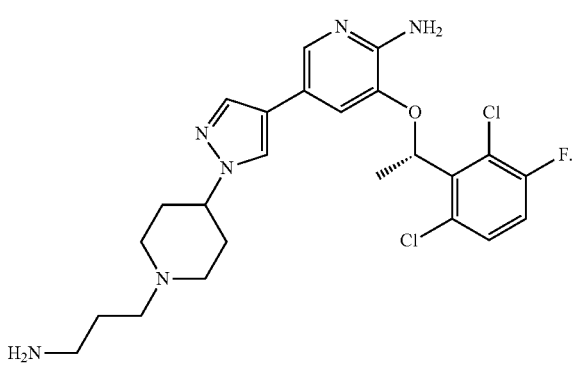

It is also envisaged that the (S)-enantiomer of an aminoheteroaryl compound of the invention may be administered to a subject as compounds per se in their use as pharmacophores or pharmaceutical compositions or may be formulated as medicaments.

Accordingly, the present invention further relates to a pharmaceutical composition comprising the compound for the use of the invention and a pharmaceutically acceptable excipient. Thus, one aspect of the invention relates to a pharmaceutical composition for use in treating and/or preventing cancer, wherein said pharmaceutical composition comprises the (S)-enantiomer of an aminoheteroaryl compound as provided herein and a pharmaceutically acceptable excipient.

One aspect of the invention relates to a pharmaceutical composition comprising the (S)-enantiomer of an aminoheteroaryl compound provided herein and a pharmaceutically acceptable excipient, for use in treating and/or preventing cancer in a subject, wherein the treatment and/or prevention is independent of the ALK-status and/or the c-Met-status of the cancer cell or tissue of said subject. Said ALK-status may be the level of ALK biological activity and/or the level of ALK expression. In line with this, said c-Met-status may be the level of c-Met biological activity and/or the level of c-Met expression. Methods for determining the level of the biological activity or the level of the expression of ALK or c-Met are described herein above and below.

Thus said cancer to be treated may be ALK-negative (i.e. may not have an activating ALK aberration) and/or c-Met-negative. In accordance with the present invention, said pharmaceutically acceptable excipient may be a carrier, diluent, filler, desintegrant, lubricating agent, binder, colorant, pigment, stabilizer, preservative or antioxidant.

As described herein, one embodiment of the invention relates to the pharmaceutical composition of the invention, comprising at least two components each having one of the chemical structures represented by Formulae (1) to (5). Another embodiment of the invention relates to the pharmaceutical composition of the invention, comprising at least two components each having one of the chemical structures represented by Formulae (2) to (5). As indicated above, the invention relates to an (S)-enantiomer of an aminoheteroaryl compound and a pharmaceutical composition for use in treating and/or preventing cancer in a subject. The invention further relates to the compound for the use of the invention, or the pharmaceutical composition of the invention, wherein the treatment and/or prevention of cancer in a subject is independent of the ALK-status and/or the c-Met-status of the cancer cell or tissue of said subject. Thus, the cancer to be treated and/or prevented may be ALK-negative (i.e. may not have an activating ALK aberration) and/or may be c-Met-negative.

Crizotinib is a dual inhibitor of anaplastic lymphoma kinase (ALK) and hepatocyte growth factor receptor kinase (c-Met).[3] At present, crizotinib is exclusively used to treat patients who have been diagnosed with ALK-positive tumours. The molecular lesions behind oncogenic ALK activity can be associated with either ALK gene amplification, mutation or chromosomal translocations such as EML4-ALK.[4] EML4-ALK is an oncogenic fusion protein consisting of the echinoderm microtubule-associated protein-like 4 and ALK genes (EML4-ALK).[5]

As indicated above, in context of the present invention it has been surprisingly found that aminoheteroaryl compounds (such as crizotinib), and preferably the (S)-enantiomer of an aminoheteroaryl compound (such as the (S)-enantiomer of crizotinib) are able to inhibit the biological activity of MTH1 and can therefore also be used to treat and/or prevent cancer in a subject independent of the ALK-status and/or c-Met-status of the cancer. Accordingly, a further embodiment of the invention relates to the compound for the use of the invention, or the pharmaceutical composition of the invention, wherein said cancer cell or tissue of said subject does not have a gene mutation and/or a chromosomal translocation of ALK. One aspect of the invention relates to the compound for the use of the invention, or the pharmaceutical composition of the invention, wherein said chromosomal translocation is EML4-ALK.

This translocation occurs in approximately 3-13% of adenocarcinomas in non-small cell lung cancer (NSCLC) and is, apart from one reported case, considered to be mutually exclusive with mutations in EGFR or KRAS.[6] Furthermore, as ALK rearrangements have been found to be mutually exclusive with mutations in RAS or EGFR family genes in lung cancer patients (Gainor (2013) Clinical Cancer Research 19, 4273-4281), the ALK kinase inhibitor (R)-crizotinib is not suited for the treatment of patients bearing mutations in KRAS or EGFR. It is noteworthy that even patients that have developed resistance toward (R)-crizotinib [Xalkori®] do not seem to acquire mutations in KRAS or EGFR (Gainor, op., cit.), which further underscores the lack of rationale to treat patients whose cancer has RAS mutations or increased EGFR expression with (R)-crizotinib [Xalkori®]. In agreement with this, the appended illustrative examples show that c-Met inhibition does not suppress growth of KRAS mutated SW480 cells. In contrast, the (S)-enantiomer of crizotinib decreases cell growth of SW480 cells in vitro as well as in an in vivo mouse model. These results demonstrate that in contrast to crizotinib (i.e (R)-crizotinib) the (S)-enantiomer of crizotinib is useful for the treatment of RAS positive cancers.

It has been surprisingly demonstrated in the appended examples that the pure (S)-enantiomer of crizotinib is a highly potent inhibitor of MTH1, an enzyme which has been linked in the prior art to the development, progression and maintenance of RAS-driven cancer.[13] It is mentioned that the prior art recently demonstrated that MTH1 might also be a promising target for adenocarcinomas expressing EGFR, as the micro-RNA MiR-145 which suppresses both EGFR and MTH1 is downregulated in these tumours.[37] As also shown in the prior art, reexpression of MiR-145 led to a downregulation of EGFR and MTH1 on both mRNA and protein level and impaired the growth of EGFR-positive cell lines. In addition, as shown in the appended examples, the (S)-enantiomer of crizotinib efficiently inhibited colony formation of human colon adenocarcinoma cells (SW480) as well as of pancreatic cancer cells (PANC1), both having an activating RAS mutation. Consistent with these results, stable knockdown of MTH1 significantly reduced colony formation of SW480 cells. Furthermore, as described herein, a mouse xenograft study using human colon adenocarcinoma cells (SW480) demonstrates that the (S)-enantiomer of crizotinib is able to impair tumour progression. In particular, administering of the (S)-enantiomer of crizotinib resulted in a reduction in tumour volume of more than 50%. As also evident from this experiment, the (S)-enantiomer of crizotinib is well-tolerated as animals behaved normally and no significant change in haematological parameters or body weight was observed.

Thus, one embodiment of the present invention relates to the compound for the use of the invention, or the pharmaceutical composition of the invention, wherein the cancer cell or tissue of said subject has an activating RAS mutation and/or an activating EGFR mutation. One particular embodiment of the invention relates to the compound for the use of the invention, or the pharmaceutical composition of the invention, wherein the cancer cell or tissue of said subject has an activating RAS mutation. Said activating RAS mutation may be an activating KRAS mutation (e.g. G12D, G12V, or G12C). Treating cells transformed with mutant RAS by targeting MTH1 is in line with the prior art showing that transformation of cells by mutant RAS can lead to increased production of ROS.[12] As for normal cells, oxidative damage caused by ROS can force cancer cells into a state of quiescence or senescence (OIS), and eventually apoptosis. To overcome senescence, RAS-transformed cells upregulate MTH1 which protects the cells from oxidative DNA damage. For instance, it has been described in the prior art that human skin fibroblasts transfected with HRAS undergo senescence, but this phenotype can be rescued by concomitant overexpression of MTH1.[12] Consequently, MTH1 suppression causes proliferative defects in cancer cells expressing mutant RAS.[13] As MTH1$^{-/-}$ knockout mice show a very mild phenotype,[14] targeting MTH1 with small molecules may provide a novel and well-tolerated therapeutic option for the difficult to treat RAS mutant cancers. Indeed, as also shown in the appended examples, clinically used (R)-enantiomer of crizotinib exhibited higher toxicity than the (S)-enantiomer of crizotinib on non-transformed cells. In agreement with this and as also shown in the appended illustrative examples, the (S)-enantiomer of crizotinib is less toxic to wildtype cells or cells which are only immortalized by telomerase as compared to transformed cells. This result underscores the cancer-specific effect of the (S)-enantiomer of crizotinib.

Activated RAS GTPase signalling is a critical driver of oncogenic transformation and malignant disease (Pylayeva-Gupta (2011) Nat Rev Cancer 11, 761-774). About 20-30% of human cancers contain mutations in one RAS isoform, (Parada (1982) Nature 297, 474-478; Der (1982) Proceedings of the National Academy of Sciences 79, 3637-3640) which is accompanied by poor prognosis and low overall survival, highlighting the urgent need to identify new inhibitors. However, the structure of the RAS proteins makes them poor targets for small molecules. As an alternative, cellular models of RAS-dependent cancers have been used in the prior art to develop specific inhibitors such as SCH51344, but the molecular targets remain mostly enigmatic (Kumar (1995) Cancer Research 55, 5106-5117). Direct modulation of RAS activity by small molecules has posed a significant challenge in drug discovery. Therefore, alternative approaches have been used in the prior art, for example to interfere with RAS processing, which is regulated via post-translational modifications, e.g. palmitoylation, to prevent maturation and translocation of the active protein to the plasma membrane (Xu (2012) Blood 119, 1032-1035; Dekker (2010) Nat Chem Biol 6, 449-456). In addition to these targeted approaches, phenotypic screens have been employed in the prior art to search for small molecules that selectively target RAS-transformed cancer cells but do not affect the growth of untransformed cells (Yagoda (2007) Nature 447, 865-869). The benefit of such a strategy is that active compounds are already being selected on the basis of their specificity for cancer cells and their cellular activity. In 1995, this approach led to the discovery of a pyrazoloquinoline compound termed SCH51344 that suppressed the anchorage-independent growth of RAS-transformed fibroblasts as well as human colon carcinoma and pancreatic cancer cell lines (Kumar (1995) Cancer Research 55, 5106-5117). Significantly, as documented in the appended examples, the herein provided (S)-enantiomer of an aminoheteroaryl compound (e.g. the (S)-enantiomer of crizotinib) is considerably more effective in the treatment of RAS-dependent cancer cells than the compound SCH51344.

Several proteins play a role in the repair of damaged DNA. These proteins include DNA ligase, PCNA (a sliding clamp), as well as p53, p21, and MLH1. Studies in model systems have shown that the antiproliferative effect of MTH1 suppression may depend on p53, a well-known tumour suppressor gene (Rai (2009) Proceedings of the National Academy of Sciences 106, 169-174; Rai (2010) Mutation Research/Genetic Toxicology and Environmental Mutagenesis 703, 71-81). In particular, loss of p53 function was demonstrated to prevent senescence induction by MTH1 genetic silencing. Therefore, it is likely that patients with functional p53 signalling may benefit preferably from MTH1 inhibitor treatment. However, the appended illustrative examples indicate that the p53 status as well as the presence or absence of functional MLH1 do not affect the activity of the (S)-enantiomer of crizotinib. However, loss of p21 increases the sensitivity of cancer cells (e.g. HCT116 cells) toward treatment with the (S)-enantiomer of crizotinib. Accordingly, it is likely that patients with non-functional p21 signalling may benefit preferably from treatment with the (S)-enantiomer of an aminoheteroaryl compound of the present invention. Thus, one aspect of the invention is directed to the herein provided (S)-enantiomer of an aminoheteroaryl compound or the herein described pharmaceutical composition for use in treating and/or preventing cancer in a subject, wherein in the cancer cell or tissue of said subject the biological activity and/or expression of p21 is reduced or absent. In this regard, the term "reduced" means that the biological activity of p21 and/or the expression of p21 is reduced as compared to the biological activity or expression of p21 in a cell or tissue sample of a healthy control subject (e.g. of a healthy control person). Human p21 inhibits cyclin-CDK2 and cyclin-CDK4 complexes, regulating cell cycle progression in G1 phase. Reduced p21 expression has been implicated in a variety of human cancers including those of the prostate, bladder, and esophagus. The tumor suppressor p21 mediates its various biological activities primarily by binding to and inhibiting the kinase activity of the cyclin-dependent kinases (CDKs) CDK2 and CDK1 (also known as CDC2). Thus, in order to determine the biological activity of p21, the ability of purified p21 to inhibit kinase activity of CDK2 or CDK1 may be determined. CDK activity (e.g. activity of CDK2) may be monitored by determining substrate phosphorylation using radioactively-labeled ATP. For example, for measurement of Cdk2 activity, the [33P]ATP Scintillation Proximity Assay of PerkinElmer may be used (see, e.g., http://www.perkinelmer.com/pages/020/proximitynews/enzymes/measurementofcdk2.xhtml). The expression of p21 may be determined, e.g., by PCR, RT-PCT or Western blot.

In one embodiment of the invention, the cancer cell or tissue of the subject to be treated with the herein provided (S)-enantiomer of an aminoheteroaryl compound or pharmaceutical composition has the genetic constitution $p21^{+/-}$ (i.e. one allele of p21 is deleted or inactivated). In another embodiment of the invention, said cancer cell or tissue has the genetic constitution $p21^{-/-}$ (i.e. both alleles of p21 are deleted or inactivated).

As described above, the present invention relates to an (S)-enantiomer of an aminoheteroaryl compound for use in treating and/or preventing cancer in a subject. One aspect of the invention relates to the compound for the use of the invention, or the pharmaceutical composition of the invention, wherein said subject is a mammal. A further aspect of the invention relates to the compound for the use of the invention, or the pharmaceutical composition of the invention, wherein said mammal is a human patient.

As described herein and illustrated in the appended examples, it has been found that crizotinib, preferably racemic crizotinib, and more preferably the (S)-enantiomer of crizotinib as well as its structural derivatives could be applied in the treatment of a variety of distinct tumour types apart from ALK/Met-driven lung cancer but also RAS-driven colon cancer, breast cancer, lung cancer, pancreatic cancer, Ewing's sarcoma and many more. As shown herein, the (S)-enantiomer of crizotinib efficiently inhibits growth and progression of RAS-dependent cancer cells. Therefore, it is prioritized to use the (S)-enantiomer of an aminoheteroaryl compound of the present invention to treat and/or prevent cancer having an activating RAS mutation. This cancer may be, e.g., colon cancer. Thus, one embodiment of the present invention relates to the compound for the use of the invention, or the pharmaceutical composition of the invention, wherein the cancer is selected from the group consisting of colon cancer, lung cancer, breast cancer, leukaemia, lymphoma, skin cancer, liver cancer, pancreatic cancer, brain cancer, kidney cancer, neuroblastoma, Ewing's sarcoma, prostate cancer, bladder cancer and esophagus cancer.

It has been shown in the prior art that triple negative breast cancer cell lines are sensitive to oxidative DNA damage and that this damage can sensitize these cancers to other chemotherapeutics such as PARP inhibitors.[18] Therefore, MTH1 inhibitors which are thought to induce oxidative DNA lesions could be used to treat these tumour types. In addition, it has been reported that the BRCA1 and BRCA2 genes which are mutated in some types of breast cancer are involved in the repair of oxidative DNA damage including 8-oxo-guanine-based lesions.[17,39] Consequently, one aspect of the invention relates to use the herein identified MTH1 inhibitors to target these tumours. In this context, the MTH1 inhibitors could also synergize with other standard-of-care agents such as PARP inhibitors. Thus, it is envisaged in context of the present invention to use MTH1 inhibitors for treating and/or preventing breast cancer, preferably triple-negative breast cancer. Accordingly, the present invention further relates to the compound for the use of the invention, or the pharmaceutical composition of the invention for treating and/or preventing breast cancer in a subject. One embodiment of the invention relates to the compound for the use of the invention, or the pharmaceutical composition of the invention, wherein said breast cancer lacks expression of estrogen receptor-α and progesterone receptor and lacks overexpression or amplification of the HER2/NEU oncogene (i. e, triple-negative breast cancer). A particular aspect of the present invention relates to the compound for the use of the invention, or the pharmaceutical composition of the invention, wherein said breast cancer has a BRCA1 and/or BRCA2 gene mutation. The breast cancer or the lung cancer which is to be treated and/or prevented with the compound for the use of the invention or the pharmaceutical composition of the invention may further be EGFR-dependent.

Based on the physiological effects of MTH1 suppression, MTH1 inhibitors are likely to synergise with radiotherapy and/or chemotherapy, preferably with DNA damaging compounds, compounds which interfere with DNA repair mechanisms, or compounds which induce the production or inhibit the clearance of ROS.

Thus, one embodiment of the invention relates to the compound for the use of the invention, or the pharmaceutical composition of the invention, wherein said compound or pharmaceutical composition is co-administered with radiation and/or chemotherapy. One aspect of the invention relates to the compound for the use of the invention, or the pharmaceutical composition of the invention, wherein said chemotherapy is a DNA damaging drug, an alkylating agent, a DNA intercalator, a topoisomerase inhibitor, an agent which confers oxidative damage to DNA, a cytotoxic compound, an antimetabolite, a compound which interferes with DNA repair mechanisms, an ATM kinase inhibitor, an ATR kinase inhibitor, a CHK1/2 kinase inhibitor, a PARP inhibitor, an EGFR inhibitor, a DNA-dependent protein kinase inhibitor, a generic base excision repair inhibitor, a DNA polymerase beta inhibitor, a O-6-methylguanine methyltransferase (MGMT) inhibitor, a survivin suppressant, a compound generating reactive oxygen species (ROS), an antimitotic compound, or a combination of any of the foregoing. As indicated above, the compound for the use of the invention, or the pharmaceutical composition of the invention may be co-administered with chemotherapy. A preferred aspect of the invention relates to the compound for the use of the invention, or the pharmaceutical composition of the invention, wherein said chemotherapy is a PARP inhibitor and/or an EGFR inhibitor. However, beside PARP inhibitors and/or EGFR inhibitors, several other chemotherapeutic drugs may be co-administered with the compound of the invention or the pharmaceutical composition of the invention. Thus, another aspect of the invention relates to the compound for the use of the invention, or the pharmaceutical composition of the invention, wherein said chemotherapy is cyclophosphamide, temozolomide, melphalan, carmustine, busulfan, cisplatin, procarbazine, anthracyclines, camptothecin, irinotecan, etoposide, hydrogen peroxide, resorcinol, quinones, methotrexate, 5-fluorouracil, thalidomide, lenalidomide, pomalidomide, olaparib, ABT-888, neocarzinostatin, bleomycin, decitabine, 5-azacytosine, methoxyamine hydrochloride (TRC102), lomeguatrib, piperlongumine, quercetin, vincristin, taxol, mitoxantrone, YM155, erlotinib, gefitinib, lapatinib, or a combination of any of the foregoing. Accordingly, as described herein, the herein defined (S)-enantiomer of an aminoheteroaryl compound can be co-administered with several chemotherapeutic drugs including DNA damaging drugs such as alkylating agents (e.g. cyclophosphamide, temozolomide, melphalan, carmustine, busulfan, cisplatin, procarbazine and others), DNA intercalators (e.g. anthracyclines) or topoisomerase inhibitors (e.g. camptothecin, irinotecan, etoposide), agents which confer oxidative damage to DNA (e.g. hydrogen peroxide, resorcinol, quinones) other cytoxic compounds (e.g. antimetabolites including methotrexate, 5-fluorouracil, thalidomide and analogues thereof, neocarzinostatin, bleomycin, decitabine, 5-azacytosine), compounds which interfere with DNA repair mechanisms (e.g. ATM-, ATR- or CHK1/2 kinase inhibitors, PARP inhibitors, DNA-dependent protein kinase inhibitors, generic base excision repair inhibitors such as methoxyamine hydrochloride (TRC102), DNA polymerase beta inhibitors, O-6-methylguanine methyltransferase (MGMT) inhibitors (e.g. lomeguatrib), compounds generating reactive oxygen species (ROS) (e.g. piperlongumine, quercetin), antimitotic compounds such as vincristin or taxol, EGFR inhibitors (e.g. erlotinib, gefitinib, lapatinib) as well as mitoxantrone and YM155.

As provided herein, crizotinib, more preferably racemic crizotinib, and even more preferably the pure (S)-enantiomer of crizotinib are highly potent inhibitors of MTH1. This is of particular interest as a) small molecule inhibitors of MTH1 have not been reported so far, b) patients who are to be treated with crizotinib are selected by their c-Met-, or more preferably, ALK-expression status whilst not considering MTH1, and c) as demonstrated in the appended examples, introduction of aminoalkyl substituents at the piperidine nitrogen of crizotinib is well tolerated with respect to both ALK and MTH1 inhibition. The latter finding also suggests that compounds disclosed in WO 2008/053157, WO 2006/021881, WO 2006/021886 and WO 2006/021884 are potent and bioavailable MTH1 inhibitors. Accordingly, one aspect of the invention relates to the use of the compounds disclosed in WO 2008/053157, WO 2006/021881, WO 2006/021886 and WO 2006/021884 for inhibiting MHT1 and thus, treating and/or preventing cancer.

As described herein, it has been found that the (S)-enantiomer of an aminoheteroaryl compound effectively inhibits the biological activity of MTH1. Therefore, the compound of the invention can be used to treat and/or prevent cancers, in particular cancers wherein MTH1 is involved in the development of the cancer and/or progression of the cancer. To determine whether a MTH1 is involved in the development and/or progression of a cancer, one can analyze the status (e.g. the genetic constitution, expression and/or activity) of MTH1. The MTH1-status of a cancer represents an appropriate indicator for the involvement of MTH1 in the development and/or progression of said cancer. Accordingly, it is a further aspect of the invention to stratify cancer patients with respect to their MTH1-status.

Thus, a further embodiment of the invention relates to an in vitro method for determining the effectiveness of the compound for the use of the invention, or the pharmaceutical composition of the invention, the method comprising the steps of:
(a) obtaining a cell or tissue sample from a subject; and
(b) determining the subject's NUDT1/MTH1-status;
wherein a NUDT1/MTH1-positive cell or tissue sample is indicative of an effective treatment and/or prevention of cancer.

In one aspect of this in vitro method, said NUDT/MTH1-status is the level of MTH1 biological activity and/or the level of MTH1 expression. The level of MTH1 biological activity may be monitored by purifying MTH1 from said cell or tissue sample from said subject and measuring the production of PPi generated by MTH1-mediated 8-oxo-dGTP hydrolysis. In particular, purified MTH1 may be contacted with 8-oxo-dGTP and the production of PPi may be measured using the PPiLight Inorganic Pyrophosphate Assay (Lonza Rockland Inc.). In order to determine whether the herein described (S)-enantiomer of crizotinib or the herein described pharmaceutical composition is suitable for the treatment of a cancer patient, the level of MTH1 biological activity (i.e. the quantity of produced PPi) of MTH1 within a sample of said cancer patient may be compared to the level of MTH1 biological activity (i.e. the quantity of produced PPi) of MTH1 within a sample of a healthy control person. The cell or tissue sample of the cancer patient is "NUDT1/MTH1-positive" if the level of MTH1 biological activity (i.e. the amount of produced PPi) is higher in the sample of the cancer patient as compared to the sample of the healthy control person. In this case the herein described (S)-enantiomer of an aminoheteroaryl compound or the herein described pharmaceutical composition is suitable for the treatment of said cancer patient.

The level of MTH1 expression may be determined, for example, by PCR, RT-PCT or western blot. The cell or tissue sample is "NUDT1/MTH1-positive" if the expression of MTH1 (i.e. the amount of the MTH1 mRNA or of the MTH1 protein) is higher in a sample of a cancer patient as compared to a sample of a healthy control person. In this case the herein described (S)-enantiomer of an aminoheteroaryl compound or the herein described pharmaceutical composition is suitable for the treatment of said cancer patient. In addition, as described in more detail below, for the determination of the status of MTH1, several other detection methods can be applied.

One aspect of the invention relates to the in vitro method of the invention, further comprising the step of:
(c) determining the subject's RAS-status;
wherein a cell or tissue sample positive for NUDT1/MTH1 and positive for an activating RAS mutation are indicative of an effective treatment and/or prevention of cancer. Accordingly, in this context, the term "RAS-status" relates to the existences of an activating RAS mutation. Accordingly, one aspect of the invention relates to the above described in vitro method, further comprising the step of:
(c) determining whether said cell or tissue sample has an activating RAS mutation;
wherein a cell or tissue sample positive for NUDT1/MTH1 and positive for an activating RAS mutation are indicative of an effective treatment and/or prevention of cancer.

An activating RAS mutation is an activating aberration of RAS. In particular, an activating RAS mutation relates to a mutation within RAS which leads to an increased biological activity (i.e. catalytic activity) of RAS. The person skilled in the art readily knows several activating RAS mutations. Examples for activating RAS mutations are, e.g., the G12 mutation (e.g. G12D, G12V, or G12C) of KRAS or the Q61 mutation (e.g. Q61H) of KRAS. These mutations may be determined, e.g., by sequencing. Further examples for a number of activating RAS mutations are also provided herein, below.

As mentioned above, in context of the present invention it has surprisingly been identified that loss of p21 increases the sensitivity of cancer cells toward treatment with the (S)-enantiomer of crizotinib. Thus, the in vitro method provided herein may further comprise the step of:
(d) determining whether in said cell or tissue sample the expression and/or biological activity of p21 is reduced or absent;
wherein a cell or tissue sample which is positive for NUDT1/MTH1 and wherein the expression and/or biological activity of p21 is reduced or absent are indicative of an effective treatment and/or prevention of cancer.

In context of the present invention it has been surprisingly identified that effective treatment of cancer by using the compound for the use of the invention is independent of the patient's ALK- and/or c-Met-status. Thus, in one specific aspect, the invention relates to the above described in vitro method, further comprising the steps of:
(d) determining the subject's c-Met-status; and/or
(e) determining the subject's ALK-status;
wherein a cell or tissue sample positive for NUDT1/MTH1 and negative for c-Met is indicative of an effective treatment and/or wherein a cell or tissue sample positive for NUDT1/MTH1 and negative for ALK is indicative of an effective treatment and/or prevention of cancer.

The cell or tissue sample which is to be obtained in context of the in vitro method of the invention may be a cancer cell or tissue sample obtained from a cancer patient. Accordingly, a further embodiment of the invention relates to the in vitro method of the invention, wherein said cell or tissue sample is a cancer cell or tissue. For the determination of the status of MTH1, RAS, c-Met and/or ALK, several detection methods can be applied. Thus, one aspect of the invention relates to the in vitro method of the invention, wherein step (b) and/or (c) comprises at least one detection method selected from the group consisting of PCR (polymerase chain reaction), gene sequencing, ARMS (Amplification Refractory Mutation System), Peptide nucleic acid-locked nucleic acid (PNA-LNA) PCR clamp, PCR-Invader, SNaPshot, PCR/HRMA/dHPLC, PCR/fIRFLP, Fluorescent In-Situ Hybridisation (FISH), Immunohistochemistry (IHC), RT-PCR, gene arrays, and gene chips. Another aspect of the invention relates to the in vitro method of the invention, wherein step (b), (c), (d) and/or (e) comprises at least one detection method selected from the group consisting of PCR (polymerase chain reaction), gene sequencing, ARMS (Amplification Refractory Mutation System), Peptide nucleic acid-locked nucleic acid (PNA-LNA) PCR clamp, PCR-Invader, SNaPshot, PCR/HRMA/dHPLC, PCR/fIRFLP, Fluorescent In-Situ Hybridisation (FISH), Immunohistochemistry (IHC), RT-PCR, gene arrays, and gene chips. These methods are well known in the art and also described herein, below.

The in vitro method provided herein may be performed prior to the administration of the herein described (S)-enantiomer of an aminoheteroaryl compound in order to evaluate whether a cancer patient will profit from the treatment with an (S)-enantiomer of an aminoheteroaryl compound. Accordingly, provided herein is a method of treating and/or preventing cancer in a subject in need of such treatment, wherein the method comprises:
(i) performing the in vitro method as described above; and
(ii) administering to said subject an effective amount of the (S)-enantiomer of an aminoheteroaryl compound provided herein if the result obtained in step (i) is indicative of an effective treatment and/or prevention of cancer.

Thus, the invention provides for a method of treating and/or preventing cancer in a subject in need of such treatment, wherein the method comprises:
(a) obtaining a cell or tissue sample from said subject;
(b) determining the subjects's NUDT1/MTH1-status;
(c) optionally, determining the subject's RAS-status;
(d) optionally, determining whether in said cell or tissue sample the expression and/or biological activity of p21 is reduced or absent;
wherein a cell or tissue sample which is positive for NUDT1/MTH1 and, optionally, which is positive for an activating RAS mutation and, optionally, wherein the expression and/or biological activity of p21 is reduced or absent, are indicative of an effective treatment and/or prevention of cancer in said subject.

The in vitro method of the invention may be realized by using an appropriate kit. Accordingly, another embodiment of the invention relates to a kit for carrying out the in vitro method of the invention, comprising polynucleotides and/or antibodies capable of detecting NUDT1/MTH1. In one aspect the invention relates to said kit, further comprising polynucleotides and/or antibodies capable of detecting RAS. The kit may additionally comprise polynucleotides and/or antibodies capable of detecting ALK and/or c-Met. The kit may further comprise polynucleotides and/or antibodies capable of detecting p21. Several polynucleotides and antibodies for the detection of NUDT1/MTH1, RAS, ALK, c-Met and p21 are known in the art and also provided herein, below.

Accordingly, the present invention relates to a kit for carrying out the in vitro method for determining the effectiveness of the compound for the use of the invention, or the pharmaceutical composition of the invention, the method comprising the steps of:
(a) obtaining a cell or tissue sample from a subject; and
(b) determining the subject's NUDT1/MTH1-status;
wherein a NUDT1/MTH1-positive cell or tissue sample is indicative of an effective treatment and/or prevention of cancer.

The embodiments disclosed in connection with the in vitro method of the present invention apply, mutatis mutandis, to the kit of the present invention.

Advantageously, the kit of the present invention further comprises, optionally (a) reaction buffer(s), storage solutions, wash solutions and/or remaining reagents or materials required for the conduction of the assays as described herein. Furthermore, parts of the kit of the invention can be packaged individually in vials or bottles or in combination in containers or multicontainer units. These vials/bottles/containers or multicontainers may, in addition to the polynucleotides and/or antibodies as described herein, comprise preservatives or buffers for storage. In addition, the kit may contain instructions for use, in particular the kit may contain an instruction manual how to carry out the determination of the patient's NUDT1/MTH1-status and optionally, also the patient's RAS-, ALK-, and/or c-Met-status.

The kit of the present invention may be advantageously used, inter alia, for carrying out the in vitro method as described herein and/or it could be employed in a variety of further applications, e.g., as diagnostic kit, as research tool or as therapeutic tool. Additionally, the kit of the invention may contain further means for detection suitable for scientific, medical and/or diagnostic purposes. The manufacture of the kit of the present invention follows preferably standard procedures which are known to the person skilled in the art.

A further embodiment of the invention relates to the use of a kit in the in vitro method of the invention, the kit comprising polynucleotides and/or antibodies capable of detecting NUDT1/MTH1. The invention further relates to said use, wherein the kit further comprises polynucleotides and/or antibodies capable of detecting RAS. In addition, the invention also relates to said use, wherein the kit further comprises polynucleotides and/or antibodies capable of detecting ALK and/or c-Met. Moreover, provided herein is the use of the herein described kit in the in vitro method provided herein, wherein said kit further comprises polynucleotides and/or antibodies capable of detecting p21.

In context of the present invention it has been surprisingly identified that MTH1 represents a novel target of an aminoheteroaryl compound (such as crizotinib). Furthermore, in the appended illustrative examples a screening method for identifying a target of the (S)-enantiomer of crizotinib is performed in SW480 cells, a colon carcinoma cell line expressing mutant KRAS. The obtained results clearly demonstrate that MTH1 (gene name NUDT1) is the main target of to (S)-enantiomer of crizotinib highlighting the specificity of the compound. Accordingly, the present invention further relates to a screening method for identifying a target of an aminoheteroaryl compound.

Thus, one embodiment of the invention relates to a screening method for identifying a target of an aminoheteroaryl compound having the following chemical structure represented by Formula (6),

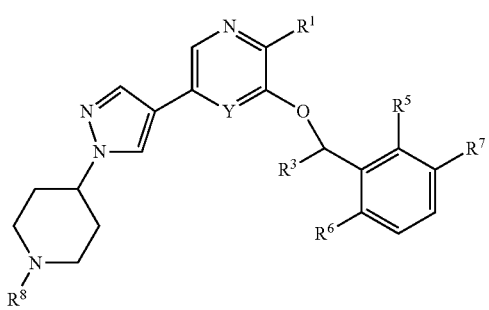

Formula (6)

wherein:
$R^1$ is —$NH_2$, —NRH, —OH or —SH;
$R^2$ is $C_{1-6}$ alkyl, $C_{2-6}$ alkenyl or $C_{2-6}$ alkynyl;
$R^3$ is $C_{1-3}$ alkyl, $C_{2-3}$ alkenyl, $C_{2-3}$ alkynyl or cyclopropyl;
Y is N or $CR^4$;
$R^4$ is hydrogen, halogen, $C_{1-6}$ alkyl, $C_{2-6}$ alkenyl, $C_{2-6}$ alkynyl or $C_{3-6}$ cycloalkyl;
each $R^5$, $R^6$ and $R^7$ is independently fluorine, chlorine, bromine or iodine;
$R^8$ is hydrogen or -A-$B_n$-X, wherein
 A is a single bond, —C(=O)— or —C(=O)$CH_2$—;
 B is $C_{1-4}$ alkylene, $C_{2-4}$ alkenylene or —(O$CH_2CH_2$)—;
 n is 0, 1, 2, 3, 4 or 5, and
 X is —$NHR^2$; —$NH_2$; —SH; —OH or O-alkyl;
or a pharmaceutically acceptable salt, solvate or prodrug thereof;
and wherein the screening method comprises the steps of:
(a) obtaining a cell lysate;
(b) contacting said aminoheteroaryl compound with said cell lysate; and
(c) determining whether a molecule binds to said aminoheteroaryl compound,
wherein, if a molecule is found to bind to said aminoheteroaryl compound, then such molecule is identified as a target of said aminoheteroaryl compound.

One aspect of the invention relates to the screening method of the invention, wherein in compound of Formula (6)
$R^1$ is —$NH_2$, —OH or —SH;
$R^3$ is methyl;
Y is $CR^4$;
$R^4$ is hydrogen or halogen;
each $R^5$, $R^6$ and $R^7$ is independently fluorine or chlorine;
$R^8$ is hydrogen or -A-$B_n$-X, wherein
 B is $C_{1-4}$ alkylene or —(O$CH_2CH_2$)—;
 n is 1, 2 or 3, and
 X is —$NH_2$.

A further aspect of the invention relates to the screening method of the invention, wherein in compound of Formula (6)
$R^8$ is hydrogen;
—C(=O) $CH_2CH_2CH_2CH_2CH_2$—$NH_2$;
—C(=O)$CH_2$—O—$CH_2CH_2$—O—$CH_2CH_2$—$NH_2$; or
—$CH_2CH_2CH_2$—$NH_2$.

Another aspect of the invention relates to the screening method of the invention, wherein the compound has one of the following chemical structures represented by Formulae (7) to (10):

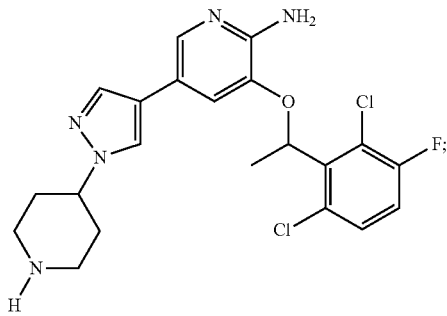

Formula (7)

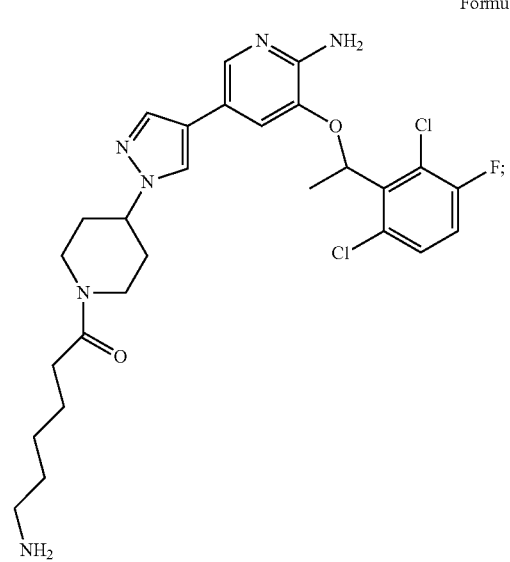

Formula (8)

Formula (9)

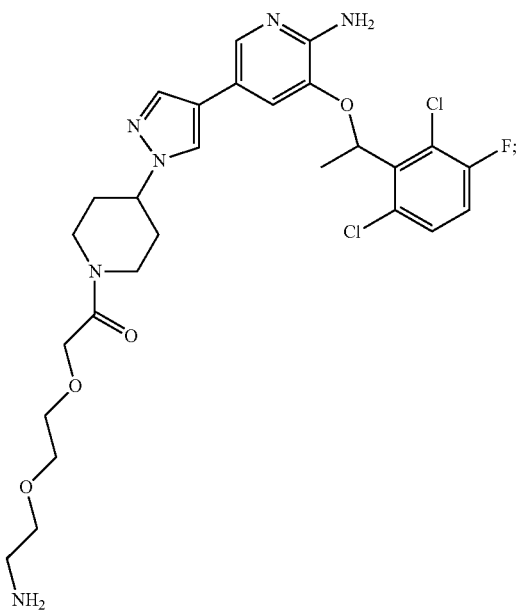

Formula (1)

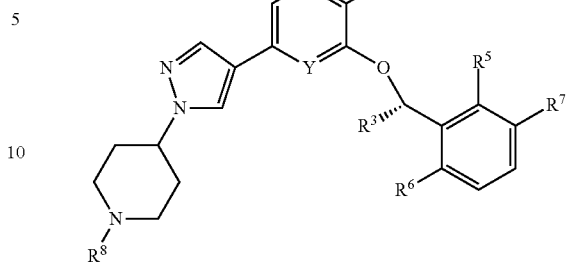

wherein:
R¹ is —NH₂, —NR²H, —OH or —SH;
R² is $C_{1-6}$ alkyl, $C_{2-6}$ alkenyl or $C_{2-6}$ alkynyl;
R³ is $C_{1-3}$ alkyl, $C_{2-3}$ alkenyl, $C_{2-3}$ alkynyl or cyclopropyl;
Y is N or CR⁴;
R⁴ is hydrogen, halogen, $C_{1-6}$ alkyl, $C_{2-6}$ alkenyl, $C_{2-6}$ alkynyl or $C_{3-6}$ cycloalkyl;
each R⁵, R⁶ and R⁷ is independently fluorine, chlorine, bromine or iodine;
R⁸ is hydrogen or -A-B$_n$-X, wherein
  A is a single bond, —C(=O)— or —C(=O)CH₂—;
  B is $C_{1-4}$ alkylene, $C_{2-4}$ alkenylene or —(OCH₂CH₂)—;
  n is 0, 1, 2, 3, 4 or 5, and
  X is —NHR²; —NH₂; —SH; —OH or O-alkyl;
or a pharmaceutically acceptable salt, solvate or prodrug thereof;
and wherein the screening method comprises the steps of:
(a) obtaining a cell lysate;
(b) contacting said aminoheteroaryl compound with said cell lysate; and
(c) determining whether a molecule binds to said aminoheteroaryl compound,
wherein, if a molecule is found to bind to said aminoheteroaryl compound, then such molecule is identified as a target of said aminoheteroaryl compound.

One embodiment of the invention relates to this screening method, wherein in compound of Formula (1)
R¹ is —NH₂, —OH or —SH;
R³ is methyl;
Y is CR⁴;
R⁴ is hydrogen or halogen;
each R⁵, R⁶ and R⁷ is independently fluorine or chlorine;
R⁸ is hydrogen or -A-B$_n$-X, wherein
  B is $C_{1-4}$ alkylene or —(OCH₂CH₂)—;
  n is 1, 2 or 3, and
  X is —NH₂.

A particular embodiment of the invention is directed to this screening method, wherein in compound of Formula (1)
R⁸ is hydrogen;
—C(=O)CH₂CH₂CH₂CH₂CH₂—NH₂;
—C(=O)CH₂—O—CH₂CH₂—O—CH₂CH₂—NH₂; or
—CH₂CH₂CH₂—NH₂.

A prioritized aspect of the invention relates to this screening method, wherein the compound has one of the following chemical structures represented by Formulae (2) to (5):

Formula (10)

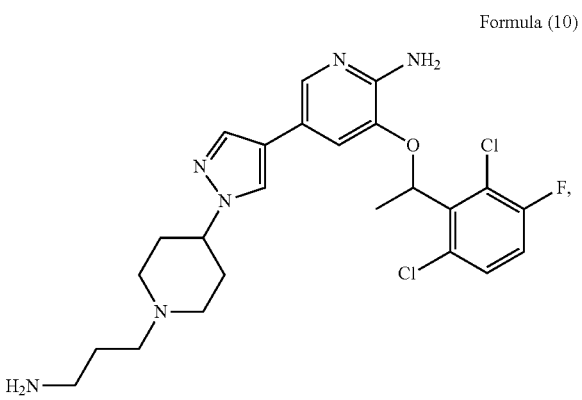

or a pharmaceutically acceptable salt, solvate or prodrug thereof.

To assess the complete interactome of the herein defined aminoheteroaryl compound considering both enantiomers, the racemic form of the aminoheteroaryl compound may be used. However, it is also envisaged to use the aminoheteroaryl compound in the (R)- or (S)-enantiomer conformation. However, in context of the invention, it is more preferred to use the (S)- than the (R)-enantiomer conformation. Accordingly, one particular embodiment of the invention is directed to the screening method of the invention, wherein said aminoheteroaryl compound is in the (S)-enantiomer conformation. Accordingly, said aminoheteroaryl compound which is to be applied in the screening method of the invention may be the herein defined (S)-enantiomer of an aminoheteroaryl compound.

Thus, a prioritized aspect of the present invention relates to a screening method for identifying a target of an (S)-enantiomer of an aminoheteroaryl compound having the following chemical structure represented by Formula (1), Formula (2)

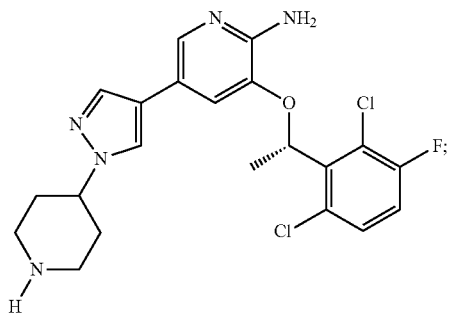

Formula (3)

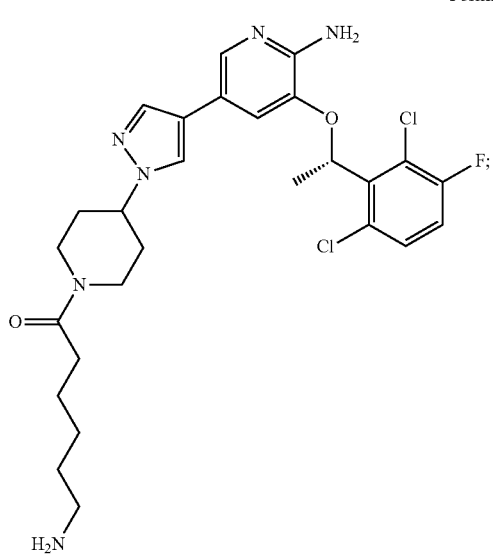

Formula (4)

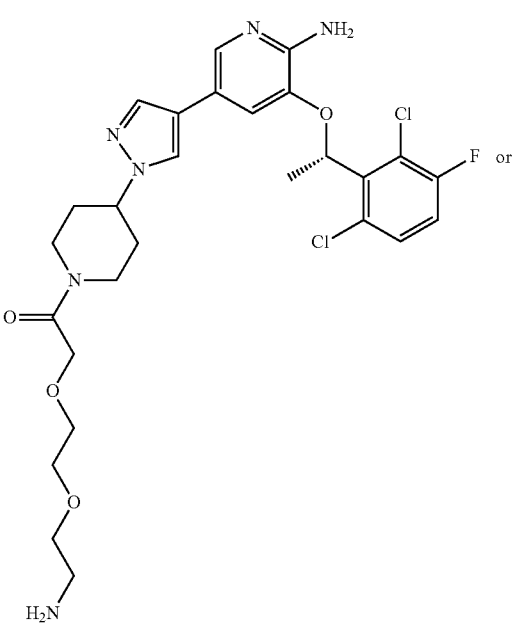

Formula (5)

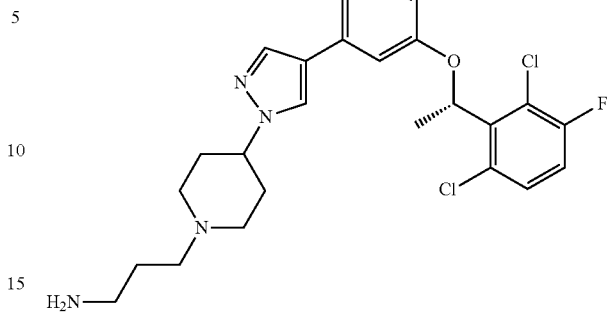

or a pharmaceutically acceptable salt, solvate or prodrug thereof.

As mentioned, the present invention relates to a screening method comprising the steps (a) to (c) as described above. A specific aspect of the invention relates to the screening method of the invention, further comprising the step of:

(d) determining whether said (S)-enantiomer of an aminoheteroaryl compound alters the biological activity of said molecule, wherein, if said (S)-enantiomer of an aminoheteroaryl compound is found to alter the biological activity of said molecule, then such molecule is identified as a target of said (S)-enantiomer of an aminoheteroaryl compound.

In context of the screening method of the invention, a cell lysate is obtained and contacted with an aminoheteroaryl compound (e.g. with the (S)-enantiomer of an aminoheteroaryl compound). The cells for generating this cell lysate may be cancer cells obtained from a human cancer patient. For example, said cells obtained from a human cancer patient may comprise biological material of biopsies. The meaning of "biopsies" is known in the art. For instance, biopsies comprise cancer cell(s) or cancer tissue(s) taken, e.g. by the attending physician, from a patient, suffering from cancer. Alternatively, the cells for generating the cell lysate may be obtained from (a) non-human animal(s), or from an established cancer cell line, such as an established human cancer cell line, or from an engineered cell line.

Accordingly, one embodiment of the present invention relates to the screening method of the invention, wherein said cell lysate is derived from a cell or tissue sample form a cancer patient, from an established cancer cell line or from a non-human animal. Preferably, for carrying out the screening method of the present invention, the cell lysate is generated by using a tumour sample obtained from a human cancer patient. For example, said cells obtained from a human cancer patient may comprise biological material of biopsies. It is also preferred that the cell lysate is generated by using an established cancer cell line, such as an established human cancer cell line. For example, for generating said cell lysate, cells of the Ewing's sarcoma family of tumours (ESFT) (such as SK-ES-1 and SK-N-MC cells) may be used. In context of the screening method of the present invention, several cell lysates may be generated and analyzed in parallel. For instance, for preparing the cell lysates, human cancer cell lines with different genetic background (such as ALK-positive and ALK-negative) may be used and analyzed in parallel.

As mentioned above, within the screening method of the invention, it may be determined whether said (S)- enantiomer of an aminoheteroaryl compound alters the biological activity of said molecule. The biological activity of said molecule may be increased or inhibited by said (S)-enantiomer of an aminoheteroaryl compound. However, it is preferred that the biological activity of said molecule is inhibited. Accordingly, one aspect of the invention relates to the screening method of the invention, wherein altering the biological activity is inhibiting the biological activity.

The gist of the present invention is that an aminoheteroaryl compound, preferably the (S)-enantiomer of an aminoheteroaryl compound is a highly potent inhibitor of MTH1. Thus, a preferred embodiment of the invention relates to the compound for the use of the invention, the pharmaceutical composition of the invention, the in vitro method of the invention, the kit of the invention, the use of the invention, or the screening method of the invention, wherein said compound inhibits the biological activity of MTH1.

As mentioned above, the present invention relates to a screening method for identifying a target of an aminoheteroaryl compound. This screening method may comprise a drug pull-down assay. Therefore, a direct chemical proteomics approach in which the compound of interest (e.g. an aminoheteroaryl compound) is immobilized on sepharose beads, may be used. Such direct chemical proteomics approaches are well known in the art and described, e.g., in Superti-Furga (2012) Designing Multi-Target Drugs. Royal Society of Chemistry: Cambridge, 2012; p 256.[8] An experimental set-up which may be used in context of the screening method of the present invention is provided in FIG. 1. Preferably, the method described as "Compound-centred chemical proteomics" in FIG. 1 is used in context of the present invention. Also activity-based probe profiling may be applied using a modified version of one of the compounds disclosed herein.

The immobilization on sepharose beads may be achieved by a chemical reaction which establishes a covalent bond between the compound and the bead matrix. Therefore the compound requires an adequate reactive functional group for the reaction to take place which in many cases enforces chemical modification of the original compound. f course, changing the molecular structure can alter the interaction behavior and target spectrum of the compound to be investigated. It should be noted that also the location within the molecule where the compound is immobilized can affect binding. Thus, a common practice is to check and confirm binding of already known targets for all coupleable derivatives. As illustrated in the appended examples, three derivatives of crizotinib (i.e. CeMM-144, CeMM-145 and CeMM-146 as defined herein) with different chemical linkers covering various linker lengths and chemical nature in terms of hydrophobicity have been prepared. Chemical synthesis of crizotinib derivatives CeMM-144, CeMM-145, and CeMM-146 is outlined in FIG. 13. Surprisingly, as shown in the illustrative appended examples, the aminopropyl-substituted CeMM-146 enriches both ALK isoforms to highest extent, followed by the PEG-derivative CeMM-145. Unmodified crizotinib and CeMM-144 bind ALK to a lesser extent than CeMM-146 and CeMM-145.

In context of the screening method of the present invention, after contacting the cell lysate with an aminoheteroaryl compound, molecules that bind to said aminoheteroaryl compound may be co-purified by affinity purification of the aminoheteroaryl compound. Methods for affinity purification are well known in the art and described, e.g., in Superti-Furga (2012) Designing Multi-Target Drugs. Royal Society of Chemistry: Cambridge, 2012; p 256.[8] After purification of the molecule (e.g. the protein) that binds to said aminoheteroaryl compound, the identity of the molecule may be determined (e.g. it may be determined which protein bound to the aminoheteroaryl compound). For this identification step, mass spectrometry may be applied. Mass spectrometry methods are well known in the art and described, e.g., in Superti-Furga (2012) Designing Multi-Target Drugs. Royal Society of Chemistry: Cambridge, 2012; p 256.[8]

As reported in the prior art, MTH1 suppression was shown to cause proliferative defects in cancer cells.[13] Thus, as indicated above, targeting MTH1 may provide a novel therapeutic option to treat cancer. In line with this, the MTH1-status (in particular the level of MTH1 activity) may be used to monitor (i.e. accessing the effectiveness of) the treatment (i.e. the therapy) of a cancer patient. Since the activity of MTH1 may be reflected by the expression of MTH1, also the level of MTH1 expression may be used to monitor (i.e. accessing the effectiveness of) the treatment (i.e. the therapy) of a cancer patient. The treatment may comprise (an) MTH1 inhibitor(s). Thus, provided herein is a method of monitoring the effectiveness of a treatment of a cancer patient, the method comprising the following steps:

(a) determining MTH1 activity and/or expression in a first tissue sample from said cancer patient at a first time point;
(b) determining MTH1 activity and/or expression in a second tissue sample from said cancer patient at a second time point, and
(c) comparing the MTH1 activity and/or expression determined in step (a) with the MTH1 activity and/or expression determined in step (b), wherein a reduced activity and/or expression of MTH1 determined in step (b) compared to the MTH1 activity and/or expression determined in step (a) is indicative of an effective treatment, and wherein an enhanced or identical activity and/or expression of MTH1 determined in step (b) compared to the MTH1 activity and/or expression determined in step (a) is indicative of an ineffective treatment.

The effectiveness of a treatment, in particular of a cancer therapy, may also be monitored by using a reference value. Thus, also provided herein is a method of monitoring the effectiveness of a treatment of a cancer patient, the method comprising the following steps:

(a) determining MTH1 activity and/or expression in a tissue sample from said cancer patient, and
(b) comparing the MTH1 activity and/or expression determined in step (a) with a reference value, wherein a reduced activity and/or expression of MTH1 determined in step (a) compared to the reference value is indicative of an effective treatment, and wherein an enhanced or identical activity and/or expression of MTH1 determined in step (a) compared to the reference value is indicative of an ineffective treatment.

As described herein, the methods of monitoring the effectiveness of a treatment of a cancer patient may be in vitro methods. In context of the above described methods of monitoring the effectiveness of a treatment of a cancer patient, said tissue sample is preferably a cancer tissue sample.

As described above, there is a strong link between MTH1 and the expression of oncogenic RAS, reactive oxygen species (ROS), oxidative damage and tumour development. Therefore, inhibitors of MTH1 represent promising agents for the treatment of cancer. Thus, provided herein is a method for identifying an anticancer substance. This method is highly useful in identifying at least one substance suspected of being an inhibitor of MTH1 activity. Potent inhibitors identified by this method can be used in the medical intervention of cancer. The method for identifying an anticancer substance comprises the steps of:
(a) contacting MTH1 or a cell, tissue or a non-human animal comprising MTH1 with at least one test substance;
(b) determining MTH1 activity and/or expression;
(c) selecting a substance that decreases MTH1 activity and/or expression;
wherein the ability to decrease MTH1 activity and/or MTH1 expression is indicative for the anticancer activity of the selected substance.

Said method for identifying an anticancer substance may be characterized in that step (a) is a cell-free composition comprising the purified MTH1 protein; and step (b) comprises determining whether the at least one test substance inhibits biological activity of MTH1. The method for identifying an anticancer substance may also be characterized in that step (a) comprises a cell, tissue or non-human animal that expresses MTH1 (said expression of MTH1 may also be the expression of MTH1 in form of a transgene), and wherein step (b) comprises determining whether the at least one test substance inhibits biological activity and/or expression of MTH1. Step (b) of the method for identifying an anticancer substance may comprise detecting a decrease in MTH1 biological activity and/or a decrease of MTH1 expression within a cell lysate derived from a cell, tissue or non-human animal.

Most of the MTH1 which is applied in step (a) of the method for identifying an anticancer substance is considered to be functional, i.e. to have the ability to hydrolyse oxidised nucleotides such as 2-OH-dATP and 8-oxo-dGTP. It is envisaged, that at least 25% or 50%, preferably at least 50%, 75% or 90%, and more preferably at least 95%, 98% or 99% of the MTH1 which is applied in step (a) is functional.

It is noted that in step (a) of the method for identifying an anticancer substance, the term "contacting MTH1 or a cell, tissue or a non-human animal comprising MTH1 with at least one test substance" also relates to "contacting a derivative of MTH1 or a functional fragment of MTH1 or a cell, tissue or a non-human animal comprising a derivative of MTH1 or a functional fragment of MTH1 with at least one test substance". A definition of the terms "derivative of MTH1" and "functional fragment of MTH1 is provided herein, below.

In accordance with the method for identifying an anticancer substance described herein, at least one test substance is contacted with a cell, tissue or non-human animal comprising MTH1. For example said cell, tissue or non-human animal may express a MTH1 gene, in particular also (an) additional (copy) copies of a MTH1 gene, (a) MTH1 mutated gene(s), a recombinant MTH1 gene construct and the like. The ability of a test substance to decrease MTH1 activity and/or expression may, accordingly, be determined by measuring the expression level (e.g. mRNA or protein) of such gene products of MTH1 or of corresponding gene constructs, wherein a low expression level (compared to a standard or reference value) is indicative for the ability of the test substance to decrease MTH1 activity and/or expression. As described herein, in one aspect of the method for identifying an anticancer substance, said cell, tissue or non-human animal is genetically modified. Said cell, tissue or non-human animal may comprise a reporter gene expression construct. In particular, said reporter gene expression construct may comprise the MTH1-promoter and/or enhancer or an MTH1-dependent promoter and or an enhancer of an MTH1-dependent factor linked to a reporter gene. A MTH1-dependent promoter (i.e. the promoter of an MTH1-dependent factor) may be the promoter of a protein that acts downstream of MTH1. For example, said protein may be transcriptionally upregulated or downregulated in response to hydrolysis of oxidised nucleotides such as 2-OH-dATP and 8-oxo-dGTP. Accordingly, if said protein is transcriptionally upregulated in response to MTH1 enzymatic activity, a reduced transcription of the reporter gene construct would be indicative for a decreased MTH1 activity and/or expression. On the other hand, if said factor is transcriptionally downregulated in response to MTH1 enzymatic activity, an enhanced transcription of the reporter gene construct would be indicative for decreased MTH1 activity and/or expression. Accordingly, as defined and disclosed herein, the term "comprising MTH1" refers not only to the MTH1 gene(s) or protein(s) known in the art and described herein. Also reporter constructs comprising a promoter and/or enhancer region of MTH1 can be used in the method for identifying an anticancer substance. Accordingly, the cell(s), tissue(s) and/or non-human animal(s) used in the context of the method for identifying an anticancer substance can comprise reporter constructs. Exemplary reporters are luciferase and fluorescent proteins, like GFP, RFP and the like. Also reporter constructs comprising a promoter and/or enhancer region of MTH1 (or of MTH1-dependent factors) can be used. Accordingly, the cell(s), tissue(s) and/or non-human animal(s) used in the context of the present invention, can be stably or transiently transfected with reporter constructs.

The used non-human animal or cell may be transgenic or non transgenic. Within said transgenic cell or non-human animal, at least one MTH1 gene may be overexpressed, thus the MTH1 activity in the non-human transgenic animal or transgenic cell may be enhanced. Generally, it is preferred herein that MTH1 is highly expressed in (a) cell(s), tissue(s), non-human animal(s) to be used in the method for identifying an anticancer substance as described herein. The term "transgenic non-human-animal", "transgenic cell" or "transgenic tissue" as used herein refers to a non-human animal, tissue or cell, that comprises different genetic material. The term "genetic material" in this context may be any kind of a nucleic acid molecule, or analogues thereof. The term "different" means that additional or fewer genetic material in comparison to the genome of the wild type animal or cell. An overview of different expression systems to be used for generating a transgenic cell/animal refers for example to Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440).

Non-limiting examples of the (transgenic) non-human animals or derived (transgenic) cells are selected from the group consisting of a mouse, a rat, a rabbit, a guinea pig and *Drosophila*. In a preferred embodiment, the (transgenic) non-human animal or (transgenic) cell is or is derived from a mammal Generally, the (transgenic) cell may be a eukaryotic cell. For example, the (transgenic) cell in accordance with the present invention may be but is not limited to yeast, fungus, plant or animal cell. The (transgenic) cell may be derived from human, e.g., from human cancer tissue. The (transgenic) cell may be an established cancer cell line. In general, the transformation or genetically engineering of a cell with a nucleic acid construct or a vector can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

In accordance with the method for identifying an anticancer substance, the determined activity and/or expression of MTH1 may be compared to a standard or reference value of MTH1 activity and/or expression, respectively. The standard/reference value may be determined in a cell, tissue, or non-human animal, which has not been contacted with a test substance. The decrease in the activity and/or expression of MTH1 may also be compared to the decrease in MTH1 activity and/or expression by (a) routinely used reference substance(s). A skilled person is easily in the position to determine/assess whether the activity and/or expression of MTH1 is (preferably statistically significant) decreased.

In context of the method for identifying an anticancer substance, the term "contacting" refers to the addition of at least one test substance to MTH1, or to a cell, tissue, or non-human animal comprising MTH1. The term "contacting" also refers to the addition of a test substance to a cell comprising MTH1 in a way that the test substance may become effective to the cell upon cellular uptake and thereby exerts its inhibitory function on MTH1.

The term "test substance" as used herein refers to a molecule or substance or composition or agent or any combination thereof to be tested by the method for identifying an anticancer substance. A test substance can, in principle, be obtained from any source. The at lease one test substance may be a naturally occurring substance or a substance produced by a transgenic organism and optionally purified to a certain degree and/or further modified. Practically, the test substance may be taken from a compound library.

The test substance may be a potential inhibitor of activity and/or expression of MTH1. A test substance can be any chemical, such as an inorganic chemical, an organic chemical, a protein, a peptide, a carbohydrate, a lipid, an siRNA against MTH1, an shRNA against MTH1, or a combination thereof or any of the compounds or compositions described herein. A test substance to be used herein may be, inter alia, a substance or composition which is of chemical or biological origin, which is naturally occurring and/or which is synthetically, recombinantly and/or chemically produced. Thus, a test substance may be a protein, protein-fragment, peptide, amino acid and/or derivatives thereof or another substance, which binds to and/or interacts with MTH1, a regulatory protein/sequence of MTH1 function or functional fragments thereof. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural substances in the form of bacterial, fungal, plant and animal extracts are available from e.g. Pan Laboratories (Bothell, Wash.) or MycoSearch (N.C.) are readily producible. Additionally, natural and synthetically produced libraries and compounds are readily modified through conventional chemical, physical, and biochemical means. Results obtained from deorphanisation programs based on phylogenetic analysis methods may aid to find natural factors that bind to or interact with MTH1 and, e.g., will allow in silico profiling of substances which potentially have the ability to decrease MTH1 activity and/or expression. Factors that bind to or interact with MTH1 may be inhibitors of MTH1 and thus, may be anticancer substances.

The generation of chemical libraries with potential factors that bind to or interact with MTH1 is well known in the art. For example, combinatorial chemistry may be used to generate a library of substances. A combinatorial chemical library is a collection of diverse chemical substances generated by either chemical synthesis or biological synthesis by combining a number of chemical "building block" reagents. For example, a linear combinatorial chemical library such as a polypeptide library is formed by combining amino acids in every possible combination to yield peptides of a given length. Millions of chemical substances can theoretically be synthesized through such combinatorial mixings of chemical building blocks. For example, one commentator observed that the systematic, combinatorial mixing of 100 interchangeable chemical building blocks results in the theoretical synthesis of 100 million tetrameric compounds or 10 billion pentameric compounds (see, e.g., Gallop, Journal of Medicinal Chemistry, Vol. 37, No. 9, 1233-1250 (1994)). Other chemical libraries known to those in the art may also be used, including natural product libraries. Once generated, combinatorial libraries are screened for substances that possess desirable biological properties. For example, substances which may be useful as drugs or to develop drugs would likely have the ability to bind to the target protein (e.g. MTH1).

In addition, in the context of the present invention, libraries of substances may be screened to identify substances that may function as an antagonist or inhibitor of MTH1. First, a library of small molecules may be generated using methods of combinatorial library formation well known in the art. U.S. Pat. No. 5,463,564 and U.S. Pat. No. 5,574,656 are two such teachings. Then the library substances may be screened to identify those substances that possess desired structural and functional properties. Methods for screening libraries are well known in the art and discussed, e.g., in U.S. Pat. No. 5,684,711. In addition, a wide variety of screening techniques are known for a large number of naturally-occurring targets when the biochemical function of the target protein is known. For example, some techniques involve the generation and use of small peptides to probe and analyze target proteins both biochemically and genetically in order to identify and develop drug leads. Such techniques include the methods described in WO 99/35494, WO 98/19162 and WO 99/54728.

Test substances may encompass numerous chemical classes, preferably they are organic compounds, and more preferably small (organic) molecules, such as the herein defined aminoheteroaryl compounds.

Test substances may comprise functional groups necessary for structural interaction with a protein (in particular with MTH1), particularly hydrogen bonding, and typically include at least an amine, carbonyl, hydroxyl or carboxyl group, preferably at least two of the functional chemical groups. The test substances often comprise carbocyclic or heterocyclic structures and/or aromatic or polyaromatic structures substituted with one or more of the above functional groups. The test substance and/or the selected anticancer substance may be modified to enhance efficacy, stability, pharmaceutical compatibility, and the like. Structural identification of an anticancer substance may be used to identify, generate, or screen additional anticancer substances.

In accordance with the herein described method for identifying an anticancer substance, the substances selected in the first screen may be subject to subsequent screens in order to verify the previous findings and to select the most potent inhibitors/antagonists of MTH1. Upon multiple screening and selection rounds those substances will be selected which show a pronounced capacity to inhibit/antagonize MTH1.

The term "decreases MTH1 activity and/or expression" in step (c) of the method for identifying an anticancer substance means that the "activity and/or expression of MTH1" is reduced upon contacting MTH1 or a cell, tissue, or non-human animal comprising MTH1 with the at least one test substance, preferably in comparison to a (control) standard or reference value, wherein a decrease of the MTH1 activity and/or expression is indicative for the anticancer activity of the selected substance (i.e. for the capacity of the selected substance to ameliorate cancer).

As described herein a substance that "decreases MTH1 activity" relates to substance that decreases the biological activity of MTH1 (i.e. the ability to hydrolyse oxidised nucleotides such as 2-OH-dATP and 8-oxo-dGTP). Methods for measuring the MTH1 biological activity are known in the art and also provided herein. In addition, a substance that "decreases MTH1 expression" relates to a decreased expression of the gene(s) encoding the MTH1 protein(s). Therefore, a quantitative assessment of the gene product (e.g. protein or spliced, unspliced or partially spliced mRNA) can be performed in order to evaluate decreased expression of the gene(s) encoding the MTH1 protein(s). The person skilled in the art is aware of standard methods to be used in this context or may deduce these methods from standard textbooks (e.g. Sambrook, Russell "Molecular Cloning, A Laboratory Manual", Cold Spring Harbor Laboratory, N.Y. (2001)). For example, quantitative data on the respective concentration/amounts of mRNA from MTH1 can be obtained by Northern Blot, Real Time PCR and the like.

Preferably, the MTH1 activity and/or expression may be decreased by at least about 10%, 20%, 30%, 40%, preferably by at least 50%, 60%, 70%, 80%, 90%, or 100% compared to a control sample. As mentioned, a person skilled in the art is aware of standard methods to be used for determining or quantitating activity of MTH1 or expression of a nucleic acid molecule encoding MTH1 (or fragments thereof). In addition, a method for determining and quantitiating activity of MTH1 is described in detail herein and in the appended examples. In addition, the expression of MTH1 can be determined on the protein level by taking advantage of immunoagglutination, immunoprecipitation (e.g. immunodiffusion, immunelectrophoresis, immune fixation), western blotting techniques (e.g. (in situ) immuno histochemistry, (in situ) immuno cytochemistry, affinitychromatography, enzyme immunoassays), and the like. Amounts of purified polypeptide in solution can be determined by physical methods, e.g. photometry. Methods of quantifying a particular polypeptide in a mixture rely on specific binding, e.g of antibodies. Specific detection and quantitation methods exploiting the specificity of antibodies comprise for example immunohistochemistry (in situ). For example, concentration/amount of MTH1 proteins in a cell, tissue or a non-human animal can be determined by enzyme linked-immunosorbent assay (ELISA). Alternatively, Western Blot analysis or immunohistochemical staining can be performed. Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction.

Expression can also be determined on the nucleic acid level (e.g. if the gene product/product of the coding nucleic acid sequence is an unspliced/partially spliced/spliced mRNA) by taking advantage of Northern blotting techniques or PCR techniques, like in-situ PCR or Real time PCR. Quantitative determination of mRNA can be performed by taking advantage of northern blotting techniques, hybridization on microarrays or DNA chips equipped with one or more probes or probe sets specific for mRNA transcripts or PCR techniques referred to above, like, for example, quantitative PCR techniques, such as Real time PCR. These and other suitable methods for detection and/or determination of the concentration/amount of (specific) mRNA or protein(s)/polypeptide(s) are well known in the art and are, for example, described in Sambrook (2001), loc. cit.).

A skilled person is capable of determining the amount of mRNA or polypeptides/proteins, in particular the gene products described herein above, by taking advantage of a correlation, preferably a linear correlation, between the intensity of a detection signal and the amount of, for example, the mRNA or polypeptides/proteins to be determined.

In accordance with the method for identifying an anticancer substance, the amount of decrease of MTH1 activity and/or expression may be statistically significant and a substance may be selected, if the MTH1 activity and/or expression (or of a corresponding reporter signal) is strongly decreased, preferably is very low or non-detectable. For example, the MTH1 activity and/or expression (or of a corresponding reporter signal) may be decreased by at least 50%, 60%, 70%, 80%, more preferably by at least 90% compared to the (control) standard value.

As used herein, in particular in the context of the embodiments relating to formulae (1) and (6), the following definitions apply:

The term "halogen" includes fluorine, chlorine, bromine and iodine.

$C_{1-6}$ alkyl refers to straight or branched alkyl. Examples include methyl, ethyl, n-propyl, isopropyl, n-butyl, isobutyl, sec-butyl, tert-butyl, n-pentyl, isopentyl, neopentyl, hexyl, isohexyl. Accordingly, $C_{1-3}$ alkyl refers to straight or branched alkyl, and for example, methyl, ethyl, n-propyl, isopropyl.

$C_{2-6}$ alkenyl refers to straight or branched alkenyl having one or more double bond(s) at any position thereof. Examples include vinyl, allyl, propenyl, isopropenyl, butenyl, isobutenyl, prenyl, butadienyl, pentenyl, isopentenyl, pentadienyl, hexenyl, isohexenyl, hexadienyl. Accordingly, $C_{2-3}$ alkenyl refers to straight or branched alkenyl having one or more double bond(s) at any position thereof. Examples include vinyl, allyl, propenyl, isopropenyl.

$C_{2-6}$ alkynyl refers to straight or branched alkynyl having one or more triple bond(s) at any position thereof. Examples include ethynyl, propynyl, butynyl, pentynyl, hexynyl. Alkynyl groups may additionally have a double bond at any position thereof. Accordingly, $C_{2-3}$ alkynyl refers to straight or branched alkynyl having one or more triple bond(s) at any position thereof. Examples include ethynyl and propynyl.

$C_{1-4}$ alkylene refers to a linear divalent hydrocarbon chain. Examples include methylene, ethylene, propylene and butylene.

$C_{2-4}$ alkenylene refers to a linear divalent hydrocarbon chain having one or more double bonds at any position thereof, and includes, for example, vinylene, propenylene and butenylene.

In accordance with the present invention, the terms "(S)-enantiomer of an aminoheteroaryl compound of the invention", "(S)-enantiomer of an aminoheteroaryl compound for the use of the invention" and "compound for the use of the invention" relate to the herein defined "(S)-enantiomer of an aminoheteroaryl compound". In addition, as used herein, the terms "(S)-enantiomer of an aminoheteroaryl compound of the invention", "(S)-enantiomer of an aminoheteroaryl compound for the use of the invention" and "compound for the use of the invention" are synonyms for the "(S)-enantiomer of an aminoheteroaryl compound" which is shown in any one of Formulae (1) to (5) and described in claim 1 of the appended claims. Preferably, the terms "(S)-enantiomer of an aminoheteroaryl compound of the invention", "(S)-enantiomer of an aminoheteroaryl compound for the use of the invention" and "compound for the use of the invention" are synonyms for the "(S)-enantiomer of an aminoheteroaryl compound" which is described in items 1 to 4, 8 to 20 and 37.

As demonstrated herein, in contrast to (R)-crizotinib, the "(S)-enantiomer of an aminoheteroaryl compound for the use of the invention" is not restricted to the use in treating ALK-positive cancer. Thus, the "(S)-enantiomer of an aminoheteroaryl compound for the use of the invention" can also be used to treat ALK-negative cancer. Accordingly, the terms "(S)-enantiomer of an aminoheteroaryl compound of the invention", "(S)-enantiomer of an aminoheteroaryl compound for the use of the invention" and "compound for the use of the invention" further relate to "an (S)-enantiomer of an aminoheteroaryl compound for use in treating and/or preventing cancer in a subject, wherein the treatment and/or prevention of cancer is independent of the ALK-status and/or the c-Met-status of the cancer cell or tissue of said subject.

More specifically, the terms "(S)-enantiomer of an aminoheteroaryl compound of the invention", "(S)-enantiomer of an aminoheteroaryl compound for the use of the invention", and "compound for the use of the invention" relate to a compound which has the ability to inhibit the biological activity (in particular the catalytic activity) of MTH1. Accordingly, the terms "(S)-enantiomer of an aminoheteroaryl compound of the invention", "(S)-enantiomer of an aminoheteroaryl compound for the use of the invention" and "compound for the use of the invention" relate to an (S)-enantiomer of an aminoheteroaryl compound which is capable of inhibiting the biological activity of MTH1 for use in treating and/or preventing cancer in a subject.

As mentioned above, the "(S)-enantiomer of an aminoheteroaryl compound of the invention" is not restricted to the use in treating ALK-positive cancer. Thus, the terms "(S)-enantiomer of an aminoheteroaryl compound of the invention", "(S)-enantiomer of an aminoheteroaryl compound for the use of the invention" and "compound for the use of the invention" further relate to an (S)-enantiomer of an aminoheteroaryl compound which has the ability to inhibit the biological activity of MTH1 for use in treating and/or preventing cancer in a subject, wherein the treatment and/or prevention of cancer is independent of the ALK-status and/or c-Met-status of the cancer cell or tissue of said subject. Means and methods for determining whether a particular compound has the ability to inhibit the biological activity of MTH1 are known in the art and provided herein, below.

The "(S)-enantiomer of an aminoheteroaryl compound for the use of the invention" may be the (S)-enantiomer of a derivative of crizotinib (such as CeMM-144, CeMM-145 or CeMM-146). Preferably, the "(S)-enantiomer of an aminoheteroaryl compound for the use of the invention" is CeMM-146. More preferably, the "(S)-enantiomer of an aminoheteroaryl compound for the use of the invention" is (S)-crizotinib (i.e. the (S)-enantiomer of the chemical substance 3-[1-(2,6-dichloro-3-fluoro-phenyl)-ethoxy]-5-(1-piperidin-4-yl-1H-pyrazol-4-yl)-pyridin-2-ylamine)

The person skilled in the art has the ability to synthesize the (S)-enantiomer of crizotinib (i.e. the (S)-enantiomer of the chemical substance 3-[1-(2,6-dichloro-3-fluoro-phenyl)-ethoxy]-5-(1-piperidin-4-yl-1H-pyrazol-4-yl)-pyridin-2-ylamine). In addition, the preparation of the (S)-enantiomer of crizotinib (i.e. the (S)-enantiomer of the chemical substance 3-[1-(2,6-dichloro-3-fluoro-phenyl)-ethoxy]-5-(1-piperidin-4-yl-1H-pyrazol-4-yl)-pyridin-2-ylamine) is described herein in FIG. 14. The synthetic strategy depends on the use of optically pure starting materials and may follow previously published procedures for synthesis of racemic and/or (R)-crizotinib. Procedures for synthesis of racemic and/or (R)-crizotinib are given in, e.g., de Koning (2011) Organic Process Research & Development, 15: 1018-1026[38], which is herein incorporated by reference in its entirety.

A "functional fragment" of MTH1 is a polypeptide comprising a fragment of MTH1 and having the biological activity of MTH1. As described herein above and below, the biological activity of MTH1 is the catalytic activity of MTH1, i.e. the ability to hydrolyse oxidised nucleotides such as 2-OH-dATP and 8-oxo-dGTP. A functional fragment of MTH1 may be a polypeptide comprising a fragment of one of the amino acid sequences of MTH1 as provided herein as SEQ ID Nos. 2, 4, 6, 8, 10, 12, 14 to 16. A functional fragment of MTH1 may also be a polypeptide which is encoded by a fragment of one of the nucleotide sequences of MTH1 as provided herein as SEQ ID Nos. 1, 3, 5, 7, 9, 11 and 13. A functional fragment of MTH1 may be a polypeptide comprising at least 50%, preferably at least 60%, more preferably at least 70%, at least 80%, or at least 90%, and most preferably at least 95% or at least 99% of one of the amino acid sequences of MTH1 as provided herein as SEQ ID Nos. 2, 4, 6, 8, 10, 12, 14 to 16. A functional fragment of MTH1 may also be a polypeptide which is encoded by a nucleotide sequence comprising at least 50%, preferably at least 60%, more preferably at least 70%, at least 80%, or at least 90%, and most preferably at least 95% or at least 99% of one of the nucleotide sequences of MTH1 as provided herein as SEQ ID Nos. 1, 3, 5, 7, 9, 11 and 13.

A "derivative" of MTH1 is a polypeptide having homology to MTH1 and having the biological activity of MTH1. A derivative of MTH1 may be a polypeptide having at least 60%, preferably at least 70% or at least 80%, more preferably at least 90% and most preferably at least 95%, at least 96%, at least 97%, at least 98% or at least 99% homology to one of the amino acid sequences of MTH1 as provided herein as SEQ ID Nos. 2, 4, 6, 8, 10, 12, 14 to 16. A derivative of MTH1 may also be a polypeptide encoded by a nucleotide sequence having at least 60%, preferably at least 70% or at least 80%, more preferably at least 90% and most preferably at least 95%, at least 96%, at least 97%, at least 98% or at least 99% homology to one of the nucleotide sequences of MTH1 as provided herein as SEQ ID Nos. 1, 3, 5, 7, 9, 11 and 13. As described herein above and below, the biological activity of MTH1 is the catalytic activity of MTH1, i.e. the ability to hydrolyse oxidised nucleotides such as 2-OH-dATP and 8-oxo-dGTP.

In context of the present invention, the term "having homology to", means that the respective amino acid or nucleotide sequences have identities of at least 60%, 70%, 80%, 90%, 95%, 96%, 97%, 98% or 99% to the sequences shown herein, e.g. those of MTH1, wherein the higher identity values are preferred upon the lower ones. In accordance with the present invention, the term "identity/identities" or "percent identity/identities" in the context of two or more nucleic acid or amino acid sequences, refers to two or more sequences or subsequences that are the same, or that have a specified percentage of amino acid residues or nucleotides that are the same (e.g., 60% or 70% identity, preferably, 70-95% identity, more preferably at least 95%, 96%, 97%, 98% or 99% identity with the nucleotide sequences of, e.g., SEQ ID Nos: 1, 3, 5, 7, 9, 11 and 13, or with the amino acid sequences of, e.g., SEQ ID Nos: 2, 4, 6, 8, 10, 12, 14 to 16), when compared and aligned for maximum correspondence over a window of comparison, or over a designated region as measured using a sequence comparison algorithm as known in the art, or by manual alignment and visual inspection.

Preferably the described identity exists over a region that is at least about 25 to 75 amino acids or nucleotides in length. It is more preferred that the described identity exists over a region that is about 75 to 150 amino acids or nucleotides in length. In case of nucleotide sequences, the described identity most preferably exists over a region that is at least about 75 to 225, and more preferred over a region that is at least about 225 to 450 nucleotides in length. Those having skill in the art will know how to determine percent identity between/among sequences using, for example, algorithms such as those based on CLUSTALW computer program (Thompson; 1994; Nucl Acids Res; 2; 4673-4680) or FASTDB (Brutlag; 1990; Comp App Biosci; 6; 237-245), as known in the art.

In accordance with the present invention it is envisaged that the (S)-enantiomer of an aminoheteroaryl compound for use in treating and/or preventing ALK-negative cancer, has the ability to inhibit the biological activity of MTH1.

The term "biological activity" as used herein relates to the functionality of a molecule (e.g. a polypeptide such as MTH1). A molecule (e.g. a polypeptide) is "functional" means, in context of the invention, that the molecule (e.g. the polypeptide) has the ability to carry out a specific "function". Accordingly, the term "biological activity" relates to the ability of a molecule (e.g. of a specific protein such as MTH1) to carry out a specific function. For instance, in context of the present invention, the biological activity of MTH1 comprises the catalytic activity of MTH1, i.e., the ability to hydrolyse oxidised nucleotides such as 2-OH-dATP and 8-oxo-dGTP, yielding the corresponding monophosphate and pyrophosphate (PPi). To analyse whether a (S)-enantiomer of an aminoheteroaryl compound has the ability to alter (e.g. to inhibit) the biological activity of MTH1, an enzymatic assay using recombinant MTH1 can be performed. For instance a luminescence-based assay which monitors the production of PPi generated by MTH1-mediated 8-oxo-dGTP hydrolysis may be used following a protocol which has been used to determine MTH1 enzyme kinetics (see, e.g. Svensson (2011) FEBS Lett. 585: 2617-2621.[15]

More specifically, for determining the ability of a compound in inhibiting biological activity of MTH1, MTH1 may be expressed in an appropriate host cell (such as a bacterial cell) and MTH1 may be purified. Subsequently, the purified MTH1 may be incubated with the (S)-enantiomer of an aminoheteroaryl compound of interest. The activity of MTH1 can be monitored by measuring the production of PPi generated by MTH1-mediated 8-oxo-dGTP hydrolysis.

Additionally, in context of the present invention, an "enhanced", or "high" biological activity of a molecule (e.g. of a protein such as MTH1) means that the biological activity of the molecule (e.g. of MTH1) is enhanced compared to a control. In line with this, in context of the present invention, an "inhibited", "reduced", "low" or "less" biological activity of a molecule (e.g. of MTH1) means that the biological activity of the molecule (e.g. of MTH1) is reduced compared to a control. For example, the reason for a reduced biological activity of a molecule (e.g. of a protein such as MTH1) compared to a control may be the presence of a compound (e.g. an (S)-enantiomer of an aminoheteroaryl compound) that inhibits the biological activity of the molecule (e.g. of MTH1). In this respect, the control could be the same sample but without the compound that inhibits the biological activity of the molecule.

The pharmaceutical composition described herein can be formulated by techniques known to the person skilled in the art, such as the techniques published in Remington's Pharmaceutical Sciences, 20th Edition. The pharmaceutical composition can be formulated as dosage forms for, e.g. oral administration. However, also parenteral, such as intramuscular, intravenous, subcutaneous, intradermal, intraarterial, rectal, nasal, topical or vaginal administration is envisaged. In context of the present invention, the most preferred route of administration of the herein defined (S)-enantiomer of an aminoheteroaryl compound (such as the (S)-enantiomer of crizotinib) is oral administration.

Dosage forms for oral administration include coated and uncoated tablets, soft gelatine capsules, hard gelatine capsules, lozenges, troches, solutions, emulsions, suspensions, syrups, elixiers, powders and granules for reconstitution, dispersible powders and granules, medicated gums, chewing tablets and effervescent tablets.

Dosage forms for parenteral administration include solutions, emulsions, suspensions, dispersions, powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler.

Pharmaceutically acceptable salts of compounds that can be used in the present invention can be formed with various organic and inorganic acids and bases. Exemplary acid addition salts comprise acetate, adipate, alginate, ascorbate, benzoate, benzenesulfonate, hydrogensulfate, borate, butyrate, citrate, caphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pectinate, persulfate, 3-phenylsulfonate, phosphate, picate, pivalate, propionate, salicylate, sulfate, sulfonate, tartrate, thiocyanate, toluenesulfonate, such as tosylate, undecanoate and the like. Exemplary base addition salts comprise ammonium salts, alkali metal salts, such as sodium, lithium and potassium salts; earth alkali metal salts, such as calcium and magnesium salts; salts with organic bases (such as organic amines), such as benzazethine, dicyclohexylamine, hydrabine, N-methyl-D-glucamine, N-methyl-D-glucamide, t-butylamine, salts with amino acids, such as arginine, lysine and the like.

Pharmaceutically acceptable solvates of compounds that can be used in the present invention may exist in the form of solvates with water, for example hydrates, or with organic solvents such as methanol, ethanol or acetonitrile, i.e. as a methanolate, ethanolate or acetonitrilate, respectively.

Pharmaceutically acceptable prodrugs of compounds that can be used in the present invention are derivatives which have chemically or metabolically cleavable groups and become, by solvolysis or under physiological conditions, the compounds of the invention which are pharmaceutically active in vivo. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985).

These pharmaceutical compositions described herein can be administered to the subject at a suitable dose. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition comprising the herein defined (S)-enantiomer of an aminoheteroaryl compound should be in the range of 0.1 µg to 5000 mg units per day, in some embodiments 0.1 µg to 1000 mg units per day. If the regimen is a orally administration, it may be in the range of 100 mg units per day to 5000 mg units per day, preferably 500 mg units per day. This 500 mg units per day may be administrated as 250 mg dosages twice daily. If the regimen is a continuous infusion, it may also be in the range of 0.1 ng to 10 µg units per kilogram of body weight per minute, respectively. Progress can be monitored by periodic assessment. It is also envisaged to use regimens which provide for escalating doses. It is in particular preferred that the patient in need of the medical intervention as provided herein receives high dosages of the herein defined (S)-enantiomer of an aminoheteroaryl compound. Such high dosages may comprise between 1 to 500 mg/kg, however, also other dosage regimens are envisaged and can be attended to by the attending physician. As shown in the appended examples, in a xenograft mouse study, 25 mg/kg body weight of the (S)-enantiomer of crizotinib was well-tolerated and led to a significant reduction of tumour volume of more than 50%. Therefore, the herein defined (S)-enantiomer of an aminoheteroaryl compound may be administered in a dosage of 25 mg/kg body weight (e.g. when administered to animals such as mice). There is further provided a regimen as a regular administration of the pharmaceutical composition comprising the herein defined (S)-enantiomer of an aminoheteroaryl compound in combination with chemotherapy, preferably with a PARP inhibitor and/or an EGFR inhibitor wherein said combined preparation is for simultaneous, separate or sequential use. It is also envisaged in context of the present invention to administer the pharmaceutical composition comprising the herein defined (S)-enantiomer of an aminoheteroaryl compound in combination with radiotherapy, wherein said combined administration is a simultaneous, separate or sequential administration.

In the context of the present invention, the following modes of administration of the (S)-enantiomer of an aminoheteroaryl compound (such as the (S)-enantiomer of crizotinib), alone or in combination with radiotherapy and/or chemotherapy (such as a PARP inhibitor and/or an EGFR inhibitor), are preferred:

Oral administration in constant or escalating doses;
Subcutaneous administration in constant or escalating doses; and/or
Intravenous administration in constant or escalating doses.

The most preferred mode of administration is oral administration in constant doses.

As described herein above and below, the invention provides for a method of treating and/or preventing cancer in a subject in need of such treatment, wherein the method comprises administering an effective amount of the (S)-enantiomer of an aminoheteroaryl compound provided herein or the pharmaceutical composition provided herein to said subject. One aspect of the present invention relates to the method of treatment and/or prevention of cancer in a subject, wherein the treatment and/or prevention is independent of the ALK-status and/or the c-Met-status of the cancer cell or tissue of said subject, comprising administering to said subject a therapeutically effective amount of the herein defined (S)-enantiomer of an aminoheteroaryl compound. Thus, the cancer to be treated and/or prevented may be ALK-negative (i.e. may not have an activating ALK aberration) and/or may be c-Met-negative.

Accordingly, the present invention provides for means and methods for the treatment of subjects in need of such a treatment (either curative or preventive) which suffer from cancer. This cancer may be an ALK-negative cancer, (i.e. a cancer wherein the cancer cells or cancer tissue do not have an activating ALK aberration) and/or a c-Met-negative cancer. The method of treatment of such disorder comprises the administration of a pharmaceutically active amount of a herein defined (S)-enantiomer of an aminoheteroaryl compound (such as the (S)-enantiomer of crizotinib) alone or in combination with radiotherapy and/or chemotherapy (such as a PARP inhibitor and/or an EGFR inhibitor). Accordingly, in context of the present invention, the herein described method of treatment may also comprise the co-administration of additional compounds/medicaments and the herein defined (S)-enantiomer of an aminoheteroaryl compound (such as the (S)-enantiomer of crizotinib). In particular, the method of treatment preferably comprises the co-administration and the herein defined (S)-enantiomer of an aminoheteroaryl compound (such as the (S)-enantiomer of crizotinib). These co-therapy approaches and combination therapy approaches are envisaged with respect to the present invention.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing and/or ameliorating a cancerous disease from occurring in a subject which may be predisposed to the disease; (b) inhibiting the disease, i.e. arresting its development like the inhibition of cancer progression and/or inhibition of the development of metastases; or (c) relieving the disease, i.e. causing regression of the disease, like the repression of a tumour and/or of metastases.

In accordance with the present invention, the term "prevention" or "preventing" of an cancer/cancerous disease means the cancer per se can be hindered of developing or to develop into an even worse situation. Accordingly, it is one of the advantages of the present invention that an (S)-enantiomer of an aminoheteroaryl compound (such as the (S)-enantiomer of crizotinib) can be employed in avoidance of cancer, cancer progression, and/or the development of metastases. Therefore, in accordance with the present invention, an (S)-enantiomer of an aminoheteroaryl compound (such as the (S)-enantiomer of crizotinib) may also be employed before a cancer develops.

However, as disclosed and provided herein, an (S)-enantiomer of an aminoheteroaryl compound (such as the (S)-enantiomer of crizotinib) may also be employed in the amelioration and/or treatment of disorders wherein the diseased status has already developed, i.e. in the treatment of an existing cancer. Accordingly, the term "treatment" as used herein also relates to medical intervention of an already manifested disorder, like the treatment of an already defined and manifested cancer.

The terms "patient" and "subject" are used interchangeably herein. A "patient" or "subject" for the purposes of the present invention may be a vertebrate. Said vertebrate may be a mammal, such as a human. Said vertebrate may also be farm animal, such as a cow, pig, sheep, goat, horse, camel, chicken, turkey or other commercially important farm animals. A "patient" or "subject" for the purposes of the present invention includes both humans and other animals, particularly mammals, and other organisms. Thus, the methods are applicable to both human therapy and veterinary applications. In the preferred embodiment the patient is a mammal, and in the most preferred embodiment the patient is human.

The "patient" or "subject" to be treated or in need of treatment according to this invention may be a vertebrate. Said vertebrate may be a mammal, such as a human. Said vertebrate may also be farm animal, such as a cow, pig, sheep, goat, horse, camel, chicken, turkey or other commercially important farm animals. The "patient" or "subject" to be treated or in need of treatment according to this invention is preferably a mammal. The "patient" or "subject" to be treated is most preferably a human. In particular, the "patient" or "subject" to be treated is a human patient that suffers from cancer.

In accordance with the present invention, the term "status", in particular "NUDT1/MTH1-status", "RAS-status", "ALK-status" or "c-Met-status" relates to the genetic constitution of the gene of the respective protein, the expression of the respective protein and/or the biological activity of the respective protein. In particular, the "status" of NUDT1/MTH1, RAS, ALK or c-Met may be reflected by the presence or absence of activating or inactivating aberrations of NUDT1/MTH1, RAS, ALK or c-Met, respectively. Accordingly, the term "status" as used herein also relates to the existence of an activating or inactivating mutation within the gene or protein of interest (e.g. within the gene or protein of NUDT1/MTH1, RAS, ALK or c-Met).

In addition, in context of the present invention, the "status" of a gene or protein also relates to the "level" of the respective gene and/or protein, i.e. the level of NUDT1/MTH1, RAS, ALK, or c-Met. Accordingly, the term "status" in context of, e.g., "NUDT1/MTH1-status" as used herein is known in the art and relates to the level of MTH1 biological activity and/or MTH1 expression (e.g. the level of MTH1 mRNA and/or MTH1 protein). Accordingly, the term "RAS-status" as used herein is known in the art and relates to the level of RAS biological activity and/or RAS expression (e.g. the level of RAS mRNA and/or RAS protein). Accordingly, the term "ALK-status" as used herein is known in the art and relates to the level of ALK biological activity and/or ALK expression (e.g. the level of ALK mRNA and/or ALK protein). Accordingly, the term "c-Met-status" as used herein is known in the art and relates to the level of c-Met biological activity and/or c-Met expression (e.g. the level of c-Met mRNA and/or c-Met protein). The level of NUDT1/MTH1, RAS, ALK or c-Met expression may be reflected by the biological activity of NUDT1/MTH1, RAS, ALK or c-Met, respectively. Accordingly, the term "status" as used herein, also relates to the biological activity of a protein, e.g. of MTH1, RAS, ALK or c-Met.

The level of a particular protein (e.g. the expression level and/or the level of the biological activity of said protein) may be increased or decreased. In particular, the level of NUDT1/MTH1, RAS, ALK or c-Met may be increased by activating aberrations of NUDT1/MTH1, RAS, ALK or c-Met, respectively. Alternatively, the level of NUDT1/MTH1, RAS, ALK or c-Met may be decreased by inactivating aberrations of NUDT1/MTH1, RAS, ALK or c-Met, respectively. Accordingly, the term "status" as used herein also relates to the existence of an activating or inactivating mutation within the gene or protein of interest. In addition, in context of the invention, an inactivating aberration may be a mutation resulting in a loss-of function mutant. An inactivating aberration may also be the deletion or partial deletion of a gene encoding the respective protein (e.g. MTH1, RAS, ALK or c-Met). In line with, in context of the invention, an activating aberration may be a mutation resulting in a protein (e.g. MTH1, RAS, ALK or c-Met) with enhanced expression or activity. Such activating aberration may be, for example, an activating ALK aberration. An activating ALK aberration may be, e.g., a gene mutation or a chromosomal translocation such as EML4-ALK.

In addition, as used herein, the term "patient's status", such as "patient's NUDT1/MTH1-status", "patient's RAS-status", "patient's ALK-status", or "patient's c-Met-status" relates to status of the cancer of said patient, such as the "cancer's NUDT1/MTH1-status", the "cancer's RAS-status", the "cancer's ALK-status" or the "cancer's c-Met-status". In particular, the term "patient's status" (such as "patient's NUDT1/MTH1-status") relates to the status of the cancer cell or tissue of said patient. Thus, the term "patient's status" (such as "patient's NUDT1/MTH1-status") relates to the status of the cancer cell or tissue of said patient regarding the genetic constitution of the genes of the respective protein, the expression of the respective protein and/or the biological activity of the respective protein.

In this context, the terms "MTH1-positive" "NUDT1/MTH1-positive", "positive for MTH1" and "positive for NUDT1/MTH1" are used interchangeably herein and relate to both, physiological (i.e. "normal") and increased expression and/or biological activity of NUDT1/MTH1. "Physiological" or "normal" expression and/or biological activity of NUDT1/MTH1 relates to the expression and/or biological activity (i.e. catalytic activity) of MTH1 in cells, which do express MTH1, but which do not have an activating or inactivating MTH1 aberration. "Increased" expression and/or biological activity of NUDT1/MTH1 relates to the expression and/or biological activity (i.e. catalytic activity) of MTH1 in cells, which do express MTH1 and have an activating MTH1 aberration. "Increased" expression and/or biological activity of NUDT1/MTH1 further relates to an increased expression and/or biological activity (i.e. catalytic activity) of MTH1 compared to cells, which do express MTH1, but which do not have an activating MTH1 aberration. An activating MTH1 aberration leads to an increased expression and/or biological activity (i.e. catalytic activity) of MTH1. Accordingly, the term "MTH1-positive" also relates to increased expression and/or biological activity of MTH1. Examples for an activating MTH1 aberration are a gene amplification, a gene mutation or a chromosomal translocation leading to an increased expression and/or biological activity (i.e. catalytic activity) of MTH1.

In line with this, the terms "MTH1-negative", "NUDT1/MTH1-negative", "negative for MTH1" and "negative for NUDT1/MTH1" are used interchangeably herein and relate reduced expression and/or biological activity of NUDT1/MTH1. "Reduced" expression and/or biological activity of MTH1 relates to the expression and/or biological activity (i.e. catalytic activity) of MTH1 in cells, which do not express MTH1. "Reduced" expression and/or biological activity of NUDT1/MTH1 further relates to reduced expression and/or biological activity (i.e. catalytic activity) of MTH1 compared to cells, which do express MTH1 and which do not have an inactivating MTH1 aberration. Additionally, "Reduced" expression and/or biological activity of MTH1 relates to the expression and/or biological activity (i.e. catalytic activity) of MTH1 in cells, which do express MTH1, and which have an inactivating MTH1 aberration. Examples for an inactivating MTH1 aberration are a gene mutation or a chromosomal translocation leading to a reduction in expression and/or biological activity (i.e. catalytic activity) of MTH1.

Similarly, as used herein, the terms "c-Met-positive" and "positive for c-Met" are used interchangeably herein and relate to both, physiological (i.e. "normal") and increased expression and/or biological activity of c-Met. C-Met-positive cells may be c-Met-dependent, i.e. cells wherein the survival and/or proliferation depends on the expression of c-Met. "Physiological" or "normal" expression and/or biological activity of c-Met relates to the expression and/or biological activity (i.e. catalytic activity) of c-Met in cells, which do express c-Met, but which do not have an activating or inactivating c-Met aberration. "Increased" expression and/or biological activity of c-Met relates to the expression and/or biological activity (i.e. catalytic activity) of c-Met in cells, which do express c-Met and have an activating c-Met aberration. "Increased" expression and/or biological activity of c-Met further relates to an increased expression and/or biological activity (i.e. catalytic activity) of c-Met compared to cells, which do express c-Met, but which do not have an activating c-Met aberration. An activating c-Met aberration leads to an increased expression and/or biological activity (i.e. catalytic activity) of c-Met. Accordingly, the term "c-Met-positive" also relates to an increased expression and/or biological activity of c-Met. Examples for an activating c-Met aberration are a gene amplification, a gene mutation or a chromosomal translocation leading to an increased expression and/or biological activity (i.e. catalytic activity) of c-Met. In line with this, the terms "c-Met-negative" and "negative for c-Met" are used interchangeably herein and relate to reduced expression and/or biological activity of c-Met. C-Met-negative cells are c-Met-independent, i.e. cells wherein the survival and/or proliferation does not depend on the expression of c-Met. "Reduced" expression and/or biological activity of c-Met relates to the expression and/or biological activity (i.e. catalytic activity) of c-Met in cells, which do not express c-Met. "Reduced" expression and/or biological activity of c-Met further relates to a reduced expression and/or biological activity (i.e. catalytic activity) of c-Met compared to cells, which do express MTH1 and which do not have an inactivating c-Met aberration. Additionally, "Reduced" expression and/or biological activity of c-Met relates to the expression and/or biological activity (i.e. catalytic activity) of c-Met in cells, which do express c-Met, and which have an inactivating c-Met aberration. Examples for an inactivating c-Met aberration are a gene mutation or a chromosomal translocation leading to a reduction in expression and/or biological activity (i.e. catalytic activity) of c-Met.

It is noted that the terms "ALK-negative", "negative for ALK" and "do/does not have an activating ALK-aberration" are used interchangeably herein. Accordingly, term "ALK-negative" relates to both, physiological (i.e. "normal") and reduced expression and/or biological activity of ALK. "Physiological" or "normal" expression and/or biological activity of ALK relates to ALK expression and/or ALK biological activity (i.e. catalytic activity) in cells, which do express ALK, but which do not have an activating ALK aberration. "Physiological" or "normal" expression and/or biological activity of ALK further relates to ALK expression and/or ALK biological activity in a healthy, non-cancerous cell or tissue. This non-cancerous cell or tissue is to be considered as not having an activating ALK-aberration.

"Reduced" expression and/or biological activity of ALK relates, in one aspect, to no expression and/or biological activity (i.e. catalytic activity) of the ALK kinase. "Reduced" expression and/or biological activity of ALK further relates to qualitatively or quantitatively reduced expression and/or biological activity (i.e. catalytic activity) of ALK as compared to physiological ALK expression and/or physiological ALK biological activity as defined herein above.

The terms "ALK-positive", "positive for ALK" and "do/does have an activating ALK-aberration" are used interchangeably herein and relate to a cancer cell or tissue that has an activating ALK aberration. ALK-positive cells may be ALK-dependent, i.e. (cancer and/or tumour) cells wherein the survival and/or proliferation depends on the expression of ALK. An activating ALK aberration leads to an increased expression and/or biological activity (i.e. catalytic activity) of ALK. "Increased" expression and/or biological activity of ALK relates to an increased expression and/or biological activity (i.e. catalytic activity) of ALK as compared to cells, which do express ALK, but which do not have an activating ALK aberration. In addition, "increased" ALK expression and/or ALK biological activity relates to an enhanced expression and/or biological activity of ALK as compared to physiological expression and/or biological activity of the ALK kinase in healthy, non-cancerous cells. Accordingly, the term "ALK-positive" relates to enhanced expression and/or biological activity of ALK. Examples for an activating ALK aberration are a gene amplification, a gene mutation or a chromosomal translocation leading to an increased expression and/or biological activity (i.e. catalytic activity) of ALK. An example for a chromosomal translocation which represents an activating ALK aberration is EML4-ALK.

The gene name of the protein MTH1 is NUDT1. At present, four isoforms of NUDT1/MTH1 (p18, p21, p22 and p26) have been reported of which p18 is considered the dominant isoform. The isoform p18 has been used in the experiments described herein. Nucleotide and amino acid sequences of NUDT1/MTH1 are provided herein, below. Mutations for MTH1 have been reported, however, their physiological or clinical relevance has not been elucidated. Methods for determining the NUDT/MTH1-status (e.g. for detecting the level (such as the expression level) of NUDT/MTH1 or for determining whether the nucleotide or amino acid sequence of NUDT/MTH1 contains a specific mutation) are known in the art and described herein below. With respect to RAS, several genes exist (i.e. HRAS, KRAS, NRAS, and MRAS). Due to alternative splicing there are several existing isoforms. Known activating RAS mutations include mutations of KRAS, e.g., the G12 mutation (e.g. G12C) or the Q61 mutation (e.g. Q61H). Nucleotide and amino acid sequences of RAS are provided herein, below. In addition, the amino acid sequence for mutant G12C KRAS, which is found, e.g., in lung cancer, is provided herein as SEQ ID No. 23, below. Methods for determining the RAS-status (e.g. for detecting the level (e.g. the expression level) of RAS or determining whether the nucleotide or amino acid sequence of RAS contains a specific mutation) are known in the art and described herein below. In addition, herein disclosed are nucleotide and amino acid sequences of ALK and c-Met (see below). Furthermore, disclosed herein are sequence annotations of the amino acid sequences of RAS, ALK and c-Met, providing several aberration and mutations of RAS, ALK and c-Met, respectively (see below).

Activating and inactivating aberrations include genetic aberrations such as gene mutation, gene copy number increase, aberration of gene expression, and aberration of mRNA expression. A general overview of genetic aberration techniques for detecting said aberrations is shown in Table 1, below.

TABLE 1

General overview of genetic aberrations and techniques for detecting genetic aberrations.

| Aberration | Test material | Location | Method of detection |
|---|---|---|---|
| Gene mutation | DNA | nucleus | Mutation analysis such as sequencing etc. |
| Gene copy number increase | DNA | nucleus | Fluorescent In-Situ Hybridisation (FISH) |
| Gene expression | Protein | depending on gene | Immunohistochemistry (IHC) |
| Gene mRNA expression | RNA | nucleus | RT-PCR |

Other techniques that can be used to detect NUDT1/MTH1, ALK, RAS or c-Met aberrations (e.g. genetic aberrations), such as amplifications or mutations in DNA derived from tumour biopsies, include Peptide nucleic acid-locked nucleic acid (PNA-LNA) PCR clamp, PCR-Invader, SNaPshot, PCR/HRMA/dHPLC, PCR/fIRFLP, Fluorescent In-Situ Hybridisation (FISH) and Immunohistochemistry (IHC) as described herein, below.

Peptide nucleic acid-locked nucleic acid (PNA-LNA) PCR clamp is a rapid and sensitive detection system for mutations that can detect, for instance, EGFR mutations in the presence of 100-1000-fold background of wild-type EGFR from non-tumour cells.[24] This method is known in the art and described, e.g., in Nagai (2005) Cancer Res 65: 7276-7282.[24]

PCR-Invader. This system uses two simultaneous reactions to identify known single nucleic acid changes in DNA sequence and to amplify the signal. This method is commonly known in the art and described, e.g., in Tadokoro (2011) Transl Res. 158:169-79 as well as on http://www.twt.com/invader/invader.html.

SNaPshot. SNaPshot is a single nucleotide primer extension assay that can be used to detect known single nucleotide mutations. This method is commonly known in the art and described, e.g., in Hurst (2009) BMC Research Notes 2:66 as well as on https://products.appliedbiosystems.com/ab/en/US/adirect/ab?cmd=catNavigate2&catID=600762&tab=DetailInfo.

PCR/HRMA/dHPLC. Biopsy DNA is amplified by PCR and subjected to high resolution melting analysis and/or denaturing high performance liquid chromatography to detect mutations.[25,26] This method is commonly known in the art and described, e.g., in Jänne (2006) Clin Cancer Res 12: 751-758[25] and in Nomoto (2006) Am J Clin Pathol 126: 608-615.[26]

PCR/fIRFLP. DNA is amplified using PCR with fluorescently labelled primers. The fragment is digested with restriction enzymes targeting the region containing the mutation, and the product undergoes fragment analysis to detect digested and undigested fragments.[27] This method is commonly known in the art and described, e.g., in Pao (2005) PLoS Med 2 (3): e73.[27]

Fluorescent In-Situ Hybridisation (FISH) and Immunohistochemistry (IHC). FISH measures the number of copies of DNA of the gene of interest and IHC measures the expression of the according protein within the cell. FISH is commonly known in the art and described, e.g., in Koivunen (2008) Clinical Cancer Research 14: 4275-4283. IHC is also commonly known in the art and described in, e.g., in Chen (2010) Cancer Research 70: 9827-9836. For ALK there is a specific FISH kit available (Abbott Laboratories' Vysis ALK Break Apart FISH Probe Kit (Product Name: Vysis ALK Break Apart FISH Probe Kit, Abbott Order Number: 06N38-020).

For the detection of cytogenetic aberrations several detection methods are known in the art and reviewed, e.g., in Speicher (2005) Nat Rev Genet 6 (10): 782-792.[29]

All Mutation detection methods should be performed in best practice. This means that all mutation detection methods should be robust and performed to the highest standards with established Standard Operating Procedures (SOPs). Quality control of each step in the process should be in place. How to perform mutation detection methods in best practice is known in the art and described, e.g., in Eberhard (2008) Clin Oncol 26 (6): 983-993.[28]

Antibodies, Probes and Primers which may be Used for Detecting a Patient's NUDT1/MTH1-Status are Commonly Known in the Art and also Shown in the Following:

An antibody for detecting a patient's NUDT1/MTH1-status is, e.g., Novus Biologicals MTH1 Antibody (NB100-109).

Primers for detecting a patient's NUDT1/MTH1-status are shown, e.g. in Kennedy (1998) FEBS Lett. 429 (1): 17-20,[36] which is herein incorporated by reference in its entirety. In addition, primers for detecting a patient's NUDT1/MTH1-status are also provided herein, below and in the appended Sequence Listing.

```
Primer Sequence for the Detection of NUDT1/MTH1
                                      (SEQ ID No. 17)
5P-AGCCTCAGCGAGTTCTCCTG-3P Primer Sequence for the Detection of NUDT1/MTH1
                                      (SEQ ID No. 18)
5P-GATCTGGCCCACCTTGTGC-3P
```

Antibodies, Probes and Primers which may be used for Detecting a Patient's RAS-status are Commonly Known in the Art and also Shown in the Following:

An antibody for detecting a patient's RAS-status is, e.g., Cell Signaling Ras Antibody #3965. Primers for detecting a patient's RAS-status are shown, e.g. in Keohavong (1996) Clin. Cancer. Res. 2 (2): 411-418[33]; and Gerry (1999) Mol. Biol. 292 (2): 251-262,[34] which are herein incorporated by reference in their entirety.

Antibodies, Probes and Primers which may be Used for Detecting a Patient's c-Met-status are Commonly Known in the Art and also Shown in the Following:

An antibody for detecting a patient's c-Met-status is, e.g., Cell Signaling Met Antibody #4560

Primers and probes for detecting a patient's c-Met-status are shown, e.g. in Kubo (2009) Int. J. Cancer 124 (8): 1778-1784,[35] which is herein incorporated by reference in its entirety.

Antibodies, Probes and Primers which may be Used for Detecting a Patient's ALK-status are Commonly Known in the Art and also Shown in the Following:

Antibodies for detecting a patient's ALK-status are, e.g., Cell Signaling #3633 ALK (D5F3) XP® Rabbit mAb, and ALK (C26G7) Rabbit mAb #3333.

Probes and primers for detecting a patient's ALK-status are shown, e.g. in Koivunen (2008) Clin. Cancer. Res. 14 (13): 4275-4283[30]; and Lin (2009) Mol. Cancer Res. 7 (9): 1466-1476,[31] which are herein incorporated by reference in their entirety.

Further primers for detecting a patient's ALK-status are shown, e.g., in Chen (2008) Nature 455 (7215): 971-974,[32] which is herein incorporated by reference in their entirety.

Antibodies, Probes and Primers which may be Used for Detecting a Patient's p21-status are Commonly Known in the Art and also Shown in the Following:

Polynucleotides capable of detecting p21 (e.g. by using qPCR) are the human p21/WAF1-oligonucleotides which have the following sequence:

```
                                              (SEQ ID No. 49)
5'-CTGTGATGCGCTAATGGCG-3'

(SEQ ID No. 50)
5'-AAGTCGAAGTTCCATCGCTCA-3'
```

(See, e.g., Zeng (2006) Cancer Research 66, 10701-10708)

Antibodies capable of detecting p21 are, e.g., the anti-p21 antibody (ab7960), Abcam, and the p21 Waf1/Cip1 (DCS60) Mouse mAb #2946, Cell Signaling.

It is noted that the term "polynucleotide(s)" as used herein encompasses primer(s) and probe(s). Accordingly, the term "polynucleotide(s)" as used herein means both, primer(s) and probe(s). Primers (e.g. primers for detecting a patient's NUDT1/MTH1-status, a patient's RAS-status, a patient's ALK-status and/or a patient's c-Met-status) can, e.g., be designed using available software, such as Primer3Plus (available the following URL: bioinformatics.nl/cgi-bin/primer3plus/primer3plus.cgi; see Rozen and Skaletsky, In: Krawetz S, Misener S (eds) Bioinformatics Methods and Protocols: Methods in Molecular Biology. Humana Press, Totowa, N.J., pp. 365-386, 2000) and Invitrogen Vector NTI proprietary software. Other methods for designing primers are known to those of skill in the art.

The following figures show and illustrate the present invention:

FIG. 1: Chemical proteomics workflow (The Figure is a modified version of a Figure taken from Superti-Furga (2012) Designing Multi-target Drugs, (eds. Richard Morphy and John Harris), Drug Discovery Series, Royal Society of Chemistry, Cambridge, which is herein incorporated by reference in its entirety).

Figure 2:
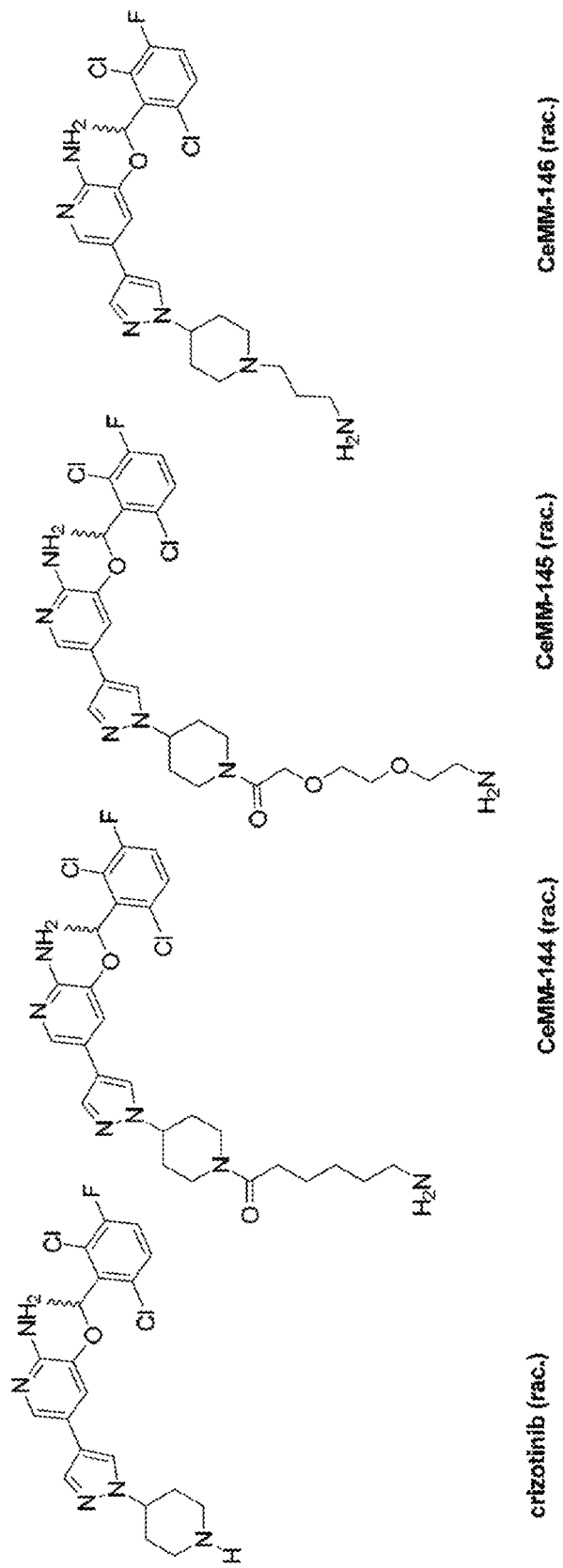

FIG. 2: Structure of crizotinib and the newly synthesised coupleable derivatives.

Figure 3:
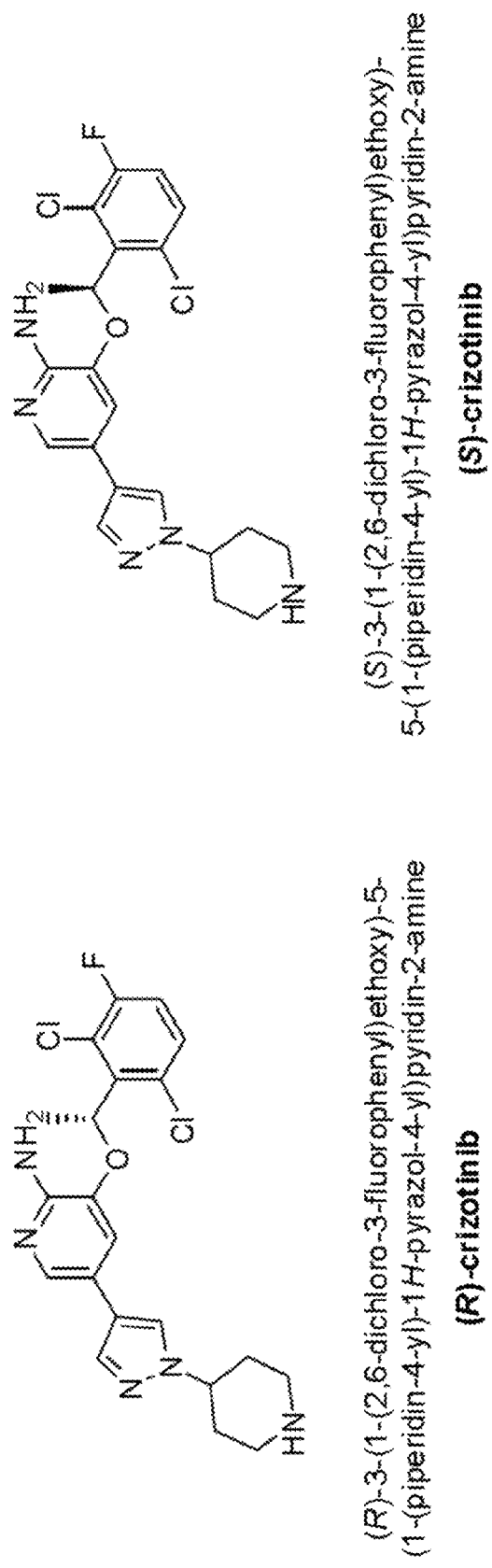

FIG. 3: Chemical structures of both crizotinib enantiomers.

Figure 4:
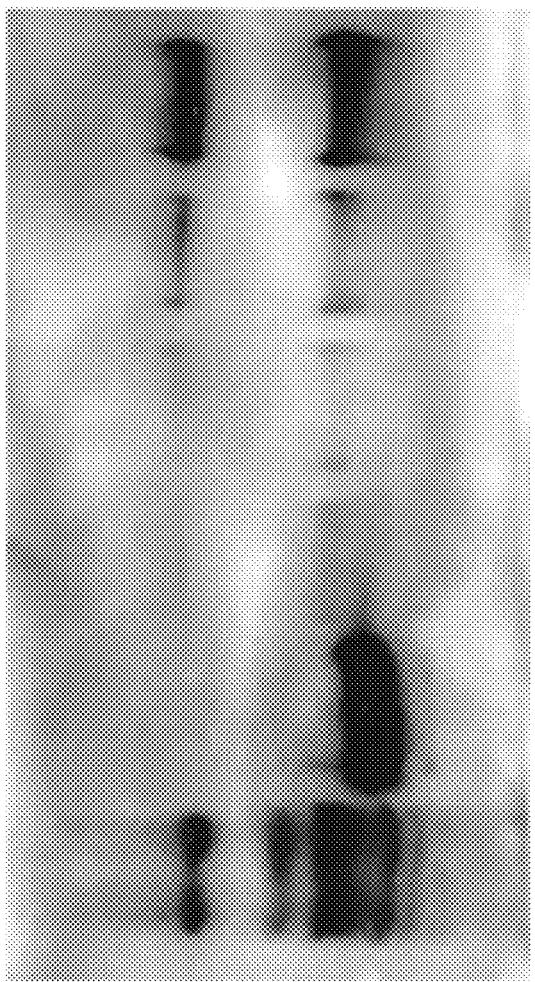

FIG. 4: Evaluation of immobilized compounds with respect to their ability to bind ALK. Only CeMM-146 effectively enriches for both ALK isoforms expressed in SH-SY5Y cells.

Figure 5:
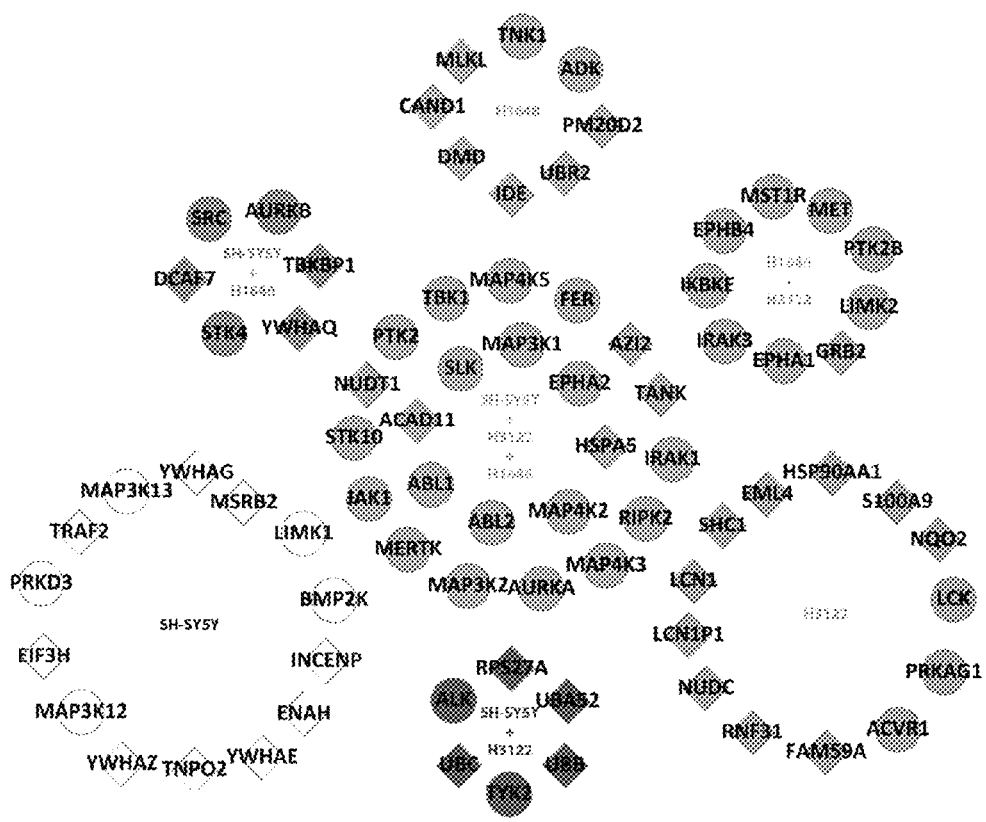

FIG. 5: Identified interactors of crizotinib (labels are official gene symbols). Kinases are depicted as circles, non-kinase proteins are shown as diamonds.

Figure 6:
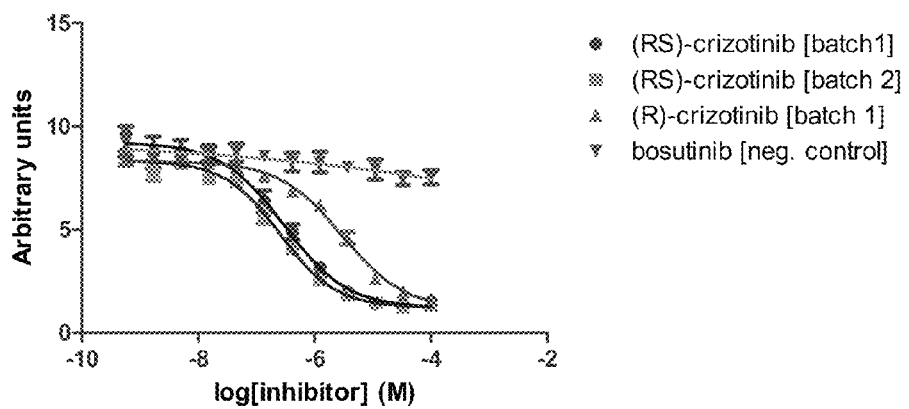

FIG. 6: MTH1 inhibition assay. Two different batches of racemic crizotinib are approx. 10-fold more potent than optically pure (R)-crizotinib in inhibiting MTH1 catalytic activity. In contrast, the promiscuous BCR-Abl kinase inhibitor bosutinib does not exhibit any significant MTH1 inhibition.

Figure 7:
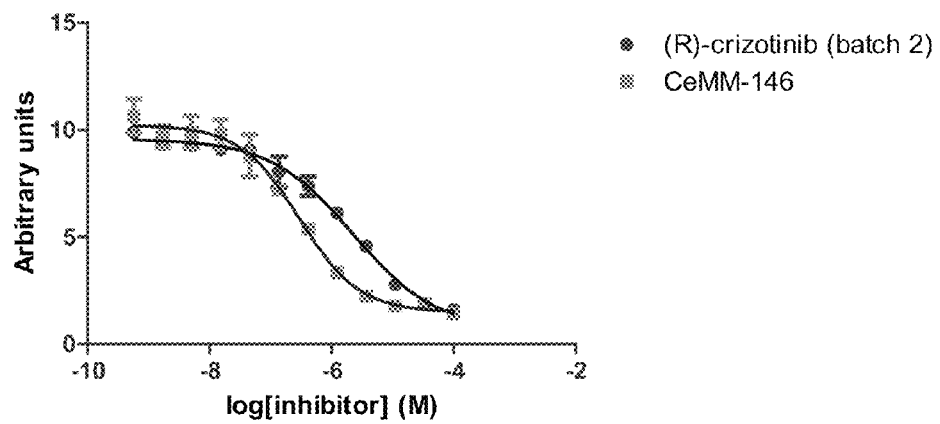

FIG. 7: MTH1 inhibition assay. The N-aminopropyl-substituted crizotinib derivative CeMM-146 which was prepared from racemic crizotinib also exhibits nanomolar inhibition of MTH1 catalytic activity and is more potent than optically pure (R)-crizotinib.

Figure 8:
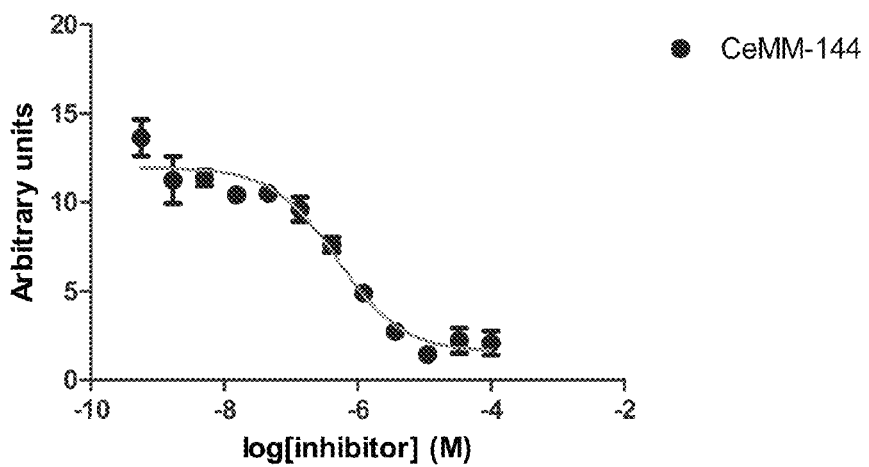

FIG. 8: MTH1 inhibition assay. The N-aminohexylcarboxylic acid derivative CeMM-144 prepared from racemic crizotinib inhibits MTH1 catalytic activity with an IC50 value of approximately 500 nM.

Figure 9:
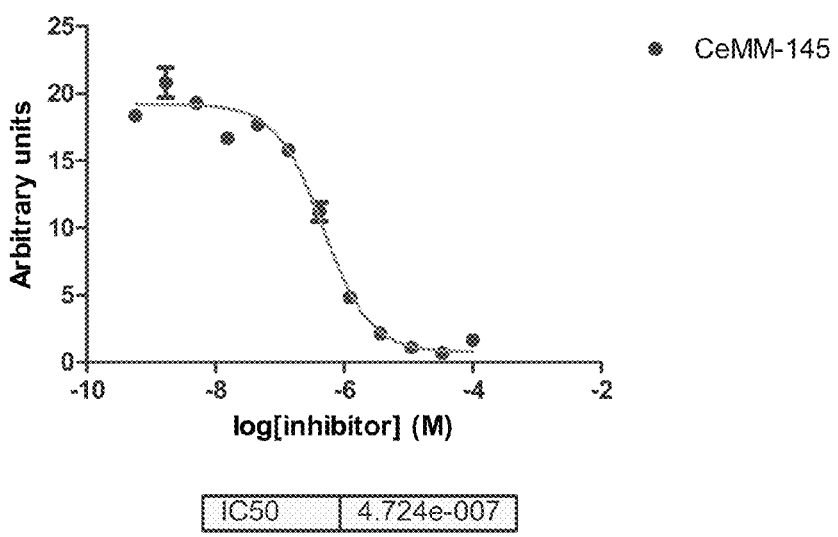

FIG. 9: MTH1 inhibition assay. Introduction of a PEG-based aminoalkyl substitutent at the piperidine ring of racemic crizotinib does not interfere with MTH1 inhibitory activity.

Figure 10:
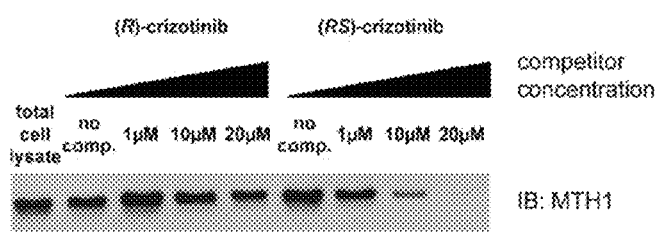

FIG. 10: Western blot analysis of SK-ES-1 Ewing's sarcoma cell lysates showing differential MTH1 binding potencies for optically pure (R)-crizotinib versus the racemate.

Figure 11:
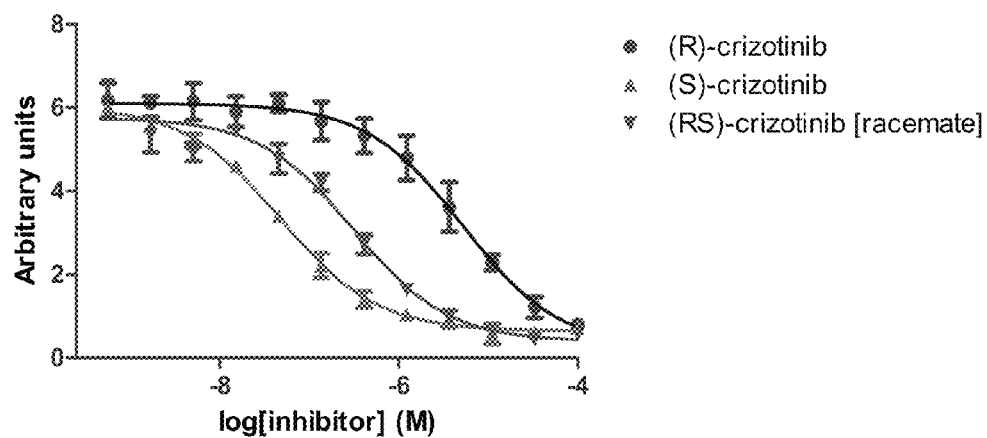

FIG. 11: MTH1 inhibition assay. The (S)-enantiomer of crizotinib is a low nanomolar inhibitor of MTH1 catalytic activity. The (S)-enantiomer of crizotinib gives a significantly lower IC50 value when compared to the (R)-enantiomer or the racemate, indicating that the (S)-configuration leads to an increased affinity of the compound. Results indicate technical replicates±SEM representative for at least duplicate experiments (n>2).

Figure 12:
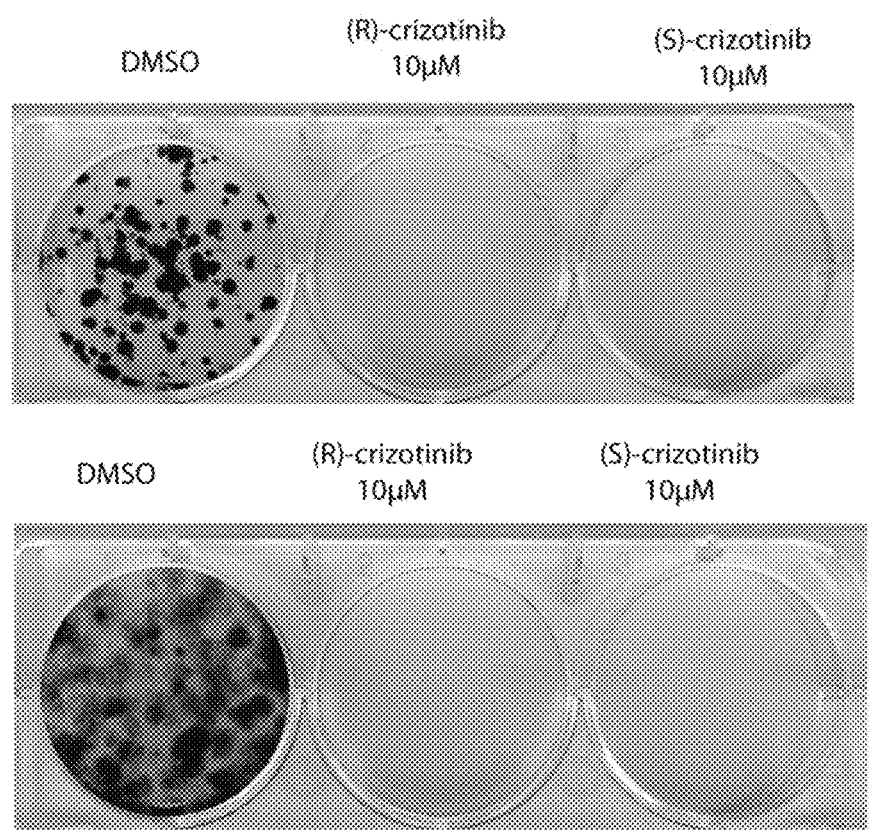

FIG. 12: Colony formation assay. MCF 7 (top) and MDA-MB-231 (bottom) human breast cancer cells were seeded in 6-well format followed by drug or mock treatment at the indicated concentrations 24 hours after plating. After four weeks, cells were fixed and stained with crystal violet.

Figure 13:
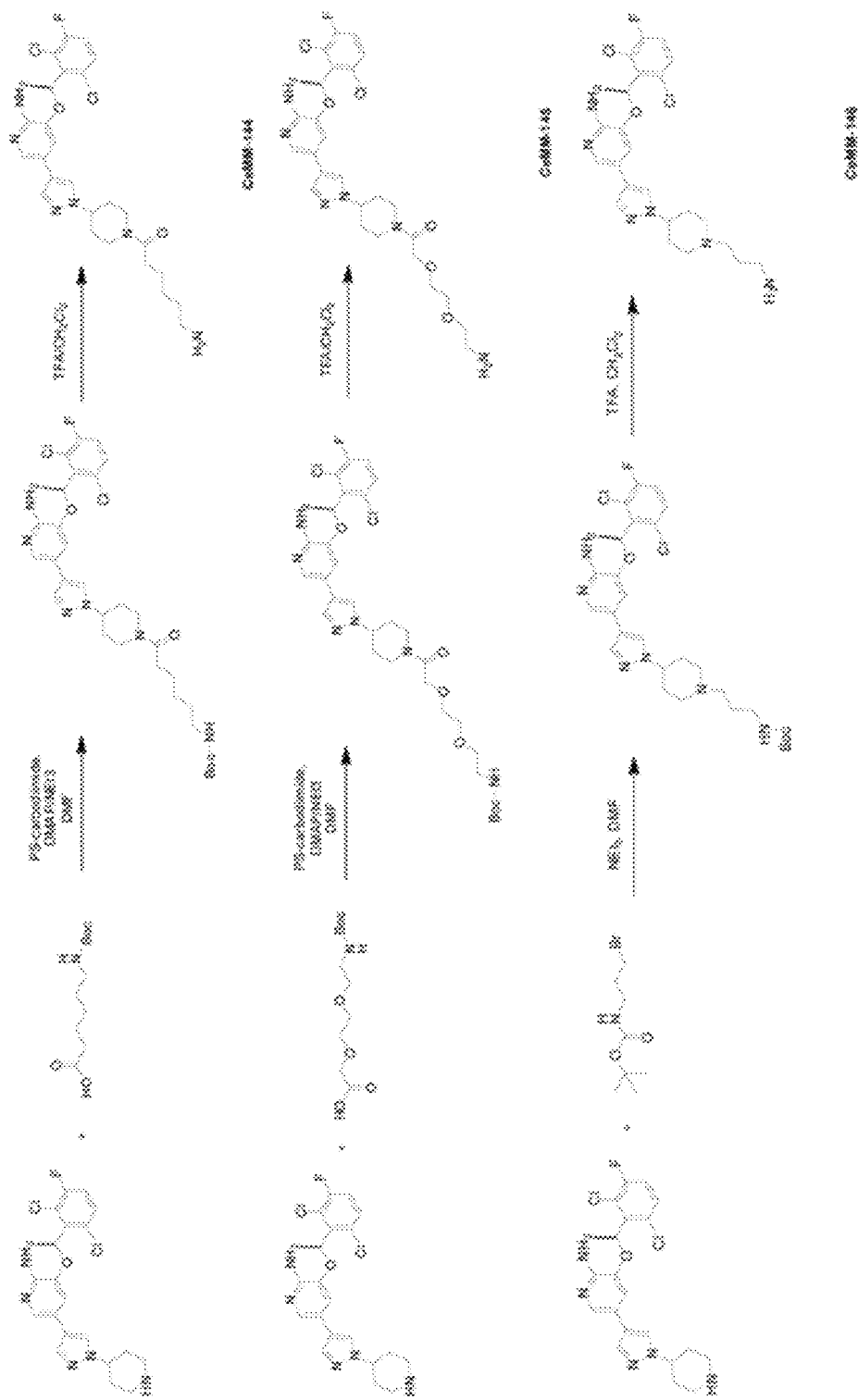

FIG. 13: Preparation of CeMM-144, CeMM-145, and CeMM-146.

Figure 14:
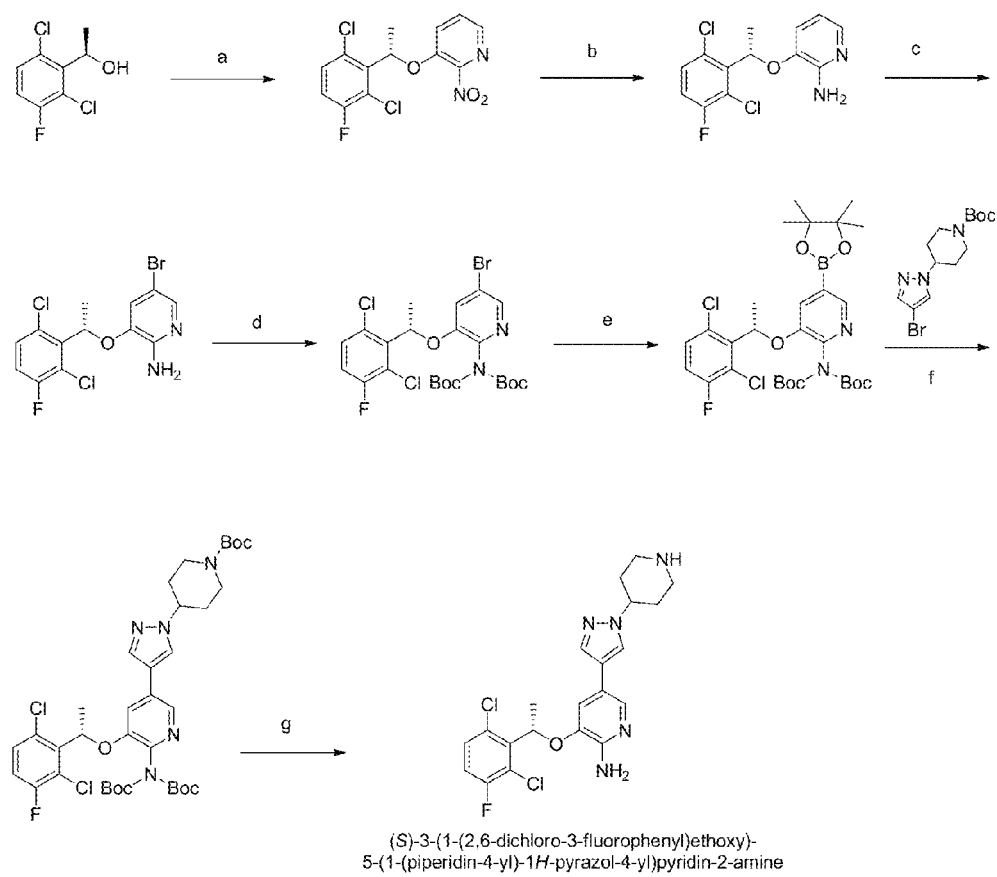

FIG. 14: Stereoselective preparation of the (S)-enantiomer of crizotinib. Reagents and conditions: (a) $Ph_3P$, DIAD, THF, 0° C., 4 h; (b) Fe, AcOH/EtOH, reflux, 1 h; (c) NBS, MeCN, 0° C., 15 min; (d) $(Boc)_2O$, DMAP, DMF, ambient temperature, 18 h; (e) $Pd(dppf)_2Cl_2$, KOAc, DMSO, 80° C., 18 h; (f) $Pd(Ph_3P)_2Cl_2$, $Na_2CO_3$, $DME/H_2O$, 87° C., 16 h; (g) deprotection (e.g. 4 N HCl, 1,4-dioxane/$CH_2Cl_2$, 40° C., 12 h).

Figure 15:
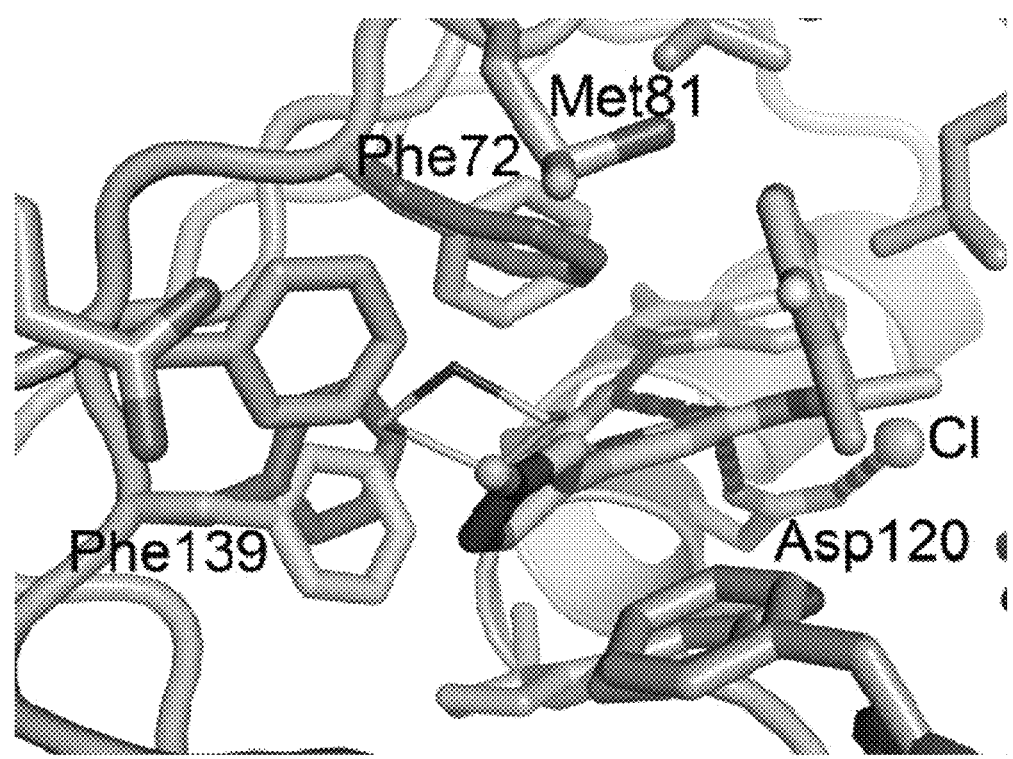

FIG. 15: Cocrystal structure of the (S)-enantiomer of crizotinib bound to human MTH1.

Figure 16:
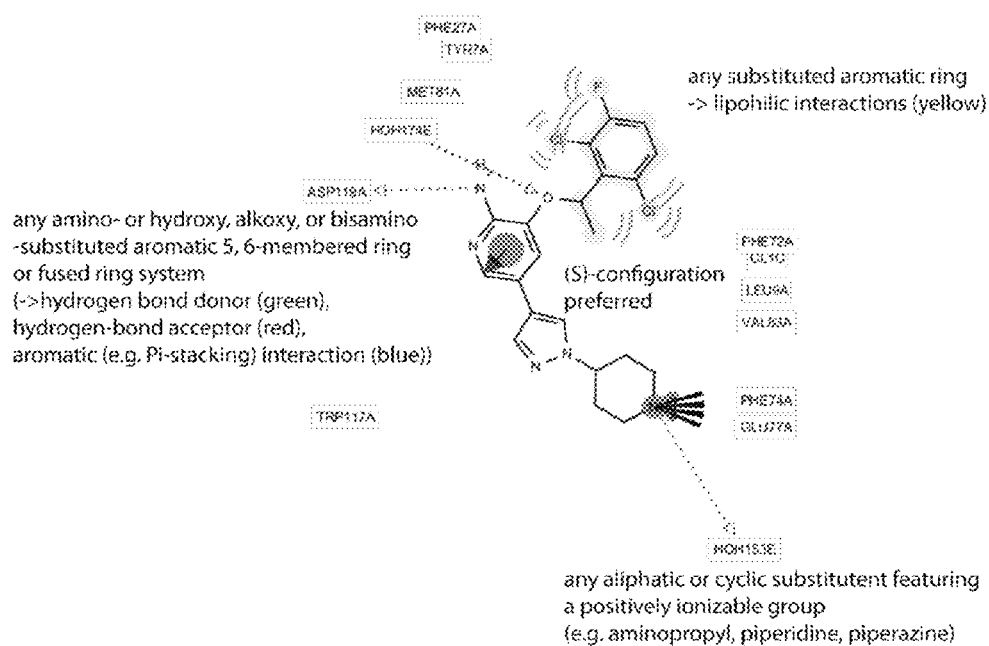

FIG. 16: MTH1 inhibitor pharmacophore showing preferred structural features of aminoheteroaryl-based MTH1 inhibitors.

Figure 17A:
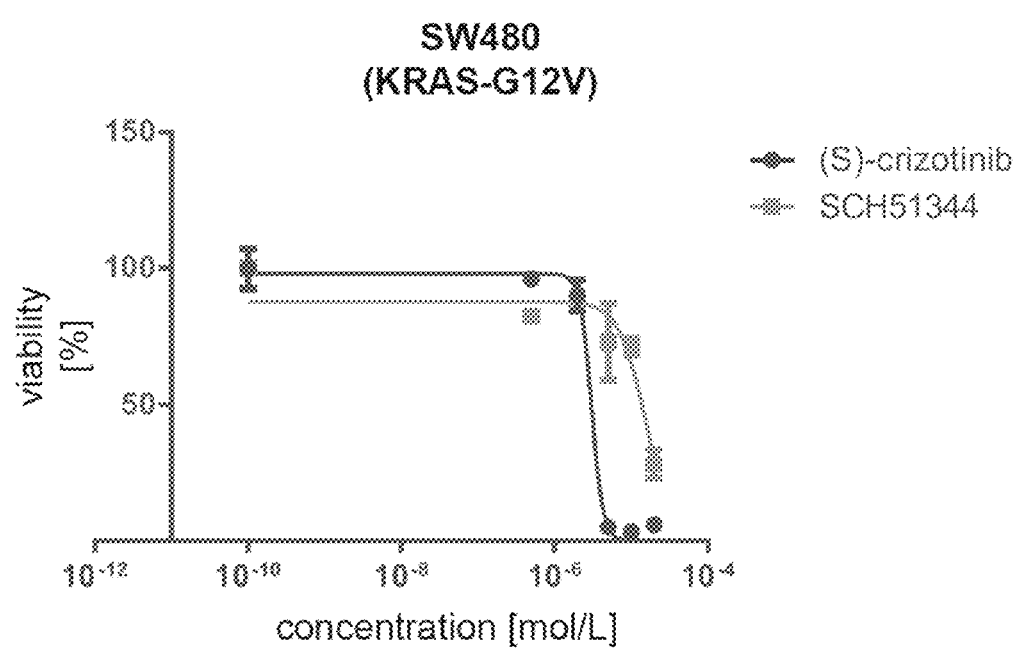
Figure 17C:
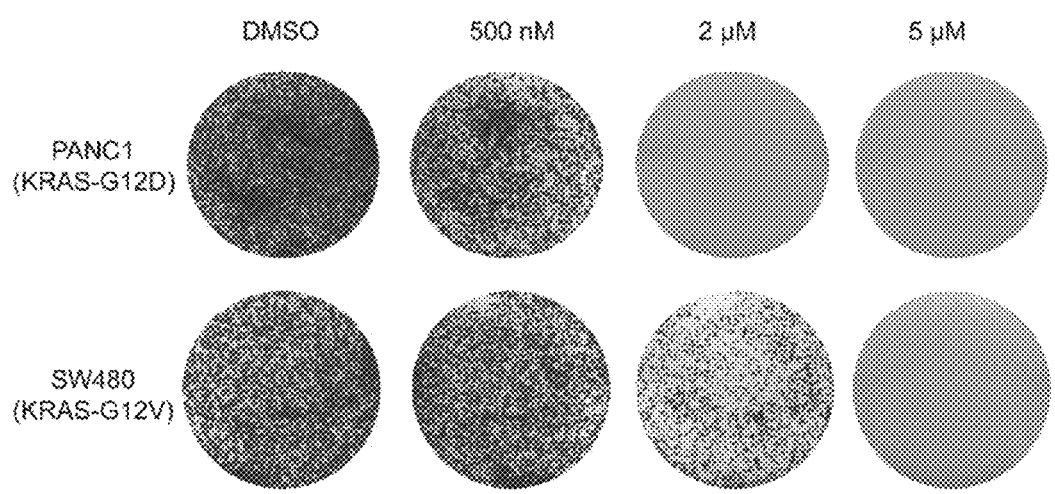

FIGS. 17A-C: A) Comparison of antiproliferative efficacy of the (S)-enantiomer of crizotinib versus SCH51344 against SW480 cells. B) ITC for MTH1 with (R)-crizotinib and the (S)-enantiomer of crizotinib. C) The (S)-enantiomer of crizotinib inhibits colony formation of PANC1 (pancreatic cancer) and SW480 (colon carcinoma) cells.

FIGS. 18A-E: A) Comet assay. Both SCH51344 and the (S)-enantiomer of crizotinib, but not (R)-crizotinib, induce single strand breaks (positive control=$H_2O_2$ (150 µM, 10 min; MTM, mean tail moment.), and B) increase 53BP1 foci in SW480 cells. C) Cocrystal structure of the (S)-enantiomer of crizotinib bound to human MTH1. Hydrogen-bonding interactions are shown by dashed lines. D) MTH1 interactions with (R)-crizotinib and the (S)-enantiomer of crizotinib. Left panel shows (R)-crizotinib; the thinner lines indicate part of the (R)-crizotinib that was not resolved in the electron density. Right panel shows the (S)-enantiomer of crizotinib; alternate protein conformations in the absence of the (S)-enantiomer of crizotinib are shown in darker colour.

E) Results from SW480 mouse xenograft study. Top panel: Effect on tumour growth following 35 days treatment with the MTH1 inhibitor (S)-crizotinib (i.e. the (S)-enantiomer of crizotinib) (25 mg/kg qd, sc daily) (Survival curves significant different, p<0.01 (Mantel-Cox test)). Bottom panel: Effect on tumour growth on termination day (35 days treatment) (data shown as mean±SEM).

Figure 19:
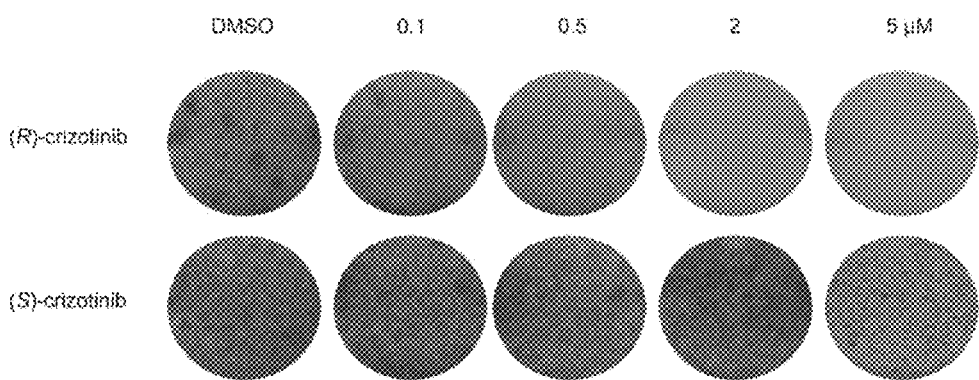

FIG. 19: The (S)-enantiomer of crizotinib does not exhibit any increased unspecific cytotoxicity compared to (R)-crizotinib. In contrast, the (R)-enantiomer significantly impairs the growth of untransformed BJ skin fibroblasts at low micromolar concentrations in a colony formation assay. Compounds were added 24 h after seeding the cells and plates were incubated for 10 days, washed, fixed, and stained with crystal violet. Images are representative for duplicate experiments.

Figure 20:
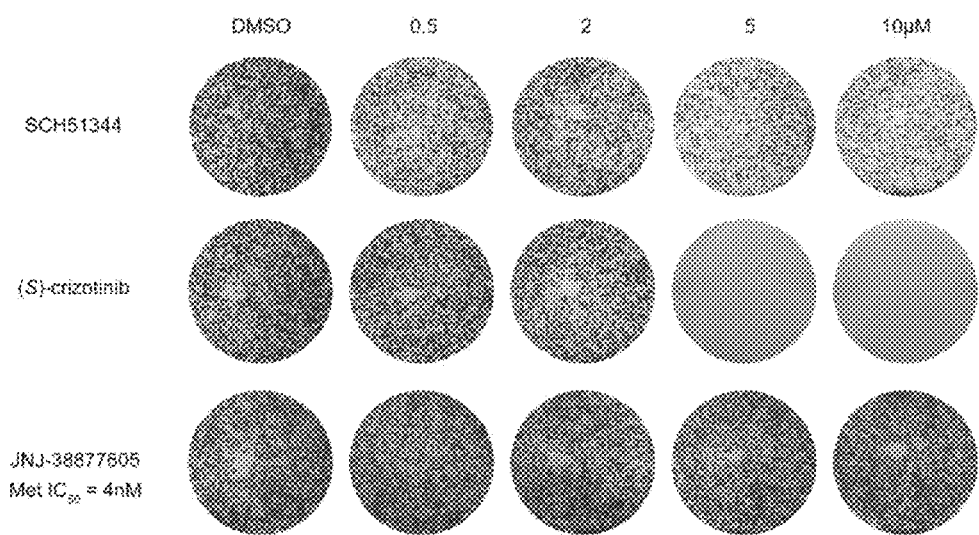

FIG. 20: Pharmacologic c-Met kinase inhibition by a highly potent inhibitor (JNJ-38877605) does not suppress growth of K-Ras-mutated SW480 cells in contrast to the MTH1 inhibitors SCH51344 and the (S)-enantiomer of crizotinib.

FIGS. 21A-B: A) The MTH1 inhibitors SCH51344 and the (S)-enantiomer of crizotinib, but not (R)-crizotinib, increase the number of 53BP1 foci in SW480 cells. B) Similarly, transient knock-down of MTH1 also induces formation of 53BP1 foci in SW480 cells.

FIGS. 22A-B: A) MTH1 crystal structure overview with the (S)-enantiomer of crizotinib. B) As A) with a molecular surface shown covering MTH1 apart from the binding site loops.

FIGS. 23A-B: MTH1 crystal structures with (R)-crizotinib and the (S)-enantiomer of crizotinib showing $2F_o-F_c$ electron density maps contoured at 1σ. A) (R)-Crizotinib B) the (S)-enantiomer of crizotinib.

Figure 24:
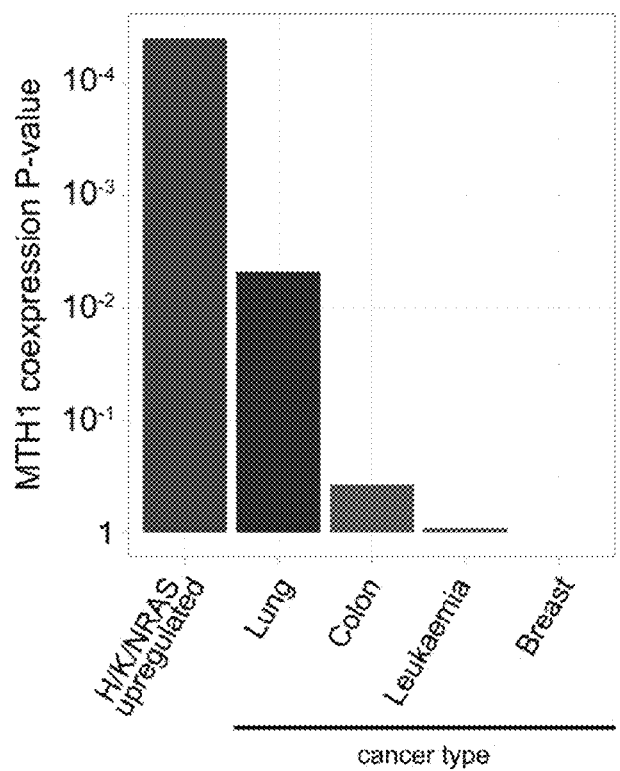

FIG. 24: Meta-analysis of Oncomine data. MTH1 expression strongly correlates with upregulated Ras which is also reflected by the fact that cancers with high prevalence of Ras mutations such as lung and colon carcinoma express higher levels of MTH1 than other unrelated cancer types.

Figure 25:
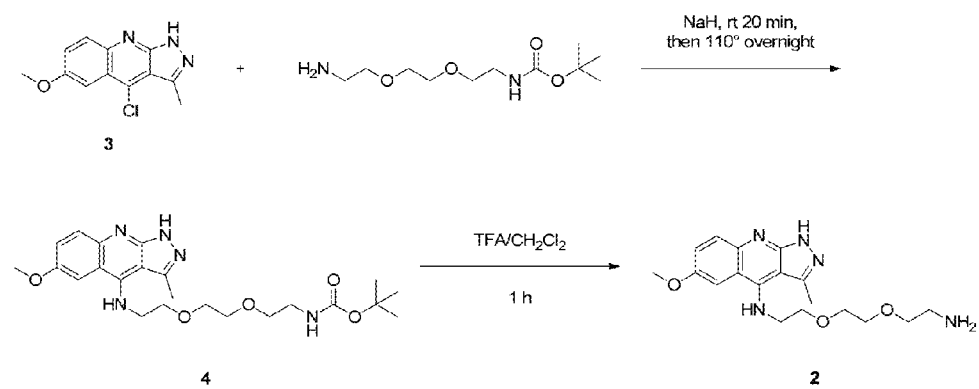

FIG. 25: Synthesis of compound 2. tert-Butyl (2-(2-(2-((6-methoxy-3-methyl-1H-pyrazolo[3,4-b]quinolin-4-yl)amino)ethoxy)ethoxy)ethyl)carbamate (4). According to literature (U.S. Pat. No. 5,608,067A) sodium hydride (3.3 mg, 0.087 mmol, 60% dispersion) was added to N-Boc-2,2'-(ethylenedioxy)diethylamine (723 mg, 2.8 mmol) and the mixture stirred for 20 min at room temperature. Upon addition of 4-chloro-6-methoxy-3-methyl-1H-pyrazolo[3,4-b]quinoline (3) (Yang (2012) Bioorganic & Medicinal Chemistry Letters 22, 235-239) (18 mg, 0.07 mmol) the reaction was heated to 110° C. and stirred overnight. After cooling, water (5 mL) was added followed by extraction with ethyl acetate (3×10 mL). The organic layer was dried over sodium sulphate, filtered, and concentrated in vacuo. Flash column chromatography (dichloromethane/ethanol 10:1) gave a yellowish crystalline solid. Yield: 12.2 mg (37%). $^1$H NMR (400 MHz, DMSO) δ 12.50 (s, 1H), 7.64 (d, J=9.3 Hz, 1H), 7.55 (d, J=2.7 Hz, 1H), 7.30 (dd, J=9.3, 2.7 Hz, 1H), 6.68 (s, 1H), 6.21 (s, 1H), 3.88 (s, 3H), 3.82 (q, J=5.5 Hz, 2H), 3.67 (t, J=5.5 Hz, 2H), 3.55-3.49 (m, 2H), 3.44 (dd, J=5.9, 3.5 Hz, 2H), 3.35-3.29 (m, 2H), 3.01 (q, J=11.9, 6.0 Hz, 2H), 2.70 (s, 3H), 1.35 (s, 9H); MS ESI m/z (relative intensity, %) 360 [M$^+$+H] (100).

N-(2-(2-(2-Aminoethoxy)ethoxy)ethyl)-6-methoxy-3-methyl-1H-pyrazolo[3,4-b]quinolin-4-amine (2). Trifluoroacetic acid (40 μL) was added to a solution of compound 4 (8 mg, y mmol) in dichloromethane (4 mL) and the mixture was stirred at room temperature for 45 min. After removal of solvents, the crude product was purified by MPLC (dichloro-methane/methanol 9:1) to give a yellow wax-like solid. Yield: 3 mg (48%). $^1$H NMR (400 MHz, DMSO) δ 12.53 (s, 1H), 7.65 (d, J=9.3 Hz, 1H), 7.57 (d, J=2.7 Hz, 1H), 7.31 (dd, J=9.3, 2.7 Hz, 1H), 6.25 (s, 2H), 3.89 (s, 3H), 3.83 (t, J=5.6 Hz, 2H), 3.68 (t, J=5.5 Hz, 2H), 3.61-3.37 (m, 7H), 2.83 (t, J=5.3 Hz, 2H), 2.70 (s, 3H); MS ESI m/z (relative intensity, %) 460 [M$^{+.}$+H] (97), 404 (100), 360 (47).

FIG. 26: Stable knockdown of MTH1 impairs colony formation of SW480 cells. Stable knockdown of MTH1 significantly reduced colony formation of SW480 cells.

Figure 27:
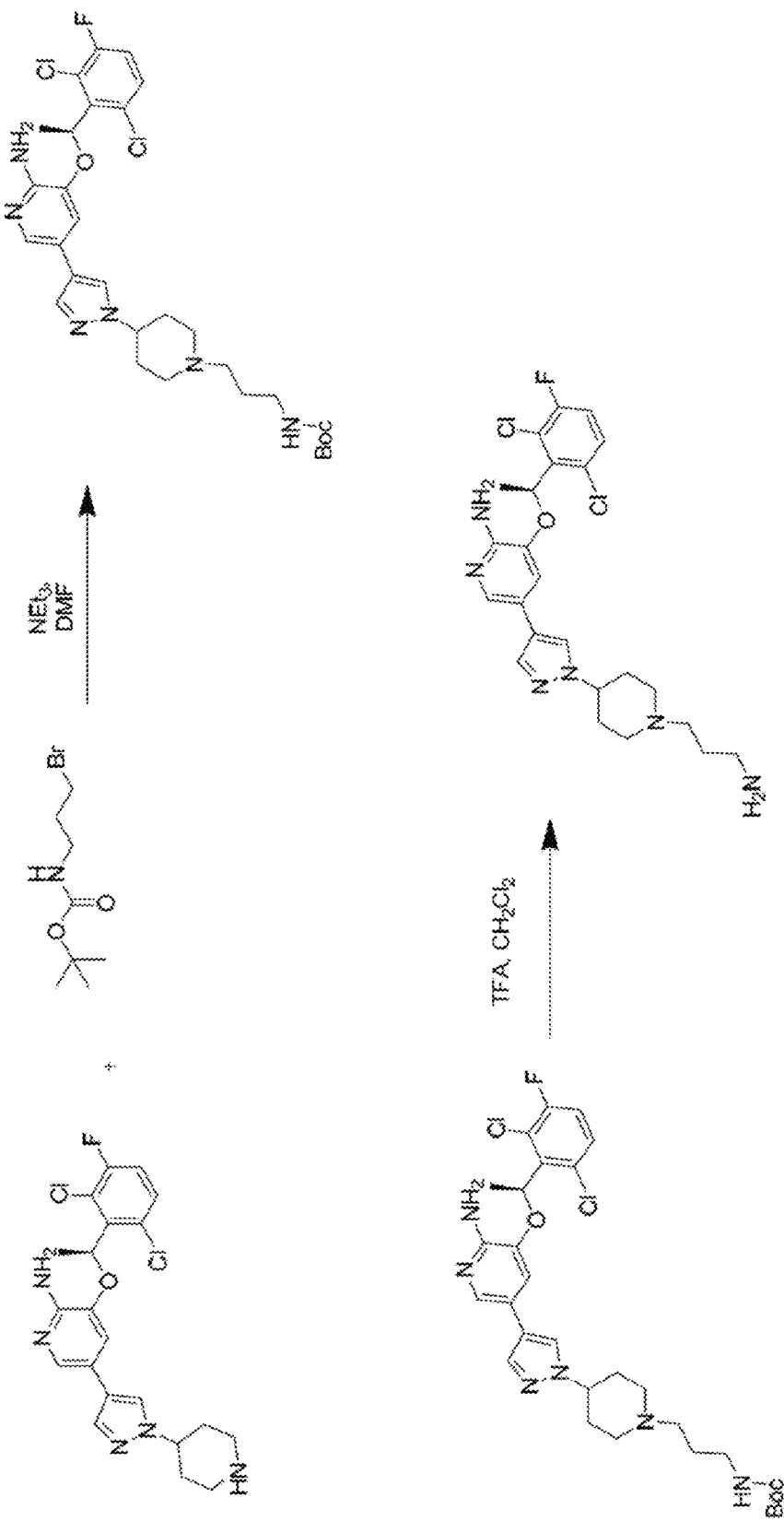

FIG. 27: Derivatisation of (S)-3-(1-(2,6-dichloro-3-fluorophenyl)ethoxy)-5-(1-(piperidin-4-yl)-1H-pyrazol-3-yl)pyridin-2-amine to yield (5)-5-(1-(1-(3-aminopropyl)piperidin-4-yl)-1H-pyrazol-3-yl)-3-(1-(2,6-dichloro-3-fluorophenyl)ethoxy)pyridin-2-amine The Figure shows (S)-tert-butyl (3-(4-(3-(6-amino-5-(1-(2,6-dichloro-3-fluorophenyl)ethoxy)pyridin-3-yl)-1H-pyrazol-1-yl)piperidin-1-yl)propyl)carbamate. 1H NMR (400 MHz, CDCl3) δ 7.74 (d, J=1.7 Hz, 1H), 7.58-7.46 (m, 2H), 7.30 (dd, J=8.9, 4.8 Hz, 1H), 7.04 (dd, J=8.9, 7.9 Hz, 1H), 6.87 (d, J=1.7 Hz, 1H), 6.07 (q, J=6.7 Hz, 1H), 4.78 (s, 2H), 4.18-4.02 (m, 1H), 3.48 (s, 1H), 3.20 (d, J=6.0 Hz, 2H), 3.05 (d, J=11.8 Hz, 2H), 2.47 (t, J=6.7 Hz, 2H), 2.27-1.95 (m, 6H), 1.85 (d, J=6.7 Hz, 3H), 1.75-1.62 (m, 2H), 1.44 (s, 9H); ESI-MS: 607 (M+H).

The Figure further shows (S)-5-(1-(1-(3-aminopropyl)piperidin-4-yl)-1H-pyrazol-3-yl)-3-(1-(2,6-dichloro-3-fluorophenyl)ethoxy)pyridin-2-amine. 1H NMR (400 MHz, CDCl3) δ 7.76 (d, J=1.5 Hz, 1H), 7.61-7.46 (m, 2H), 7.30 (dd, J=8.9, 4.8 Hz, 1H), 7.04 (dd, J=8.9, 7.9 Hz, 1H), 6.87 (d, J=1.6 Hz, 1H), 6.07 (q, J=6.7 Hz, 1H), 4.76 (s, 2H), 4.20-4.01 (m, 1H), 3.07 (d, J=11.7 Hz, 2H), 2.81 (t, J=6.5 Hz, 2H), 2.47 (t, J=7.1 Hz, 2H), 2.23-1.94 (m, 6H), 1.85 (d, J=6.7 Hz, 3H), 1.80 (s, 2H), 1.73-1.63 (m, 2H). ESI-MS: 507 (M+H).

Figure 28:
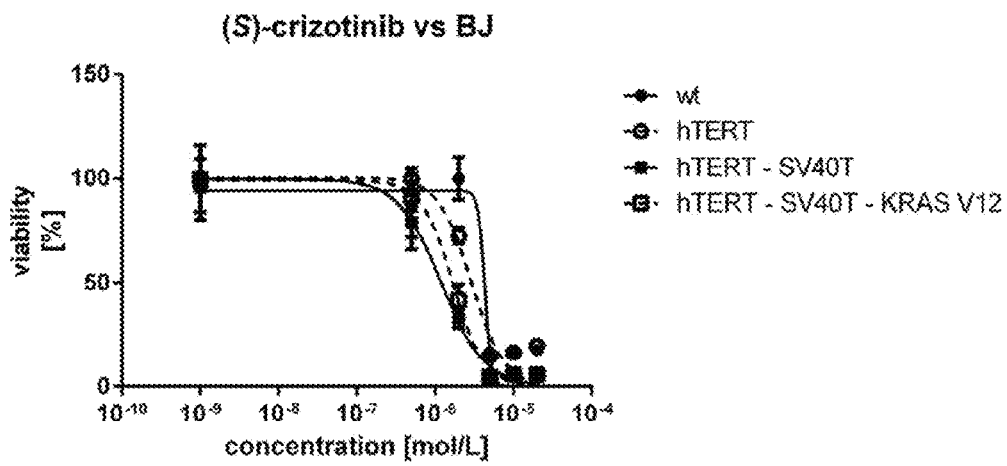

FIG. 28: Anti-cancer specificity. Various isogenic BJ fibroblast cell lines were treated with several concentrations of the (S)-enantiomer of crizotinib in colony formation assays. As indicated, the investigated cell line panel comprised non-transformed ("wildtype") cells, cells immortalized with telomerase (hTERT), cells transformed with hTERT and SV40 Large T antigen (SV40T), and cells transformed with hTERT, SV40T, and the KRAS mutant V12.

Figure 29:
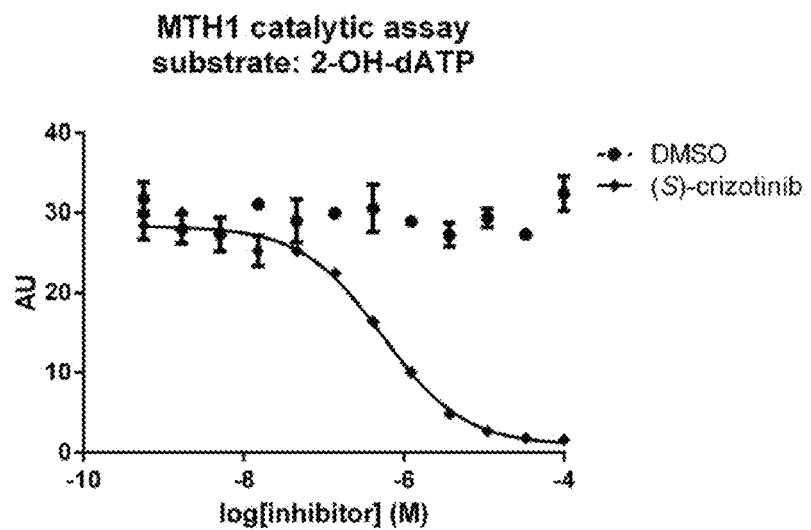

FIG. 29: Inhibition of MTH1-catalytic activity by the (S)-enantiomer of crizotinib is not substrate-dependent. The Figure shows that the (S)-enantiomer of crizotinib also inhibits hydrolysis 2-OH-dATP by MTH1 in a dose-dependent manner.

Figure 30:
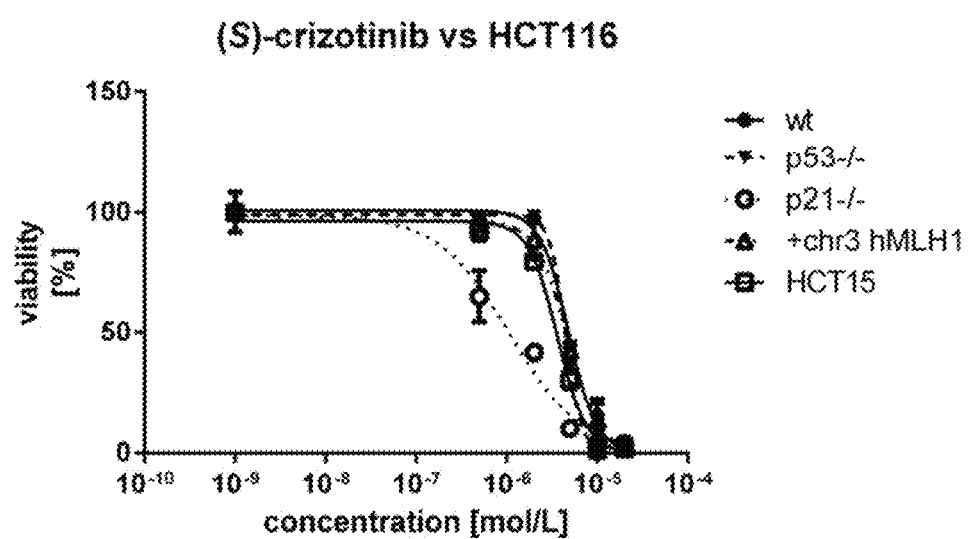

FIG. 30: Effect of p53-/p21-status and mismatch repair pathways on the activity of the (S)-enantiomer of crizotinib. The Figure shows that p53 status and presence or absence of functional MLH1 do not affect the activity of the (S)-enantiomer of crizotinib. However, loss of p21 seems to increase the sensitivity of HCT116 cells toward treatment with the (S)-enantiomer of crizotinib.

Figure 31B:
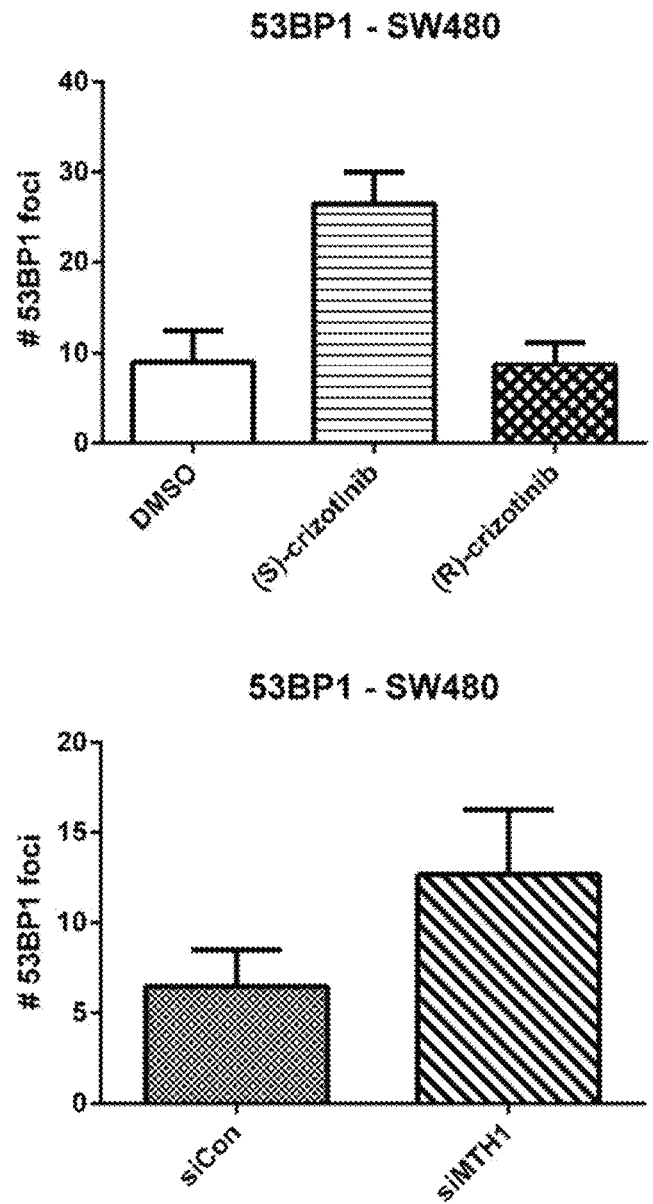

FIGS. 31A-B: MTH1 enzymatic function increases the content of 8-oxo-guanine in DNA. A) and B) Treatment of BJ fibroblasts with (S)-, but not (R)-crizotinib, increased staining of an anti-8-oxo-guanine mouse monoclonal antibody. At the same time, staining for 53BP1, a specific marker for DNA damage, is increased, which is in line with the effect observed for anti-MTH1 siRNA.

Figure 32:
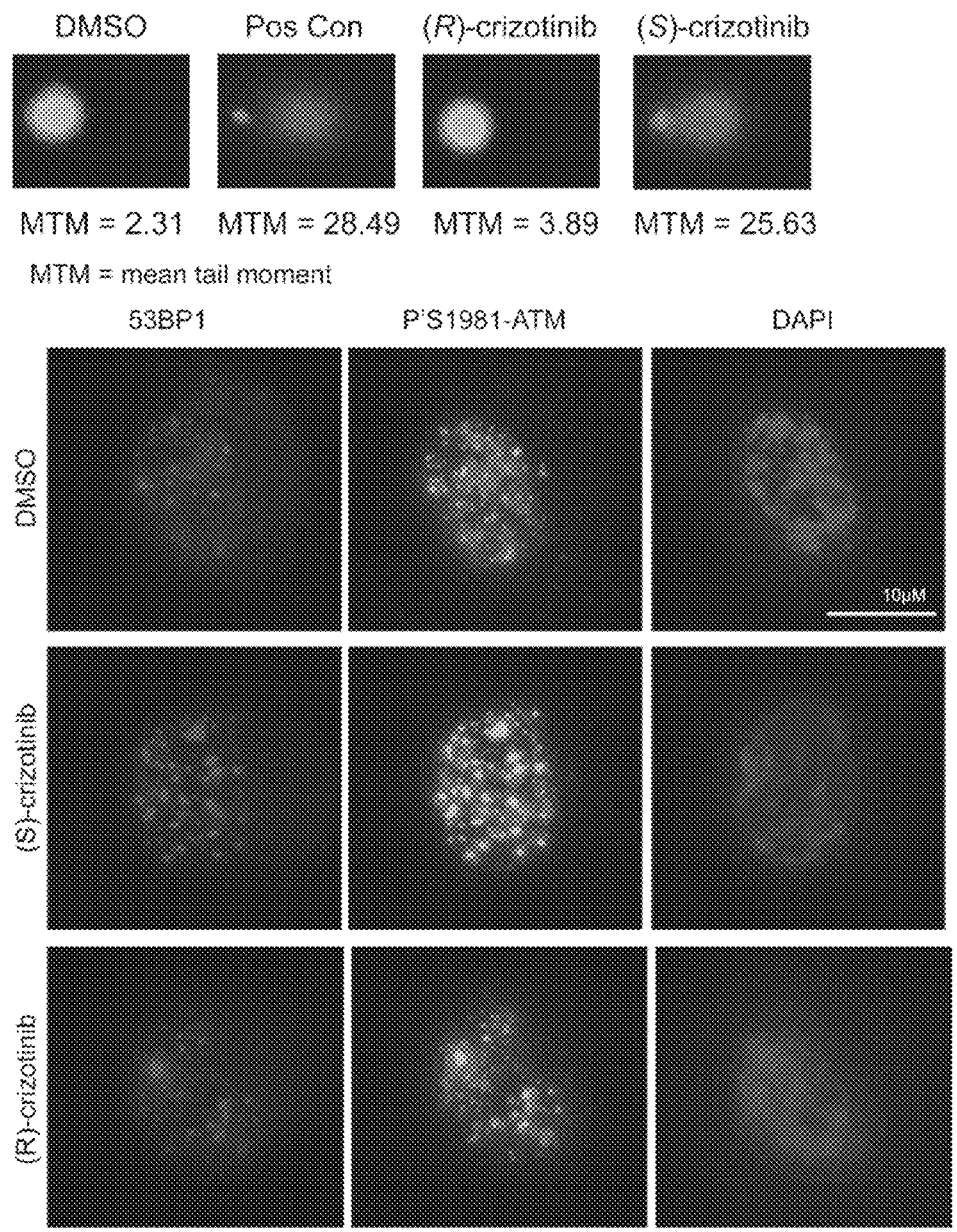

FIG. 32: The (S)-enantiomer of crizotinib activates DNA repair mechanisms and induces the formation of single strand breaks due to activated base excision repair (BER).

The (S)-enantiomer of crizotinib has been investigated in an alkaline comet assay, which reveals DNA single strand breaks by single cell electrophoresis. Using SW480 cells it was found that both (S)-crizotinib, but not (R)-crizotinib, yields a significant tail moment in the comet assay. Also an increase of ATM phosphorylation was observed indicating DNA damage pathway activation, again demonstrating an (S)-crizotinib-specific effect.

The following non-limiting examples illustrate the invention:

Materials and Methods:

General Information. NMR spectra were recorded on a Bruker Avance III 400 (Bruker, Billerica, Mass., U.S). Chemical shifts are given in ppm, and coupling constants are given in hertz. Mass spectra were recorded using a XeVo-UPLC-TQ-MS system (Waters, Milford, Mass., U.S.). Purification by flash column chromatography (FCC) was done using silica gel 60 (Merck, Darmstadt, Germany), MPLC was performed on a Biotage Isolera system (Biotage, Uppsala, Sweden). The purity of the synthesized compounds was determined and confirmed by UPLC analysis.

All synthesis chemicals were purchased from Sigma-Aldrich and Santa Cruz and used without further purification.

Chemicals. All chemicals were purchased from Sigma Aldrich or Fluka (Sigma Aldrich Austria) and used without further purification. Racemic (RS)-crizotinib and JNJ-38877605 were obtained from Selleck Chemicals (Selleck Chemicals LLC, Houston, Tex., USA), (R)-crizotinib was purchased from Selleck Chemicals, Tocris (Tocris Bioscience, Bristol, UK), and ChemieTek (ChemieTek, Indianapolis, Ind., USA). The (S)-enantiomer of crizotinib was obtained from ChemFuture (ChemFuture PharmaTech Ltd, Jiangsu, China). SCH51344 was purchased from Calbiochem (EMD Millipore, Billerica, Mass., USA). Synthesis of compound 2 is shown in FIG. 25.

Immobilization and Affinity Purification. Drug-affinity matrices were prepared essentially as described previously (Rix (2007) Blood 110, 4055-4063). Briefly, 25 nmol of compound was immobilised on 50 µL NHS-activated Sepharose 4 Fast Flow beads (GE Healthcare Bio-Sciences AB, Uppsala, Sweden). Affinity chromatography and elution were performed in duplicate as reported previously, (Fernbach (2009) Journal of Proteome Research 8, 4753-4765) using 10 mg total cell lysate as protein input per replicate.

Solution Tryptic Digestion and Peptide Purification. After elution, enriched proteins were reduced with dithiothreitol, cysteine residues alkylated by incubation with iodoacetamide and the samples digested with modified porcine trypsin (Promega, Madison, Wis.). Three percent (and multiples thereof) of the digested eluates were purified and concentrated by C18 reversed-phase material for subsequent duplicate analysis by gel-free one-dimensional liquid chromatography mass spectrometry (1D-LCMS). Details of the LCMS methodology are as previously described (Maurer (2012) Journal of Proteome Research 12, 1040-1048).

Protein Identification. Peak extraction and conversion of RAW files into the MGF format for subsequent protein identification was performed with msconvert (ProteoWizard Library v2.1.2708). An initial database search was performed with broader mass tolerance to re-calibrate the mass lists for optimal final protein identification. For the initial protein database search, Mascot (www.matrixscience.com, version 2.3.02) was used. Error tolerances on the precursor and fragment ions were ±10 ppm and ±0.6 Da, respectively, and the database search limited to fully-tryptic peptides with maximum 1 missed cleavage, carbamidomethyl cysteine and methionine oxidation set as fixed and variable modifications, respectively. The Mascot peptide ion score threshold was set to 30, and at least 3 peptide identifications per protein were required. Searches were performed against the human UniProtKB/SwissProt database (www.uniprot.org release 2012-05) including all protein isoforms.

The initial peptide identifications were used to deduce independent linear transformations for precursor and fragment masses that would minimize the mean square deviation of measured masses from theoretical. Re-calibrated mass list files were searched against the same human protein database by a combination of Mascot and Phenyx (GeneBio, SA, version 2.5.14) search engines using narrower mass tolerances (±4 ppm and ±0.3 Da). One missed tryptic cleavage site was allowed. Carbamidomethyl cysteine was set as a fixed modification and oxidized methionine was set as a variable modification. To validate the proteins, Mascot and Phenyx output files were processed by internally-developed parsers. Proteins with >2 unique peptides above a score $T_1$, or with a single peptide above a score $T_2$ were selected as unambiguous identifications. Additional peptides for these validated proteins with score >$T_3$ were also accepted. For Mascot searches, the following thresholds were used: $T_1=14$, $T_2=40$ and $T_3=10$; Phenyx thresholds were set to 4.2, 4.75 and 3.5, respectively (P-value<$10^{-3}$). The validated proteins retrieved by the two algorithms were merged, any spectral conflicts discarded and grouped according to shared peptides. A false discovery rate (FDR) of <1% for protein identifications and <0.1% for peptides (including the ones exported with lower scores) was determined by applying the same procedure against a database of reversed protein sequences.

Bioinformatic Analysis. Non-specific binders were filtered from the drug pull-downs using the SAINT software (version 2.3.4) (Choi (2011) Nat Meth 8, 70-73). Using protein spectral counts as a measure of protein abundance and comparing the data of a real pull-down versus the negative control experiments, SAINT calculates the probability of a prey protein to be a real bait interactor.

The SAINT probability cut-off threshold was set to 0.99 as TUBA1B and RPS3A, known contaminants observed in more than thousand MS experiments at our institution, had probability of 0.9993 and 0.9882, respectively.

Expression and Purification of MTH1 for Crystallization. The expression construct was transformed into E. coli BL21 (DE3) competent cells containing the pRARE2 plasmid from commercial Rosetta cells. Colonies from the transformation were used to inoculate 100 mL of LB media containing 34 µg/ml chloramphenicol and 50 µg/ml kanamycin. The culture was grown overnight in a baffled shaker flask at 37° C. with shaking. This culture was used to inoculate LB media by adding 10 ml of culture to 1 L of LB (containing 50 µg/ml kanamycin) in baffled shaker flasks. When the culture had an OD600 of approximately 0.6 the temperature was reduced to 18° C. and protein expression was induced by addition of isopropyl β-D-1-thiogalactopyranoside to 0.5 mM. The culture was left shaking at 18° C. overnight before the cell pellets were harvested by centrifugation. The cells were resuspended in Binding Buffer (20 mM Imidazole, 500 mM NaCl, 50 mM Hepes pH 7.4, 5% Glycerol) with the addition of 0.5 mM tris(2-carboxyethyl)phosphine (TCEP) and 0.2 mM phenylmethanesulphonyl fluoride (PMSF). The resuspended cells were stored at −20° C. The resuspended cells were thawed and lysed by sonication. Polyethyleneimine was added to a concentration of 0.15% and the lysate was centrifuged at 4° C. to remove insoluble material. The supernatant was loaded onto 7.5 ml of nickel-chelating resin. The resin was washed with Binding Buffer, and Binding Buffer containing 40 mM imidazole and then 60 mM imidazole. The protein was eluted with Binding Buffer containing 250 mM imidazole. The hexahistidine tag was removed by overnight treatment with TEV protease at 4° C. The digested sample was concentrated to 5 ml volume and loaded onto a Superdex200 gel filtration column (HiLoad 16/60, GE Healthcare) pre-equilibrated in GF Buffer (50 mM Hepes pH 7.5, 300 mM NaCl, 0.5 mM TCEP). Fractions containing MTH1 were pooled and passed through a column of 2.5 ml nickel-chelating resin. The flow-through and an elution with GF Buffer containing 10 mM imidazole were combined. The protein identity was verified by electrospray ionization time-of-flight mass spectrometry (Agilent LC/MSD).

The MTH1 complexes were prepared by adding (R)-crizotinib or the (S)-enantiomer of crizotinib to dilute protein solution at an approximate molar ratio of 10:1. The MTH1:crizotinib complexes were concentrated together by ultrafiltration to a protein concentration of 20 mg/ml.

Crystallization and Data Collection. MTH1 complexes were crystallised by the sitting drop vapour diffusion method using 150 nL drops as detailed in Table 3. All crystals were cryo-protected in reservoir solution with the addition of 25% (v/v) ethylene glycol and flash-frozen in liquid nitrogen. X-ray diffraction data was collected at 100 K at the DIAMOND synchrotron.

Structure Determination and Refinement. The diffraction images were processed using MOSFLM (Leslie in Evolving Methods for Macromolecular Crystallography Vol. 245 NATO Science Series; eds RandyJ Read & JoelL Sussman; Ch. 4, 41-51; Springer Netherlands, 2007). The integrated data were scaled and merged using AIMLESS (Evans (2006) Acta Crystallographica Section D 62, 72-82) and the CCP4 suite of programs (Winn (2011) Acta Crystallographica Section D 67, 235-242). The structures were solved by molecular replacement using PHASER (McCoy (2007) J. Appl. Crystallogr. 40, 658-674). All structural models were built using COOT (Emsley (2010) Acta Crystallographica Section D 66, 486-501) and refined using REFMACS (Murshudov (2011) Acta Crystallographica Section D 67, 355-367). Ligand restraints were generated with PRODRG (Schuttelkopf (2004) Acta Crystallographica Section D 60, 1355-1363). Molprobity (Chen (2010) Acta Crystallographica Section D 66, 12-21) was used for structure validation. Data collection and refinement statistics can be seen in Table 4.

Cell Culture and Immunoblotting. BJ cells were obtained from ATCC. SW480 and DLD1 were kindly provided by Walter Berger, PANC1 were a generous gift from Rudolf Oehler. All other cell lines were obtained from the American Type Culture Collection (ATCC) or Leibniz-Institut DSMZ-Deutsche Sammlung von Mikroorganismen and Zellkulturen GmbH (DSMZ). SW480, PANC1 and BJ cells were cultivated in DMEM, DLD1 in RPMI. All media contained 10% fetal bovine serum (FBS) and 10 U/mL penicillin/streptomycin (Gibco). MCF-7 were cultivated in DMEM containing 10% FBS, 10 U/mL penicillin/streptomycin, and 0.01 mg/ml bovine insulin. MDA-MB-231 were grown in Leibovitz's L-15 containing 10% FBS and 10 U/mL penicillin/streptomycin. Antibodies. Anti-ALK antibody was obtained from Cell Signaling Technology, anti-MTH1 was purchased from Novus (Novus Biologicals, Littleton, Colo., USA). The following antibodies were used according to manufacturer's instructions: rabbit anti-MTH1 (NB100-109, Novus Biologicals), rabbit anti-actin (AAN01, Cytoskeleton), rabbit anti-ALK (C26G7, Cell Signaling Technology, and 513900, Invitrogen, Life Technologies).

Expression of Recombinant MTH1. Codon-optimised human MTH1 cDNA subloned into a pETM-11 vector (Gunther Stier, EMBL) featuring a His-tag and TEV site was obtained from GenScript (GenScript, NJ, USA) and expressed in the *E. coli* strain BL21 DE3 (Life Technologies). After harvesting, bacteria were lysed using buffer (50 mM Tris-HCl pH 7.5, 500 mM NaCl, 5% glycerol, 5 mM/β-mercaptoethanol, 1 mM PMSF) containing lysozyme (Sigma-Aldrich) and DNase I (Roche). His-tagged protein was purified with NiNTA agarose (Qiagen), washed with buffer, and eluted with an imidazole gradient. Following removal of the His-tag by incubation with TEV protease, fractions were dialysed and purified using size-exclusion chromatography (Sephadex, GE Healthcare). Protein concentration of the purified fractions was determined by UV ($A_{280}$). The identity of the protein was confirmed by MALDI-TOF and protein activity determined by $K_m$ measurement which gave values in accordance with literature data (Svensson (2011) FEBS Letters 585, 2617-2621).

Chemical Proteomics Experiments. Drug pull-down experiments were essentially carried out as described previously using 10 mg total lysate protein per replicate. For competition experiments, the lysate was preincubated with unmodified, genuine crizotinib (final concentration 20 µM) for 30 minutes. Pull-down eluates were digested with trypsin, labeled with iTRAQ reagent, fractionated by LC, and analysed on an OrbiTrap Velos mass spectrometer. Peak list information was extracted from the acquired MS data and searched against the human SwissProt database version v2010.09_20100812 (including isoforms as obtained from varsplic.p1) with the search engines MASCOT (v2.3.02, MatrixScience, London, UK) and Phenyx (v2.5.14, GenBio, Geneva, Switzerland).[20] Details of the protein database search criteria are given elsewhere.[21] Analysis of quantitative proteomics data was performed with the R/Bioconductor package isobar.[22]

MTH1 Assay. cDNA encoding human MTH1 (NUDT1) and optimized for expression in *E. coli* was purchased from Genscript. His-tagged MTH1 was expressed from pETM-11 in *E. coli* BL-21(DE3) (Stratagene). The bacteria were harvested, lysed and His tagged MTH1 was purified using Ni-NTA agarose (Qiagen). The His-tag was removed by TEV cleavage and the MTH1 protein further purified using anion exchange chromatography at pH 7.5 using a Sephadex column (GE Healthcare). The identity and purity of the protein was confirmed using mass spectrometry. The activity of MTH1 was monitored using 8-oxo-dGTP (TriLink Biotechnologies) using the PPiLight Inorganic Pyrophosphate Assay (Lonza Rockland Inc.). IC50 values were determined using non-linear regression analysis utilizing GraphPad Prism Software.

More specifically, the MTH1 catalytic assay was performed as follows. Half-maximal inhibitory concentrations ($IC_{50}$) were determined using a luminescence-based assay as described previously (Svensson (2011) FEBS Letters 585, 2617-2621) with some minor modifications. Briefly, serial dilutions of compounds were dissolved in assay buffer (100 mM Tris-acetate pH 8.0, 40 mM NaCl and 10 mM $Mg(OAc)_2$ containing 0.005% Tween-20 and 2 mM dithiothreitol (DTT). Upon addition of MTH1 recombinant protein (final concentration 2 nM), plates were incubated on a plate shaker for 15 min at room temperature. After addition of 8-oxo-dGTP (TriLink Biotechnologies, final concentration 16 µM) the generation of pyrophosphate (PPi) as a result of 8-oxo-dGTP hydrolysis by MTH1 was monitored over a time course of 15 min using the PPiLight Inorganic Pyrophosphate Assay kit (Lonza Rockland). $IC_{50}$ values were determined by fitting a dose response curve to the data points using non-linear regression analysis utilizing the GraphPad Prism software.

siRNA Experiments. Both a commercial anti-MTH1 siRNA set (SMARTpool ON-TARGETplus, Dharmacon) as well as a custom-synthesised siRNA (Sigma-Aldrich) were obtained. The custom siRNA sequence was CGACGACAGCUACUGGUUU, AllStars Negative Control siRNA (Qiagen) was used as control. For transfections, cells were seeded in 24-well plates at approximately 30% confluency 24 h prior to siRNA treatment. The next day, medium was aspirated and transfections were performed with INTERFERin (Polyplus) according to manufacturer's instructions using a final siRNA concentration of 10 nM. Cells were incubated for 2-3 days, washed, detached with trypsin and replated in 6-well plates. After 7-10 days, medium was aspirated, cells were washed with PBS, fixed with ice-cold methanol, stained with crystal violet solution (0.5% in 25% methanol) and left to dry overnight. For quantification of results, UV absorbance of crystal violet was determined at 595 nm after solubilisation by 70% ethanol. Data were analysed using the GraphPad Prism software (t test, P<0.05).

Colony Formation Assay Using SW480 Cells. One day before treatment, $10^4$ cells were seeded per well in 6-well plates and incubated for 24 h. The next day DMSO (equal to highest amount of compound dilution, maximum 0.2%) or compounds in increasing concentrations were added and cells incubated at 37° C., 5% CO2, for 7-10 days. After washing with PBS (Gibco), cells were fixed with ice-cold methanol, stained with crystal violet solution (0.5% in 25% methanol) and left to dry overnight. For quantification of results, UV absorbance of crystal violet was determined at 595 nm after solubilisation by 70% ethanol. Data were analysed using non-linear regression analysis utilizing the GraphPad Prism software. (This colony formation assay has also been performed by using MCF 7 and MDA-MB-231 cells leading to comparable results as shown in FIG. 12.)

Colony Formation Assay Using MCF 7 and MDA-MB-231 Cells. 1000 cells per well were seeded in 2 mL complete medium (day 0). Drugs or DMSO (mock) were added 24 h later (day 1) with renewal of medium and drugs on day 15 and day 21. Four weeks after plating cells were fixed with methanol followed by staining with crystal violet.

Comet Assay. Cells were treated with compounds for 6 days, upon which DNA single-strand breaks were assayed using the comet assay under alkali conditions. For the $H_2O_2$ control, cells were treated with $H_2O_2$ (Sigma-Aldrich) in PBS at 150 µM for 10 minutes. Cells were washed twice with PBS, harvested using a rubber scraper, pelleted by centrifugation, resuspended in PBS and mixed with 1% low-gelling-temperature agarose (Sigma type VII) that was maintained at 37° C. The mixture of cells and agarose was layered onto frosted glass slides pre-coated with 0.5% agarose and slides were placed on ice to gel. Slides were maintained in the dark for all subsequent steps. Slides were immersed in pre-chilled lysis buffer (2.5 M NaCl, 0.1 M EDTA, 10 mM Tris-HCl pH 7.70, 1% Triton X-100, 1% DMSO) for 1 hour, washed in pre-chilled distilled water 3 times for 20 minutes and incubated for 45 minutes in pre-chilled alkaline electrophoresis buffer (50 mM NaOH, 1 mM EDTA, 1% DMSO, pH 12.8). After electrophoresis for 25 minutes at 25 volts, slides were placed at 4° C. overnight, in the dark. The following day, slides were neutralized with 0.4 M Tris-HCl pH 7.0 for 1 hour and stained with SYBR Gold (Invitrogen, diluted 1:10,000 in distilled water) for 30 minutes. Comet tail moments (defined as the average distance migrated by the DNA multiplied by the fraction of DNA in the comet tail) were scored using the CellProfiler cell image analysis software.

Indirect Immunofluorescence. Cells were treated with compounds for 6 days, following which they were adhered to glass coverslips, washed with PBS and then fixed with 3% paraformaldehyde in PBS for 20 minutes. Fixed cells were rinsed with PBS and permebealised with 0.5% Triton-X-100 for 5 minutes. PBS washed slides were incubated for 1 hour with 10% FCS and 0.1% Triton-X-100 in PBS following which cells were stained with an anti-53BP1 monoclonal antibody (H-300, Santa Cruz, diluted 1:600), in 10% FCS and 0.1% Triton-X-100 in PBS. After rinsing with PBS coverslips were incubated with an Alexa Fluor® 568 goat anti-rabbit IgG secondary antibody for 1 hour (Invitrogen, diluted 1:400) in 10% FCS and 0.1% Triton-X-100 in PBS. After a PBS wash, DNA was counterstained with DAPI (Sigma-Aldrich) for 10 minutes and the coverslips were mounted in Fluorescent Mounting Medium (Dako). Images were analysed with a Zeiss fluorescent microscope at 63 times magnification with supporting software.

Xenograft Study. SCID mice (female, 5-6 weeks, Scanbur, Germany) were s.c. injected with $1 \times 10^6$ SW480 cells together with a matrix gel (1:1) in the sacral area. Treatment was initiated one day after cell inoculation. Vehicle or MTH1 inhibitor was administered subcutaneously once daily at 25 mg/kg for 35 days. MTH1 inhibitor was diluted in 1% DMSO, 10% ethanol, 10% cremaphore, 10% Tween 80, 69% PBS. Tumour size was measured twice weekly and body weight once weekly. At termination, a gross postmortem inspection was performed; blood was collected for haematological parameters and ASAT, ALAT, creatinine measurements and tumours collected in paraformaldehyde (4%) and later paraffin inbedded for immunohistology analysis. All experiments involving animals followed protocols approved by Stockholms Norra djurfOrsoksetiska namnd (laboratory animal ethical committee Stockholm). All animals were acclimatised for one week, and had free access to water and food during the experiment. Animals were under a 12-hour lightcycle, and temperature and humidity according to laboratory animal guidelines and regulations.

8-oxo-quanine Staining. 5000 BJ cells were seeded per well in a 24-well plate and after 24 h treated with compounds or DMSO as indicated. Cells were fixed 72 h later and stained with the respective antibody (anti-oxoguanine 8 antibody [2Q2311] (ab64548), abcam).

EXPERIMENTS AND RESULTS

Example 1

Immobilization of Crizotinib and Derivatives of Crizotinib and their Binding to ALK To examine crizotinib's cellular interactors a direct chemical proteomics approach has been pursued in which the compound of interest is immobilized on sepharose beads (FIG. 1, "Compound-centred chemical proteomics").[8] The immobilization is achieved by a chemical reaction which establishes a covalent bond between the compound and the bead matrix. Therefore the compound requires an adequate reactive functional group for the reaction to take place which is why in many cases enforces chemical modification of the original compound. Of course, changing the molecular structure can alter the interaction behavior and target spectrum of the compound to be investigated. It should be noted that also the location within the molecule where the compound is immobilized can affect binding. Thus, a common practice is to check and confirm binding of already known targets for all coupleable derivatives. Three derivatives of crizotinib have been prepared with different chemical linkers covering various linker lengths and chemical nature in terms of hydrophobicity (FIG. 2).

Crizotinib has a chiral centre at the carbon to which the methyl (CH3) group is attached. Therefore there are two enantiomers of crizotinib, i.e. (R)-crizotinib and the (S)-enantiomer of crizotinib (FIG. 3). Clinically, only (R)-crizotinib is used as this enantiomer has been shown to be considerably more potent than the (S)-enantiomer in inhibiting c-Met kinase activity (c-Met Ki (R)=0.002 µM, Ki (S)=0.161 µM).[9] In fact, crizotinib was actually developed as a specific c-Met kinase inhibitor. To assess the complete interactome considering both enantiomers, racemic crizotinib (a 1:1 mixture of (R)- and (S)-enantiomer) was used in the drug pull-down-assays.

Chemical synthesis of crizotinib derivatives CeMM-144, CeMM-145, and CeMM-146 is outlined in FIG. 13.

As crizotinib itself is also compatible with the immobilization procedure due to the presence of an N-unsubstituted piperidine moiety it was included in the linker evaluation experiment with CeMM-144, CeMM-145 and CeMM-146. To confirm that the immobilization did not interfere with crizotinib's ability to bind its cognate targets, drug-bead matrices were generated for all four compounds followed by pull-down experiments using ALK-positive SH-SY5Y neuroblastoma cells. Bosutinib, a promiscuous BCR-Abl kinase inhibitor which also binds ALK,[10] was used as positive control. The eluates were analysed by SDS-PAGE and Western blot (FIG. 4).

As shown in FIG. 4, SH-SY5Y cells express two ALK isoforms with different molecular weight. The aminopropyl-substituted CeMM-146 enriches both ALK isoforms to highest extent, followed by the PEG-derivative CeMM-145. Unmodified crizotinib and CeMM-144 bind ALK to a lesser extent than CeMM-146 and CeMM-145. Based on these results it was decided to use CeMM-146 in all future experiments.

Example 2

The Identification of Interactors of Crizotinib: MTH1 as a New Target of Crizotinib For the profiling, three human cancer cell lines with different genetic background were selected: SH-SY5Y (NB, ALK-positive), NCI-H3122 (NSCLC, EML4-ALK-positive), and NCI-H1648 (c-Met amplification, ALK-negative). To distinguish direct binders from indirect or unspecific binders competition experiments were conducted in which the cell lysates were preincubated with unmodified crizotinib for 30 minutes at a final concentration of 20 µM before the affinity purification step. Isobaric tag for relative and absolute quantification (iTRAQ) labeling was used to quantify peptides in MS experiments. All experiments were carried out in duplicates. Comparing the ratio of labeled peptides in normal versus competitive pull-downs an affinity ranking was generated, prioritizing the most efficiently competed proteins as they are likely to be the top direct interactors of crizotinib. The results of the analyses for the top identified proteins from all three cell lines are summarized in FIG. 5.

As expected, ALK could be identified as a target in both the ALK-positive SH-SY5Y and H3122 samples whereas c-Met was captured in H1648 and H3122 pull-downs confirming the overall experimental strategy. Interestingly, apart from several unknown kinase targets the 7,8-dihydro-8-oxoguanine-triphosphatase MTH1 (gene symbol: NUDT1) was discovered as a common target of crizotinib in all samples.

The result that MTH1 interacts with crizotinib has been confirmed by screening a small kinase inhibitor collection in a thermal shift stability assay using recombinant MTH1 protein. By applying this thermal shift stability assay, the inventors discovered that the dual Met/ALK inhibitor crizotinib exhibits high affinity toward MTH1 (data not shown).

Human MutT homologue 1 (MTH1) depicts the major clearance enzyme for oxidised nucleotides such as 2-OH-dATP and 8-oxo-dGTP.[11] Oxidised nucleotides, which are generated by attack of reactive oxygen species (ROS) on DNA or the nucleotide pool, can cause DNA damage and mutations. Sources of ROS include mitochondrial respiration, chemicals or radiation. The frequently occurring 8-oxo-guanine (8-oxo-G), for example, can lead to transversion mutations during replication. In contrast to unoxidised guanine, 8-oxo-G is able to pair with either cytosine or adenine with almost equal efficiency, thereby generating mutations if 8-oxo-G is inserted opposite A in a nascent DNA strand or vice versa. If the misincorporated oxidised nucleotide is recognised by the DNA repair system the lesion can be repaired by base excision repair (BER). BER involves induction of a temporary single strand break to remove the falsely inserted base and subsequent replacement. However, high amounts of 8-oxo-G can lead to accumulation of single strand breaks which eventually progress to double strand breaks (DSB), thus inducing cell cycle arrest (quiescence or senescence) and apoptosis. By converting the oxidised triphosphate nucleotides into the corresponding monophosphates which can no longer be used as substrates by DNA polymerases, MTH1 prevents integration of oxidised bases into DNA and therefore mutations and oxidative DNA damage induced by ROS. Transformation of cells by oncogenes such as mutant RAS which occurs in about 20% of all tumours can also lead to increased production of ROS.[12] As for normal cells, oxidative damage caused by ROS can force cancer cells into a state of quiescence or senescence (OIS), and eventually apoptosis. To overcome senescence, RAS-transformed cells upregulate MTH1 which protects the cells from oxidative DNA damage. For instance, it has been shown that human skin fibroblasts transfected with HRAS undergo senescence, but this phenotype can be rescued by concomitant overexpression of MTH1.[12] Consequently, reports indicate that MTH1 suppression causes proliferative defects in cancer cells expressing mutant RAS.[13] As MTH1-/- knockout mice show a very mild phenotype,[14] targeting MTH1 with small molecules may provide a novel and well-tolerated therapeutic option for the difficult to treat RAS mutant cancers.

Example 3

Crizotinib Inhibits the Catalytic Activity of MTH1

Publicly available protein-protein interaction databases were examined to check if MTH1 might be interacting with a kinase target of crizotinib which could lead to "piggy-backing", i.e. an indirect interaction which could also cause an enrichment of MTH1 peptides in our analysis. However, no such interactions have been reported. This investigation was extended to a different type of cancer, the Ewing's sarcoma family of tumours (ESFT) as it was found that crizotinib inhibited the growth of these cells at low nanomolar concentrations. Again, MTH1 was identified in all pull-downs interrogating SK-ES-1 and SK-N-MC cells, both of which are thought to be driven by the EWS-FLI1 oncogene. To confirm that crizotinib is indeed inhibiting the catalytic activity of MTH1, an enzymatic assay was performed using recombinant MTH1. In cells, MTH1 hydrolyses oxidised nucleotides such as 2-OH-dATP and 8-oxo-dGTP, yielding the corresponding monophosphate and pyrophosphate (PPi). A luminescence-based assay was performed which monitors the production of PPi generated by MTH1-mediated 8-oxo-dGTP hydrolysis following a protocol which has been used to determine MTH1 enzyme kinetics.[15] IC50 values were determined for crizotinib considering both the clinically applied, optically pure (R)-enantiomer as well as the racemic mixture containing both (R)- and (S)-enantiomer (FIGS. 6-9). Confirming the pull-down results, both racemic and pure (R)-crizotinib inhibited MTH1's ability to hydrolyse 8-oxo-dGTP. However, the inhibitory potency of the racemate was about 10 times higher than the one observed for the enantiomerically pure (R)-crizotinib. These results were validated by analysis of different batches of both pure (R)- and racemic crizotinib which had been obtained from distinct vendors. A different ALK inhibitor, NVP-TAE684,[16] was also examined which did not exhibit any significant inhibition of MTH1 catalytic activity at concentrations of 100 µM (data not shown). This suggests that MTH1 inhibition is not a general phenomenon for ALK kinase inhibitors but is a feature of the particular chemotype of crizotinib. However, as kinase inhibitors mimic ATP when binding to the kinase active site it is likely that other kinase inhibitors are also potent MTH1 inhibitors as its natural substrates are derivatives of ATP and GTP.

In addition, competitive pull-down experiments in SK-ES-1 cells were performed using racemic CeMM-147 as bait and increasing concentrations of either optically pure (R)-crizotinib or the racemate (FIG. 10). As suggested by the IC50 results, only racemic crizotinib effectively prevented binding of MTH1 at preincubation concentrations up to 20 µM.

To confirm the preference of the (S)-enantiomer of crizotinib to bind and inhibit MTH1, we resynthesised an optically pure batch of the (S)-enantiomer of crizotinib (FIG. 14). The synthetic strategy depends on the use of optically pure starting materials and follow previously published procedures for synthesis of racemic and/or (R)-crizotinib (see de Koning (2011) Organic Process Research & Development, 15: 1018-1026[38], which is herein incorporated by reference in its entirety). Indeed, when evaluated in the MTH1 catalytic assay, the $IC_{50}$ value determined for the (S)-enantiomer of crizotinib indicated more than 100-fold higher potency for the (S)- versus (R)-enantiomer (FIG. 11).

The inventors prepared and tested both the pure, clinically used (R)- as well as the so far unexplored (S)-enantiomer of crizotinib. Analysis of both enantiomers in the MTH1 catalytic assay suggested that the screening hit batch contained a racemic mixture as the inventors found that the pure (S)-enantiomer of crizotinib is a low nanomolar MTH1 inhibitor whereas the (R)-enantiomer gave $IC_{50}$ values in the micromolar range (FIG. 11). Results were confirmed by direct binding assays (ITC) indicating a 16-fold higher affinity of the (S)-enantiomer for MTH1 (FIG. 17).

To assess the antiproliferative activity of the (S)-enantiomer against human cancer cells, we conducted colony formation assays using the two breast cancer cell lines MCF-7 and MDA-MB-231 (FIG. 12), the latter bearing a KRAS mutation (G13D). At 10 µM concentration both the (R)- and (S)-enantiomer significantly decreased the growth of both cell lines in comparison to DMSO-treated cells.

Consistent with these data, the (S)-enantiomer of crizotinib efficiently inhibited colony formation of SW480 colon carcinoma and K-Ras mutated PANC1 pancreatic cancer cells, similar to SCH51344 (FIGS. 17A and 17C). Importantly, when the inventors treated normal human BJ skin fibroblasts with increasing concentrations of either (R)-crizotinib or the (S)-enantiomer of crizotinib, the inventors found that the clinically used (R)-enantiomer exhibited higher toxicity than the (S)-enantiomer of crizotinib on non-transformed cells (FIG. 19). Thus, the antiproliferative effects observed for the (S)-enantiomer of crizotinib were not due to any increased non-specific cytotoxicity. The inventors also tested another two ALK and three commercially available Met inhibitors for their ability to inhibit MTH1, but no other compound displayed comparable potency (data not shown). Considering the published c-Met $K_i$ value for the (S)-enantiomer of crizotinib, the data of the present invention suggest that the (S)-enantiomer of crizotinib is at least 4-fold more selective for MTH1 (Cui (2011) Journal of Medicinal Chemistry 54, 6342-6363). To exclude that the antiproliferative effects of the (S)-enantiomer of crizotinib are mediated by inhibition of the potential off-target c-Met the inventors treated SW480 cells with a specific, low nanomolar c-Met inhibitor, but did not detect significant effects on proliferation (FIG. 20). Thus, the (S)-enantiomer of crizotinib is a novel and potent MTH1 inhibitor with antiproliferative activity against Ras transformed cancer cells.

Since MTH1 is thought to sanitise the nucleotide pool of oxidised nucleotides including 8-oxo-dGTP, thereby preventing its incorporation into DNA, the inventors reasoned that inhibition of MTH1 enzymatic function should increase the content of 8-oxo-guanine in DNA. Consequently, this should in turn activate DNA repair mechanisms and induce the formation of single strand breaks due to activated base excision repair (BER) (Rai (2009) Proceedings of the National Academy of Sciences 106, 169-174). To test this the inventors investigated the (S)-enantiomer of crizotinib and SCH51344 in an alkaline comet assay, which reveals DNA single strand breaks by single cell electrophoresis. The inventors found that both the (S)-enantiomer of crizotinib as well as SCH51344, but not (R)-crizotinib, yielded a significant tail moment in the comet assay (FIG. 18A). At the same time, staining for 53BP1, a specific marker for DNA damage, was increased, which was in line with the effect observed for anti-MTH1 siRNA (FIGS. 18B and 21).

Example 4

Preferred Structural Features of Aminoheteroaryl-Based MTH1 Inhibitors

To determine the molecular requirements for the inhibitors to bind MTH1 the inventors cocrystallised both (R)-crizotinib and the (S)-enantiomer of crizotinib with MTH1. The structure revealed that an unfavourable eclipsed conformation of the methyl group at the chiral centre and the halogen substituents on the benzyl ring may reduce the energetic favourability of binding (R)-crizotinib in the active site (FIGS. 18C, D, 22, 23, and Tables 3, 4). This observation is also supported by the ITC data which suggest that the difference in binding between (R)-crizotinib and the (S)- enantiomer of crizotinib is entirely entropic and therefore not due to different binding interactions with the protein.

As noted above, a cocrystal structure of the (S)-enantiomer of crizotinib bound to human MTH1 was generated (see FIG. 15). On the basis of the cocrystal structure of the (S)-enantiomer of crizotinib bound to human MTH1, the MTH1 inhibitor pharmacophore model as shown in FIG. 16 was developed. This pharmacophore model illustrates the preferred structural features of aminoheteroaryl compound-based MTH1 inhibitors. In particular, as shown in FIG. 16, the MTH1 inhibitor pharmacophore comprises a 5- or 6-membered heteroaromatic ring with one hydrogen bond acceptor (e.g. —NH2, —RNH, —RNR, —OH, —OR, —SH, —SR) and one hydrogen bond donor (e.g. —NH2, —RNH, —OH, —SH) in ortho position to each other. The hydrogen bond acceptor bears preferably lipohilic benzyl substituents such as halogenated benzyls. The benzyl substituent preferably has an additional methyl group at the CH2-carbon. With regard to the resulting chiral centre, (S)-configuration is preferred with regard to MTH1 inhibition. In para position to the main heteroaromatic ring additional aryl substituents may be introduced such as 5-membered heteroaromatic rings (e.g. pyrazol). The 5-membered ring preferably bears an aliphatic or cyclic substituent featuring a positively ionizable functional group which may also be capable of acting as a hydrogen bond donor (e.g. aminopropyl, piperidine, piperazine).

This pharmacophore model is in line with the following Formula (1) of an MTH1 inhibitor, which is an (S)-enantiomer of an aminoheteroaryl compound.

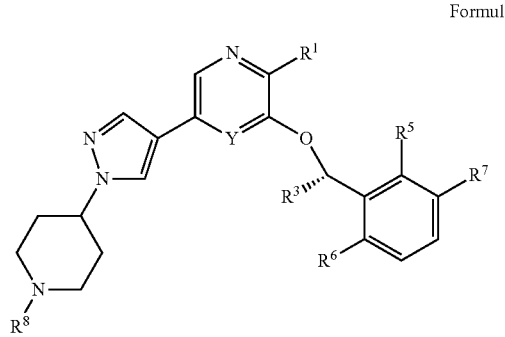

Formula (1)

wherein:

$R^1$ is —NH$_2$, —NR$^2$H, —OH or —SH;

$R^2$ is C$_{1-6}$ alkyl, C$_{2-6}$ alkenyl or C$_{2-6}$ alkynyl;

$R^3$ is C$_{1-3}$ alkyl, C$_{2-3}$ alkenyl, C$_{2-3}$ alkynyl or cyclopropyl;

Y is N or CR$^4$;

$R^4$ is hydrogen, halogen, C$_{1-6}$ alkyl, C$_{2-6}$ alkenyl, C$_{2-6}$ alkynyl or C$_{3-6}$ cycloalkyl;

each $R^5$, $R^6$ and $R^7$ is independently fluorine, chlorine, bromine or iodine;

$R^8$ is hydrogen or -A-B$_n$-X, wherein

A is a single bond, —C(=O)— or —C(=O)CH$_2$—;

B is C$_{1-4}$ alkylene, C$_{2-4}$ alkenylene or —(OCH$_2$CH$_2$)—;

n is 0, 1, 2, 3, 4 or 5, and

X is —NHR$^2$; —NH$_2$; —SH; —OH or O-alkyl;

TABLE 2

| Isothermal titration calorimetry | | | |
|---|---|---|---|
| | (R)-crizotinib | (S)-enantiomer of crizotinib | SCH51344 |
| Molar ratio (n) | 0.72 | 0.76 | 0.99 |
| ΔH (cal/mol)# | −7306 ± 66 | −7328 ± 38 | −6479 ± 45 |
| TΔS (cal/mol) | +710 | 2330 | 3170 |
| K$_d$ (nM)# | 781 ± 39 | 48 ± 3.9 | 49 ± 5.6 |

Data were measured at 15° C. in 50 mM Tris-HCl pH 7.8, 150 mM NaCl.
Error given in the table represent the error of the nonlinear least squares fit to the experimental data.

TABLE 3

| Crystallization of MTH1 complexes | | |
|---|---|---|
| | MTH1: (R)-crizotinib | MTH1: (S)-enantiomer of crizotinib |
| Reservoir solution | 30% PEG4000, 0.2M (NH$_4$)$_2$SO$_4$ | 24% PEG4000, 0.2M (NH$_4$)$_2$SO$_4$ |
| Volume of protein: Volume of reservoir (nL) | 50:100 | 50:100 |
| Temperature (° C.) | 4 | 20 |

TABLE 4

| Data Collection and Refinement Statistics | | |
|---|---|---|
| Dataset | MTH1: (R)-crizotinib | MTH1: (S)-enantiomer of crizotinib |
| Unit Cell (a, b, c (Å)) | 36.2, 60.0, 66.9 | 36.2, 60.0, 67.0 |
| Spacegroup | P2$_1$2$_1$2$_1$ | P2$_1$2$_1$2$_1$ |
| Number of molecules/ asymmetric unit | 1 | 1 |
| Data Collection | | |
| Beamline | Diamond I04 | Diamond I02 |
| Resolution range$^a$ (Å) | 44.64-1.65 (1.68-1.65) | 36.20-1.20 (1.22-1.20) |
| Completeness$^a$ (%) | 99.8 (97.4) | 99.6 (99.8) |
| Multiplicity$^a$ | 4.2 (3.2) | 3.9 (4.0) |
| R$_{merge}^a$ (%) | 0.077 (0.369) | 0.054 (0.566) |
| <I/σ(I)>$^a$ | 8.2 (2.6) | 10.4 (2.2) |
| Refinement | | |
| R factor (%) | 16.7 | 15.6 |
| R$_{free}$ (%) | 22.7 | 19.2 |
| Rmsd bond length (Å) (angle (°)) | 0.009 (1.34) | 0.008 (1.30) |

$^a$Values in parentheses are for the highest resolution shell.

Example 5

Mouse Xenograft Study

Figure 18E:
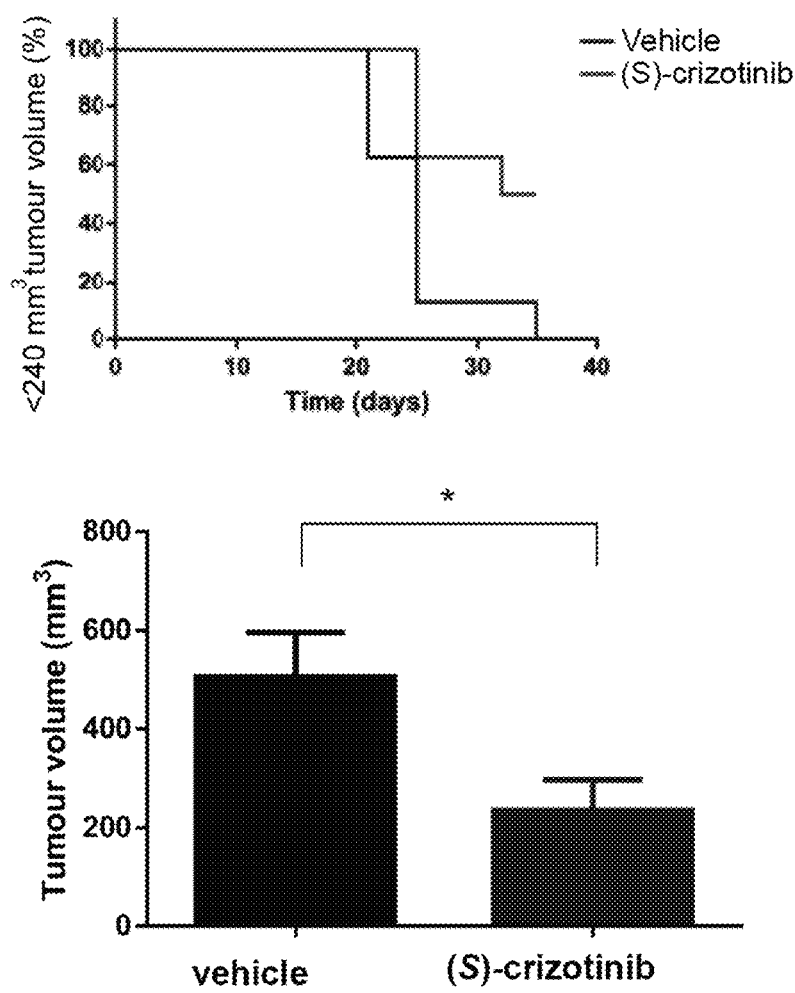

To explore the in vivo potential of the (S)-enantiomer of crizotinib to abrogate tumour growth the inventors performed a mouse xenograft study using SW480 cells indicating that the (S)-enantiomer of crizotinib is able to impair tumour progression as shown by a reduction in tumour volume of more than 50% (FIG. 18E). The (S)-enantiomer was well-tolerated as animals behaved normally and no significant change in haematological parameters (Table 5) or body weight was observed (18.8 mg±1.2 (S)-crizotinib vs 19.1 mg±2.0 vehicle group).

In summary the data suggest MTH1 is a critical component of Ras-transformed cells that can be readily targeted by drug-like small molecule inhibitors. It is well established that cancer cells are subject to high levels of oxidative stress due to increased proliferation leading to production of ROS as a result of mitochondrial respiration. The nucleotide pool represents a major target of ROS and oxidation of DNA bases contributes significantly to mutations and DNA damage. Consequently, tumour cells which bear a considerable amount of genetic aberrations and concomitant defects in DNA repair mechanisms are particularly sensitive to ROS-induced DNA damage. By removing oxidised nucleotides and thus maintaining nucleotide pool homeostasis, MTH1 relieves cancer cells of proliferative stress and is therefore a potential target for antitumoural compounds. Indeed, MTH1 levels are increased in Ras-expressing cancers (FIG. 24) ranging from lung cancer (Speina (2005) Journal of the National Cancer Institute 97, 384-395; Kennedy (1998) FEBS Letters 429, 17-20) to renal carcinoma (Okamoto (1996) Int J Cancer 65, 437-441) indicating that there is a connection between oncogenic transformation and oxidative stress. This is also supported by the fact that SCH51344 was also shown to prevent growth of fibroblasts infected with a variety of different oncogenes such as v-ab1 prompting further exploration of a potential global role of MTH1. Remarkably, MTH1 deficiency in knockout mice confers a mild phenotype suggesting there is a potential therapeutic window for MTH1 inhibitors (Tsuzuki (2001) Proceedings of the National Academy of Sciences 98, 11456-11461). The identification of SCH51344 as a direct and functional inhibitor of MTH1 reveals genome integrity-related proteins as a new and druggable target class. Furthermore, our finding that the (S)-enantiomer of crizotinib, a clinically approved kinase inhibitor applied to patients with ALK aberrations, is a first-in-class low nanomolar MTH1 inhibitor that provides benefit in a K-Ras-positive colon carcinoma xenograft model may open a new therapeutic option in the treatment of cancer.

TABLE 5

SCID mouse hematology and liver/heart/kidney parameters

| Test Name (test unit) | (S)-enantiomer of crizotinib (mean ± SD) | (S)-enantiomer of crizotinib Fold of control | p-value (t test) |
|---|---|---|---|
| WBC (10^9/l) | 1.90 ± 0.64 | 1.08 ± 0.35 | 0.33 |
| RBC (10^12/l) | 9.51 ± 0.37 | 1.00 ± 0.04 | 0.48 |
| Neutrophils (10^9/l) | 1.50 ± 0.51 | 1.24 ± 0.43 | 0.15 |
| Lymphocytes (10^9/l) | 0.23 ± 0.06 | 0.67 ± 0.19 | 0.11 |
| Monocytes (10^9/l) | 0.16 ± 0.11 | 0.95 ± 0.51 | 0.42 |
| MCV (fl) | 43.02 ± 1.07 | 1.01 ± 0.02 | 0.26 |
| MCH (pg) | 14.07 ± 0.30 | 1.0 ± 0.02 | 0.38 |
| MCHC (g/l) | 327 ± 4.90 | 0.98 ± 0.02 | 0.019 |
| Thrombocytes (10^9/l) | 828 ± 160 | 0.84 ± 0.16 | 0.21 |
| HBG (g/l) | 134 ± 6.25 | 0.99 ± 0.046 | 0.4 |
| p-Creatinine (uM) | 18.6 ± 4.24 | 0.93 ± 0.21 | 0.15 |
| p-ASAT (mCat/l) | 1.10 ± 0.32 | 0.72 ± 0.21 | 0.068 |
| P-ALAT (mCat/l) | 0.26 ± 0.07 | 0.81 ± 0.21 | 0.15 |

Mouse hematology and liver/heart/kidney parameters comparing treatment versus controls. SCID mice were subcutaneously administered vehicle or the (S)-enantiomer of crizotinib (25 mg/kg) for 35 days. Blood samples were obtained by orbital bleeding (under anaesthesia), blood parameters were analysed using whole blood and ASAT, ALAT and creatinine were analysed in EDTA collected plasma by the Karolinska Universitetslaboratoriet, Clinical Chemistry. The mean values of white blood cells (WBC), red blood cells (RBC), neutrophils, lymphocytes, monocytes, mean corpuscular volume (MCV), mean cell haemoglobin (MCH), mean cell haemoglobin concentration (MCHC) from the different groups are presented in the table. The results did not show any significant differences in the hematology parameters or the liver/heart/kidney parameters between control and treated groups apart from a minor change in MCHC.

Example 6

Stable Knockdown of MTH1 Impairs Colony Formation of SW480 Cells

To corroborate our finding that MTH1 gene silencing by anti-MTH1 siRNA impairs viability of SW480 colon carcinoma cells expressing mutant KRAS, we also created stable cell lines expressing shRNA targeting either eGFP (control) or MTH1 (Rai (2009) Proceedings of the National Academy of Sciences 106, 169-174). Consistent with previous results stable knockdown of MTH1 significantly reduced colony formation of SW480 cells (FIG. 26).

Example 7

Global Cellular Target Profile of (S)-crizotinib

To determine the specificity of the (S)-enantiomer of crizotinib to target the MTH1 protein in cells, a chemical proteomics drug pull-down was performed using shotgun mass spectrometry as described above. For immobilization of (S)-crizotinib, derivatisation of (S)-3-(1-(2,6-dichloro-3-fluorophenyl)ethoxy)-5-(1-(piperidin-4-yl)-1H-pyrazol-3-yl)pyridin-2-amine was carried out as described for CeMM-146 to yield (S)-5-(1-(1-(3-aminopropyl)piperidin-4-yl)-1H-pyrazol-3-yl)-3-(1-(2,6-dichloro-3-fluorophenyl)ethoxy)pyridin-2-amine (FIG. 27).

Chemoproteomic analyses were performed as shown using SW480 colon carcinoma cells which express an oncogenic KRAS mutant. Results are presented in Table 6:

TABLE 6

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| NUDT1 | 0.9997 | 32 | 32 | 23 | 30 | 117 | 4 | 2 | 2 | 2 | 10 |
| PLIN3 | 0.8429 | 4 | 3 | 3 | 3 | 13 | 0 | 0 | 1 | 0 | 1 |
| DDX3X | 0.7764 | 2 | 2 | 1 | 2 | 7 | 0 | 0 | 0 | 0 | 0 |
| ANP32A | 0.5951 | 1 | 1 | 1 | 3 | 6 | 0 | 0 | 0 | 0 | 0 |
| KPNB1 | 0.5773 | 7 | 6 | 1 | 0 | 14 | 0 | 0 | 2 | 0 | 2 |
| ANP32B | 0.5116 | 0 | 1 | 4 | 4 | 9 | 0 | 0 | 0 | 0 | 0 |
| UBA1 | 0.4997 | 15 | 15 | 0 | 0 | 30 | 0 | 0 | 2 | 2 | 4 |
| PDIA3 | 0.4952 | 8 | 7 | 0 | 0 | 15 | 0 | 0 | 1 | 0 | 1 |
| TLN1 | 0.4939 | 7 | 7 | 0 | 0 | 14 | 0 | 0 | 0 | 1 | 1 |
| GARS | 0.4818 | 6 | 7 | 0 | 0 | 13 | 0 | 0 | 2 | 0 | 2 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| PGAM1 | 0.4721 | 6 | 6 | 0 | 0 | 12 | 0 | 0 | 2 | 0 | 2 |
| AHCY | 0.4716 | 4 | 4 | 0 | 0 | 8 | 0 | 0 | 0 | 0 | 0 |
| HSPH1 | 0.4697 | 7 | 5 | 0 | 0 | 12 | 0 | 0 | 0 | 0 | 0 |
| SET | 0.4696 | 3 | 3 | 4 | 3 | 13 | 0 | 0 | 2 | 3 | 5 |
| SARS | 0.4649 | 4 | 4 | 0 | 0 | 8 | 0 | 0 | 0 | 0 | 0 |
| MDH1 | 0.4615 | 5 | 6 | 0 | 0 | 11 | 0 | 0 | 0 | 2 | 2 |
| TARS | 0.4614 | 5 | 4 | 0 | 0 | 9 | 0 | 0 | 0 | 0 | 0 |
| ADK | 0.4613 | 4 | 3 | 0 | 0 | 7 | 0 | 0 | 0 | 0 | 0 |
| ANXA3 | 0.461 | 4 | 4 | 0 | 0 | 8 | 0 | 0 | 0 | 0 | 0 |
| TXN | 0.4587 | 4 | 5 | 2 | 1 | 12 | 0 | 0 | 1 | 3 | 4 |
| IQGAP2 | 0.4584 | 9 | 9 | 0 | 0 | 18 | 0 | 0 | 0 | 0 | 0 |
| PARK7 | 0.4547 | 6 | 7 | 0 | 0 | 13 | 0 | 0 | 0 | 0 | 0 |
| PAICS | 0.4488 | 7 | 5 | 0 | 0 | 12 | 0 | 0 | 2 | 1 | 3 |
| NME1 | 0.4442 | 6 | 4 | 0 | 0 | 10 | 0 | 0 | 0 | 0 | 0 |
| MDH2 | 0.4441 | 5 | 5 | 0 | 0 | 10 | 0 | 0 | 0 | 2 | 2 |
| PDIA6 | 0.4427 | 3 | 4 | 0 | 0 | 7 | 0 | 0 | 0 | 0 | 0 |
| COTL1 | 0.4372 | 5 | 4 | 0 | 0 | 9 | 0 | 0 | 0 | 0 | 0 |
| ATIC | 0.4369 | 3 | 4 | 0 | 0 | 7 | 0 | 0 | 0 | 0 | 0 |
| PSMD2 | 0.4359 | 6 | 5 | 0 | 0 | 11 | 0 | 2 | 2 | 0 | 4 |
| CDC37 | 0.4343 | 3 | 3 | 0 | 0 | 6 | 0 | 0 | 0 | 0 | 0 |
| ANXA5 | 0.4332 | 9 | 6 | 0 | 0 | 15 | 0 | 0 | 2 | 2 | 4 |
| PSMC3 | 0.4297 | 3 | 3 | 0 | 0 | 6 | 0 | 0 | 0 | 0 | 0 |
| RUVBL2 | 0.4297 | 3 | 3 | 0 | 0 | 6 | 0 | 0 | 0 | 0 | 0 |
| RBM39 | 0.4214 | 4 | 3 | 0 | 0 | 7 | 0 | 0 | 0 | 0 | 0 |
| TPM3 | 0.4204 | 2 | 3 | 0 | 0 | 5 | 0 | 0 | 0 | 0 | 0 |
| TPM4 | 0.4193 | 5 | 2 | 0 | 0 | 7 | 0 | 0 | 0 | 0 | 0 |
| RCN1 | 0.4191 | 4 | 4 | 0 | 0 | 8 | 0 | 0 | 0 | 2 | 2 |
| STMN1 | 0.4156 | 3 | 3 | 0 | 0 | 6 | 0 | 0 | 0 | 0 | 0 |
| ARHGDIA | 0.4128 | 2 | 3 | 0 | 0 | 5 | 0 | 0 | 0 | 0 | 0 |
| ANXA2 | 0.41 | 13 | 13 | 0 | 0 | 26 | 0 | 0 | 5 | 6 | 11 |
| EIF4H | 0.4095 | 3 | 2 | 0 | 0 | 5 | 0 | 0 | 0 | 0 | 0 |
| MAPRE1 | 0.4084 | 2 | 3 | 0 | 0 | 5 | 0 | 0 | 0 | 0 | 0 |
| PHGDH | 0.4081 | 5 | 7 | 0 | 0 | 12 | 0 | 0 | 2 | 2 | 4 |
| FSCN1 | 0.4044 | 2 | 3 | 0 | 0 | 5 | 0 | 0 | 0 | 0 | 0 |
| PPP2R1A | 0.4042 | 3 | 3 | 0 | 0 | 6 | 0 | 0 | 0 | 0 | 0 |
| KRT14 | 0.4038 | 4 | 2 | 0 | 0 | 6 | 0 | 0 | 1 | 0 | 1 |
| GPI | 0.3986 | 4 | 5 | 0 | 0 | 9 | 0 | 0 | 1 | 2 | 3 |
| P4HB | 0.3981 | 3 | 4 | 0 | 0 | 7 | 0 | 0 | 1 | 1 | 2 |
| SND1 | 0.3957 | 3 | 5 | 0 | 0 | 8 | 0 | 0 | 0 | 0 | 0 |
| EIF1AY | 0.3949 | 2 | 3 | 0 | 0 | 5 | 0 | 0 | 0 | 0 | 0 |
| FASN | 0.394 | 8 | 8 | 0 | 0 | 16 | 0 | 0 | 0 | 0 | 0 |
| CACYBP | 0.392 | 2 | 2 | 0 | 0 | 4 | 0 | 0 | 0 | 0 | 0 |
| PSAT1 | 0.3916 | 3 | 3 | 0 | 0 | 6 | 0 | 0 | 1 | 0 | 1 |
| CYCS | 0.391 | 2 | 3 | 0 | 0 | 5 | 0 | 0 | 0 | 0 | 0 |
| S100A4 | 0.3894 | 3 | 2 | 0 | 0 | 5 | 0 | 0 | 0 | 0 | 0 |
| SOD1 | 0.3882 | 3 | 3 | 0 | 0 | 6 | 0 | 0 | 0 | 1 | 1 |
| CFL1 | 0.3871 | 12 | 11 | 1 | 0 | 24 | 0 | 0 | 7 | 5 | 12 |
| RUVBL1 | 0.3864 | 2 | 3 | 0 | 0 | 5 | 0 | 0 | 0 | 0 | 0 |
| PFDN2 | 0.3862 | 2 | 2 | 0 | 0 | 4 | 0 | 0 | 0 | 0 | 0 |
| SERPINH1 | 0.3843 | 5 | 6 | 0 | 0 | 11 | 0 | 0 | 1 | 3 | 4 |
| HMGB1P1 | 0.3829 | 2 | 2 | 0 | 0 | 4 | 0 | 0 | 0 | 0 | 0 |
| NPC2 | 0.3813 | 2 | 2 | 0 | 0 | 4 | 0 | 0 | 0 | 0 | 0 |
| PPIB | 0.381 | 2 | 2 | 0 | 0 | 4 | 0 | 0 | 0 | 0 | 0 |
| LUC7L2 | 0.3775 | 3 | 3 | 0 | 0 | 6 | 0 | 0 | 0 | 1 | 1 |
| S100A11 | 0.3773 | 4 | 5 | 0 | 0 | 9 | 0 | 0 | 1 | 2 | 3 |
| TALDO1 | 0.3739 | 2 | 2 | 0 | 0 | 4 | 0 | 0 | 0 | 0 | 0 |
| PPP1CA | 0.3721 | 2 | 2 | 0 | 0 | 4 | 0 | 0 | 0 | 0 | 0 |
| PTMA | 0.3707 | 2 | 2 | 0 | 0 | 4 | 0 | 0 | 0 | 0 | 0 |
| DPYSL2 | 0.3678 | 6 | 4 | 0 | 0 | 10 | 0 | 0 | 2 | 2 | 4 |
| HARS | 0.3676 | 3 | 3 | 0 | 0 | 6 | 0 | 0 | 2 | 0 | 2 |
| KRT1 | 0.3569 | 26 | 24 | 5 | 3 | 58 | 9 | 8 | 6 | 3 | 26 |
| HSPA9 | 0.3567 | 2 | 3 | 0 | 0 | 5 | 0 | 0 | 0 | 0 | 0 |
| ARF4 | 0.352 | 3 | 3 | 0 | 0 | 6 | 0 | 0 | 2 | 0 | 2 |
| TMSB10 | 0.3518 | 2 | 2 | 0 | 0 | 4 | 0 | 0 | 0 | 0 | 0 |
| PSMD12 | 0.35 | 2 | 2 | 0 | 0 | 4 | 0 | 0 | 0 | 0 | 0 |
| CAD | 0.3483 | 2 | 3 | 0 | 0 | 5 | 0 | 0 | 0 | 1 | 1 |
| FARSB | 0.3413 | 3 | 2 | 0 | 0 | 5 | 0 | 0 | 0 | 0 | 0 |
| MIF | 0.3362 | 0 | 1 | 2 | 2 | 5 | 0 | 1 | 1 | 1 | 3 |
| C1QBP | 0.33 | 3 | 3 | 0 | 0 | 6 | 0 | 0 | 1 | 1 | 2 |
| PEBP1 | 0.3266 | 3 | 3 | 0 | 0 | 6 | 0 | 0 | 1 | 1 | 2 |
| PGD | 0.3262 | 4 | 2 | 0 | 0 | 6 | 0 | 0 | 1 | 1 | 2 |
| PRDX2 | 0.3255 | 4 | 4 | 0 | 0 | 8 | 0 | 0 | 2 | 1 | 3 |
| 09-Sep | 0.323 | 1 | 2 | 0 | 2 | 5 | 1 | 0 | 1 | 0 | 2 |
| MANF | 0.3221 | 2 | 1 | 0 | 0 | 3 | 0 | 0 | 0 | 0 | 0 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| CTSZ | 0.3217 | 2 | 2 | 0 | 0 | 4 | 0 | 0 | 0 | 1 | 1 |
| HSD17B4 | 0.3179 | 2 | 3 | 0 | 0 | 5 | 0 | 0 | 0 | 0 | 0 |
| PCNA | 0.3137 | 2 | 1 | 0 | 0 | 3 | 0 | 0 | 0 | 0 | 0 |
| NQO1 | 0.3104 | 2 | 1 | 0 | 0 | 3 | 0 | 0 | 0 | 0 | 0 |
| CAP1 | 0.3081 | 3 | 2 | 0 | 0 | 5 | 0 | 0 | 0 | 2 | 2 |
| RAN | 0.3036 | 5 | 6 | 0 | 0 | 11 | 0 | 0 | 3 | 2 | 5 |
| LIN28A | 0.3021 | 2 | 2 | 2 | 0 | 6 | 2 | 0 | 1 | 0 | 3 |
| DCTN2 | 0.2964 | 2 | 3 | 0 | 0 | 5 | 0 | 1 | 0 | 1 | 2 |
| 07-Sep | 0.2962 | 3 | 3 | 0 | 0 | 6 | 0 | 0 | 1 | 2 | 3 |
| HNRNPA2B1 | 0.2944 | 2 | 2 | 0 | 2 | 6 | 1 | 1 | 0 | 1 | 3 |
| ACTN4 | 0.2923 | 4 | 4 | 0 | 0 | 8 | 0 | 0 | 3 | 2 | 5 |
| ACOT7 | 0.2785 | 1 | 2 | 0 | 0 | 3 | 0 | 0 | 0 | 0 | 0 |
| MTHFD1 | 0.2666 | 2 | 2 | 0 | 0 | 4 | 0 | 0 | 0 | 0 | 0 |
| SRP9 | 0.2561 | 2 | 1 | 0 | 2 | 5 | 2 | 0 | 1 | 0 | 3 |
| CRABP2 | 0.2533 | 4 | 1 | 0 | 0 | 5 | 0 | 0 | 0 | 2 | 2 |
| YARS | 0.2511 | 2 | 1 | 0 | 0 | 3 | 0 | 0 | 0 | 0 | 0 |
| PGK1 | 0.2466 | 14 | 12 | 0 | 0 | 26 | 0 | 0 | 9 | 6 | 15 |
| DYNC1H1 | 0.2458 | 13 | 13 | 2 | 2 | 30 | 1 | 2 | 3 | 2 | 8 |
| TGM2 | 0.2455 | 6 | 5 | 0 | 0 | 11 | 0 | 0 | 3 | 3 | 6 |
| CAPRIN1 | 0.2355 | 2 | 2 | 0 | 0 | 4 | 0 | 0 | 0 | 1 | 1 |
| HIST1H1E | 0.2298 | 0 | 2 | 0 | 2 | 4 | 0 | 3 | 0 | 0 | 3 |
| MSN | 0.2291 | 11 | 11 | 0 | 0 | 22 | 0 | 0 | 7 | 6 | 13 |
| ALDOA | 0.2283 | 12 | 12 | 2 | 0 | 26 | 0 | 0 | 8 | 6 | 14 |
| HSP90B1 | 0.228 | 13 | 8 | 0 | 0 | 21 | 0 | 0 | 8 | 5 | 13 |
| SLC1A5 | 0.227 | 1 | 0 | 3 | 2 | 6 | 2 | 2 | 0 | 1 | 5 |
| NAP1L1 | 0.2244 | 1 | 2 | 0 | 0 | 3 | 0 | 0 | 1 | 0 | 1 |
| ENO1 | 0.2209 | 29 | 28 | 7 | 7 | 71 | 3 | 3 | 17 | 18 | 41 |
| PDXK | 0.2207 | 3 | 0 | 0 | 0 | 3 | 0 | 0 | 0 | 0 | 0 |
| ACTN1 | 0.2142 | 3 | 1 | 0 | 0 | 4 | 0 | 0 | 0 | 0 | 0 |
| FAU | 0.2109 | 2 | 4 | 0 | 2 | 8 | 2 | 1 | 1 | 1 | 5 |
| COPB1 | 0.2093 | 1 | 3 | 0 | 0 | 4 | 0 | 0 | 0 | 0 | 0 |
| SUB1 | 0.206 | 5 | 5 | 2 | 4 | 16 | 0 | 2 | 3 | 3 | 8 |
| EIF3H | 0.2043 | 3 | 0 | 0 | 0 | 3 | 0 | 0 | 0 | 0 | 0 |
| DBF4B | 0.2 | 0 | 0 | 2 | 0 | 2 | 0 | 0 | 0 | 0 | 0 |
| PRDX6 | 0.1992 | 8 | 8 | 0 | 0 | 16 | 0 | 0 | 5 | 5 | 10 |
| IDH1 | 0.1991 | 3 | 0 | 0 | 0 | 3 | 0 | 0 | 0 | 0 | 0 |
| KRT9 | 0.1979 | 18 | 15 | 4 | 6 | 43 | 8 | 10 | 2 | 0 | 20 |
| BLVRB | 0.1915 | 0 | 2 | 0 | 0 | 2 | 0 | 0 | 0 | 0 | 0 |
| TPD52L2 | 0.191 | 0 | 2 | 0 | 0 | 2 | 0 | 0 | 0 | 0 | 0 |
| HN1L | 0.1898 | 0 | 2 | 0 | 0 | 2 | 0 | 0 | 0 | 0 | 0 |
| HPRT1 | 0.1891 | 2 | 0 | 0 | 0 | 2 | 0 | 0 | 0 | 0 | 0 |
| ARF3 | 0.1881 | 2 | 0 | 0 | 0 | 2 | 0 | 0 | 0 | 0 | 0 |
| PSMB4 | 0.1875 | 2 | 0 | 0 | 0 | 2 | 0 | 0 | 0 | 0 | 0 |
| TXNDC17 | 0.1862 | 2 | 3 | 0 | 0 | 5 | 0 | 0 | 2 | 1 | 3 |
| GDI2 | 0.1854 | 4 | 0 | 0 | 0 | 4 | 0 | 0 | 2 | 1 | 3 |
| CTSB | 0.1845 | 0 | 2 | 0 | 0 | 2 | 0 | 0 | 0 | 0 | 0 |
| ERP29 | 0.1841 | 2 | 0 | 0 | 0 | 2 | 0 | 0 | 0 | 0 | 0 |
| SLC2A3 | 0.1834 | 3 | 0 | 0 | 0 | 3 | 0 | 0 | 0 | 0 | 0 |
| TAGLN2 | 0.1795 | 6 | 5 | 0 | 0 | 11 | 0 | 0 | 4 | 3 | 7 |
| APEX1 | 0.1792 | 2 | 0 | 0 | 0 | 2 | 0 | 0 | 0 | 0 | 0 |
| TOMM34 | 0.1791 | 0 | 2 | 0 | 0 | 2 | 0 | 0 | 0 | 0 | 0 |
| LDHA | 0.176 | 14 | 11 | 0 | 2 | 27 | 0 | 0 | 7 | 9 | 16 |
| COPB2 | 0.1753 | 2 | 4 | 0 | 0 | 6 | 2 | 2 | 0 | 0 | 4 |
| PRMT1 | 0.1736 | 2 | 0 | 0 | 0 | 2 | 0 | 0 | 0 | 0 | 0 |
| GLOD4 | 0.1735 | 2 | 0 | 0 | 0 | 2 | 0 | 0 | 0 | 0 | 0 |
| RPN1 | 0.1727 | 0 | 3 | 0 | 0 | 3 | 0 | 2 | 0 | 0 | 2 |
| UBB | 0.1726 | 3 | 4 | 1 | 2 | 10 | 1 | 2 | 1 | 1 | 5 |
| GANAB | 0.1726 | 3 | 0 | 0 | 0 | 3 | 0 | 0 | 0 | 0 | 0 |
| TPI1 | 0.1723 | 14 | 18 | 6 | 5 | 43 | 0 | 0 | 12 | 11 | 23 |
| ST13 | 0.169 | 2 | 2 | 0 | 0 | 4 | 0 | 0 | 2 | 1 | 3 |
| ALDOC | 0.1677 | 2 | 2 | 0 | 0 | 4 | 0 | 0 | 2 | 1 | 3 |
| STIP1 | 0.1665 | 1 | 2 | 0 | 0 | 3 | 0 | 0 | 2 | 0 | 2 |
| PSMC2 | 0.1654 | 0 | 2 | 0 | 0 | 2 | 0 | 0 | 0 | 0 | 0 |
| PSMD11 | 0.1638 | 2 | 0 | 0 | 0 | 2 | 0 | 0 | 0 | 0 | 0 |
| TXNDC5 | 0.1605 | 0 | 2 | 0 | 0 | 2 | 0 | 0 | 0 | 0 | 0 |
| GSTP1 | 0.156 | 6 | 3 | 0 | 0 | 9 | 0 | 0 | 3 | 3 | 6 |
| GEMIN4 | 0.1509 | 0 | 1 | 2 | 0 | 3 | 2 | 1 | 0 | 0 | 3 |
| PSMA4 | 0.1477 | 1 | 1 | 2 | 1 | 5 | 2 | 0 | 1 | 1 | 4 |
| WDR1 | 0.1469 | 0 | 2 | 0 | 0 | 2 | 0 | 0 | 0 | 0 | 0 |
| PFN1 | 0.1469 | 9 | 9 | 1 | 3 | 22 | 0 | 2 | 6 | 6 | 14 |
| ABCE1 | 0.1467 | 2 | 0 | 0 | 0 | 2 | 0 | 0 | 0 | 0 | 0 |
| PDIA4 | 0.1432 | 2 | 0 | 0 | 0 | 2 | 0 | 0 | 0 | 0 | 0 |
| EIF5A | 0.1427 | 6 | 7 | 0 | 0 | 13 | 0 | 0 | 6 | 3 | 9 |
| XRCC5 | 0.1426 | 2 | 0 | 0 | 0 | 2 | 0 | 0 | 0 | 0 | 0 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| DYNLRB1 | 0.1409 | 2 | 2 | 2 | 2 | 8 | 2 | 1 | 1 | 1 | 5 |
| CARS | 0.1394 | 0 | 2 | 0 | 0 | 2 | 0 | 0 | 0 | 0 | 0 |
| FKBP4 | 0.1375 | 3 | 2 | 0 | 0 | 5 | 0 | 0 | 2 | 2 | 4 |
| FABP3 | 0.1374 | 4 | 3 | 0 | 0 | 7 | 0 | 0 | 2 | 3 | 5 |
| PKM | 0.1356 | 23 | 22 | 6 | 6 | 57 | 0 | 2 | 13 | 14 | 29 |
| RARS | 0.1343 | 5 | 6 | 3 | 0 | 14 | 2 | 3 | 1 | 2 | 8 |
| PSMB6 | 0.1336 | 0 | 2 | 0 | 0 | 2 | 0 | 0 | 0 | 2 | 2 |
| CAST | 0.1312 | 2 | 0 | 0 | 0 | 2 | 0 | 0 | 0 | 0 | 0 |
| PRKCSH | 0.1291 | 2 | 0 | 0 | 0 | 2 | 0 | 0 | 1 | 0 | 1 |
| GSN | 0.1286 | 0 | 2 | 0 | 0 | 2 | 0 | 0 | 0 | 0 | 0 |
| DSTN | 0.1269 | 0 | 2 | 0 | 0 | 2 | 0 | 0 | 2 | 0 | 2 |
| YWHAH | 0.1244 | 1 | 2 | 0 | 0 | 3 | 0 | 0 | 3 | 0 | 3 |
| CNN2 | 0.1239 | 2 | 0 | 0 | 0 | 2 | 0 | 0 | 1 | 1 | 2 |
| TKT | 0.1231 | 5 | 7 | 0 | 0 | 12 | 0 | 0 | 4 | 5 | 9 |
| YWHAE | 0.1176 | 10 | 10 | 0 | 0 | 20 | 0 | 2 | 6 | 6 | 14 |
| EZR | 0.1136 | 4 | 6 | 0 | 0 | 10 | 0 | 0 | 5 | 3 | 8 |
| PSMD1 | 0.1117 | 0 | 2 | 0 | 0 | 2 | 0 | 0 | 0 | 0 | 0 |
| PDCD6IP | 0.1109 | 2 | 0 | 0 | 0 | 2 | 0 | 0 | 0 | 0 | 0 |
| AIMP1 | 0.1089 | 0 | 0 | 2 | 0 | 2 | 0 | 1 | 1 | 2 | 4 |
| ACLY | 0.1061 | 2 | 0 | 0 | 0 | 2 | 0 | 0 | 0 | 0 | 0 |
| EIF4A1 | 0.1044 | 4 | 5 | 0 | 0 | 9 | 0 | 1 | 4 | 2 | 7 |
| ATP2A2 | 0.1039 | 2 | 0 | 0 | 0 | 2 | 0 | 0 | 0 | 0 | 0 |
| COPA | 0.1038 | 0 | 2 | 0 | 0 | 2 | 0 | 0 | 0 | 0 | 0 |
| HNRNPAB | 0.1024 | 1 | 2 | 0 | 0 | 3 | 2 | 1 | 0 | 0 | 3 |
| CLTA | 0.1023 | 2 | 0 | 4 | 2 | 8 | 2 | 3 | 2 | 1 | 8 |
| PLOD3 | 0.1017 | 2 | 0 | 0 | 0 | 2 | 0 | 0 | 1 | 0 | 1 |
| IQGAP1 | 0.1001 | 6 | 4 | 0 | 0 | 10 | 0 | 2 | 2 | 5 | 9 |
| GART | 0.0981 | 0 | 2 | 0 | 0 | 2 | 0 | 0 | 0 | 0 | 0 |
| HINT1 | 0.0956 | 0 | 2 | 0 | 3 | 5 | 1 | 0 | 2 | 3 | 6 |
| HSPD1 | 0.0865 | 8 | 8 | 0 | 0 | 16 | 0 | 0 | 7 | 5 | 12 |
| PFAS | 0.0861 | 0 | 2 | 0 | 0 | 2 | 0 | 0 | 0 | 0 | 0 |
| PSMA6 | 0.0839 | 3 | 3 | 0 | 1 | 7 | 2 | 1 | 1 | 1 | 5 |
| NACA | 0.0792 | 2 | 2 | 1 | 0 | 5 | 0 | 0 | 2 | 2 | 4 |
| PSMA1 | 0.0751 | 0 | 2 | 0 | 0 | 2 | 0 | 1 | 1 | 1 | 3 |
| EEF2 | 0.0725 | 15 | 15 | 0 | 0 | 30 | 0 | 0 | 11 | 11 | 22 |
| RPS28 | 0.0702 | 2 | 3 | 1 | 3 | 9 | 3 | 2 | 1 | 1 | 7 |
| PRDX1 | 0.0697 | 6 | 6 | 0 | 2 | 14 | 0 | 0 | 4 | 6 | 10 |
| PDCD5 | 0.0686 | 2 | 2 | 0 | 0 | 4 | 0 | 0 | 2 | 2 | 4 |
| CALM2, CALM1, CALM3 | 0.063 | 2 | 2 | 0 | 0 | 4 | 0 | 2 | 0 | 2 | 4 |
| RPS20 | 0.0628 | 0 | 2 | 2 | 3 | 7 | 2 | 3 | 2 | 0 | 7 |
| RANBP1 | 0.0579 | 2 | 2 | 0 | 0 | 4 | 0 | 0 | 2 | 2 | 4 |
| CCT6A | 0.053 | 9 | 8 | 0 | 2 | 19 | 3 | 3 | 4 | 3 | 13 |
| ARFGEF2 | 0.051 | 0 | 2 | 2 | 3 | 7 | 4 | 3 | 0 | 0 | 7 |
| STRAP | 0.0503 | 4 | 4 | 0 | 3 | 11 | 3 | 3 | 2 | 0 | 8 |
| XPO7 | 0.0419 | 5 | 4 | 6 | 4 | 19 | 3 | 6 | 2 | 2 | 13 |
| GAPDH | 0.0389 | 17 | 14 | 4 | 4 | 39 | 2 | 4 | 10 | 8 | 24 |
| IPO5 | 0.0381 | 4 | 4 | 4 | 6 | 18 | 4 | 4 | 2 | 3 | 13 |
| PSMA7 | 0.0354 | 2 | 2 | 1 | 2 | 7 | 2 | 2 | 1 | 1 | 6 |
| CALR | 0.0304 | 0 | 2 | 0 | 0 | 2 | 0 | 0 | 2 | 2 | 4 |
| RPL21 | 0.0299 | 2 | 2 | 2 | 1 | 7 | 1 | 2 | 2 | 1 | 6 |
| HIST1H4J, HIST1H4D, HIST1H4K, HIST1H4C, HIST2H4A, HIST4H4, HIST1H4E, HIST1H4A, HIST1H4B, HIST1H4I, HIST2H4B, HIST1H4H, HIST1H4L, HIST1H4F | 0.0286 | 2 | 3 | 0 | 0 | 5 | 2 | 2 | 2 | 0 | 6 |
| ACTB | 0.0283 | 19 | 18 | 6 | 3 | 46 | 3 | 3 | 12 | 12 | 30 |
| EIF5B | 0.0275 | 3 | 2 | 0 | 2 | 7 | 2 | 0 | 2 | 2 | 6 |
| RPL38 | 0.0262 | 4 | 2 | 2 | 3 | 11 | 2 | 4 | 1 | 2 | 9 |
| RBP1 | 0.0261 | 3 | 2 | 0 | 0 | 5 | 0 | 0 | 3 | 3 | 6 |
| STAU1 | 0.0255 | 2 | 2 | 0 | 3 | 7 | 3 | 3 | 0 | 2 | 8 |
| EIF3G | 0.0243 | 2 | 2 | 0 | 2 | 6 | 2 | 2 | 0 | 2 | 6 |
| SLC7A5 | 0.0239 | 3 | 2 | 2 | 2 | 9 | 3 | 2 | 0 | 2 | 7 |
| PSMB3 | 0.0232 | 4 | 4 | 0 | 0 | 8 | 2 | 2 | 2 | 2 | 8 |
| YWHAZ | 0.0192 | 4 | 6 | 1 | 1 | 12 | 0 | 0 | 6 | 5 | 11 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| EIF3J | 0.0189 | 3 | 2 | 0 | 2 | 7 | 2 | 3 | 2 | 0 | 7 |
| LDHB | 0.0184 | 9 | 8 | 2 | 3 | 22 | 0 | 0 | 7 | 9 | 16 |
| YWHAB | 0.0173 | 4 | 4 | 0 | 0 | 8 | 0 | 0 | 5 | 4 | 9 |
| RPL36AL | 0.0168 | 3 | 0 | 2 | 0 | 5 | 2 | 3 | 0 | 2 | 7 |
| HNRNPK | 0.0165 | 6 | 5 | 3 | 0 | 14 | 2 | 1 | 4 | 4 | 11 |
| VCP | 0.01631 | 5 | 14 | 3 | 4 | 36 | 4 | 5 | 6 | 9 | 24 |
| CLIC1 | 0.0151 | 8 | 8 | 0 | 1 | 17 | 0 | 0 | 7 | 8 | 15 |
| HDAC6 | 0.0145 | 2 | 2 | 0 | 1 | 5 | 2 | 1 | 1 | 1 | 5 |
| RPL35A | 0.0138 | 1 | 2 | 0 | 0 | 3 | 1 | 2 | 1 | 1 | 5 |
| YWHAG | 0.0136 | 3 | 3 | 1 | 2 | 9 | 0 | 0 | 4 | 4 | 8 |
| SYNE1 | 0.0134 | 3 | 4 | 0 | 0 | 7 | 0 | 0 | 0 | 0 | 0 |
| XPO1 | 0.0132 | 4 | 2 | 2 | 0 | 8 | 5 | 3 | 1 | 0 | 9 |
| RPL27A | 0.0111 | 7 | 2 | 3 | 2 | 14 | 3 | 3 | 4 | 3 | 13 |
| PRKDC | 0.0073 | 10 | 8 | 4 | 9 | 31 | 15 | 7 | 0 | 0 | 22 |
| MAP4 | 0.0072 | 6 | 5 | 4 | 6 | 21 | 4 | 4 | 3 | 4 | 15 |
| HNRNPU | 0.0071 | 2 | 3 | 2 | 3 | 10 | 2 | 2 | 2 | 3 | 9 |
| SSB | 0.0068 | 2 | 2 | 0 | 0 | 4 | 2 | 1 | 2 | 1 | 6 |
| KARS | 0.0068 | 1 | 1 | 0 | 2 | 4 | 3 | 2 | 2 | 0 | 7 |
| CCT3 | 0.0066 | 7 | 7 | 4 | 5 | 23 | 3 | 4 | 4 | 3 | 14 |
| RPL35 | 0.0065 | 2 | 0 | 2 | 2 | 6 | 2 | 2 | 2 | 2 | 8 |
| EIF3F | 0.0064 | 3 | 2 | 0 | 0 | 5 | 3 | 2 | 2 | 0 | 7 |
| RPL34 | 0.0057 | 0 | 2 | 0 | 0 | 2 | 2 | 0 | 2 | 2 | 6 |
| RPS26 | 0.0053 | 3 | 3 | 3 | 4 | 13 | 3 | 3 | 3 | 3 | 12 |
| 02-Sep | 0.0051 | 6 | 2 | 1 | 2 | 11 | 2 | 4 | 3 | 3 | 12 |
| RPL29 | 0.005 | 0 | 0 | 2 | 2 | 4 | 2 | 2 | 2 | 2 | 8 |
| YWHAQ | 0.0042 | 6 | 6 | 0 | 0 | 12 | 0 | 0 | 7 | 7 | 14 |
| MARS | 0.0042 | 3 | 2 | 3 | 1 | 9 | 3 | 3 | 1 | 3 | 10 |
| CCT4 | 0.0041 | 10 | 10 | 2 | 2 | 24 | 4 | 2 | 7 | 6 | 19 |
| SYNE2 | 0.0039 | 2 | 0 | 0 | 0 | 2 | 0 | 0 | 0 | 0 | 0 |
| HSPA5 | 0.0033 | 18 | 14 | 4 | 4 | 40 | 4 | 5 | 11 | 10 | 30 |
| VDAC1 | 0.0033 | 5 | 3 | 7 | 5 | 20 | 6 | 7 | 3 | 2 | 18 |
| THADA | 0.0025 | 2 | 0 | 3 | 2 | 7 | 4 | 7 | 0 | 0 | 11 |
| EIF2S1 | 0.0022 | 2 | 2 | 1 | 4 | 9 | 3 | 3 | 3 | 3 | 12 |
| RPL27 | 0.002 | 4 | 5 | 0 | 3 | 12 | 3 | 3 | 4 | 3 | 13 |
| RPLP1 | 0.0019 | 3 | 2 | 0 | 0 | 5 | 2 | 2 | 2 | 3 | 9 |
| EIF3M | 0.0019 | 2 | 2 | 0 | 0 | 4 | 2 | 1 | 2 | 2 | 7 |
| EPDR1 | 0.0018 | 4 | 3 | 5 | 4 | 16 | 5 | 4 | 3 | 3 | 15 |
| RPS23 | 0.0016 | 1 | 2 | 2 | 1 | 6 | 2 | 3 | 2 | 2 | 9 |
| RPS13 | 0.0016 | 4 | 4 | 3 | 3 | 14 | 2 | 4 | 2 | 4 | 12 |
| HIST1H2AB, HIST1H2AE | 0.0014 | 2 | 3 | 2 | 2 | 9 | 3 | 3 | 2 | 2 | 10 |
| SLC2A1 | 0.0014 | 2 | 2 | 2 | 2 | 8 | 3 | 3 | 3 | 1 | 10 |
| RPL14 | 0.0013 | 3 | 2 | 3 | 2 | 10 | 3 | 4 | 2 | 2 | 11 |
| MYL6 | 0.0012 | 5 | 4 | 2 | 4 | 15 | 4 | 4 | 3 | 3 | 14 |
| RPL19 | 0.0012 | 4 | 2 | 2 | 2 | 10 | 2 | 5 | 0 | 4 | 11 |
| RPL9, RPL9P8, RPL9P7, RPL9P9 | 0.0011 | 2 | 2 | 1 | 2 | 7 | 3 | 4 | 2 | 1 | 10 |
| RPL22 | 0.0011 | 3 | 3 | 1 | 1 | 8 | 4 | 2 | 2 | 2 | 10 |
| EIF3D | 0.0009 | 5 | 4 | 3 | 3 | 15 | 5 | 2 | 2 | 4 | 13 |
| RPL31 | 0.0008 | 3 | 3 | 4 | 3 | 13 | 3 | 3 | 4 | 4 | 14 |
| EIF3I | 0.0008 | 3 | 2 | 0 | 0 | 5 | 3 | 3 | 2 | 1 | 9 |
| MLST8 | 0.0008 | 7 | 7 | 6 | 8 | 28 | 8 | 7 | 3 | 3 | 21 |
| EEF1D | 0.0007 | 3 | 4 | 3 | 2 | 12 | 4 | 3 | 3 | 2 | 12 |
| RPS9 | 0.0007 | 5 | 4 | 2 | 2 | 13 | 2 | 4 | 3 | 4 | 13 |
| PA2G4 | 0.0005 | 10 | 11 | 4 | 4 | 29 | 5 | 5 | 6 | 7 | 23 |
| KRT5 | 0.0004 | 5 | 5 | 1 | 0 | 11 | 6 | 3 | 3 | 2 | 14 |
| RPL5 | 0.0004 | 3 | 3 | 4 | 3 | 13 | 5 | 5 | 2 | 2 | 14 |
| RPL18 | 0.0004 | 4 | 4 | 5 | 6 | 19 | 6 | 4 | 3 | 6 | 19 |
| PSMB2 | 0.0003 | 0 | 3 | 0 | 0 | 3 | 2 | 3 | 2 | 3 | 10 |
| LARS | 0.0003 | 5 | 6 | 3 | 3 | 17 | 7 | 3 | 2 | 3 | 15 |
| HSPB1 | 0.0002 | 6 | 7 | 2 | 4 | 19 | 4 | 4 | 5 | 5 | 18 |
| PSMB1 | 0.0002 | 2 | 2 | 0 | 0 | 4 | 3 | 3 | 1 | 2 | 9 |
| RPL13A | 0.0002 | 4 | 4 | 2 | 3 | 13 | 4 | 2 | 3 | 4 | 13 |
| RPS11 | 0.0002 | 4 | 4 | 5 | 4 | 17 | 6 | 4 | 3 | 4 | 17 |
| RPL30 | 0.0002 | 3 | 2 | 2 | 3 | 10 | 2 | 4 | 3 | 4 | 13 |
| RPL18A | 0.0002 | 3 | 3 | 4 | 2 | 12 | 4 | 3 | 4 | 4 | 15 |
| KRT8 | 0.0001 | 12 | 8 | 3 | 4 | 27 | 6 | 7 | 5 | 6 | 24 |
| XRCC6 | 0.0001 | 5 | 4 | 0 | 3 | 12 | 5 | 4 | 2 | 4 | 15 |
| PSMB5 | 0.0001 | 4 | 4 | 3 | 4 | 15 | 5 | 4 | 4 | 3 | 16 |
| RPS19 | 0.0001 | 8 | 7 | 3 | 6 | 24 | 5 | 6 | 5 | 4 | 20 |
| CCT5 | 0.0001 | 6 | 4 | 0 | 0 | 10 | 3 | 3 | 5 | 5 | 16 |
| RPS25 | 0.0001 | 6 | 6 | 5 | 5 | 22 | 4 | 5 | 4 | 6 | 19 |
| PCBP2 | 0.0001 | 3 | 3 | 0 | 0 | 6 | 4 | 3 | 2 | 3 | 12 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| CCT7 | 0.0001 | 10 | 10 | 2 | 3 | 25 | 4 | 6 | 6 | 6 | 22 |
| NA | 0 | 69 | 67 | 53 | 61 | 250 | 75 | 69 | 61 | 63 | 268 |
| NA | 0 | 7 | 5 | 1 | 0 | 13 | 38 | 12 | 3 | 1 | 54 |
| PSMD14 | 0 | 0 | 1 | 0 | 0 | 1 | 0 | 0 | 0 | 0 | 0 |
| SLC9A3R1 | 0 | 1 | 0 | 0 | 0 | 1 | 0 | 0 | 0 | 0 | 0 |
| TAX1BP3 | 0 | 1 | 0 | 0 | 0 | 1 | 0 | 0 | 0 | 0 | 0 |
| MYL12B | 0 | 4 | 3 | 3 | 2 | 12 | 3 | 3 | 4 | 4 | 14 |
| SURF4 | 0 | 1 | 1 | 1 | 1 | 4 | 6 | 3 | 1 | 1 | 11 |
| PSMD3 | 0 | 0 | 1 | 0 | 0 | 1 | 0 | 0 | 0 | 0 | 0 |
| SYNCRIP | 0 | 7 | 8 | 3 | 5 | 23 | 10 | 8 | 7 | 7 | 32 |
| HNRNPCL1 | 0 | 1 | 0 | 0 | 0 | 1 | 0 | 0 | 0 | 0 | 0 |
| PFDN1 | 0 | 0 | 1 | 0 | 0 | 1 | 0 | 0 | 0 | 0 | 0 |
| GGCT | 0 | 0 | 1 | 0 | 0 | 1 | 0 | 0 | 0 | 0 | 0 |
| FLNB | 0 | 28 | 29 | 9 | 11 | 77 | 21 | 19 | 14 | 16 | 70 |
| BANF1 | 0 | 1 | 1 | 0 | 0 | 2 | 0 | 0 | 0 | 0 | 0 |
| IPO7 | 0 | 12 | 9 | 6 | 5 | 32 | 8 | 9 | 5 | 6 | 28 |
| MT2A | 0 | 1 | 1 | 0 | 0 | 2 | 0 | 0 | 0 | 0 | 0 |
| CSTB | 0 | 1 | 0 | 0 | 0 | 1 | 0 | 0 | 0 | 0 | 0 |
| CAPNS1 | 0 | 0 | 1 | 0 | 0 | 1 | 0 | 0 | 0 | 0 | 0 |
| RPLP2 | 0 | 4 | 4 | 6 | 7 | 21 | 8 | 8 | 5 | 6 | 27 |
| RPLP0 | 0 | 12 | 10 | 6 | 10 | 38 | 13 | 12 | 10 | 12 | 47 |
| KRT18 | 0 | 7 | 3 | 5 | 3 | 18 | 4 | 6 | 5 | 5 | 20 |
| NPM1 | 0 | 2 | 2 | 1 | 1 | 6 | 3 | 4 | 4 | 3 | 14 |
| CTSD | 0 | 1 | 1 | 0 | 0 | 2 | 0 | 0 | 0 | 0 | 0 |
| TUBB | 0 | 18 | 20 | 10 | 9 | 57 | 19 | 22 | 18 | 22 | 81 |
| EPRS | 0 | 3 | 4 | 0 | 2 | 9 | 5 | 6 | 1 | 2 | 14 |
| HSP90AA1 | 0 | 19 | 21 | 6 | 7 | 53 | 3 | 5 | 17 | 17 | 42 |
| HSPA1A, HSPA1B | 0 | 11 | 10 | 5 | 5 | 31 | 7 | 8 | 9 | 9 | 33 |
| HSP90AB1 | 0 | 19 | 21 | 9 | 8 | 57 | 7 | 6 | 21 | 19 | 53 |
| RPS17 | 0 | 2 | 3 | 0 | 0 | 5 | 3 | 3 | 5 | 3 | 14 |
| RPSA | 0 | 5 | 7 | 4 | 5 | 21 | 6 | 5 | 5 | 6 | 22 |
| ENO2 | 0 | 1 | 0 | 0 | 0 | 1 | 1 | 0 | 5 | 5 | 11 |
| SNRPA1 | 0 | 0 | 0 | 0 | 1 | 1 | 2 | 0 | 0 | 0 | 2 |
| PARP1 | 0 | 0 | 1 | 0 | 0 | 1 | 0 | 0 | 0 | 0 | 0 |
| HSPA8 | 0 | 16 | 18 | 8 | 9 | 51 | 11 | 14 | 11 | 16 | 52 |
| PABPC1 | 0 | 7 | 10 | 7 | 5 | 29 | 10 | 11 | 6 | 8 | 35 |
| IMPDH2 | 0 | 1 | 0 | 0 | 0 | 1 | 0 | 0 | 0 | 0 | 0 |
| CKB | 0 | 1 | 1 | 0 | 0 | 2 | 0 | 0 | 0 | 0 | 0 |
| RNH1 | 0 | 0 | 1 | 0 | 0 | 1 | 0 | 0 | 0 | 0 | 0 |
| KRT10 | 0 | 16 | 14 | 0 | 0 | 30 | 12 | 12 | 7 | 7 | 38 |
| DARS | 0 | 6 | 6 | 0 | 1 | 13 | 2 | 5 | 5 | 6 | 18 |
| RPS2 | 0 | 6 | 6 | 5 | 5 | 22 | 9 | 8 | 6 | 5 | 28 |
| HIST1H1B | 0 | 1 | 0 | 0 | 0 | 1 | 1 | 1 | 1 | 1 | 4 |
| CSDA | 0 | 2 | 2 | 2 | 2 | 8 | 5 | 5 | 3 | 3 | 16 |
| HSPA6 | 0 | 1 | 1 | 1 | 1 | 4 | 5 | 6 | 6 | 7 | 24 |
| TCP1 | 0 | 11 | 8 | 4 | 4 | 27 | 8 | 4 | 7 | 6 | 25 |
| RPL7 | 0 | 4 | 4 | 2 | 2 | 12 | 7 | 5 | 4 | 5 | 21 |
| VCL | 0 | 1 | 0 | 0 | 0 | 1 | 0 | 0 | 0 | 0 | 0 |
| RPL17 | 0 | 3 | 4 | 3 | 3 | 13 | 4 | 4 | 3 | 5 | 16 |
| NCL | 0 | 13 | 14 | 8 | 9 | 44 | 12 | 14 | 15 | 14 | 55 |
| HK1 | 0 | 1 | 0 | 0 | 0 | 1 | 0 | 0 | 0 | 0 | 0 |
| EIF2S2 | 0 | 4 | 6 | 2 | 4 | 16 | 4 | 5 | 6 | 5 | 20 |
| PTMS | 0 | 1 | 1 | 0 | 0 | 2 | 0 | 0 | 0 | 0 | 0 |
| FLNA | 0 | 43 | 43 | 32 | 30 | 148 | 47 | 51 | 34 | 36 | 168 |
| RPS3 | 0 | 9 | 9 | 7 | 8 | 33 | 8 | 8 | 5 | 7 | 28 |
| EEF1B2 | 0 | 2 | 3 | 2 | 3 | 10 | 4 | 4 | 4 | 3 | 15 |
| ACP1 | 0 | 5 | 5 | 4 | 3 | 17 | 5 | 6 | 6 | 5 | 22 |
| RPS12 | 0 | 6 | 5 | 4 | 6 | 21 | 5 | 6 | 5 | 5 | 21 |
| RPL13 | 0 | 6 | 6 | 4 | 6 | 22 | 7 | 7 | 6 | 7 | 27 |
| PTBP1 | 0 | 1 | 0 | 0 | 0 | 1 | 0 | 0 | 0 | 0 | 0 |
| EEF1G | 0 | 7 | 9 | 9 | 7 | 32 | 9 | 10 | 10 | 10 | 39 |
| RPL12 | 0 | 7 | 12 | 8 | 7 | 34 | 9 | 11 | 9 | 8 | 37 |
| HSPA4 | 0 | 13 | 16 | 2 | 4 | 35 | 7 | 8 | 9 | 11 | 35 |
| PHB | 0 | 8 | 9 | 5 | 4 | 26 | 12 | 10 | 8 | 5 | 35 |
| MYH9 | 0 | 32 | 33 | 15 | 18 | 98 | 18 | 19 | 22 | 24 | 83 |
| FUS | 0 | 1 | 0 | 0 | 0 | 1 | 1 | 0 | 0 | 0 | 1 |
| KRT2 | 0 | 8 | 8 | 0 | 0 | 16 | 9 | 8 | 6 | 4 | 27 |
| RPL4 | 0 | 8 | 4 | 5 | 5 | 22 | 5 | 6 | 8 | 8 | 27 |
| SRP14 | 0 | 1 | 1 | 1 | 1 | 4 | 1 | 1 | 1 | 1 | 4 |
| RPL3 | 0 | 5 | 5 | 4 | 4 | 18 | 5 | 7 | 6 | 6 | 24 |
| EIF2S3 | 0 | 5 | 4 | 3 | 4 | 16 | 3 | 3 | 7 | 4 | 17 |
| IARS | 0 | 4 | 4 | 2 | 3 | 13 | 4 | 4 | 3 | 4 | 15 |
| MTOR | 0 | 9 | 10 | 9 | 11 | 39 | 24 | 19 | 3 | 4 | 50 |
| RPS27 | 0 | 0 | 0 | 0 | 1 | 1 | 2 | 2 | 0 | 0 | 4 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| VDAC2 | 0 | 1 | 0 | 0 | 0 | 1 | 1 | 1 | 0 | 0 | 2 |
| RPL28 | 0 | 4 | 2 | 0 | 0 | 6 | 6 | 4 | 3 | 4 | 17 |
| RPS5 | 0 | 5 | 4 | 3 | 2 | 14 | 5 | 6 | 5 | 4 | 20 |
| RPS10 | 0 | 7 | 5 | 5 | 3 | 20 | 7 | 7 | 7 | 8 | 29 |
| MAP1B | 0 | 21 | 20 | 14 | 12 | 67 | 26 | 25 | 23 | 22 | 96 |
| PPT1 | 0 | 1 | 0 | 0 | 0 | 1 | 0 | 0 | 0 | 0 | 0 |
| CCT8 | 0 | 8 | 8 | 4 | 4 | 24 | 5 | 4 | 6 | 6 | 21 |
| CSE1L | 0 | 11 | 12 | 6 | 7 | 36 | 14 | 14 | 5 | 4 | 37 |
| EIF3B | 0 | 3 | 3 | 2 | 3 | 11 | 5 | 4 | 5 | 4 | 18 |
| EIF6 | 0 | 2 | 2 | 1 | 0 | 5 | 3 | 4 | 3 | 3 | 13 |
| MTPN | 0 | 0 | 1 | 0 | 0 | 1 | 0 | 0 | 0 | 1 | 1 |
| EIF3E | 0 | 2 | 2 | 2 | 2 | 8 | 3 | 4 | 3 | 2 | 12 |
| RAB10 | 0 | 1 | 0 | 0 | 0 | 1 | 0 | 0 | 0 | 0 | 0 |
| UBE2N | 0 | 1 | 1 | 0 | 0 | 2 | 0 | 0 | 0 | 0 | 0 |
| RPS3A | 0 | 9 | 6 | 6 | 6 | 27 | 5 | 7 | 5 | 8 | 25 |
| RPL26 | 0 | 3 | 3 | 2 | 2 | 10 | 3 | 5 | 6 | 4 | 18 |
| RPL15 | 0 | 4 | 4 | 4 | 3 | 15 | 5 | 6 | 4 | 4 | 19 |
| RPL37A | 0 | 3 | 4 | 3 | 4 | 14 | 4 | 5 | 4 | 4 | 17 |
| HSPE1 | 0 | 1 | 1 | 0 | 0 | 2 | 0 | 0 | 0 | 0 | 0 |
| RPS7 | 0 | 5 | 7 | 2 | 2 | 16 | 7 | 5 | 7 | 5 | 24 |
| PSMC5 | 0 | 1 | 1 | 0 | 1 | 3 | 1 | 1 | 0 | 0 | 2 |
| RPS8 | 0 | 7 | 6 | 5 | 6 | 24 | 8 | 8 | 6 | 5 | 27 |
| RPS16 | 0 | 6 | 4 | 6 | 5 | 21 | 6 | 7 | 5 | 4 | 22 |
| RPS14 | 0 | 6 | 6 | 5 | 5 | 22 | 6 | 6 | 5 | 5 | 22 |
| RPS18 | 0 | 8 | 7 | 4 | 8 | 27 | 6 | 6 | 7 | 9 | 28 |
| TMSB4X | 0 | 1 | 1 | 0 | 0 | 2 | 0 | 0 | 0 | 0 | 0 |
| RPL7A | 0 | 3 | 3 | 5 | 3 | 14 | 6 | 7 | 6 | 4 | 23 |
| RPS4X | 0 | 8 | 7 | 3 | 6 | 24 | 10 | 10 | 11 | 7 | 38 |
| PPP2CB | 0 | 1 | 1 | 0 | 0 | 2 | 0 | 0 | 0 | 0 | 0 |
| ACTA2 | 0 | 2 | 1 | 0 | 0 | 3 | 3 | 2 | 7 | 10 | 22 |
| RPL23A | 0 | 3 | 3 | 2 | 3 | 11 | 5 | 3 | 5 | 4 | 17 |
| RPS6 | 0 | 5 | 4 | 3 | 3 | 15 | 3 | 4 | 4 | 5 | 16 |
| RAB1A | 0 | 0 | 1 | 0 | 0 | 1 | 0 | 0 | 0 | 1 | 1 |
| RPL23 | 0 | 5 | 5 | 4 | 4 | 18 | 5 | 5 | 5 | 6 | 21 |
| RPL10A | 0 | 5 | 4 | 3 | 4 | 16 | 4 | 4 | 3 | 5 | 16 |
| RPL32 | 0 | 1 | 1 | 1 | 1 | 4 | 1 | 2 | 1 | 1 | 5 |
| RPL11 | 0 | 3 | 4 | 3 | 4 | 14 | 5 | 5 | 5 | 4 | 19 |
| RPL8 | 0 | 6 | 5 | 5 | 6 | 22 | 6 | 5 | 7 | 7 | 25 |
| PPIA | 0 | 13 | 13 | 4 | 3 | 33 | 8 | 6 | 10 | 10 | 34 |
| FKBP1A | 0 | 1 | 1 | 1 | 0 | 3 | 1 | 0 | 0 | 1 | 1 |
| GNB2L1 | 0 | 12 | 13 | 9 | 11 | 45 | 13 | 14 | 12 | 14 | 53 |
| YBX1 | 0 | 2 | 2 | 2 | 2 | 8 | 6 | 5 | 4 | 3 | 18 |
| EEF1A1 | 0 | 23 | 21 | 8 | 8 | 60 | 12 | 11 | 16 | 16 | 55 |
| TUBA1B | 0 | 1 | 1 | 0 | 0 | 2 | 22 | 20 | 19 | 21 | 82 |
| TUBA4A | 0 | 22 | 20 | 14 | 12 | 68 | 18 | 16 | 16 | 17 | 67 |
| TUBB4B | 0 | 8 | 8 | 2 | 4 | 22 | 16 | 19 | 16 | 18 | 69 |
| PAFAH1B2 | 0 | 1 | 1 | 0 | 0 | 2 | 0 | 0 | 0 | 1 | 1 |
| CCT2 | 0 | 9 | 11 | 3 | 3 | 26 | 6 | 5 | 9 | 6 | 26 |
| RPL24 | 0 | 4 | 4 | 3 | 4 | 15 | 4 | 4 | 4 | 4 | 16 |
| CLTC | 0 | 16 | 14 | 5 | 7 | 42 | 16 | 17 | 12 | 10 | 55 |
| EWSR1 | 0 | 0 | 1 | 0 | 0 | 1 | 1 | 0 | 0 | 0 | 1 |
| RPL6 | 0 | 7 | 11 | 4 | 6 | 28 | 9 | 8 | 10 | 6 | 33 |
| SSBP1 | 0 | 1 | 1 | 0 | 0 | 2 | 1 | 0 | 0 | 0 | 1 |
| GFPT1 | 0 | 1 | 1 | 0 | 0 | 2 | 0 | 0 | 0 | 0 | 0 |
| BAX | 0 | 1 | 1 | 1 | 1 | 4 | 1 | 1 | 1 | 1 | 4 |
| AHNAK | 0 | 5 | 6 | 6 | 6 | 23 | 4 | 7 | 6 | 5 | 22 |
| MTAP | 0 | 1 | 1 | 0 | 0 | 2 | 0 | 0 | 0 | 0 | 0 |
| G3BP1 | 0 | 2 | 2 | 3 | 2 | 9 | 4 | 4 | 4 | 2 | 14 |
| PDAP1 | 0 | 1 | 1 | 0 | 0 | 2 | 0 | 0 | 0 | 0 | 0 |
| TUBB2A | 0 | 5 | 4 | 2 | 2 | 13 | 15 | 17 | 14 | 16 | 62 |
| EIF3A | 0 | 9 | 7 | 7 | 6 | 29 | 9 | 7 | 7 | 8 | 31 |
| EIF4A2 | 0 | 1 | 1 | 0 | 1 | 3 | 2 | 2 | 4 | 3 | 11 |
| FLNC | 0 | 0 | 0 | 0 | 1 | 1 | 2 | 4 | 3 | 3 | 12 |
| LASP1 | 0 | 0 | 1 | 0 | 0 | 1 | 0 | 0 | 0 | 2 | 2 |
| PAFAH1B3 | 0 | 1 | 1 | 0 | 0 | 2 | 0 | 0 | 0 | 0 | 0 |
| PCBP1 | 0 | 0 | 1 | 0 | 0 | 1 | 1 | 1 | 3 | 3 | 8 |
| ACTBL2 | 0 | 1 | 1 | 0 | 0 | 2 | 0 | 0 | 4 | 4 | 8 |
| KRT79 | 0 | 0 | 1 | 0 | 0 | 1 | 2 | 1 | 1 | 3 | 7 |
| TUBA1A | 0 | 12 | 11 | 9 | 10 | 42 | 21 | 20 | 18 | 20 | 79 |
| RPS27L | 0 | 0 | 1 | 0 | 0 | 1 | 0 | 2 | 2 | 2 | 6 |
| KRT74 | 0 | 1 | 1 | 0 | 0 | 2 | 0 | 0 | 0 | 0 | 0 |
| MYH14 | 0 | 1 | 1 | 0 | 0 | 2 | 0 | 0 | 0 | 0 | 0 |
| SERBP1 | 0 | 8 | 10 | 5 | 6 | 29 | 8 | 7 | 10 | 8 | 33 |
| GCN1L1 | 0 | 37 | 34 | 37 | 37 | 145 | 60 | 61 | 17 | 12 | 150 |

TABLE 6-continued

Global cellular target profile of (S)-crizotinib

| PreyGene | AvgP | SC.Exp. 1-1 | SC.Exp. 1-2 | SC.Exp. 2-1 | SC.Exp. 2-2 | Sum | SC.Neg Ctrl. 1-1 | SC.Neg Ctrl. 1-2 | SC.Neg Ctrl. 2-1 | SC.Neg Ctrl. 2-2 | Sum |
|---|---|---|---|---|---|---|---|---|---|---|---|
| TNPO1 | 0 | 9 | 7 | 6 | 6 | 28 | 14 | 8 | 5 | 6 | 33 |
| S100A16 | 0 | 1 | 0 | 0 | 0 | 1 | 1 | 0 | 0 | 0 | 1 |
| EIF3C, EIF3CL | 0 | 4 | 6 | 7 | 7 | 24 | 10 | 7 | 3 | 3 | 23 |
| PHB2 | 0 | 9 | 8 | 3 | 5 | 25 | 14 | 11 | 8 | 7 | 40 |
| TUBA1C | 0 | 1 | 1 | 0 | 1 | 3 | 20 | 19 | 18 | 19 | 76 |
| TUBB2B | 0 | 4 | 3 | 1 | 2 | 10 | 16 | 18 | 15 | 17 | 66 |
| TMEM109 | 0 | 1 | 1 | 0 | 1 | 3 | 2 | 1 | 0 | 1 | 4 |
| NACAP1 | 0 | 0 | 0 | 1 | 0 | 1 | 0 | 0 | 0 | 0 | 0 |
| OLA1 | 0 | 1 | 1 | 0 | 0 | 2 | 0 | 0 | 0 | 1 | 1 |
| IGF2BP1 | 0 | 4 | 8 | 4 | 6 | 22 | 8 | 7 | 4 | 6 | 25 |
| STOML2 | 0 | 5 | 4 | 2 | 2 | 13 | 8 | 8 | 2 | 3 | 21 |
| EIF3L | 0 | 9 | 7 | 6 | 4 | 26 | 9 | 11 | 7 | 8 | 35 |
| NUDC | 0 | 0 | 1 | 0 | 0 | 1 | 0 | 0 | 0 | 0 | 0 |
| CNPY2 | 0 | 1 | 0 | 0 | 0 | 1 | 0 | 0 | 0 | 0 | 0 |

The results clearly indicate that MTH1 (gene name NUDT1) is the main target of (S)-crizotinib in SW480 cells, a colon carcinoma cell line expressing mutant KRAS highlighting the specificity of the compound.

Example 8

Anti-cancer Specificity

To further evaluate the anti-cancer specificity of the (S)-enantiomer of crizotinib in vitro, various isogenic BJ fibroblast cell lines were treated with several concentrations of the (S)-enantiomer of crizotinib in colony formation assays. The investigated cell line panel comprised non-transformed ("wildtype") cells, cells immortalized with telomerase (hTERT), cells transformed with hTERT and SV40 Large T antigen (SV40T), and cells transformed with hTERT, SV40T, and the KRAS mutant V12 (FIG. 28).

The data suggest that (S)-crizotinib is more toxic to transformed cells than to wildtype cells or cells which are only immortalized by telomerase thus underscoring a cancer-specific effect.

Example 9

Inhibition of MTH1-catalytic Activity by the (S)-enantiomer of Crizotinib is not Substrate-dependent It is known that MTH1 does not only hydrolyse 8-oxo-dGTP but also is able to cleave another potentially mutagenic DNA precursor, 2-hydroxy-deoxyadenosine triphosphate (2-OH-dATP) (Fujikawa (1999) Journal of Biological Chemistry 274, 18201-18205). Therefore we investigated whether the (S)-enantiomer of crizotinib affects hydrolysis of 2-OH-dATP by MTH1 in vitro using the previously described luciferase-based PPiLight assay. As shown in FIG. 29, the (S)-enantiomer of crizotinib also inhibits hydrolysis 2-OH-dATP by MTH1 in a dose-dependent manner.

Example 10

Effect of p53-/p21-status and Mismatch Repair Pathways on the Activity of the (S)-enantiomer of Crizotinib The tumor suppressor gene p53 is mutated or defective in a large number of various cancer types and can impact therapeutic outcome. Therefore we examined how p53 function and its downstream mediator p21 might affect the anticancer activity of the (S)-enantiomer of crizotinib in mutant KRAS HCT116 colon carcinoma cells. Furthermore, as inhibition of MTH1 is supposed to induce mispairing of base during DNA replication we sought to evaluate how deficiencies in mismatch repair genes such as MLH1 might alter sensitivity toward the (S)-enantiomer of crizotinib using the established HCT116 isogenic cell line system (FIG. 30). HCT116 wildtype cells have functional p53 but are deficient in MLH1 whereas the derivative HCT116+chr3 has a functional MLH1 gene due to chromosomal transfer.

The results indicate that p53 status and presence or absence of functional MLH1 do not affect the activity of the (S)-enantiomer of crizotinib. However, loss of p21 seems to increase the sensitivity of HCT116 cells toward treatment with the (S)-enantiomer of crizotinib.

Example 11

Induction of DNA Damage as a Result of MTH1 Inhibition

Since MTH1 is thought to sanitise the nucleotide pool of oxidised nucleotides including 8-oxo-dGTP, thereby preventing its incorporation into DNA, we reasoned that inhibition of MTH1 enzymatic function should increase the content of 8-oxo-guanine in DNA. Indeed, treatment of BJ fibroblasts with (S)-, but not (R)-crizotinib, increased staining of an anti-8-oxo-guanine mouse monoclonal antibody. At the same time, staining for 53BP1, a specific marker for DNA damage, was increased, which was in line with the effect observed for anti-MTH1 siRNA (FIG. 31).

Consequently, this should in turn activate DNA repair mechanisms and induce the formation of single strand breaks due to activated base excision repair (BER). To test this we investigated the (S)-enantiomer of crizotinib in an alkaline comet assay, which reveals DNA single strand breaks by single cell electrophoresis. Using SW480 cells we found that both (S)-crizotinib, but not (R)-crizotinib, yielded a significant tail moment in the comet assay. We also observed an increase of ATM phosphorylation indicating DNA damage pathway activation again demonstrating an (S)-crizotinib-specific effect (FIG. 32).

SUMMARY

Taken together, the data indicate that crizotinib, more preferably racemic crizotinib, and even more preferably the pure (S)-enantiomer of crizotinib are highly potent inhibitors of MTH1, an enzyme which has been linked to the development, progression and maintenance of RAS-driven cancer.[13] This is of particular interest as a) small molecule inhibitors of MTH1 have not been reported so far, b) patients who are to be treated with crizotinib are selected by their c-Met-, or more preferably, ALK-expression status whilst not considering MTH1, and c) introduction of aminoalkyl substituents at the piperidine nitrogen of crizotinib is well tolerated with respect to both ALK and MTH1 inhibition. Thus, also compounds prepared by the procedures described in WO2008053157 are potent and bioavailable MTH1 inhibitors.

Based on the physiological effects of MTH1 suppression, MTH1 inhibitors are concluded to synergise with DNA damaging compounds, compounds which interfere with DNA repair mechanisms, or compounds which induce the production or inhibit the clearance of ROS. Furthermore, MTH1 inhibitors are concluded to exhibit synthetic lethalities with tumours bearing lesions in DNA repair pathway genes or which produce considerable amounts of ROS. For example, breast cancer cells deficient in the genes BRCA1 or BRCA2 which have been associated with repair of 8-oxo-G lesions[17] are particularly sensitive towards oxidative DNA damage.[18] Recently, it has been shown that MTH1 specifically assists RAS-induced tumours in preventing tumour-suppressive effects such as senescence whilst enabling maintenance and progression of the tumour. Therefore, MTH1 inhibition, may help in impairing tumour growth by abrogating mitogenic signalling, epithelial-mesenchymal transition (EMT), a hallmark of progressing and aggressive tumours, anoikis inhibition and PI3K/Akt-mediated pro-survival signalling.[19] Recent data also suggests that MTH1 might be a promising target for adenocarcinomas expressing EGFR as the micro-RNA MiR-145 which suppresses both EGFR and MTH1 is downregulated in these tumours.[37] Reexpression of MiR-145 led to a downregulation of EGFR and MTH1 on both mRNA and protein level and impaired the growth of EGFR-positive cell lines. In summary, crizotinib and its enantiomers as well as structural derivatives thereof can be applied to the treatment of a variety of distinct tumour types apart from ALK/Met-driven lung cancer but also RAS-driven lung or breast cancer, colon cancer, pancreatic cancer, Ewing's sarcoma and many more.

The present invention refers to the following nucleotide and amino acid sequences:

1. Sequences Relating to NUDT1/MTH1

1.1 NM_002452.3→NP_002443.3 7,8-dihydro-8-oxoguanine triphosphatase isoform p18:
   Description
   Transcript Variant: This variant (1) encodes the predominant isoform (p18, also known as MTH1d). Variants 1, 2A, 3A, and 4A encode the same isoform.
   SEQ ID No. 1: Nucleotide Sequence (471 nt) of NUDT1/MTH1, Isoform p18, Transcript Variant (1)
   SEQ ID No. 2: Amino Acid Sequence (156 aa) of NUDT1/MTH1, Isoform p18, Transcript Variant (1)

1.2 NM_198948.1→NP_945186.1 7,8-dihydro-8-oxoguanine triphosphatase isoform p18:
   Description
   Transcript Variant: This variant (2A) differs in the 5' UTR compared to variant 1. Variants 1, 2A, 3A, and 4A encode the same isoform (p18, also known as MTH1d).
   SEQ ID No. 3: Nucleotide Sequence (471 nt) of NUDT1/MTH1, Isoform p18, Transcript Variant (2A)
   SEQ ID No. 4: Amino Acid Sequence (156 aa) of NUDT1/MTH1, Isoform p18, Transcript Variant (2A)

1.3 NM_198949.1→NP_945187.1 7,8-dihydro-8-oxoguanine triphosphatase isoform p22:
   Description
   Transcript Variant: This variant (2B) differs in the 5' UTR and 5' coding region compared to variant 1, resulting in translation initiation at an upstream ATG and an isoform (p22, also known as MTH1b) with a longer N-terminus compared to isoform p18. Variants 2B, 3B, and 4B encode the same isoform.
   SEQ ID No. 5: Nucleotide Sequence (540 nt) of NUDT1/MTH1, Isoform p22, Transcript Variant (2B)
   SEQ ID No. 6: Amino Acid Sequence (179 aa) of NUDT1/MTH1, Isoform p22, Transcript Variant (2B)

1.4 NM_198950.1→NP_945188.1 7,8-dihydro-8-oxoguanine triphosphatase isoform p18:
   Description
   Transcript Variant: This variant (3A) differs in the 5' UTR compared to variant 1. Variants 1, 2A, 3A, and 4A encode the same isoform (p18, also known as MTH1d).
   SEQ ID No. 7: Nucleotide Sequence (471 nt) of NUDT1/MTH1, Isoform p18, Transcript Variant (3A)
   SEQ ID No. 8: Amino Acid Sequence (156 aa) of NUDT1/MTH1, Isoform p18, Transcript Variant (3A)

1.5 NM_198952.1→NP_945190.1 7,8-dihydro-8-oxoguanine triphosphatase isoform p22:
   Description
   Transcript Variant: This variant (3B) differs in the 5' UTR and 5' coding region compared to variant 1, resulting in translation initiation at an upstream ATG and an isoform (p22, also known as MTH1b) with a longer N-terminus compared to isoform p18. Variants 2B, 3B, and 4B encode the same isoform.
   SEQ ID No. 9: Nucleotide Sequence (540 nt) of NUDT1/MTH1, Isoform p22, Transcript Variant (3B)
   SEQ ID No. 10: Amino Acid Sequence (179 aa) of NUDT1/MTH1, Isoform p22, Transcript Variant (3B)

1.6 NM_198953.1→NP_945191.1 7,8-dihydro-8-oxoguanine triphosphatase isoform p18:
   Description
   Transcript Variant: This variant (4A) differs in the 5' UTR compared to variant 1. Variants 1, 2A, 3A, and 4A encode the same isoform (p18, also known as MTH1d).
   SEQ ID No. 11: Nucleotide Sequence (471 nt) of NUDT1/MTH1, Isoform p18, Transcript Variant (4A)
   SEQ ID No. 12: Amino Acid Sequence (156 aa) of NUDT1/MTH1, Isoform p18, Transcript Variant (4A)

1.7 NM_198954.1→NP_945192.1 7,8-dihydro-8-oxoguanine triphosphatase isoform p22:
   Description
   Transcript Variant: This variant (4B) differs in the 5' UTR and 5' coding region compared to variant 1, resulting in translation initiation at an upstream ATG and an isoform (p22, also known as MTH1b) with a longer N-terminus compared to isoform p18. Variants 2B, 3B, and 4B encode the same isoform.
   SEQ ID No. 13: Nucleotide Sequence (540 nt) of NUDT1/MTH1, Isoform p22, Transcript Variant (4B)
   SEQ ID No. 14: Amino Acid Sequence (179 aa) of NUDT1/MTH1, Isoform p22, Transcript Variant (4B)
   SEQ ID No. 15: Amino Acid Sequence of NUDT1/MTH1, p26 isoform
   >sp|P36639|8ODP_HUMAN 7,8-dihydro-8-oxoguanine triphosphatase OS=*Homo sapiens* GN=NUDT1 PE=1 SV=3
   SEQ ID No. 16: Amino Acid Sequence of NUDT1/MTH1, p21 isoform >sp|P36639-3|8ODP_HUMAN Isoform p21 of 7,8-di-hydro-8-oxoguanine triphosphatase OS=*Homo sapiens* GN=NUDT1

Primer Sequences:

SEQ ID No. 17: Primer Sequence for the Detection of NUDT1/MTH1

(Corresponding to bases 97-116 of the human MTH1 sequence published in Sakumi (1993) Journal of Biological Chemistry 268: 23524-30.))

5P-AGCCTCAGCGAGTTCTCCTG-3P

SEQ ID No. 18: Primer Sequence for the Detection of NUDT1/MTH1

(Corresponding to bases 248-266 of the human MTH1 sequence published in Sakumi (1993) Journal of Biological Chemistry 268: 23524-30.))

5P-GATCTGGCCCACCTTGTGC-3P

2. Sequences Relating to KRAS 2.1 NM_004985.3→NP_004976.2 GTPase KRas isoform b precursor:

Description

Transcript Variant: This variant (b) is composed of five exons and lacks exon 4a which the longer transcript variant (a) includes. This predominant variant (b) has a cds that terminates in exon 4b and encodes isoform b.

SEQ ID No. 19: Nucleotide Sequence (567 nt) of KRAS, Isoform b precursor, Transcript Variant (b)

SEQ ID No. 20: Amino Acid Sequence (188 aa) of KRAS, Isoform b precursor, Transcript Variant (b)

2.2 NM_033360.2→NP_203524.1 GTPase KRas isoform a precursor:

Description

Transcript Variant: This variant (a) is composed of six exons, including exon 4a, which the shorter transcript variant (b) lacks. This rare variant (a) has a cds that terminates in exon 4a and encodes a unique C-terminus, compared to isoform a.

SEQ ID No. 21: Nucleotide Sequence (570 nt) of KRAS, Isoform a precursor, Transcript Variant (a)

SEQ ID No. 22: Amino Acid Sequence (189 aa) of KRAS, Isoform a precursor, Transcript Variant (a)

KRAS Sequence Annotation

In this Sequence Annotation, common mutations of KRAS are indicated by the term "variant".

```
FT   CHAIN        1  186 GTPase KRas.
FT                      /FTId=PRO_0000082641.
FT   INIT_MET     1    1 Removed; alternate.
FT   CHAIN        2  186 GTPase KRas, N-terminally processed.
FT                      /FTId=PRO_0000326480.
FT   PROPEP     187  189 Removed in mature form.
FT                      /FTId=PRO_0000281291.
FT   NP_BIND     10   17 GTP.
FT   NP_BIND     57   61 GTP.
FT   NP_BIND    116  119 GTP.
FT   REGION     166  185 Hypervariable region.
FT   MOTIF       32   40 Effector region.
FT   MOD_RES      1    1 N-acetylmethionine; in GTPase KRas;
FT                      alternate.
FT   MOD_RES      2    2 N-acetylthreonine; in GTPase KRas, N-
FT                      terminally processed.
FT   MOD_RES    186  186 Cysteine methyl ester.
FT   LIPID      180  180 S-palmitoyl cysteine.
FT   LIPID      186  186 S-farnesyl cysteine.
FT   VAR_SEQ    151  153 RVE -> GVD (in isoform 2B).
FT                      /FTId=VSP_011140.
FT   VAR_SEQ    165  189 QYRLKKISKEEKTPGCVKIKKCIIM ->
FT                      KHKEKMSKDGKKKKKKSKTKCVIM
FT                      (in isoform 2B).
FT                      /FTId=VSP_011141.
FT   VARIANT      5    5 K -> E (in NS3).
FT                      /FTId=VAR_065144.
FT   VARIANT      5    5 K -> N (in GASC; found also in a patient
FT                      with Costello syndrome; exhibits only
FT                      minor alterations in its in vitro
FT                      biochemical behavior compared to wild-
FT                      type protein).
FT                      /FTId=VAR_064849.
FT   VARIANT     10   10 G -> GG (in one individual with AML;
FT                      expression in 3T3 cell causes cellular
FT                      transformation; expression in COS cells
FT                      activates the Ras-MAPK signaling pathway;
FT                      lower GTPase activity; faster GDP
FT                      dissociation rate).
FT                      /FTId=VAR_034601.
FT   VARIANT     12   12 G -> A (in a colorectal cancer sample;
FT                      somatic mutation).
FT                      /FTId=VAR_036305.
FT   VARIANT     12   12 G -> C (in lung carcinoma; somatic
FT                      mutation).
FT                      /FTId=VAR_006839.
FT   VARIANT     12   12 G -> D (in pancreatic carcinoma, GASC and
FT                      lung carcinoma; somatic mutation).
FT                      /FTId=VAR_016026.
FT   VARIANT     12   12 G -> R (in lung cancer and bladder
FT                      cancer; somatic mutation).
FT                      /FTId=VAR_016027.
FT   VARIANT     12   12 G -> S (in lung carcinoma and GASC;
FT                      somatic mutation).
FT                      /FTId=VAR_016028.
FT   VARIANT     12   12 G -> V (in lung carcinoma, pancreatic
FT                      carcinoma, colon cancer and GASC; somatic
FT                      mutation).
FT                      /FTId=VAR_006840.
FT   VARIANT     13   13 G -> D (in a breast carcinoma cell line
FT                      and GASC; somatic mutation).
FT                      /FTId=VAR_016029.
FT   VARIANT     13   13 G -> R (in pylocytic astrocytoma; somatic
FT                      mutation; increase activation of the Ras
FT                      pathway).
FT                      /FTId=VAR_065145.
FT   VARIANT     14   14 V -> I (in NS3; affects activity and
FT                      impairs responsiveness to GTPase
FT                      activating proteins; characterized by a
FT                      strong increase of both intrinsic and
FT                      guanine nucleotide exchanged factor-
FT                      catalyzed nucleotide exchange leading to
FT                      an increased level of the activated
FT                      state).
FT                      /FTId=VAR_026109.
FT   VARIANT     22   22 Q -> E (in CFC syndrome; exhibits an
FT                      increase in intrinsic and guanine
FT                      nucleotide exchange factor catalyzed
FT                      nucleotide exchange in combination with
FT                      an impaired GTPase-activating protein-
FT                      stimulated GTP hydrolysis but functional
FT                      in interaction with effectors).
FT                      /FTId=VAR_064850.
FT   VARIANT     22   22 Q -> R (in NS3; impairs GTPase-activating
FT                      protein stimulated GTP hydrolysis with
FT                      unaffected intrinsic functions and a
FT                      virtually functional effector
FT                      interaction).
FT                      /FTId=VAR_064851.
FT   VARIANT     34   34 P -> L (in NS3; characterized by a
FT                      defective GTPase-activating protein
FT                      sensitivity and a strongly reduced
FT                      interaction with effectors).
FT                      /FTId=VAR_064852.
FT   VARIANT     34   34 P -> Q (in NS3).
FT                      /FTId=VAR_064853.
FT   VARIANT     34   34 P -> R (in CFC syndrome; characterized by
FT                      a defective GTPase-activating protein
FT                      sensitivity and a strongly reduced
FT                      interaction with effectors).
FT                      /FTId=VAR_026110.
FT   VARIANT     36   36 I -> M (in NS3).
FT                      /FTId=VAR_064854.
FT   VARIANT     58   58 T -> I (in NS3; affects activity and
FT                      impairs responsiveness to GTPase
```

| | | | |
|---|---|---|---|
| FT | | | activating proteins; exhibits only minor |
| FT | | | alterations in its in vitro biochemical |
| FT | | | behavior compared to wild-type protein). |
| FT | | | /FTId=VAR_026111. |
| FT | VARIANT | 59 | 59 A -> T (in bladder cancer and GASC; |
| FT | | | somatic mutation). |
| FT | | | /FTId=VAR_016030. |
| FT | VARIANT | 60 | 60 G -> R (in CFC syndrome; characterized by |
| FT | | | a defective GTPase-activating protein |
| FT | | | sensitivity and a strongly reduced |
| FT | | | interaction with effectors). |
| FT | | | /FTId=VAR_026112. |
| FT | VARIANT | 60 | 60 G -> S (in NS3). |
| FT | | | /FTId=VAR_065146. |
| FT | VARIANT | 61 | 61 Q -> H (in lung carcinoma; |
| FT | | | dbSNP:rs17851045). |
| FT | | | /FTId=VAR_006841. |
| FT | VARIANT | 61 | 61 Q -> R (in a colorectal cancer sample; |
| FT | | | somatic mutation). |
| FT | | | /FTId=VAR_036306. |
| FT | VARIANT | 117 | 117 K -> N (in a colorectal cancer sample; |
| FT | | | somatic mutation). |
| FT | | | /FTId=VAR_036307. |
| FT | VARIANT | 146 | 146 A -> T (in a colorectal cancer sample; |
| FT | | | somatic mutation). |
| FT | | | /FTId=VAR_036308. |
| FT | MUTAGEN | 164 | 164 R -> A: Loss of GTP-binding activity. |
| FT | STRAND | 2 | 9 |
| FT | HELIX | 16 | 25 |
| FT | STRAND | 36 | 46 |
| FT | STRAND | 49 | 58 |
| FT | HELIX | 68 | 74 |
| FT | STRAND | 76 | 83 |
| FT | HELIX | 87 | 103 |
| FT | STRAND | 111 | 116 |
| FT | STRAND | 120 | 122 |
| FT | HELIX | 127 | 137 |
| FT | STRAND | 141 | 143 |
| FT | TURN | 146 | 148 |
| FT | HELIX | 152 | 164 |

SEQ ID No. 23: Amino Acid Sequence of Mutant KRAS (G12C KRAS)

3. Sequences Relating to HRAS 3.1 NM_001130442.1→NP_001123914.1 GTPase HRas isoform 1:

Description

Transcript Variant: This variant (3) differs in the 3' UTR, compared to variant 1. Variants 1 and 3 encode the same protein.

SEQ ID No. 24: Nucleotide Sequence (570 nt) of HRAS, Isoform 1, Transcript Variant (3)

SEQ ID No. 25: Amino Acid Sequence (189 aa) of HRAS, Isoform 1, Transcript Variant (3)

3.2 NM_005343.2→NP_005334.1 GTPase HRas isoform 1:

Description

Transcript Variant: This variant (1) encodes the longer isoform (1). Variants 1 and 3 encode the same protein.

SEQ ID No. 26: Nucleotide Sequence (570 nt) of HRAS, Isoform 1, Transcript Variant (1)

SEQ ID No. 27: Amino Acid Sequence (189 aa) of HRAS, Isoform 1, Transcript Variant (1)

3.3 NM_176795.3→NP_789765.1 GTPase HRas isoform 2:

Description

Transcript Variant: This variant (2) differs in the 3' UTR and includes an alternate exon in its 3' coding region, compared to variant 1. The resulting isoform (2) contains a distinct C-terminus and is shorter than isoform 1.

SEQ ID No. 28: Nucleotide Sequence (513 nt) of HRAS, Isoform 2, Transcript Variant (2)

SEQ ID No. 29: Amino Acid Sequence (170 aa) of HRAS, Isoform 2, Transcript Variant (2)

HRAS Sequence Annotation

In this Sequence Annotation, common mutations of HRAS are indicated by the term "variant".

| | | | |
|---|---|---|---|
| FT | CHAIN | 1 | 186 GTPase HRas. |
| FT | | | /FTId=PRO_0000042996. |
| FT | INIT_MET | 1 | 1 Removed; alternate. |
| FT | CHAIN | 2 | 186 GTPase HRas, N-terminally processed. |
| FT | | | /FTId=PRO_0000326476. |
| FT | PROPEP | 187 | 189 Removed in mature form. |
| FT | | | /FTId=PRO_0000042997. |
| FT | NP_BIND | 10 | 17 GTP. |
| FT | NP_BIND | 57 | 61 GTP. |
| FT | NP_BIND | 116 | 119 GTP. |
| FT | REGION | 166 | 185 Hypervariable region. |
| FT | MOTIF | 32 | 40 Effector region. |
| FT | MOD_RES | 1 | 1 N-acetylmethionine; in GTPase HRas; |
| FT | | | alternate. |
| FT | MOD_RES | 2 | 2 N-acetylthreonine; in GTPase HRas, N- |
| FT | | | terminally processed. |
| FT | MOD_RES | 118 | 118 S-nitrosocysteine. |
| FT | MOD_RES | 186 | 186 Cysteine methyl ester. |
| FT | LIPID | 181 | 181 S-palmitoyl cysteine. |
| FT | LIPID | 184 | 184 S-(15-deoxy-Delta12,14-prostaglandin J2- |
| FT | | | 9-yl)cysteine; alternate. |
| FT | LIPID | 184 | 184 S-palmitoyl cysteine; alternate. |
| FT | LIPID | 186 | 186 S-farnesyl cysteine. |
| FT | VAR_SEQ | 152 | 189 VEDAFYTLVREIRQHKLRKLNPPDESGPGCMSCKCVLS -> |
| FT | | | SRSGSSSSSGTLWDPPGPM (in isoform 2). |
| FT | | | /FTId=VSP_041597. |
| FT | VARIANT | 12 | 12 G -> A (in FCSS). |
| FT | | | /FTId=VAR_026106. |
| FT | VARIANT | 12 | 12 G -> C (in FCSS). |
| FT | | | /FTId=VAR_045975. |
| FT | VARIANT | 12 | 12 G -> E (in FCSS). |
| FT | | | /FTId=VAR_045976. |
| FT | VARIANT | 12 | 12 G -> S (in FCSS, OSCC and CMEMS). |
| FT | | | /FTId=VAR_006837. |
| FT | VARIANT | 12 | 12 G -> V (in FCSS, bladder carcinoma and |

```
FT                    CMEMS; constitutively activated;
FT                    interacts and recruits PLCE1 to plasma
FT                    membrane; loss of interaction with and
FT                    recruitment to plasma membrane of PLCE1
FT                    when associated with F-32; loss of
FT                    interaction with PLCE1 when associated
FT                    with G-26, F-32 and S-35; no effect on
FT                    interaction with PLCE1 when associated
FT                    with A-29, G-34, G-37, N-38 and C-39; no
FT                    effect on subcellular location of isoform
FT                    2).
FT                    /FTId=VAR_006836.
FT   VARIANT    13   13 G -> C (in FCSS).
FT                    /FTId=VAR_026107.
FT   VARIANT    13   13 G -> D (in FCSS).
FT                    /FTId=VAR_026108.
FT   VARIANT    22   22 Q -> K (in CMEMS).
FT                    /FTId=VAR_045977.
FT   VARIANT    58   58 T -> I (in FCSS).
FT                    /FTId=VAR_045978.
FT   VARIANT    61   61 Q -> K (in follicular thyroid carcinoma
FT                    samples; somatic mutation; increases
FT                    transformation of cultured cell lines;
FT                    dbSNP:rs28933406).
FT                    /FTId=VAR_045979.
FT   VARIANT    61   61 Q -> L (in melanoma; strongly reduced GTP
FT                    hydrolysis in the presence of RAF1;
FT                    increases transformation of cultured cell
FT                    lines).
FT                    /FTId=VAR_006838.
FT   VARIANT    63   63 E -> K (in CMEMS).
FT                    /FTId=VAR_045980.
FT   VARIANT   117  117 K -> R (in FCSS).
FT                    /FTId=VAR_045981.
FT   VARIANT   146  146 A -> T (in FCSS).
FT                    /FTId=VAR_045982.
FT   VARIANT   146  146 A -> V (in FCSS).
FT                    /FTId=VAR_045983.
FT   MUTAGEN    17   17 S->N: Dominant negative. Prevents PLCE1
FT                    EGF-induced recruitment to plasma
FT                    membrane. No effect on subcellular
FT                    location of isoform 2.
FT   MUTAGEN    26   26 N->G: Loss of interaction with PLCE1;
FT                    when associated with V-12.
FT   MUTAGEN    29   29 V->A: No effect on interaction with
FT                    PLCE1; when associated with V-12.
FT   MUTAGEN    32   32 Y->F: Loss of interaction and recruitment
FT                    to plasma membrane of PLCE1; when
FT                    associated with V-12.
FT   MUTAGEN    34   34 P->G: No effect on interaction with
FT                    PLCE1; when associated with V-12.
FT   MUTAGEN    35   35 T->S: Loss of interaction with PLCE1;
FT                    when associated with V-12.
FT   MUTAGEN    37   37 E->G: No effect on interaction with
FT                    PLCE1; when associated with V-12.
FT   MUTAGEN    38   38 D->N: No effect on interaction with
FT                    PLCE1; when associated with V-12.
FT   MUTAGEN    39   39 S->C: No effect on interaction with
FT                    PLCE1; when associated with V-12.
FT   MUTAGEN    59   59 A->T: Loss of GTPase activity and
FT                    creation of an autophosphorylation site.
FT   MUTAGEN    61   61 Q->I: Moderately increased transformation
FT                    of cultured cell lines.
FT   MUTAGEN    61   61 Q->V: Strongly increased transformation
FT                    of cultured cell lines.
FT   MUTAGEN    83   83 A->T: GTP-binding activity reduced by
FT                    factor of 30.
FT   MUTAGEN   118  118 C->S: Abolishes S-nitrosylation. No
FT                    stimulation of guanine nucleotide
FT                    exchange.
FT   MUTAGEN   119  119 D->N: Loss of GTP-binding activity.
FT   MUTAGEN   144  144 T->I: GTP-binding activity reduced by
FT                    factor of 25.
FT   MUTAGEN   164  165 RQ->AV: Loss of GTP-binding activity.
FT   MUTAGEN   181  181 C->S: Exclusively localized in Golgi.
FT                    Non-specifically localized on all
FT                    endomembranes; when associated with S-
FT                    184.
FT   MUTAGEN   184  184 C->S: Loss of S-(15-deoxy-Delta12,14-
```

| FT |  |  | prostaglandin J2-9-yl)cysteine |
|---|---|---|---|
| FT |  |  | stimulation of Ras-GTPase activity. |
| FT |  |  | Mainly localized in Golgi. Non- |
| FT |  |  | specifically localized on all |
| FT |  |  | endomembranes; when associated with S- |
| FT |  |  | 181. |
| FT | STRAND | 3 | 11 |
| FT | STRAND | 12 | 14 |
| FT | HELIX | 16 | 25 |
| FT | STRAND | 27 | 31 |
| FT | STRAND | 38 | 46 |
| FT | STRAND | 49 | 57 |
| FT | STRAND | 60 | 63 |
| FT | HELIX | 66 | 74 |
| FT | STRAND | 76 | 83 |
| FT | TURN | 84 | 86 |
| FT | HELIX | 87 | 104 |
| FT | STRAND | 105 | 107 |
| FT | STRAND | 111 | 116 |
| FT | STRAND | 120 | 122 |
| FT | HELIX | 127 | 136 |
| FT | STRAND | 141 | 144 |
| FT | TURN | 146 | 148 |
| FT | HELIX | 152 | 164 |

Sequences Relating to NRAS 3.4 NM_002524.4→NP_002515.1 GTPase NRas:

SEQ ID No. 30: Nucleotide Sequence (570 nt) of NRAS

SEQ ID No. 31: Amino Acid Sequence (189 aa) of NRAS

NRAS Sequence Annotation

In this Sequence Annotation, common mutations of NRAS are indicated by the term "variant".

| FT | CHAIN | 1 | 186 GTPase NRas. |
|---|---|---|---|
| FT |  |  | /FTId=PRO_0000043006. |
| FT | PROPEP | 187 | 189 Removed in mature form (By similarity). |
| FT |  |  | /FTId=PRO_0000043007. |
| FT | NP_BIND | 10 | 17 GTP. |
| FT | NP_BIND | 57 | 61 GTP. |
| FT | NP_BIND | 116 | 119 GTP. |
| FT | REGION | 166 | 185 Hypervariable region. |
| FT | MOTIF | 32 | 40 Effector region. |
| FT | MOD_RES | 2 | 2 Phosphothreonine. |
| FT | MOD_RES | 4 | 4 Phosphotyrosine. |
| FT | MOD_RES | 186 | 186 Cysteine methyl ester (By similarity). |
| FT | LIPID | 181 | 181 S-palmitoyl cysteine. |
| FT | LIPID | 186 | 186 S-farnesyl cysteine. |
| FT | VARIANT | 12 | 12 G -> C (in leukemia). |
| FT |  |  | /FTId=VAR_021194. |
| FT | VARIANT | 13 | 13 G -> D (in ALPS4). |
| FT |  |  | /FTId=VAR_063084. |
| FT | VARIANT | 13 | 13 G -> R (in colorectal cancer). |
| FT |  |  | /FTId=VAR_006845. |
| FT | VARIANT | 50 | 50 T -> I (in NS6; hypermorphic mutation). |
| FT |  |  | /FTId=VAR_063085. |
| FT | VARIANT | 60 | 60 G -> E (in NS6; hypermorphic mutation). |
| FT |  |  | /FTId=VAR_063086. |
| FT | VARIANT | 61 | 61 Q -> K (in neuroblastoma cell). |
| FT |  |  | /FTId=VAR_006846. |
| FT | VARIANT | 61 | 61 Q -> R (in lung carcinoma cell and melanoma; dbSNP:rs11554290). |
| FT |  |  | /FTId=VAR_006847. |
| FT | MUTAGEN | 164 | 164 R-> A: Loss of GTP-binding activity. |
| FT | STRAND | 2 | 9 |
| FT | HELIX | 16 | 25 |
| FT | STRAND | 38 | 46 |
| FT | STRAND | 49 | 57 |
| FT | STRAND | 76 | 83 |
| FT | HELIX | 87 | 104 |
| FT | STRAND | 111 | 116 |
| FT | HELIX | 127 | 137 |
| FT | STRAND | 141 | 143 |
| FT | TURN | 146 | 148 |
| FT | HELIX | 152 | 166 |

4. Sequences Relating to ALK 4.1 NM_004304.4→NP_004295.2 ALK tyrosine kinase receptor precursor:

SEQ ID No. 32:__ Nucleotide Sequence (4863 nt) of ALK tyrosine kinase receptor precursor SEQ ID No. 33: Amino Acid Sequence (1620 aa) of ALK tyrosine kinase receptor precursor Aberrations of ALK

| CC | -!- | DISEASE: Note = A chromosomal aberration involving ALK is |
|---|---|---|
| CC |  | found in a form of non-Hodgkin lymphoma. Translocation t(2;5) |
| CC |  | (p23;q35) with NPM1. The resulting chimeric NPM1-ALK protein |
| CC |  | homodimerize and the kinase becomes constitutively activated. |
| CC |  | The constitutively active fusion proteins are responsible for 5-10% |
| CC |  | of non-Hodgkin lymphomas. |
| CC | -!- | DISEASE: Note = A chromosomal aberration involving ALK is |
| CC |  | associated with inflammatory myofibroblastic tumors (IMTs). |
| CC |  | Translocation t(2;11) (p23;p15) with CARS; translocation t(2;4) |
| CC |  | (p23;q21) with SEC31A. |
| CC | -!- | DISEASE: Note = A chromosomal aberration involving ALK |
| CC |  | is associated with anaplastic large-cell lymphoma (ALCL). |
| CC |  | Translocation t(2;17) (p23;q25) with ALO17. |
| CC | -!- | DISEASE: Defects in ALK are the cause of susceptibility to |
| CC |  | neuroblastoma type 3 (NBLST3) [MIM:613014]. Neuroblastoma |
| CC |  | is a common neoplasm of early childhood arising from embryonic |
| CC |  | cells that form the primitive neural crest and give rise to the |
| CC |  | adrenal medulla and the sympathetic nervous system. |
| CC | -!- | DISEASE: Note = The ALK signaling pathway plays an important |
| CC |  | role in glioblastoma, the most common malignant brain tumor of |
| CC |  | adults and one of the most lethal cancers. It regulates both |
| CC |  | glioblastoma migration and growth. |

ALK Sequence Annotation

In this Sequence Annotation, common mutations of ALK are indicated by the term "variant".

```
FT   SIGNAL        1      18  Potential.
FT   CHAIN        19    1620  ALK tyrosine kinase receptor.
FT                             /FTId=PRO_0000016740.
FT   TOPO_DOM     19    1038  Extracellular (Potential).
FT   TRANSMEM   1039    1059  Helical; (Potential).
FT   TOPO_DOM   1060    1620  Cytoplasmic (Potential).
FT   DOMAIN      264     427  MAM 1.
FT   DOMAIN      437     473  LDL-receptor class A.
FT   DOMAIN      478     636  MAM 2.
FT   DOMAIN     1116    1392  Protein kinase.
FT   NP_BIND    1197    1199  ATP.
FT   REGION     1197    1199  Inhibitor binding.
FT   COMPBIAS    816     940  Gly-rich.
FT   ACT_SITE   1249    1249  Proton acceptor (By similarity).
FT   BINDING    1124    1124  ATP; via carbonyl oxygen.
FT   BINDING    1150    1150  ATP (By similarity).
FT   BINDING    1150    1150  Inhibitor.
FT   BINDING    1199    1199  Inhibitor; via amide nitrogen.
FT   BINDING    1203    1203  Inhibitor.
FT   BINDING    1210    1210  Inhibitor.
FT   BINDING    1270    1270  ATP.
FT   MOD_RES     211     211  Phosphoserine.
FT   MOD_RES    1078    1078  Phosphotyrosine.
FT   MOD_RES    1092    1092  Phosphotyrosine.
FT   MOD_RES    1096    1096  Phosphotyrosine.
FT   MOD_RES    1131    1131  Phosphotyrosine.
FT   MOD_RES    1278    1278  Phosphotyrosine.
FT   MOD_RES    1282    1282  Phosphotyrosine; by autocatalysis.
FT   MOD_RES    1283    1283  Phosphotyrosine.
FT   MOD_RES    1359    1359  Phosphotyrosine.
FT   MOD_RES    1507    1507  Phosphotyrosine.
FT   MOD_RES    1584    1584  Phosphotyrosine.
FT   MOD_RES    1604    1604  Phosphotyrosine.
FT   CARBOHYD    169     169  N-linked (GlcNAc...) (Potential).
FT   CARBOHYD    244     244  N-linked (GlcNAc...) (Potential).
FT   CARBOHYD    285     285  N-linked (GlcNAc...) (Potential).
FT   CARBOHYD    324     324  N-linked (GlcNAc...) (Potential).
FT   CARBOHYD    411     411  N-linked (GlcNAc...) (Potential).
FT   CARBOHYD    424     424  N-linked (GlcNAc...) (Potential).
FT   CARBOHYD    445     445  N-linked (GlcNAc...) (Potential).
FT   CARBOHYD    563     563  N-linked (GlcNAc...) (Potential).
FT   CARBOHYD    571     571  N-linked (GlcNAc...) (Potential).
FT   CARBOHYD    627     627  N-linked (GlcNAc...) (Potential).
FT   CARBOHYD    709     709  N-linked (GlcNAc...) (Potential).
FT   CARBOHYD    808     808  N-linked (GlcNAc...) (Potential).
FT   CARBOHYD    863     863  N-linked (GlcNAc...) (Potential).
FT   CARBOHYD    864     864  N-linked (GlcNAc...) (Potential).
FT   CARBOHYD    886     886  N-linked (GlcNAc...) (Potential).
FT   CARBOHYD    986     986  N-linked (GlcNAc...) (Potential).
FT   VARIANT      90      90  S -> L (in dbSNP:rs34617074).
FT                             /FTId=VAR_041477.
FT   VARIANT     163     163  V -> L (in dbSNP:rs55697431).
FT                             /FTId=VAR_041478.
FT   VARIANT     296     296  E -> Q (in dbSNP:rs56077855).
FT                             /FTId=VAR_041479.
FT   VARIANT     476     476  V -> A (in dbSNP:rs35093491).
FT                             /FTId=VAR_041480.
FT   VARIANT     560     560  L -> F (in a breast pleomorphic lobu-
FT                             lar carcinoma sample; somatic mutation).
FT                             /FTId=VAR_041481.
FT   VARIANT     680     680  T -> I (in dbSNP:rs35228363).
FT                             /FTId=VAR_041482.
FT   VARIANT     704     704  A -> T (in dbSNP:rs34829159).
FT                             /FTId=VAR_041483.
FT   VARIANT     868     868  L -> Q (in dbSNP:rs55941323).
FT                             /FTId=VAR_061288.
FT   VARIANT     877     877  A -> S (in an ovarian serous carci-
FT                             noma sample; somatic mutation).
FT                             /FTId=VAR_041484.
FT   VARIANT    1012    1012  T -> M (in dbSNP:rs35073634).
FT                             /FTId=VAR_041485.
FT   VARIANT    1091    1091  D -> N (in NBLST3; somatic mutation).
FT                             /FTId=VAR_063850.
FT   VARIANT    1121    1121  G -> D (in dbSNP:rs55760835).
FT                             /FTId=VAR_041486.
FT   VARIANT    1128    1128  G -> A (in NBLST3).
FT                             /FTId=VAR_063851.
FT   VARIANT    1151    1151  T -> M (in NBLST3).
FT                             /FTId=VAR_063852.
FT   VARIANT    1166    1166  M -> R (in NBLST3; somatic mutation).
FT                             /FTId=VAR_063853.
FT   VARIANT    1171    1171  I -> N (in NBLST3; somatic mutation).
FT                             /FTId=VAR_063854.
FT   VARIANT    1174    1174  F -> C (in NBLST3).
FT                             /FTId=VAR_063855.
FT   VARIANT    1174    1174  F -> I (in NBLST3; somatic mutation).
FT                             /FTId=VAR_063856.
FT   VARIANT    1174    1174  F -> L (in NBLST3; somatic mutation).
FT                             /FTId=VAR_063857.
FT   VARIANT    1174    1174  F -> V (in NBLST3; somatic mutation).
FT                             /FTId=VAR_063858.
FT   VARIANT    1192    1192  R -> P (in NBLST3).
FT                             /FTId=VAR_063859.
FT   VARIANT    1234    1234  A -> T (in NBLST3; somatic mutation).
FT                             /FTId=VAR_063860.
FT   VARIANT    1245    1245  F -> C (in NBLST3; somatic mutation).
FT                             /FTId=VAR_063861.
FT   VARIANT    1245    1245  F -> V (in NBLST3; somatic mutation).
FT                             /FTId=VAR_063862.
FT   VARIANT    1250    1250  I -> T (in NBLST3; somatic mutation).
FT                             /FTId=VAR_063863.
FT   VARIANT    1274    1274  A -> T (in dbSNP:rs45502292).
FT                             /FTId=VAR_041487.
FT   VARIANT    1275    1275  R -> L (observed in neuroblastoma).
FT                             /FTId=VAR_063864.
FT   VARIANT    1275    1275  R -> Q (in NBLST3).
FT                             /FTId=VAR_063865.
FT   VARIANT    1278    1278  Y -> S (in NBLST3; somatic mutation).
FT                             /FTId=VAR_063866.
FT   VARIANT    1328    1328  M -> L (in dbSNP:rs56160491).
FT                             /FTId=VAR_041488.
FT   VARIANT    1376    1376  F -> S (in dbSNP:rs17694720).
FT                             /FTId=VAR_055987.
FT   VARIANT    1416    1416  K -> N (in dbSNP:rs55782189).
FT                             /FTId=VAR_041489.
FT   VARIANT    1419    1419  E -> K (in dbSNP:rs56181542).
FT                             /FTId=VAR_041490.
FT   VARIANT    1429    1429  Q -> R (in dbSNP:rs55906201).
FT                             /FTId=VAR_041491.
FT   VARIANT    1461    1461  I -> V (in dbSNP:rs1670283).
FT                             /FTId=VAR_031042.
FT   VARIANT    1491    1491  K -> R (in dbSNP:rs1881420).
FT                             /FTId=VAR_031043.
FT   VARIANT    1529    1529  D -> E (in dbSNP:rs1881421).
FT                             /FTId=VAR_031044.
FT   VARIANT    1599    1599  P -> H (in dbSNP:rs1881423).
FT                             /FTId=VAR_055988.
FT   MUTAGEN    1507    1507  Y -> F: Impairs interaction with SHC1.
FT   CONFLICT     36      36  P -> S (in Ref. 1; AAB71619).
FT   HELIX      1087    1092
FT   STRAND     1096    1098
FT   STRAND     1101    1103
FT   HELIX      1105    1107
FT   HELIX      1113    1115
FT   STRAND     1117    1121
FT   STRAND     1126    1128
FT   STRAND     1130    1134
FT   STRAND     1137    1140
FT   STRAND     1146    1151
FT   HELIX      1158    1173
FT   STRAND     1182    1186
FT   STRAND     1188    1191
FT   STRAND     1193    1197
FT   HELIX      1204    1210
```

-continued

| FT | STRAND | 1215 | 1217 |
| --- | --- | --- | --- |
| FT | HELIX | 1223 | 1242 |
| FT | HELIX | 1252 | 1254 |
| FT | STRAND | 1255 | 1258 |
| FT | STRAND | 1260 | 1263 |
| FT | STRAND | 1266 | 1268 |
| FT | HELIX | 1272 | 1278 |
| FT | STRAND | 1280 | 1282 |
| FT | HELIX | 1288 | 1290 |
| FT | HELIX | 1293 | 1295 |
| FT | HELIX | 1298 | 1303 |
| FT | HELIX | 1308 | 1323 |
| FT | HELIX | 1335 | 1343 |
| FT | HELIX | 1356 | 1365 |
| FT | HELIX | 1370 | 1372 |
| FT | HELIX | 1376 | 1388 |
| FT | HELIX | 1390 | 1393 |
| FT | STRAND | 1574 | 1576 |
| FT | STRAND | 1582 | 1584 |

SEQ ID No. 34: Nucleotide Sequence of EML4-ALK
>ENA|EU236948|EU236948.1 *Homo sapiens* EML4/ALK fusion protein variant 3 (EML4/ALK fusion) mRNA, complete cds.: Location:1 . . . 2391

SEQ ID No. 35: Amino Acid Sequence of EML4-ALK

SEQ ID No. 36: Nucleotide Sequence of EML4-ALK variant 6
>ENA|AB462411|AB462411.1 *Homo sapiens* EML4-ALK variant 6 mRNA for fusion protein EML4-ALK variant 6, complete cds.: Location:1 . . . 3365

SEQ ID No. 37: Amino Acid Sequence of EML4-ALK variant 6

SEQ ID No. 38: Nucleotide Sequence of EML4-ALK variant 7
>ENA|AB462412|AB462412.1 *Homo sapiens* EML4-ALK variant 7 mRNA for fusion protein EML4-ALK variant 7, complete cds.: Location:1 . . . 3435

SEQ ID No. 39: Amino Acid Sequence of EML4-ALK variant 7

SEQ ID No. 40: Nucleotide Sequence of EML4-ALK fusion protein variant 8a
>ENA|GU797894|GU797894.1 *Homo sapiens* EML4-ALK fusion protein variant 8a mRNA, partial cds.: Location:1 . . . 171

SEQ ID No. 41: Amino Acid Sequence of EML4-ALK fusion protein variant 8a

SEQ ID No. 42: EML4-ALK fusion protein variant 8b
>ENA|GU797895|GU797895.1 *Homo sapiens* EML4-ALK fusion protein variant 8b mRNA, partial cds.: Location:1 . . . 236

SEQ ID No. 43: Amino Acid Sequence of EML4-ALK fusion protein variant 8b

5. Sequences Relating to MET (Also Known as c-Met)

5.1 NM_000245.2→NP_000236.2 hepatocyte growth factor receptor isoform b precursor:
Description
Transcript Variant: This variant (2) uses an alternate in-frame splice junction at the end of an exon compared to variant 1. The resulting isoform (b) has the same N- and C-termini but is shorter compared to isoform a.

SEQ ID No. 44: Nucleotide Sequence (4173 nt) of MET, hepatocyte growth factor receptor isoform b precursor, Transcript Variant (2)

SEQ ID No. 45: Amino Acid Sequence (1390 aa) of MET, hepatocyte growth factor receptor isoform b precursor, Transcript Variant (2)

5.2 NM_001127500.1→NP_001120972.1 hepatocyte growth factor receptor isoform a precursor:
Description
Transcript Variant: This variant (1) represents the longer transcript and encodes the longer isoform (a).

SEQ ID No. 46: Nucleotide Sequence (4227 nt) of MET, hepatocyte growth factor receptor isoform a precursor, Transcript Variant (1)

SEQ ID No. 47: Amino Acid Sequence (1408 aa) of MET, hepatocyte growth factor receptor isoform a precursor, Transcript Variant (1)

Aberrations of MET

| | | |
| --- | --- | --- |
| CC | -!- | DISEASE: Note = Activation of MET after rearrangement with |
| CC | | the TPR gene produces an oncogenic protein. |
| CC | -!- | DISEASE: Note = Defects in MET may be associated with gastric |
| CC | | cancer. |
| CC | -!- | DISEASE: Defects in MET are a cause of hepatocellular carcinoma |
| CC | | (HCC) [MIM:114550]. |
| CC | -!- | DISEASE: Defects in MET are a cause of renal cell carcinoma |
| CC | | papillary (RCCP) [MIM:605074]. It is a subtype of renal cell |
| CC | | carcinoma tending to show a tubulo-papillary architecture formed |
| CC | | by numerous, irregular, finger-like projections of connective |
| CC | | tissue. Renal cell carcinoma is a heterogeneous group of sporadic |
| CC | | or hereditary carcinoma derived from cells of the proximal renal |
| CC | | tubular epithelium. It is subclassified into common renal cell |
| CC | | carcinoma (clear cell, non-papillary carcinoma), papillary renal |
| CC | | cell carcinoma, chromophobe renal cell carcinoma, collecting duct |
| CC | | carcinoma with medullary carcinoma of the kidney, and unclassified |
| CC | | renal cell carcinoma. |
| CC | -!- | DISEASE: Note = A common allele in the promoter region of |
| CC | | the MET shows genetic association with susceptibility to autism |
| CC | | in some families. Functional assays indicate a decrease in MET |
| CC | | promoter activity and altered binding of specific transcription factor |
| CC | | complexes. |
| CC | -!- | DISEASE: Note = MET activating mutations may be involved |
| CC | | in the development of a highly malignant, metastatic syndrome |
| CC | | known as cancer of unknown primary origin (CUP) or primary |
| CC | | occult malignancy. Systemic neoplastic spread is generally a late |
| CC | | event in cancer progression. However, in some instances, distant |
| CC | | dissemination arises at a very early stage, so that metastases |
| CC | | reach clinical relevance before primary lesions. Sometimes, the |
| CC | | primary lesions cannot be identified in spite of the progresses in |
| CC | | the diagnosis of malignancies. |

MET Sequence Annotation

In this Sequence Annotation, common mutations of MET are indicated by the term "variant".

| FT | SIGNAL | 1 | 24 | Potential. |
| --- | --- | --- | --- | --- |
| FT | CHAIN | 25 | 1390 | Hepatocyte growth factor receptor. |
| FT | | | | /FTId=PRO_0000024440. |
| FT | TOPO_DOM | 25 | 932 | Extracellular (Potential). |
| FT | TRANSMEM | 933 | 955 | Helical; (Potential). |
| FT | TOPO_DOM | 956 | 1390 | Cytoplasmic (Potential). |
| FT | DOMAIN | 27 | 515 | Sema. |
| FT | DOMAIN | 563 | 655 | IPT/TIG 1. |
| FT | DOMAIN | 657 | 739 | IPT/TIG 2. |
| FT | DOMAIN | 742 | 836 | IPT/TIG 3. |
| FT | DOMAIN | 1078 | 1345 | Protein kinase. |
| FT | NP_BIND | 1084 | 1092 | ATP (By similarity). |
| FT | REGION | 1212 | 1390 | Interaction with RANBP9. |
| FT | REGION | 1320 | 1359 | Interaction with MUC20. |
| FT | ACT_SITE | 1204 | 1204 | Proton acceptor (By similarity). |
| FT | BINDING | 1110 | 1110 | ATP. |
| FT | SITE | 307 | 308 | Cleavage (Potential). |
| FT | SITE | 1009 | 1010 | Breakpoint for translocation to form |
| FT | | | | TPR-MET oncogene. |
| FT | MOD_RES | 966 | 966 | Phosphoserine. |
| FT | MOD_RES | 977 | 977 | Phosphothreonine. |

-continued

| FT | MOD_RES | 988 | 988 | Phosphoserine. |
|---|---|---|---|---|
| FT | MOD_RES | 990 | 990 | Phosphoserine. |
| FT | MOD_RES | 997 | 997 | Phosphoserine. |
| FT | MOD_RES | 1000 | 1000 | Phosphoserine. |
| FT | MOD_RES | 1003 | 1003 | Phosphotyrosine. |
| FT | MOD_RES | 1230 | 1230 | Phosphotyrosine. |
| FT | MOD_RES | 1234 | 1234 | Phosphotyrosine; by autocatalysis. |
| FT | MOD_RES | 1235 | 1235 | Phosphotyrosine; by autocatalysis. |
| FT | MOD_RES | 1289 | 1289 | Phosphothreonine. |
| FT | MOD_RES | 1349 | 1349 | Phosphotyrosine; by autocatalysis. |
| FT | MOD_RES | 1356 | 1356 | Phosphotyrosine; by autocatalysis. |
| FT | MOD_RES | 1365 | 1365 | Phosphotyrosine. |
| FT | CARBOHYD | 45 | 45 | N-linked (GlcNAc...) (Potential). |
| FT | CARBOHYD | 106 | 106 | N-linked (GlcNAc...). |
| FT | CARBOHYD | 149 | 149 | N-linked (GlcNAc...) (Potential). |
| FT | CARBOHYD | 202 | 202 | N-linked (GlcNAc...) (Potential). |
| FT | CARBOHYD | 399 | 399 | N-linked (GlcNAc...) (Potential). |
| FT | CARBOHYD | 405 | 405 | N-linked (GlcNAc...) (Potential). |
| FT | CARBOHYD | 607 | 607 | N-linked (GlcNAc...) (Potential). |
| FT | CARBOHYD | 635 | 635 | N-linked (GlcNAc...) (Potential). |
| FT | CARBOHYD | 785 | 785 | N-linked (GlcNAc...) (Potential). |
| FT | CARBOHYD | 879 | 879 | N-linked (GlcNAc...) (Potential). |
| FT | CARBOHYD | 930 | 930 | N-linked (GlcNAc...) (Potential). |
| FT | DISULFID | 95 | 101 | |
| FT | DISULFID | 98 | 160 | |
| FT | DISULFID | 133 | 141 | |
| FT | DISULFID | 172 | 175 | |
| FT | DISULFID | 298 | 363 | |
| FT | DISULFID | 385 | 397 | |
| FT | DISULFID | 520 | 538 | |
| FT | DISULFID | 526 | 561 | |
| FT | DISULFID | 529 | 545 | |
| FT | DISULFID | 541 | 551 | |
| FT | VAR_SEQ | 755 | 764 | SGGSTITGVG -> RHVNIALIQR (in isoform 3). |
| FT | | | | /FTId=VSP_042447. |
| FT | VAR_SEQ | 755 | 755 | S -> STWWKEPLNIVSFLFCFAS (in isoform 2). |
| FT | | | | /FTId=VSP_005005. |
| FT | VAR_SEQ | 765 | 1390 | Missing (in isoform 3). |
| FT | | | | /FTId=VSP_042448. |
| FT | VARIANT | 143 | 143 | R -> Q (in dbSNP:rs35469582). |
| FT | | | | /FTId=VAR_041738. |
| FT | VARIANT | 150 | 150 | H -> Y (found in a case of cancer of unknown primary origin; the mutated receptor is still functional and can sustain the transformed phenotype; somatic mutation). |
| FT | | | | /FTId=VAR_064855. |
| FT | VARIANT | 156 | 156 | S -> L (in dbSNP:rs56311081). |
| FT | | | | /FTId=VAR_041739. |
| FT | VARIANT | 168 | 168 | E -> D (found in a case of cancer of unknown primary origin; the mutated receptor is still functional and can sustain the transformed phenotype; somatic mutation; dbSNP: rs55985569). |
| FT | | | | /FTId=VAR_041740. |
| FT | VARIANT | 238 | 238 | L -> S (in dbSNP:rs34349517). |
| FT | | | | /FTId=VAR_032478. |
| FT | VARIANT | 316 | 316 | I -> M (in dbSNP:rs35225896). |
| FT | | | | /FTId=VAR_032479. |
| FT | VARIANT | 320 | 320 | A -> V (in dbSNP:rs35776110). |
| FT | | | | /FTId=VAR_006285. |
| FT | VARIANT | 375 | 375 | N -> S (in dbSNP:rs33917957). |
| FT | | | | /FTId=VAR_032480. |
| FT | VARIANT | 385 | 385 | C -> Y (found in a case of cancer of unknown primary origin; the mutated receptor is still functional and can sustain the transformed phenotype; somatic mutation). |
| FT | | | | /FTId=VAR_064856. |
| FT | VARIANT | 773 | 773 | P -> L (in gastric cancer). |
| FT | | | | /FTId=VAR_032481. |
| FT | VARIANT | 970 | 970 | R -> C (in dbSNP:rs34589476). |
| FT | | | | /FTId=VAR_032482. |
| FT | VARIANT | 991 | 991 | P -> S (in gastric cancer; prolonged tyrosine phosphorylation in response to HGF/SF; transforming activity in athymic nude mice). |
| FT | | | | /FTId=VAR_032483. |
| FT | VARIANT | 992 | 992 | T -> I (found in a case of cancer of unknown primary origin; the mutated receptor is still functional and can sustain the transformed phenotype; somatic mutation; dbSNP: rs56391007). |
| FT | | | | /FTId=VAR_032484. |
| FT | VARIANT | 1092 | 1092 | V -> I (in RCCP; constitutive autophosphorylation). |
| FT | | | | /FTId=VAR_032485. |
| FT | VARIANT | 1094 | 1094 | H -> L (in RCCP; constitutive autophosphorylation; causes malignant transformation in cell lines). |
| FT | | | | /FTId=VAR_032486. |
| FT | VARIANT | 1094 | 1094 | H -> R (in RCCP; causes malignant transformation in cell lines). |
| FT | | | | /FTId=VAR_032487. |
| FT | VARIANT | 1094 | 1094 | H -> Y (in RCCP; constitutive autophosphorylation; causes malignant transformation in cell lines). |
| FT | | | | /FTId=VAR_032488. |
| FT | VARIANT | 1106 | 1106 | H -> D (in RCCP; constitutive autophosphorylation; causes malignant transformation in cell lines). |
| FT | | | | /FTId=VAR_032489. |
| FT | VARIANT | 1131 | 1131 | M -> T (in RCCP; germline mutation). |
| FT | | | | /FTId=VAR_006286. |
| FT | VARIANT | 1173 | 1173 | T -> I (in HCC). |
| FT | | | | /FTId=VAR_032490. |
| FT | VARIANT | 1188 | 1188 | V -> L (in RCCP; germline mutation). |
| FT | | | | /FTId=VAR_006287. |
| FT | VARIANT | 1195 | 1195 | L -> V (in RCCP; somatic mutation). |
| FT | | | | /FTId=VAR_006288. |
| FT | VARIANT | 1220 | 1220 | V -> I (in RCCP; germline mutation). |
| FT | | | | /FTId=VAR_006289. |
| FT | VARIANT | 1228 | 1228 | D -> H (in RCCP; somatic mutation). |
| FT | | | | /FTId=VAR_006291. |
| FT | VARIANT | 1228 | 1228 | D -> N (in RCCP; germline mutation). |
| FT | | | | /FTId=VAR_006290. |
| FT | VARIANT | 1230 | 1230 | Y -> C (in RCCP; germline mutation). |
| FT | | | | /FTId=VAR_006292. |
| FT | VARIANT | 1230 | 1230 | Y -> D (in RCCP; constitutive autophosphorylation; causes malignant transformation in cell lines). |
| FT | | | | /FTId=VAR_032491. |
| FT | VARIANT | 1230 | 1230 | Y -> H (in RCCP; somatic mutation). |
| FT | | | | /FTId=VAR_006293. |
| FT | VARIANT | 1244 | 1244 | K -> R (in HCC). |
| FT | | | | /FTId=VAR_032492. |
| FT | VARIANT | 1250 | 1250 | M -> I (in HCC). |
| FT | | | | /FTId=VAR_032493. |
| FT | VARIANT | 1250 | 1250 | M -> T (in RCCP; somatic mutation). |
| FT | | | | /FTId=VAR_006294. |
| FT | VARIANT | 1294 | 1294 | V -> I (found in a case of cancer of unknown primary origin; the mutated receptor is still functional and can sustain the transformed phenotype; somatic mutation). |
| FT | | | | /FTId=VAR_064857. |
| FT | CONFLICT | 237 | 237 | V -> A (in Ref. 3; ACF47606). |
| FT | CONFLICT | 508 | 508 | K -> R (in Ref. 3; ACF47606). |
| FT | CONFLICT | 720 | 720 | F -> S (in Ref. 3; ACF47606). |
| FT | CONFLICT | 1191 | 1191 | G -> A (in Ref. 1; AAA59591). |
| FT | CONFLICT | 1272 | 1272 | L -> V (in Ref. 1; AAA59591, 2; CAB56793 and 6; AAA59590). |
| FT | STRAND | 45 | 47 | |
| FT | STRAND | 52 | 58 | |
| FT | STRAND | 61 | 66 | |
| FT | STRAND | 69 | 74 | |
| FT | TURN | 75 | 77 | |
| FT | STRAND | 80 | 84 | |
| FT | STRAND | 89 | 91 | |
| FT | STRAND | 93 | 95 | |
| FT | STRAND | 97 | 99 | |
| FT | STRAND | 102 | 104 | |
| FT | STRAND | 111 | 113 | |
| FT | STRAND | 119 | 123 | |
| FT | STRAND | 125 | 133 | |

| | | | |
|---|---|---|---|
| FT | STRAND | 135 | 139 |
| FT | STRAND | 141 | 145 |
| FT | STRAND | 154 | 160 |
| FT | STRAND | 182 | 189 |
| FT | STRAND | 192 | 199 |
| FT | STRAND | 213 | 219 |
| FT | HELIX | 231 | 233 |
| FT | HELIX | 239 | 241 |
| FT | TURN | 242 | 244 |
| FT | STRAND | 247 | 255 |
| FT | STRAND | 258 | 268 |
| FT | STRAND | 272 | 274 |
| FT | STRAND | 277 | 281 |
| FT | STRAND | 284 | 286 |
| FT | STRAND | 292 | 300 |
| FT | STRAND | 312 | 314 |
| FT | STRAND | 316 | 323 |
| FT | HELIX | 327 | 333 |
| FT | STRAND | 341 | 349 |
| FT | STRAND | 356 | 366 |
| FT | HELIX | 367 | 374 |
| FT | HELIX | 387 | 390 |
| FT | STRAND | 392 | 394 |
| FT | TURN | 395 | 398 |
| FT | STRAND | 418 | 422 |
| FT | STRAND | 424 | 427 |
| FT | TURN | 429 | 436 |
| FT | STRAND | 439 | 447 |
| FT | STRAND | 450 | 457 |
| FT | STRAND | 462 | 466 |
| FT | STRAND | 469 | 471 |
| FT | STRAND | 490 | 493 |
| FT | TURN | 496 | 498 |
| FT | STRAND | 501 | 506 |
| FT | STRAND | 509 | 514 |
| FT | HELIX | 517 | 520 |
| FT | HELIX | 526 | 531 |
| FT | HELIX | 534 | 536 |
| FT | STRAND | 538 | 540 |
| FT | STRAND | 545 | 548 |
| FT | STRAND | 552 | 554 |
| FT | STRAND | 557 | 559 |
| FT | STRAND | 564 | 572 |
| FT | STRAND | 580 | 586 |
| FT | STRAND | 590 | 592 |
| FT | STRAND | 595 | 598 |
| FT | STRAND | 602 | 605 |
| FT | HELIX | 614 | 616 |
| FT | STRAND | 619 | 625 |
| FT | STRAND | 637 | 641 |
| FT | STRAND | 646 | 650 |
| FT | TURN | 1048 | 1052 |
| FT | HELIX | 1055 | 1057 |
| FT | HELIX | 1060 | 1066 |
| FT | HELIX | 1067 | 1069 |
| FT | HELIX | 1073 | 1075 |
| FT | STRAND | 1076 | 1087 |
| FT | STRAND | 1090 | 1097 |
| FT | STRAND | 1100 | 1102 |
| FT | STRAND | 1105 | 1112 |
| FT | HELIX | 1118 | 1132 |
| FT | STRAND | 1144 | 1146 |
| FT | STRAND | 1149 | 1151 |
| FT | STRAND | 1154 | 1158 |
| FT | HELIX | 1165 | 1170 |
| FT | TURN | 1172 | 1174 |
| FT | HELIX | 1178 | 1197 |
| FT | HELIX | 1207 | 1209 |
| FT | STRAND | 1210 | 1212 |
| FT | STRAND | 1218 | 1220 |
| FT | HELIX | 1224 | 1226 |
| FT | HELIX | 1232 | 1234 |
| FT | HELIX | 1237 | 1239 |
| FT | STRAND | 1241 | 1245 |
| FT | HELIX | 1247 | 1249 |
| FT | HELIX | 1252 | 1257 |
| FT | HELIX | 1262 | 1277 |
| FT | STRAND | 1285 | 1287 |
| FT | TURN | 1289 | 1291 |
| FT | HELIX | 1292 | 1297 |
| FT | HELIX | 1310 | 1319 |
| FT | HELIX | 1324 | 1326 |
| FT | HELIX | 1330 | 1342 |
| FT | TURN | 1354 | 1358 |

SEQ ID No. 48: Anti-MTH1 siRNA
CGACGACAGCUACUGGUUU

SEQ ID No. 49: qPCR-oligonucleotide for detecting p21
5'-CTGTGATGCGCTAATGGCG-3'

SEQ ID No. 50: pPCR-oligonucleotide for detecting p21
5'-AAGTCGAAGTTCCATCGCTCA-3'

REFERENCES

1. Rix, Eur. J. Clin. Invest. 2009, 39 (12), 1098-1109.
2. Knight, Nat Rev Cancer 2010, 10 (2), 130-137.
3. Zou, Cancer Res. 2007, 67 (9), 4408-4417.
4. Grande, Mol. Cancer Ther. 2011, 10 (4), 569-579.
5. Soda, Nature 2007, 448 (7153), 561-566.
6. Hallberg, F1000 Med Rep 2011, 3, 21.
7. Butrynski, New Engl. J. Med. 2011, 364 (8), 775-776.
8. Superti-Furga, Royal Society of Chemistry: Cambridge, 2012; p 256.
9. Cui, J. Med. Chem. 2011, 54 (18), 6342-6363.
10. Remsing Rix, Leukemia 2008, 23 (3), 477-485.
11. Nakabeppu, Mutation Research/Genetic Toxicology and Environmental Mutagenesis 2010, 703 (1), 51-58.
12. Rai, Oncogene 2011, 30 (12), 1489-1496.
13. Rai, Mutation Research/Genetic Toxicology and Environmental Mutagenesis 2010, 703 (1), 71-81.
14. Tsuzuki, Proceedings of the National Academy of Sciences 2001, 98 (20), 11456-11461.
15. Svensson, FEBS Lett. 2011, 585 (16), 2617-2621.
16. Galkin, Proceedings of the National Academy of Sciences 2007, 104 (1), 270-275.
17. Le Page, Cancer Res. 2000, 60 (19), 5548-5552.
18. Alli, Cancer Res. 2009, 69 (8), 3589-3596.
19. Rai, Proteomics 2003, 3 (8), 1454-1463.
21. Bennett, Journal of Proteomics 2011, 74 (2), 151-166.
22. Breitwieser, Journal of Proteome Research 2011, 10 (6), 2758-2766.
23. Christensen, Mol Cancer Ther. 2007, 6(12 Pt 1), 3314-3322.
24. Nagai, Cancer Res 2005; 65: 7276-7282.
25. Jänne, Clin Cancer Res 2006; 12: 751-758.
26. Nomoto, Am J Clin Pathol 2006; 126: 608-615.
27. Pao, PLoS Med 2005; 2 (3): e73.
28. Eberhard, J Clin Oncol 2008; 26 (6): 983-993.
29. Speicher, Nat Rev Genet 2005, 6 (10), 782-792.
30. Koivunen, 31. Lin, Mol. Cancer Res. 2009, 7 (9), 1466-1476.
32. Chen, Nature 2008, 455 (7215), 971-974.
33. Keohavong, Clin. Cancer. Res. 1996, 2 (2), 411-418.
34. Gerry, J. Mol. Biol. 1999, 292 (2), 251-262.
35. Kubo, Int. J. Cancer 2009, 124 (8), 1778-1784.
36. Kennedy, FEBS Lett. 1998, 429 (1), 17-20.
37. Cho, RNA Biology 2011, 8 (1), 125-131.

38. de Koning, Organic Process Research & Development 2011, 15 (5), 1018-1026.
39. Saha, Journal of Biological Chemistry 2010, 285 (25), 19092-19105.
40. World Health Organization. The Global Burden of Disease: 2004 Update. Geneva: World Health Organization; 2008.
41. Jemal, CA Cancer J Clin. 2011, 61(2):69-90.

The invention claimed is:

1. A method of treatment of cancer in a subject in need of such a treatment, comprising administering to said subject a therapeutically effective amount of an (S)-enantiomer of an aminoheteroaryl compound, wherein the compound has the following chemical structure represented by Formula (1)

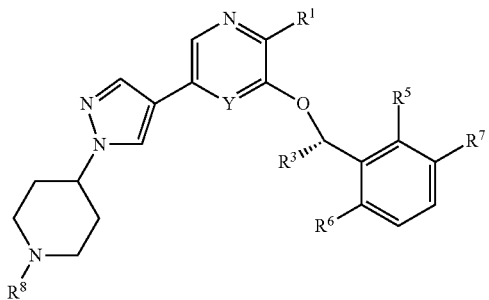

Formula (1)

Formula (1)
wherein:
$R^1$ is —$NH_2$ or —$NR^2H$;
$R^2$ is $C_{1-6}$ alkyl, $C_{2-6}$ alkenyl or $C_{2-6}$ alkynyl;
$R^3$ is $C_{1-3}$ alkyl, $C_{2-3}$ alkenyl, $C_{2-3}$ alkynyl or cyclopropyl;
Y is N or $CR^4$;
$R^4$ is hydrogen, halogen, $C_{1-6}$ alkyl, $C_{2-6}$ alkenyl, $C_{2-6}$ alkynyl or $C_{3-6}$ cycloalkyl;
each $R^5$, $R^6$ and $R^7$ is independently fluorine, chlorine, bromine or iodine;
$R^8$ is hydrogen or -A-$B_n$-X, wherein
  A is a single bond, —C(=O)— or —C(=O)$CH_2$—;
  B is $C_{1-4}$ alkylene, $C_{2-4}$ alkenylene or —(O$CH_2CH_2$)—;
  n is 0, 1, 2, 3, 4 or 5, and
  X is —$NHR^2$; —$NH_2$; —SH; —OH or O-alkyl;
or a pharmaceutically acceptable salt or solvate thereof.

2. The treatment method according to claim 1, wherein
$R^1$ is —$NH_2$;
$R^3$ is methyl;
Y is $CR^4$;
$R^4$ is hydrogen or halogen;
each $R^5$, $R^6$ and $R^7$ is independently fluorine or chlorine;
$R^8$ is hydrogen or -A-$B_n$-X, wherein
  B is $C_{1-4}$ alkylene or —(O$CH_2CH_2$)—;
  n is 1, 2 or 3, and
  X is —$NH_2$;
or a pharmaceutically acceptable salt or solvate thereof.

R⁸ is hydrogen;

—C(=O)CH₂CH₂CH₂CH₂CH₂—NH₂;

—C(=O)CH₂—O—CH₂CH₂—O—CH₂CH₂—NH₂; or

—CH₂CH₂CH₂—NH₂;

or a pharmaceutically acceptable salt or solvate thereof.

4. The treatment method according to claim 1, wherein the compound has one of the following chemical structures represented by Formulae (2) to (5):

Formula (2)

Formula (3)

Formula (4)

Formula (5)

5. The treatment method according to claim 1, wherein the cancer cell or tissue of said subject has an activating RAS mutation and/or an activating EGFR mutation.

6. The treatment method according to claim 5, wherein said activating RAS mutation is an activating KRAS mutation.

7. The treatment method according to claim 1, wherein the treatment of cancer in a subject is independent of the ALK status and/or the c-Met status of the cancer cell or tissue of said subject.

8. The treatment method according to claim 7, wherein said ALK-status is the level of ALK biological activity and/or the level of ALK expression.

9. The treatment method according to claim 7, wherein said c-Met-status is the level of c-Met biological activity and/or the level of c-Met expression.

10. The treatment method according to claim 1, wherein the cancer cell or tissue of said subject does not have a gene mutation and/or a chromosomal translocation of ALK.

11. The treatment method according to claim 10, wherein said chromosomal translocation is EML4-ALK.

12. The treatment method according to claim 1, wherein in the cancer cell or tissue of said subject the biological activity and/or expression of p21 is reduced or absent.

13. The treatment method according to claim 1, wherein said subject is a human patient.

14. The treatment method according to claim 1, wherein said cancer is selected from the group consisting of colon cancer, lung cancer, breast cancer, leukaemia, lymphoma, skin cancer, liver cancer, pancreatic cancer, brain cancer, kidney cancer, neuroblastoma, Ewing's sarcoma, prostate cancer, bladder cancer and esophagus cancer.

15. The treatment method according to claim 14, wherein said breast cancer:
(i) lacks expression of estrogen receptor-a and progesterone receptor and lacks overexpression or amplification of the HER2/NEU oncogene; and/or
(ii) has a BRCA1 and/or BRCA2 gene mutation.

16. The treatment method according to claim 1, wherein said compound is co-administered with radiation and/or chemotherapy.

17. The treatment method according to claim 12, wherein said chemotherapy is a DNA damaging drug, an alkylating agent, a DNA intercalator, a topoisomerase inhibitor, an agent which confers oxidative damage to DNA, a cytoxic compound, an antimetabolite, a compound which interferes with DNA repair mechanisms, an ATM kinase inhibitor, an ATR kinase inhibitor, a CHK1/2 kinase inhibitor, a PARP inhibitor, an EGFR inhibitor, a DNA-dependent protein kinase inhibitor, a generic base excision repair inhibitor, a DNA polymerase beta inhibitor, a O-6-methylguanine methyltransferase (MGMT) inhibitor, a survivin suppressant, a compound generating reactive oxygen species (ROS), an antimitotic compound, or a combination of any of the foregoing.

18. The treatment method according to claim 17, wherein said chemotherapy is cyclophosphamide, temozolomide, melphalan, carmustine, busulfan, cisplatin, procarbazine, anthracyclines, camptothecin, irinotecan, etoposide, hydrogen peroxide, resorcinol, quinones, methotrexate, 5-fluorouracil, thalidomide, lenalidomide, pomalidomide, olaparib, ABT-888, neocarzinostatin, bleomycin, decitabine, 5-azacytosine, methoxyamine hydrochloride (TRC102), lomeguatrib, piperlongumine, quercetin, vincristin, taxol, mitoxantrone, YM155, erlotinib, gefitinib, lapatinib, or a combination of any of the foregoing.

19. An in vitro method for determining the effectiveness of the compound, wherein the compound has the following chemical structure represented by Formula (1)

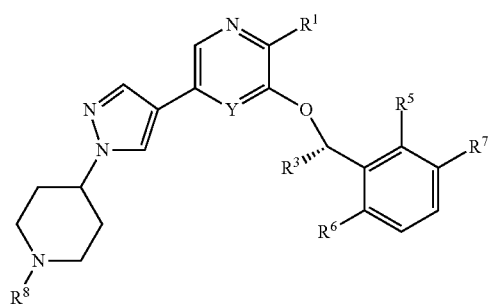

Formula (1)

Formula (1)
wherein:
$R^1$ is $-NH_2$ or $-NR^2$;
$R^2$ is $C_{1-6}$ alkyl, $C_{2-6}$ alkenyl or $C_{2-6}$ alkynyl;
$R^3$ is $C_{1-3}$ alkyl, $C_{2-3}$ alkenyl, $C_{2-3}$ alkynyl or cyclopropyl;
Y is N or $CR^4$;

$R^4$ is hydrogen, halogen, $C_{1-6}$ alkyl, $C_{2-6}$ alkenyl, $C_{2-6}$ alkynyl or $C_{3-6}$ cycloalkyl;

each $R^5$, $R^6$ and $R^7$ is independently fluorine, chlorine, bromine or iodine;

$R^8$ is hydrogen or $-A-B_n-X$, wherein
A is a single bond, $-C(=O)-$ or $-C(=O)CH_2-$;
B is $C_{1-4}$ alkylene, $C_{2-4}$ alkenylene or $-(OCH_2CH_2)-$;
n is 0, 1, 2, 3, 4 or 5, and
X is $-NHR^2$; $-NH_2$; $-SH$; $-OH$ or O-alkyl;

or a pharmaceutically acceptable salt or solvate thereof, the method comprising the steps of:
(a) administering the compound to the subject;
(b) obtaining a cell or tissue sample from a subject; and
(c) determining the subject's NUDT1/MTH1-status;
wherein a NUDT1/MTH1-positive cell or tissue sample is indicative of an effective treatment of cancer.

20. The in vitro method of claim 19, wherein said NUDT/MTH1-status is the level of MTH1 biological activity and/or the level of MTH1 expression.

21. The in vitro method of claim 19, further comprising the step of:
(d) determining the subject's RAS-status;
wherein a cell or tissue sample positive for NUDT1/MTH1 and positive for an activating RAS mutation are indicative of an effective treatment and/or prevention of cancer.

22. The in vitro method of claim 19, further comprising the step of:
(d) determining whether said cell or tissue sample has an activating RAS mutation;
wherein a cell or tissue sample positive for NUDT1/MTH1 and positive for an activating RAS mutation are indicative of an effective treatment and/or prevention of cancer.

23. The in vitro method of claim 19, further comprising the step of:
(e) determining whether in said cell or tissue sample the expression and/or biological activity of p21 is reduced or absent;
wherein a cell or tissue sample which is positive for NUDT1/MTH1 and wherein the expression and/or biological activity of p21 is reduced or absent are indicative of an effective treatment and/or prevention of cancer.

24. The in vitro method of claim 19, wherein said cell or tissue sample is a cancer cell or tissue.

25. The in vitro method of claim 19, wherein step (b) and/or (c) and/or (d) comprises at least one detection method selected from the group consisting of PCR (polymerase chain reaction), gene sequencing, ARMS (Amplification Refractory Mutation System), Peptide nucleic acid-locked nucleic acid (PNA-LNA) PCR clamp, PCR-Invader, SNaP-shot, PCR/HRMA/dHPLC, PCR/flRFLP, Fluorescent In-Situ Hybridisation (FISH), Immunohistochemistry (IHC), RT-PCR, gene arrays, and gene chips.

26. A screening method for identifying a target of an (S)-enantiomer of an aminoheteroaryl compound having the following chemical structure represented by Formula (1),

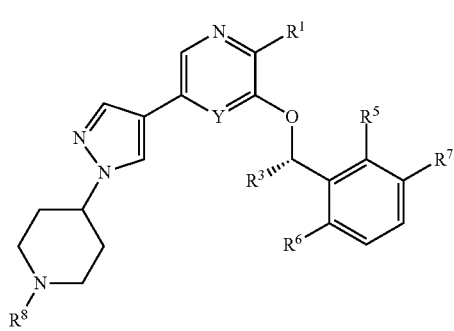

Formula (1)

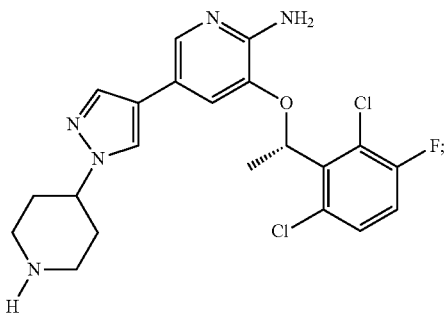

Formula (2)

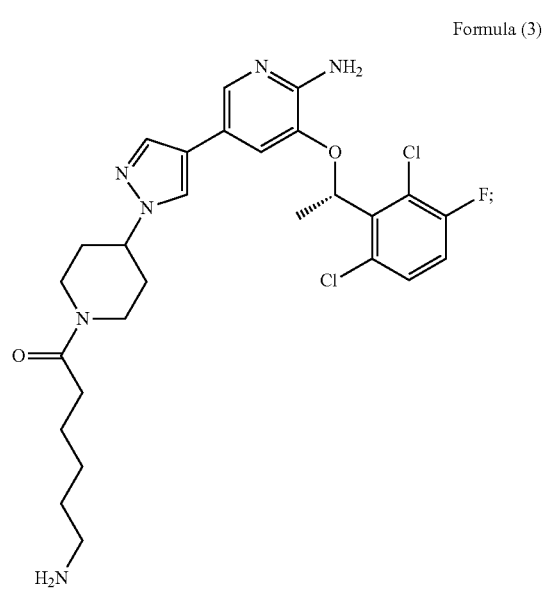

Formula (3)

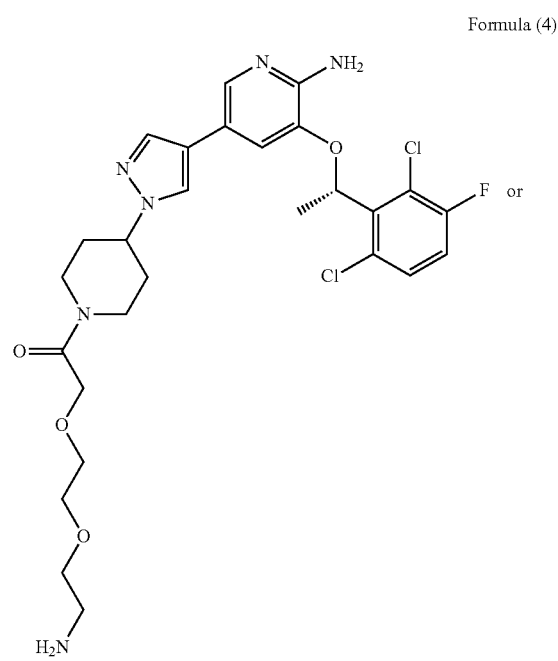

Formula (4)

wherein:
$R^1$ is —NH$_2$ or —NR$^2$H;
$R^2$ is C$_{1-6}$ alkyl, C$_{2-6}$ alkenyl or C$_{2-6}$ alkynyl;
$R^3$ is C$_{1-3}$ alkyl, C$_{2-3}$ alkenyl, C$_{2-3}$ alkynyl or cyclopropyl;
Y is N or CR$^4$;
$R^4$ is hydrogen, halogen, C$_{1-6}$ alkyl, C$_{2-6}$ alkenyl, C$_{2-6}$ alkynyl or C$_{3-6}$ cycloalkyl;
each $R^5$, $R^6$ and $R^7$ is independently fluorine, chlorine, bromine or iodine;
$R^8$ is hydrogen or -A-B$_n$-X, wherein
  A is a single bond, —C(=O)— or —C(=O)CH$_2$—;
  B is C$_{1-4}$ alkylene, C$_{2-4}$ alkenylene or —(OCH$_2$CH$_2$)—;
  n is 0, 1, 2, 3, 4 or 5, and
  X is —NHR$^2$; —NH$_2$; —SH; —OH or O-alkyl;
or a pharmaceutically acceptable salt or solvate thereof;
and wherein the screening method comprises the steps of:
(a) obtaining a cell lysate;
(b) contacting said aminoheteroaryl compound with said cell lysate; and
(c) determining whether a molecule binds to said aminoheteroaryl compound,
wherein, if a molecule is found to bind to said aminoheteroaryl compound, then such molecule is identified as a target of said aminoheteroaryl compound.

27. The screening method of claim 26, wherein in compound of Formula (1)
$R^1$ is —NH$_2$;
$R^3$ is methyl;
Y is CR$^4$;
$R^4$ is hydrogen or halogen;
each $R^5$, $R^6$ and $R^7$ is independently fluorine or chlorine;
$R^8$ is hydrogen or -A-B$_n$—X, wherein
  B is C$_{1-4}$ alkylene or —(OCH$_2$CH$_2$)—;
  n is 1, 2 or 3, and
  X is —NH$_2$.

28. The screening method of claim 26, wherein in compound of Formula (1)
$R^8$ is hydrogen;
  —C(=O)CH$_2$CH$_2$CH$_2$CH$_2$CH$_2$—NH$_2$;
  —C(=O)CH$_2$—O—CH$_2$CH$_2$—O—CH$_2$CH$_2$—NH$_2$; or
  —CH$_2$CH$_2$CH$_2$—NH$_2$.

29. The screening method of claim 26, wherein the compound has one of the following chemical structures represented by Formulae (2) to (5):

Formula (5)

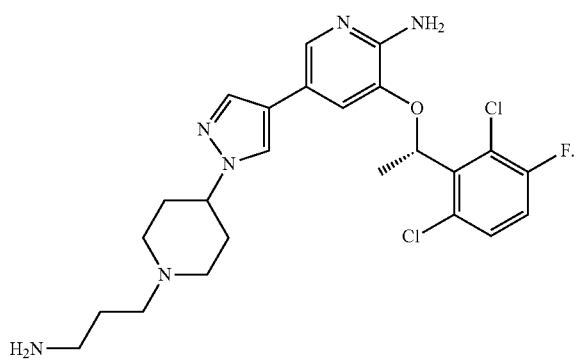

or a pharmaceutically acceptable salt or solvate thereof.

30. The screening method of claim 26, further comprising the step of:

(d) determining whether said (s)-enantiomer of an aminoheteroaryl compound alters the biological activity of said molecule, wherein, if said (S)-enantiomer of an aminoheteroaryl compound is found to alter the biological activity of said molecule, then such molecule is identified as a target of said (S)-enantiomer of an aminoheteroaryl compound.

31. The screening method of claim 26, wherein said cell lysate is derived from a cell or tissue sample from a cancer patient, from an established cancer cell line or from a non-human animal.

32. The screening method of claim 30, wherein altering the biological activity is inhibiting the biological activity.

33. The treatment method according to claim 1, wherein said compound inhibits the biological activity of MTH1.

34. The treatment method according to claim 1, wherein said compound is the (S)-enantiomer of the chemical substance 3-[1-(2,6-dichloro-3-fluoro-phenyl)-ethoxy]-5-(1-piperidin-4-yl-1H-pyrazol-4-yl)-pyridin-2-ylamine.

* * * * *

UNITED STATES PATENT AND TRADEMARK OFFICE
CERTIFICATE OF CORRECTION

| | | |
|---|---|---|
| PATENT NO. | : 9,446,039 B2 | Page 1 of 1 |
| APPLICATION NO. | : 14/424595 | |
| DATED | : September 20, 2016 | |
| INVENTOR(S) | : Kilian Huber et al. | |

It is certified that error appears in the above-identified patent and that said Letters Patent is hereby corrected as shown below:

In the Claims

In Claim 3, Column 187, Line 1, before "$R^8$ is hydrogen;" insert --3. The treatment method according to claim 1, wherein--.

In Claim 15, Column 189, Line 9, delete "receptor-a" and insert --receptor-α-- therefor.

Signed and Sealed this
Third Day of January, 2017

Michelle K. Lee
*Director of the United States Patent and Trademark Office*

SEQUENCE LISTING

```
<160> NUMBER OF SEQ ID NOS: 50

<210> SEQ ID NO 1
<211> LENGTH: 471
<212> TYPE: DNA
<213> ORGANISM: Homo sapiens
<220> FEATURE:
<221> NAME/KEY: source
<222> LOCATION: 1..471
<223> OTHER INFORMATION: /mol_type="unassigned DNA"
      /organism="Homo sapiens"

<400> SEQUENCE: 1
atgggcgcct ccaggctcta taccctggtg ctggtcctgc agcctcagcg agttctcctg      60
ggcatgaaaa agcgaggctt cggggccggc cggtggaatg gctttggggg caaagtgcaa     120
gaaggagaga ccatcgagga tggggctagg agggagctgc aggaggagag cggtctgaca     180
gtggacgccc tgcacaaggt gggccagatc gtgtttgagt tcgtgggcga gcctgagctc     240
atggacgtgc atgtcttctg cacagacagc atccagggga cccccgtgga gagcgacgaa     300
atgcgcccat gctggttcca gctggatcag atccccttca aggacatgtg gcccgacgac     360
agctactggt ttccactcct gcttcagaag aagaaattcc acgggtactt caagttccag     420
ggtcaggaca ccatcctgga ctacacactc cgcgaggtgg acacggtcta g              471

<210> SEQ ID NO 2
<211> LENGTH: 156
<212> TYPE: PRT
<213> ORGANISM: Homo sapiens

<400> SEQUENCE: 2

Met Gly Ala Ser Arg Leu Tyr Thr Leu Val Leu Val Leu Gln Pro Gln
1               5                   10                  15

Arg Val Leu Leu Gly Met Lys Lys Arg Gly Phe Gly Ala Gly Arg Trp
            20                  25                  30

Asn Gly Phe Gly Gly Lys Val Gln Glu Gly Glu Thr Ile Glu Asp Gly
        35                  40                  45

Ala Arg Arg Glu Leu Gln Glu Glu Ser Gly Leu Thr Val Asp Ala Leu
    50                  55                  60

His Lys Val Gly Gln Ile Val Phe Glu Phe Val Gly Glu Pro Glu Leu
65                  70                  75                  80

Met Asp Val His Val Phe Cys Thr Asp Ser Ile Gln Gly Thr Pro Val
                85                  90                  95

Glu Ser Asp Glu Met Arg Pro Cys Trp Phe Gln Leu Asp Gln Ile Pro
            100                 105                 110

Phe Lys Asp Met Trp Pro Asp Asp Ser Tyr Trp Phe Pro Leu Leu Leu
        115                 120                 125

Gln Lys Lys Lys Phe His Gly Tyr Phe Lys Phe Gln Gly Gln Asp Thr
    130                 135                 140

Ile Leu Asp Tyr Thr Leu Arg Glu Val Asp Thr Val
145                 150                 155

<210> SEQ ID NO 3
```

```
<211> LENGTH: 471
<212> TYPE: DNA
<213> ORGANISM: Homo sapiens
<220> FEATURE:
<221> NAME/KEY: source
<222> LOCATION: 1..471
<223> OTHER INFORMATION: /mol_type="unassigned DNA"
      /organism="Homo sapiens"

<400> SEQUENCE: 3
atgggcgcct ccaggctcta taccctggtg ctggtcctgc agcctcagcg agttctcctg      60
ggcatgaaaa agcgaggctt cggggccggc cggtggaatg gctttggggg caaagtgcaa     120
gaaggagaga ccatcgagga tggggctagg agggagctgc aggaggagag cggtctgaca     180
gtggacgccc tgcacaaggt gggccagatc gtgtttgagt tcgtgggcga gcctgagctc     240
atggacgtgc atgtcttctg cacagacagc atccagggga cccccgtgga gagcgacgaa     300
atgcgcccat gctggttcca gctggatcag atccccttca aggacatgtg gcccgacgac     360
agctactggt ttccactcct gcttcagaag aagaaattcc acgggtactt caagttccag     420
ggtcaggaca ccatcctgga ctacacactc cgcgaggtgg acacggtcta g              471

<210> SEQ ID NO 4
<211> LENGTH: 156
<212> TYPE: PRT
<213> ORGANISM: Homo sapiens

<400> SEQUENCE: 4

Met Gly Ala Ser Arg Leu Tyr Thr Leu Val Leu Val Leu Gln Pro Gln
1               5                   10                  15

Arg Val Leu Leu Gly Met Lys Lys Arg Gly Phe Gly Ala Gly Arg Trp
            20                  25                  30

Asn Gly Phe Gly Gly Lys Val Gln Glu Gly Glu Thr Ile Glu Asp Gly
        35                  40                  45

Ala Arg Arg Glu Leu Gln Glu Glu Ser Gly Leu Thr Val Asp Ala Leu
    50                  55                  60

His Lys Val Gly Gln Ile Val Phe Glu Phe Val Gly Glu Pro Glu Leu
65                  70                  75                  80

Met Asp Val His Val Phe Cys Thr Asp Ser Ile Gln Gly Thr Pro Val
                85                  90                  95

Glu Ser Asp Glu Met Arg Pro Cys Trp Phe Gln Leu Asp Gln Ile Pro
            100                 105                 110

Phe Lys Asp Met Trp Pro Asp Asp Ser Tyr Trp Phe Pro Leu Leu Leu
        115                 120                 125

Gln Lys Lys Lys Phe His Gly Tyr Phe Lys Phe Gln Gly Gln Asp Thr
    130                 135                 140

Ile Leu Asp Tyr Thr Leu Arg Glu Val Asp Thr Val
145                 150                 155

<210> SEQ ID NO 5
<211> LENGTH: 540
<212> TYPE: DNA
<213> ORGANISM: Homo sapiens
<220> FEATURE:
<221> NAME/KEY: source
<222> LOCATION: 1..540
<223> OTHER INFORMATION: /mol_type="unassigned DNA"
      /organism="Homo sapiens"

<400> SEQUENCE: 5
atgagtggaa ttagccctca gcagatgggg gagccagaag gcagttggag tgggaagaac      60
```

```
ccagggacca tgggcgcctc caggctctat accctggtgc tggtcctgca gcctcagcga    120
gttctcctgg gcatgaaaaa gcgaggcttc ggggccggcc ggtggaatgg ctttgggggc    180
aaagtgcaag aaggagagac catcgaggat ggggctagga gggagctgca ggaggagagc    240
ggtctgacag tggacgccct gcacaaggtg gccagatcg tgtttgagtt cgtgggcgag     300
cctgagctca tggacgtgca tgtcttctgc acagacagca tccaggggac ccccgtggag    360
agcgacgaaa tgcgcccatg ctggttccag ctggatcaga tccccttcaa ggacatgtgg    420
cccgacgaca gctactggtt tccactcctg cttcagaaga agaaattcca cgggtacttc    480
aagttccagg gtcaggacac catcctggac tacacactcc gcgaggtgga cacggtctag    540
```

<210> SEQ ID NO 6
<211> LENGTH: 179
<212> TYPE: PRT
<213> ORGANISM: Homo sapiens

<400> SEQUENCE: 6

```
Met Ser Gly Ile Ser Pro Gln Gln Met Gly Glu Pro Glu Gly Ser Trp
1               5                   10                  15

Ser Gly Lys Asn Pro Gly Thr Met Gly Ala Ser Arg Leu Tyr Thr Leu
            20                  25                  30

Val Leu Val Leu Gln Pro Gln Arg Val Leu Leu Gly Met Lys Lys Arg
        35                  40                  45

Gly Phe Gly Ala Gly Arg Trp Asn Gly Phe Gly Lys Val Gln Glu
    50                  55                  60

Gly Glu Thr Ile Glu Asp Gly Ala Arg Arg Glu Leu Gln Glu Glu Ser
65                  70                  75                  80

Gly Leu Thr Val Asp Ala Leu His Lys Val Gly Gln Ile Val Phe Glu
                85                  90                  95

Phe Val Gly Glu Pro Glu Leu Met Asp Val His Val Phe Cys Thr Asp
            100                 105                 110

Ser Ile Gln Gly Thr Pro Val Glu Ser Asp Glu Met Arg Pro Cys Trp
        115                 120                 125

Phe Gln Leu Asp Gln Ile Pro Phe Lys Asp Met Trp Pro Asp Asp Ser
    130                 135                 140

Tyr Trp Phe Pro Leu Leu Leu Gln Lys Lys Lys Phe His Gly Tyr Phe
145                 150                 155                 160

Lys Phe Gln Gly Gln Asp Thr Ile Leu Asp Tyr Thr Leu Arg Glu Val
                165                 170                 175

Asp Thr Val
```

<210> SEQ ID NO 7
<211> LENGTH: 471
<212> TYPE: DNA
<213> ORGANISM: Homo sapiens
<220> FEATURE:
<221> NAME/KEY: source
<222> LOCATION: 1..471
<223> OTHER INFORMATION: /mol_type="unassigned DNA"
      /organism="Homo sapiens"

<400> SEQUENCE: 7

```
atgggcgcct ccaggctcta taccctggtg ctggtcctgc agcctcagcg agttctcctg    60
ggcatgaaaa agcgaggctt cggggccggc cggtggaatg gctttggggg caaagtgcaa    120
gaaggagaga ccatcgagga tggggctagg agggagctgc aggaggagag cggtctgaca    180
```

| | |
|---|---|
| gtggacgccc tgcacaaggt gggccagatc gtgtttgagt tcgtgggcga gcctgagctc | 240 |
| atggacgtgc atgtcttctg cacagacagc atccagggga ccccgtggga gagcgacgaa | 300 |
| atgcgcccat gctggttcca gctggatcag atccccttca aggacatgtg gcccgacgac | 360 |
| agctactggt tccactcct gcttcagaag aagaaattcc acgggtactt caagttccag | 420 |
| ggtcaggaca ccatcctgga ctacacactc cgcgaggtgg acacggtcta g | 471 |

<210> SEQ ID NO 8
<211> LENGTH: 156
<212> TYPE: PRT
<213> ORGANISM: Homo sapiens

<400> SEQUENCE: 8

Met Gly Ala Ser Arg Leu Tyr Thr Leu Val Leu Val Leu Gln Pro Gln
1               5                   10                  15

Arg Val Leu Leu Gly Met Lys Lys Arg Gly Phe Gly Ala Gly Arg Trp
            20                  25                  30

Asn Gly Phe Gly Gly Lys Val Gln Glu Gly Glu Thr Ile Glu Asp Gly
        35                  40                  45

Ala Arg Arg Glu Leu Gln Glu Glu Ser Gly Leu Thr Val Asp Ala Leu
    50                  55                  60

His Lys Val Gly Gln Ile Val Phe Glu Phe Val Gly Glu Pro Glu Leu
65                  70                  75                  80

Met Asp Val His Val Phe Cys Thr Asp Ser Ile Gln Gly Thr Pro Val
                85                  90                  95

Glu Ser Asp Glu Met Arg Pro Cys Trp Phe Gln Leu Asp Gln Ile Pro
            100                 105                 110

Phe Lys Asp Met Trp Pro Asp Asp Ser Tyr Trp Phe Pro Leu Leu Leu
        115                 120                 125

Gln Lys Lys Lys Phe His Gly Tyr Phe Lys Phe Gln Gly Gln Asp Thr
    130                 135                 140

Ile Leu Asp Tyr Thr Leu Arg Glu Val Asp Thr Val
145                 150                 155

<210> SEQ ID NO 9
<211> LENGTH: 540
<212> TYPE: DNA
<213> ORGANISM: Homo sapiens
<220> FEATURE:
<221> NAME/KEY: source
<222> LOCATION: 1..540
<223> OTHER INFORMATION: /mol_type="unassigned DNA"
      /organism="Homo sapiens"

<400> SEQUENCE: 9

| | |
|---|---|
| atgagtggaa ttagccctca gcagatgggg gagccagaag gcagttggag tgggaagaac | 60 |
| ccagggacca tgggcgcctc caggctctat accctggtgc tggtcctgca gcctcagcga | 120 |
| gttctcctgg gcatgaaaaa gcgaggcttc ggggccggcc ggtggaatgg ctttgggggc | 180 |
| aaagtgcaag aaggagagac catcgaggat ggggctagga gggagctgca ggaggagagc | 240 |
| ggtctgacag tggacgccct gcacaaggtg ggccagatcg tgtttgagtt cgtgggcgag | 300 |
| cctgagctca tggacgtgca tgtcttctgc acagacagca tccaggggac ccccgtggag | 360 |
| agcgacgaaa tgcgcccatg ctggttccag ctggatcaga tccccttcaa ggacatgtgg | 420 |
| cccgacgaca gctactggtt ccactcctg cttcagaaga agaaattcca cgggtacttc | 480 |
| aagttccagg gtcaggacac catcctggac tacacactcc gcgaggtgga cacggtctag | 540 |

<210> SEQ ID NO 10
<211> LENGTH: 179
<212> TYPE: PRT
<213> ORGANISM: Homo sapiens

<400> SEQUENCE: 10

```
Met Ser Gly Ile Ser Pro Gln Gln Met Gly Glu Pro Glu Gly Ser Trp
1               5                   10                  15

Ser Gly Lys Asn Pro Gly Thr Met Gly Ala Ser Arg Leu Tyr Thr Leu
            20                  25                  30

Val Leu Val Leu Gln Pro Gln Arg Val Leu Leu Gly Met Lys Lys Arg
        35                  40                  45

Gly Phe Gly Ala Gly Arg Trp Asn Gly Phe Gly Gly Lys Val Gln Glu
    50                  55                  60

Gly Glu Thr Ile Glu Asp Gly Ala Arg Arg Glu Leu Gln Glu Glu Ser
65                  70                  75                  80

Gly Leu Thr Val Asp Ala Leu His Lys Val Gly Gln Ile Val Phe Glu
                85                  90                  95

Phe Val Gly Glu Pro Glu Leu Met Asp Val His Val Phe Cys Thr Asp
            100                 105                 110

Ser Ile Gln Gly Thr Pro Val Glu Ser Asp Glu Met Arg Pro Cys Trp
        115                 120                 125

Phe Gln Leu Asp Gln Ile Pro Phe Lys Asp Met Trp Pro Asp Asp Ser
    130                 135                 140

Tyr Trp Phe Pro Leu Leu Leu Gln Lys Lys Lys Phe His Gly Tyr Phe
145                 150                 155                 160

Lys Phe Gln Gly Gln Asp Thr Ile Leu Asp Tyr Thr Leu Arg Glu Val
                165                 170                 175

Asp Thr Val
```

<210> SEQ ID NO 11
<211> LENGTH: 471
<212> TYPE: DNA
<213> ORGANISM: Homo sapiens
<220> FEATURE:
<221> NAME/KEY: source
<222> LOCATION: 1..471
<223> OTHER INFORMATION: /mol_type="unassigned DNA"
      /organism="Homo sapiens"

<400> SEQUENCE: 11

```
atgggcgcct ccaggctcta taccctggtg ctggtcctgc agcctcagcg agttctcctg      60
ggcatgaaaa agcgaggctt cggggccggc cggtggaatg gctttggggg caaagtgcaa     120
gaaggagaga ccatcgagga tggggctagg agggagctgc aggaggagag cggtctgaca     180
gtggacgccc tgcacaaggt gggccagatc gtgtttgagt tcgtgggcga gcctgagctc     240
atggacgtgc atgtcttctg cacagacagc atccagggga ccccgtggga gagcgacgaa     300
atgcgcccat gctggttcca gctggatcag atccccttca aggacatgtg gcccgacgac     360
agctactggt ttccactcct gcttcagaag aagaaattcc acgggtactt caagttccag     420
ggtcaggaca ccatcctgga ctacacactc cgcgaggtgg acacggtcta g              471
```

<210> SEQ ID NO 12
<211> LENGTH: 156
<212> TYPE: PRT
<213> ORGANISM: Homo sapiens

<400> SEQUENCE: 12

```
Met Gly Ala Ser Arg Leu Tyr Thr Leu Val Val Leu Gln Pro Gln
1               5                   10                  15

Arg Val Leu Leu Gly Met Lys Lys Arg Gly Phe Gly Ala Gly Arg Trp
            20                  25                  30

Asn Gly Phe Gly Gly Lys Val Gln Glu Gly Glu Thr Ile Glu Asp Gly
            35                  40                  45

Ala Arg Arg Glu Leu Gln Glu Glu Ser Gly Leu Thr Val Asp Ala Leu
        50                  55                  60

His Lys Val Gly Gln Ile Val Phe Glu Phe Val Gly Glu Pro Glu Leu
65                  70                  75                  80

Met Asp Val His Val Phe Cys Thr Asp Ser Ile Gln Gly Thr Pro Val
                85                  90                  95

Glu Ser Asp Glu Met Arg Pro Cys Trp Phe Gln Leu Asp Gln Ile Pro
                100                 105                 110

Phe Lys Asp Met Trp Pro Asp Asp Ser Tyr Trp Phe Pro Leu Leu Leu
            115                 120                 125

Gln Lys Lys Lys Phe His Gly Tyr Phe Lys Phe Gln Gly Gln Asp Thr
        130                 135                 140

Ile Leu Asp Tyr Thr Leu Arg Glu Val Asp Thr Val
145                 150                 155
```

<210> SEQ ID NO 13
<211> LENGTH: 540
<212> TYPE: DNA
<213> ORGANISM: Homo sapiens
<220> FEATURE:
<221> NAME/KEY: source
<222> LOCATION: 1..540
<223> OTHER INFORMATION: /mol_type="unassigned DNA"
      /organism="Homo sapiens"

<400> SEQUENCE: 13

```
atgagtggaa ttagccctca gcagatgggg gagccagaag gcagttggag tgggaagaac    60
ccagggacca tgggcgcctc caggctctat accctggtgc tggtcctgca gcctcagcga   120
gttctcctgg gcatgaaaaa gcgaggcttc ggggccggcc ggtggaatgg ctttgggggc   180
aaagtgcaag aaggagagac catcgaggat ggggctagga gggagctgca ggaggagagc   240
ggtctgacag tggacgccct gcacaaggtg ggccagatcg tgtttgagtt cgtgggcgag   300
cctgagctca tggacgtgca tgtcttctgc acagacagca tccaggggac ccccgtggag   360
agcgacgaaa tgcgcccatg ctggttccag ctggatcaga tccccttcaa ggacatgtgg   420
cccgacgaca gctactggtt ccactcctg cttcagaaga agaaattcca cgggtacttc   480
aagttccagg gtcaggacac catcctggac tacacactcc gcgaggtgga cacggtctag   540
```

<210> SEQ ID NO 14
<211> LENGTH: 179
<212> TYPE: PRT
<213> ORGANISM: Homo sapiens

<400> SEQUENCE: 14

```
Met Ser Gly Ile Ser Pro Gln Gln Met Gly Glu Pro Glu Gly Ser Trp
1               5                   10                  15

Ser Gly Lys Asn Pro Gly Thr Met Gly Ala Ser Arg Leu Tyr Thr Leu
            20                  25                  30

Val Leu Val Leu Gln Pro Gln Arg Val Leu Leu Gly Met Lys Lys Arg
        35                  40                  45
```

```
Gly Phe Gly Ala Gly Arg Trp Asn Gly Phe Gly Lys Val Gln Glu
         50                  55                  60

Gly Glu Thr Ile Glu Asp Gly Ala Arg Arg Glu Leu Gln Glu Ser
 65                  70                  75                  80

Gly Leu Thr Val Asp Ala Leu His Lys Val Gly Gln Ile Val Phe Glu
                 85                  90                  95

Phe Val Gly Glu Pro Glu Leu Met Asp Val His Val Phe Cys Thr Asp
                100                 105                 110

Ser Ile Gln Gly Thr Pro Val Glu Ser Asp Glu Met Arg Pro Cys Trp
             115                 120                 125

Phe Gln Leu Asp Gln Ile Pro Phe Lys Asp Met Trp Pro Asp Asp Ser
130                 135                 140

Tyr Trp Phe Pro Leu Leu Leu Gln Lys Lys Phe His Gly Tyr Phe
145                 150                 155                 160

Lys Phe Gln Gly Gln Asp Thr Ile Leu Asp Tyr Thr Leu Arg Glu Val
                165                 170                 175

Asp Thr Val

<210> SEQ ID NO 15
<211> LENGTH: 197
<212> TYPE: PRT
<213> ORGANISM: Homo sapiens

<400> SEQUENCE: 15

Met Tyr Trp Ser Asn Gln Ile Thr Arg Arg Leu Gly Glu Arg Val Gln
 1               5                  10                  15

Gly Phe Met Ser Gly Ile Ser Pro Gln Met Gly Pro Glu Gly
                 20                  25                  30

Ser Trp Ser Gly Lys Asn Pro Gly Thr Met Gly Ala Ser Arg Leu Tyr
             35                  40                  45

Thr Leu Val Leu Val Leu Gln Pro Gln Arg Val Leu Leu Gly Met Lys
 50                  55                  60

Lys Arg Gly Phe Gly Ala Gly Arg Trp Asn Gly Phe Gly Lys Val
 65                  70                  75                  80

Gln Glu Gly Glu Thr Ile Glu Asp Gly Ala Arg Arg Glu Leu Gln Glu
                 85                  90                  95

Glu Ser Gly Leu Thr Val Asp Ala Leu His Lys Val Gly Gln Ile Val
                100                 105                 110

Phe Glu Phe Val Gly Glu Pro Glu Leu Met Asp Val His Val Phe Cys
             115                 120                 125

Thr Asp Ser Ile Gln Gly Thr Pro Val Glu Ser Asp Glu Met Arg Pro
130                 135                 140

Cys Trp Phe Gln Leu Asp Gln Ile Pro Phe Lys Asp Met Trp Pro Asp
145                 150                 155                 160

Asp Ser Tyr Trp Phe Pro Leu Leu Leu Gln Lys Lys Phe His Gly
                165                 170                 175

Tyr Phe Lys Phe Gln Gly Gln Asp Thr Ile Leu Asp Tyr Thr Leu Arg
                180                 185                 190

Glu Val Asp Thr Val
            195

<210> SEQ ID NO 16
<211> LENGTH: 171
<212> TYPE: PRT
<213> ORGANISM: Homo sapiens
```

-continued

<400> SEQUENCE: 16

```
Met Gly Glu Pro Glu Gly Ser Trp Ser Gly Lys Asn Pro Gly Thr Met
1               5                   10                  15

Gly Ala Ser Arg Leu Tyr Thr Leu Val Leu Val Leu Gln Pro Gln Arg
            20                  25                  30

Val Leu Leu Gly Met Lys Lys Arg Gly Phe Gly Ala Gly Arg Trp Asn
        35                  40                  45

Gly Phe Gly Gly Lys Val Gln Glu Gly Glu Thr Ile Glu Asp Gly Ala
    50                  55                  60

Arg Arg Glu Leu Gln Glu Glu Ser Gly Leu Thr Val Asp Ala Leu His
65                  70                  75                  80

Lys Val Gly Gln Ile Val Phe Glu Phe Val Gly Glu Pro Glu Leu Met
                85                  90                  95

Asp Val His Val Phe Cys Thr Asp Ser Ile Gln Gly Thr Pro Val Glu
            100                 105                 110

Ser Asp Glu Met Arg Pro Cys Trp Phe Gln Leu Asp Gln Ile Pro Phe
        115                 120                 125

Lys Asp Met Trp Pro Asp Asp Ser Tyr Trp Phe Pro Leu Leu Leu Gln
    130                 135                 140

Lys Lys Lys Phe His Gly Tyr Phe Lys Phe Gln Gly Gln Asp Thr Ile
145                 150                 155                 160

Leu Asp Tyr Thr Leu Arg Glu Val Asp Thr Val
                165                 170
```

<210> SEQ ID NO 17
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Primer Sequence for the Detection of NUDT1/MTH1"
      /organism="Artificial Sequence"

<400> SEQUENCE: 17
agcctcagcg agttctcctg                                           20

<210> SEQ ID NO 18
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="Primer Sequence for the Detection of NUDT1/MTH1"
      /organism="Artificial Sequence"

<400> SEQUENCE: 18
gatctggccc accttgtgc                                            19

<210> SEQ ID NO 19
<211> LENGTH: 567
<212> TYPE: DNA
<213> ORGANISM: Homo sapiens
<220> FEATURE:
<221> NAME/KEY: source
<222> LOCATION: 1..567
<223> OTHER INFORMATION: /mol_type="unassigned DNA"
      /organism="Homo sapiens"

<400> SEQUENCE: 19

```
atgactgaat ataaacttgt ggtagttgga gctggtggcg taggcaagag tgccttgacg        60
atacagctaa ttcagaatca ttttgtggac gaatatgatc caacaataga ggattcctac       120
aggaagcaag tagtaattga tggagaaacc tgtctcttgg atattctcga cacagcaggt       180
caagaggagt acagtgcaat gagggaccag tacatgagga ctggggaggg ctttctttgt       240
gtatttgcca taataatac taaatcattt gaagatattc accattatag agaacaaatt        300
aaaagagtta aggactctga agatgtacct atggtcctag taggaaataa atgtgatttg       360
ccttctagaa cagtagacac aaaacaggct caggacttag caagaagtta tggaattcct       420
tttattgaaa catcagcaaa gacaagacag ggtgttgatg atgccttcta tacattagtt       480
cgagaaattc gaaaacataa agaaagatg agcaagatg gtaaaagaa gaaaagaag          540 tcaaagacaa agtgtgtaat tatgtaa                                          567
```

<210> SEQ ID NO 20
<211> LENGTH: 188
<212> TYPE: PRT
<213> ORGANISM: Homo sapiens

<400> SEQUENCE: 20

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 21
<211> LENGTH: 570
<212> TYPE: DNA
<213> ORGANISM: Homo sapiens
<220> FEATURE:
<221> NAME/KEY: source
<222> LOCATION: 1..570
<223> OTHER INFORMATION: /mol_type="unassigned DNA"
      /organism="Homo sapiens"

<400> SEQUENCE: 21

```
atgactgaat ataaacttgt ggtagttgga gctggtggcg taggcaagag tgccttgacg        60
```

-continued

```
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag agagtggagg atgcttttta tacattggtg    480
agggagatcc gacaatacag attgaaaaaa atcagcaaag aagaaagac tcctggctgt    540 gtgaaaatta aaaatgcat tataatgtaa                                      570
```

<210> SEQ ID NO 22
<211> LENGTH: 189
<212> TYPE: PRT
<213> ORGANISM: Homo sapiens

<400> SEQUENCE: 22

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

<210> SEQ ID NO 23
<211> LENGTH: 189
<212> TYPE: PRT
<213> ORGANISM: Homo sapiens

<400> SEQUENCE: 23

```
Met Thr Glu Tyr Lys Leu Val Val Gly Ala Cys Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45
```

```
Glu Thr Cys Leu Leu Asp Ile Leu Asp Thr Ala Gly Gln Glu Glu Tyr
         50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

```
<210> SEQ ID NO 24
<211> LENGTH: 570
<212> TYPE: DNA
<213> ORGANISM: Homo sapiens
<220> FEATURE:
<221> NAME/KEY: source
<222> LOCATION: 1..570
<223> OTHER INFORMATION: /mol_type="unassigned DNA"
      /organism="Homo sapiens"

<400> SEQUENCE: 24
atgacggaat ataagctggt ggtggtgggc gccggcggtg tgggcaagag tgcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
caggaggagt acagcgccat gcgggaccag tacatgcgca ccggggaggg cttcctgtgt     240
gtgtttgcca tcaacaacac caagtctttt gaggacatcc accagtacag ggagcagatc     300
aaacgggtga aggactcgga tgacgtgccc atggtgctgg tggggaacaa gtgtgacctg     360
gctgcacgca ctgtggaatc tcggcaggct caggacctcg cccgaagcta cggcatcccc     420
tacatcgaga cctcggccaa gacccggcag ggagtggagg atgccttcta cacgttggtg     480
cgtgagatcc ggcagcacaa gctgcggaag ctgaaccctc tgatgagag tggccccggc     540 tgcatgagct gcaagtgtgt gctctcctga                                      570
```

```
<210> SEQ ID NO 25
<211> LENGTH: 189
<212> TYPE: PRT
<213> ORGANISM: Homo sapiens

<400> SEQUENCE: 25

Met Thr Glu Tyr Lys Leu Val Val Val Gly Ala Gly Gly Val Gly Lys
 1               5                   10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
         35                  40                  45

Glu Thr Cys Leu Leu Asp Ile Leu Asp Thr Ala Gly Gln Glu Glu Tyr
```

```
Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His Gln Tyr
                 85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 26
<211> LENGTH: 570
<212> TYPE: DNA
<213> ORGANISM: Homo sapiens
<220> FEATURE:
<221> NAME/KEY: source
<222> LOCATION: 1..570
<223> OTHER INFORMATION: /mol_type="unassigned DNA"
      /organism="Homo sapiens"

<400> SEQUENCE: 26

```
atgacggaat ataagctggt ggtggtgggc gccggcggtg tgggcaagag tgcgctgacc    60
atccagctga tccagaacca ttttgtggac gaatacgacc ccactataga ggattcctac   120
cggaagcagg tggtcattga tggggagacg tgcctgttgg acatcctgga taccgccggc   180
caggaggagt acagcgccat gcgggaccag tacatgcgca ccggggaggg cttcctgtgt   240
gtgtttgcca tcaacaacac caagtctttt gaggacatcc accagtacag ggagcagatc   300
aaacgggtga aggactcgga tgacgtgccc atggtgctgg tggggaacaa gtgtgacctg   360
gctgcacgca ctgtggaatc tcggcaggct caggacctcg cccgaagcta cggcatcccc   420
tacatcgaga cctcggccaa gacccggcag ggagtggagg atgccttcta cacgttggtg   480
cgtgagatcc ggcagcacaa gctgcggaag ctgaaccctc ctgatgagag tggccccggc   540
tgcatgagct gcaagtgtgt gctctcctga                                    570
```

<210> SEQ ID NO 27
<211> LENGTH: 189
<212> TYPE: PRT
<213> ORGANISM: Homo sapiens

<400> SEQUENCE: 27

```
Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gln Glu Glu Tyr
 50                  55                  60
```

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
                115                 120                 125

Gln Ala Gln Asp Leu Ala Arg Ser Tyr Gly Ile Pro Tyr Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 28
<211> LENGTH: 513
<212> TYPE: DNA
<213> ORGANISM: Homo sapiens
<220> FEATURE:
<221> NAME/KEY: source
<222> LOCATION: 1..513
<223> OTHER INFORMATION: /mol_type="unassigned DNA"
    /organism="Homo sapiens"

<400> SEQUENCE: 28
atgacggaat ataagctggt ggtggtgggc gccggcggtg tgggcaagag tgcgctgacc      60
atccagctga tccagaacca ttttgtggac gaatacgacc ccactataga ggattcctac     120
cggaagcagg tggtcattga tggggagacg tgcctgttgg acatcctgga taccgccggc     180
caggaggagt acagcgccat gcgggaccag tacatgcgca ccggggaggg cttcctgtgt     240
gtgtttgcca tcaacaacac caagtctttt gaggacatcc accagtacag ggagcagatc     300
aaacgggtga aggactcgga tgtgtgccc atggtgctgg tggggaacaa gtgtgacctg     360
gctgcacgca ctgtggaatc tcggcaggct caggacctcg cccgaagcta cggcatcccc     420
tacatcgaga cctcggccaa gacccggcag ggcagccgct ctggctctag ctccagctcc     480 gggacccctct gggaccccccc gggacccatg tga                                513

<210> SEQ ID NO 29
<211> LENGTH: 170
<212> TYPE: PRT
<213> ORGANISM: Homo sapiens

<400> SEQUENCE: 29

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr

```
                        85                  90                  95

Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Ser Arg Ser Gly Ser Ser Ser Ser Ser
145                 150                 155                 160

Gly Thr Leu Trp Asp Pro Pro Gly Pro Met
                165                 170

<210> SEQ ID NO 30
<211> LENGTH: 570
<212> TYPE: DNA
<213> ORGANISM: Homo sapiens
<220> FEATURE:
<221> NAME/KEY: source
<222> LOCATION: 1..570
<223> OTHER INFORMATION: /mol_type="unassigned DNA"
      /organism="Homo sapiens"

<400> SEQUENCE: 30
atgactgagt acaaactggt ggtggttgga gcaggtggtg ttgggaaaag cgcactgaca     60
atccagctaa tccagaacca ctttgtagat gaatatgatc ccaccataga ggattcttac    120
agaaaacaag tggttataga tggtgaaacc tgtttgttgg acatactgga tacagctgga    180
caagaagagt acagtgccat gagagaccaa tacatgagga caggcgaagg cttcctctgt    240
gtatttgcca tcaataatag caagtcattt gcggatatta acctctacag ggagcagatt    300
aagcgagtaa aagactcgga tgatgtacct atggtgctag tgggaaacaa gtgtgatttg    360
ccaacaagga cagttgatac aaaacaagcc cacgaactgg ccaagagtta cgggattcca    420
ttcattgaaa cctcagccaa gaccagacag ggtgttgaag atgcttttta cacactggta    480
agagaaatac gccagtaccg aatgaaaaaa ctcaacagca gtgatgatgg gactcagggt    540
tgtatgggat tgccatgtgt ggtgatgtaa                                     570

<210> SEQ ID NO 31
<211> LENGTH: 189
<212> TYPE: PRT
<213> ORGANISM: Homo sapiens

<400> SEQUENCE: 31

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
                100                 105                 110
```

```
Leu Val Gly Asn Lys Cys Asp Leu Pro Thr Arg Thr Val Asp Thr Lys
        115                 120                 125
Gln Ala His Glu Leu Ala Lys Ser Tyr Gly Ile Pro Phe Ile Glu Thr
    130                 135                 140
Ser Ala Lys Thr Arg Gln Gly Val Glu Asp Ala Phe Tyr Thr Leu Val
145                 150                 155                 160
Arg Glu Ile Arg Gln Tyr Arg Met Lys Lys Leu Asn Ser Ser Asp Asp
                165                 170                 175
Gly Thr Gln Gly Cys Met Gly Leu Pro Cys Val Val Met
                180                 185

<210> SEQ ID NO 32
<211> LENGTH: 4863
<212> TYPE: DNA
<213> ORGANISM: Homo sapiens
<220> FEATURE:
<221> NAME/KEY: source
<222> LOCATION: 1..4863
<223> OTHER INFORMATION: /mol_type="unassigned DNA"
      /organism="Homo sapiens"

<400> SEQUENCE: 32
```

| | | | | | |
|---|---|---|---|---|---|
| atgggagcca | tcgggctcct | gtggctcctg | ccgctgctgc | tttccacggc | agctgtgggc | 60 |
| tccgggatgg | ggaccggcca | gcgcgcgggc | tccccagctg | cggggccgcc | gctgcagccc | 120 |
| cgggagccac | tcagctactc | cgcctgcag | aggaagagtc | tggcagttga | cttcgtggtg | 180 |
| ccctcgctct | tccgtgtcta | cgcccgggac | ctactgctgc | caccatcctc | ctcggagctg | 240 |
| aaggctggca | ggcccgaggc | ccgcggctcg | ctagctctgg | actgcgcccc | gctgctcagg | 300 |
| ttgctggggc | cggcgccggg | ggtctcctgg | accgccggtt | caccagcccc | ggcagaggcc | 360 |
| cggacgctgt | ccagggtgct | gaagggcggc | tccgtgcgca | agctccggcg | tgccaagcag | 420 |
| ttggtgctgg | agctgggcga | ggaggcgatc | ttggagggtt | gcgtcgggcc | ccccggggag | 480 |
| gcggctgtgg | ggctgctcca | gttcaatctc | agcgagctgt | tcagttggtg | gattcgccaa | 540 |
| ggcgaaggc | gactgaggat | ccgcctgatg | cccgagaaga | aggcgtcgga | agtgggcaga | 600 |
| gagggaaggc | tgtccgcggc | aattcgcgcc | tcccagcccc | gccttctctt | ccagatcttc | 660 |
| gggactggtc | atagctcctt | ggaatcacca | acaaacatgc | cttctccttc | tcctgattat | 720 |
| tttacatgga | atctcacctg | gataatgaaa | gactccttcc | cttccctgtc | tcatcgcagc | 780 |
| cgatatggtc | tggagtgcag | cttttgacttc | ccctgtgagc | tggagtattc | ccctccactg | 840 |
| catgacctca | ggaaccagag | ctggtcctgg | cgccgcatcc | cctccgagga | ggcctcccag | 900 |
| atggacttgc | tggatgggcc | tggggcagag | cgttctaagg | agatgcccag | aggctccttt | 960 |
| ctccttctca | cacctcagc | tgactccaag | cacaccatcc | tgagtccgtg | atgaggagc | 1020 |
| agcagtgagc | actgcacact | ggccgtctcg | gtgcacaggc | acctgcagcc | ctctggaagg | 1080 |
| tacattgccc | agctgctgcc | ccacaacgag | gctgcaagag | gatcctcct | gatgcccact | 1140 |
| ccagggaagc | atggttggac | agtgctccag | ggaagaatcg | ggcgtccaga | caacccattt | 1200 |
| cgagtggccc | tggaatacat | ctccagtgga | aaccgcagct | tgtctgcagt | ggacttcttt | 1260 |
| gccctgaaga | actgcagtga | aggaacatcc | ccaggctcca | agatggccct | gcagagctcc | 1320 |
| ttcacttgtt | ggaatgggac | agtcctccag | cttgggcagg | cctgtgactt | ccaccaggac | 1380 |
| tgtgcccagg | gagaagatga | gagccagatg | tgccggaaac | tgcctgtggg | ttttactgc | 1440 |
| aactttgaag | atggcttctg | tggctggacc | caaggcacac | tgtcacccca | cactcctcaa | 1500 |
| tggcaggtca | ggaccctaaa | ggatgcccgg | ttccaggacc | accaagacca | tgctctattg | 1560 |

```
ctcagtacca ctgatgtccc cgcttctgaa agtgctacag tgaccagtgc tacgtttcct    1620
gcaccgatca agagctctcc atgtgagctc cgaatgtcct ggctcattcg tggagtcttg    1680
aggggaaacg tgtccttggt gctagtggag aacaaaaccg ggaaggagca aggcaggatg    1740
gtctggcatg tcgccgccta tgaaggcttg agcctgtggc agtggatggt gttgcctctc    1800
ctcgatgtgt ctgacaggtt ctggctgcag atggtcgcat ggtggggaca aggatccaga    1860
gccatcgtgg cttttgacaa tatctccatc agcctggact gctacctcac cattagcgga    1920
gaggacaaga tcctgcagaa tacagcaccc aaatcaagaa acctgtttga gagaaaccca    1980
aacaaggagc tgaaacccgg ggaaaattca ccaagacaga ccccccatctt tgaccctaca    2040 gttcattggc tgttcaccac atgtggggcc agcgggcccc atggccccac ccaggcacag    2100
tgcaacaacg cctaccagaa ctccaacctg agcgtggagg tggggagcga gggcccctg     2160 aaaggcatcc agatctggaa ggtgccagcc accgacacct acagcatctc gggctacgga    2220
gctgctggcg ggaaaggcgg gaagaacacc atgatgcggt cccacggcgt gtctgtgctg    2280
ggcatcttca acctggagaa ggatgacatg ctgtacatcc tggttgggca gcagggagag    2340
gacgcctgcc ccagtacaaa ccagttaatc cagaaagtct gcattggaga gaacaatgtg    2400
atagaagaag aaatccgtgt gaacagaagc gtgcatgagt gggcaggagg cggaggagga    2460
gggggtggag ccacctacgt atttaagatg aaggatggag tgccggtgcc cctgatcatt    2520
gcagccggag gtggtggcag ggcctacggg gccaagacag acacgttcca cccagagaga    2580
ctggagaata actcctcggt tctagggcta acggcaatt ccggagccgc aggtggtgga    2640
ggtggctgga atgataacac ttccttgctc tgggccggaa aatctttgca ggagggtgcc    2700
accggaggac attcctgccc ccaggccatg aagaagtggg ggtgggagac aagaggggt    2760 ttcggagggg gtggagggg gtgctcctca ggtggaggag gcggaggata tataggcggc    2820
aatgcagcct caaacaatga ccccgaaatg gatgggaag atggggtttc cttcatcagt    2880
ccactgggca tcctgtacac cccagctta aaagtgatgg aaggccacgg ggaagtgaat    2940
attaagcatt atctaaactg cagtcactgt gaggtagacg aatgtcacat ggaccctgaa    3000
agccacaagg tcatctgctt ctgtgaccac gggacggtgc tggctgagga tggcgtctcc    3060
tgcattgtgt cacccacccc ggagccacac ctgccactct cgctgatcct ctctgtggtg    3120
acctctgccc tcgtggccgc cctggtcctg gcttctccg gcatcatgat tgtgtaccgc    3180
cggaagcacc aggagctgca agccatgcag atggagctgc agagccctga gtacaagctg    3240
agcaagctcc gcacctcgac catcatgacc gactacaacc ccaactactg ctttgctggc    3300
aagacctcct ccatcagtga cctgaaggag gtgccgcgga aaacatcac cctcattcgg    3360 ggtctgggcc atggcgcctt tggggaggtg tatgaaggcc aggtgtccgg aatgcccaac    3420
gacccaagcc cctgcaagt ggctgtgaag acgctgcctg aagtgtgctc tgaacaggac    3480
gaactggatt tcctcatgga agccctgatc atcagcaaat tcaaccacca gaacattgtt    3540
cgctgcattg gggtgagcct gcaatccctg ccccggttca tcctgctgga gctcatggcg    3600
gggggagacc tcaagtcctt cctccgagag accgccctc gcccgagcca gccctcctcc    3660
ctggccatgc tggaccttct gcacgtggct cgggacattg cctgtggctg tcagtatttg    3720
gaggaaaacc acttcatcca ccgagacatt gctgccagaa actgcctctt gacctgtcca    3780
ggccctggaa gagtggccaa gattggagac ttcgggatgg cccagacat ctacagggcg    3840 agctactata gaaagggagg ctgtgccatg ctgccagtta agtggatgcc cccagaggcc    3900
```

```
ttcatggaag gaatattcac ttctaaaaca gacacatggt cctttggagt gctgctatgg    3960
gaaatctttt ctcttggata tatgccatac cccagcaaaa gcaaccagga agttctggag    4020
tttgtcacca gtggaggccg gatggaccca cccaagaact gccctgggcc tgtataccgg    4080
ataatgactc agtgctggca acatcagcct gaagacaggc ccaactttgc catcattttg    4140
gagaggattg aatactgcac ccaggacccg gatgtaatca acaccgcttt gccgatagaa    4200
tatggtccac ttgtggaaga ggaagagaaa gtgcctgtga ggcccaagga ccctgagggg    4260
gttcctcctc tcctggtctc tcaacaggca aaacgggagg aggagcgcag cccagctgcc    4320
ccaccacctc tgcctaccac ctcctctggc aaggctgcaa agaaacccac agctgcagag    4380
atctctgttc gagtccctag agggccggcc gtggaagggg acacgtgaa tatggcattc    4440
tctcagtcca accctccttc ggagttgcac aaggtccacg gatccagaaa caagcccacc    4500
agcttgtgga acccaacgta cggctcctgg tttacagaga aacccaccaa aaagaataat    4560
cctatagcaa agaaggagcc acacgacagg ggtaacctgg ggctggaggg aagctgtact    4620
gtcccaccta acgttgcaac tgggagactt ccgggggcct cactgctcct agagccctct    4680
tcgctgactg ccaatatgaa ggaggtacct ctgttcaggc tacgtcactt cccttgtggg    4740
aatgtcaatt acggctacca gcaacagggc ttgcccttag aagccgctac tgcccctgga    4800
gctggtcatt acgaggatac cattctgaaa agcaagaata gcatgaacca gcctgggccc    4860
tga                                                                 4863

<210> SEQ ID NO 33
<211> LENGTH: 1620
<212> TYPE: PRT
<213> ORGANISM: Homo sapiens

<400> SEQUENCE: 33

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Pro Ser Ser Ser Glu Leu
65                  70                  75              80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
```

```
                    195                 200                 205
Arg Ala Ser Gln Pro Arg Leu Leu Phe Gln Ile Phe Gly Thr Gly His
210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
    530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
    610                 615                 620
```

-continued

```
Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
            645                 650                 655

Glu Arg Asn Pro Asn Lys Glu Leu Lys Pro Gly Glu Asn Ser Pro Arg
                660                 665                 670

Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
            725                 730                 735

Ser Gly Tyr Gly Ala Ala Gly Gly Lys Gly Gly Lys Asn Thr Met Met
                740                 745                 750

Arg Ser His Gly Val Ser Val Leu Gly Ile Phe Asn Leu Glu Lys Asp
            755                 760                 765

Asp Met Leu Tyr Ile Leu Val Gly Gln Gln Gly Glu Asp Ala Cys Pro
770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Gly Arg Ala
835                 840                 845

Tyr Gly Ala Lys Thr Asp Thr Phe His Pro Glu Arg Leu Glu Asn Asn
850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
            885                 890                 895

Gln Glu Gly Ala Thr Gly Gly His Ser Cys Pro Gln Ala Met Lys Lys
                900                 905                 910

Trp Gly Trp Glu Thr Arg Gly Gly Phe Gly Gly Gly Gly Gly Cys
            915                 920                 925

Ser Ser Gly Gly Gly Gly Gly Tyr Ile Gly Gly Asn Ala Ala Ser
930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
                980                 985                 990

Asp Glu Cys His Met Asp Pro Glu Ser His Lys Val Ile Cys Phe Cys
            995                 1000                1005

Asp His Gly Thr Val Leu Ala Glu Asp Gly Val Ser Cys Ile Val Ser
        1010                1015                1020

Pro Thr Pro Glu Pro His Leu Pro Leu Ser Leu Ile Leu Ser Val Val
1025                1030                1035                1040
```

```
Thr Ser Ala Leu Val Ala Ala Leu Val Leu Ala Phe Ser Gly Ile Met
                 1045                1050                1055

Ile Val Tyr Arg Arg Lys His Gln Glu Leu Gln Ala Met Gln Met Glu
            1060                1065                1070

Leu Gln Ser Pro Glu Tyr Lys Leu Ser Lys Leu Arg Thr Ser Thr Ile
        1075                1080                1085

Met Thr Asp Tyr Asn Pro Asn Tyr Cys Phe Ala Gly Lys Thr Ser Ser
    1090                1095                1100

Ile Ser Asp Leu Lys Glu Val Pro Arg Lys Asn Ile Thr Leu Ile Arg
1105                1110                1115                1120

Gly Leu Gly His Gly Ala Phe Gly Glu Val Tyr Glu Gly Gln Val Ser
                1125                1130                1135

Gly Met Pro Asn Asp Pro Ser Pro Leu Gln Val Ala Val Lys Thr Leu
            1140                1145                1150

Pro Glu Val Cys Ser Glu Gln Asp Glu Leu Asp Phe Leu Met Glu Ala
        1155                1160                1165

Leu Ile Ile Ser Lys Phe Asn His Gln Asn Ile Val Arg Cys Ile Gly
    1170                1175                1180

Val Ser Leu Gln Ser Leu Pro Arg Phe Ile Leu Leu Glu Leu Met Ala
1185                1190                1195                1200

Gly Gly Asp Leu Lys Ser Phe Leu Arg Glu Thr Arg Pro Arg Pro Ser
                1205                1210                1215

Gln Pro Ser Ser Leu Ala Met Leu Asp Leu Leu His Val Ala Arg Asp
            1220                1225                1230

Ile Ala Cys Gly Cys Gln Tyr Leu Glu Glu Asn His Phe Ile His Arg
        1235                1240                1245

Asp Ile Ala Ala Arg Asn Cys Leu Leu Thr Cys Pro Gly Pro Gly Arg
    1250                1255                1260

Val Ala Lys Ile Gly Asp Phe Gly Met Ala Arg Asp Ile Tyr Arg Ala
1265                1270                1275                1280

Ser Tyr Tyr Arg Lys Gly Gly Cys Ala Met Leu Pro Val Lys Trp Met
                1285                1290                1295

Pro Pro Glu Ala Phe Met Glu Gly Ile Phe Thr Ser Lys Thr Asp Thr
            1300                1305                1310

Trp Ser Phe Gly Val Leu Leu Trp Glu Ile Phe Ser Leu Gly Tyr Met
        1315                1320                1325

Pro Tyr Pro Ser Lys Ser Asn Gln Glu Val Leu Glu Phe Val Thr Ser
    1330                1335                1340

Gly Gly Arg Met Asp Pro Pro Lys Asn Cys Pro Gly Pro Val Tyr Arg
1345                1350                1355                1360

Ile Met Thr Gln Cys Trp Gln His Gln Pro Glu Asp Arg Pro Asn Phe
                1365                1370                1375

Ala Ile Ile Leu Glu Arg Ile Glu Tyr Cys Thr Gln Asp Pro Asp Val
            1380                1385                1390

Ile Asn Thr Ala Leu Pro Ile Glu Tyr Gly Pro Leu Val Glu Glu Glu
        1395                1400                1405

Glu Lys Val Pro Val Arg Pro Lys Asp Pro Glu Gly Val Pro Pro Leu
    1410                1415                1420

Leu Val Ser Gln Gln Ala Lys Arg Glu Glu Arg Ser Pro Ala Ala
1425                1430                1435                1440

Pro Pro Pro Leu Pro Thr Thr Ser Ser Gly Lys Ala Ala Lys Lys Pro
                1445                1450                1455

Thr Ala Ala Glu Ile Ser Val Arg Val Pro Arg Gly Pro Ala Val Glu
```

```
                1460                1465                1470
Gly Gly His Val Asn Met Ala Phe Ser Gln Ser Asn Pro Pro Ser Glu
        1475                1480                1485
Leu His Lys Val His Gly Ser Arg Asn Lys Pro Thr Ser Leu Trp Asn
        1490                1495                1500
Pro Thr Tyr Gly Ser Trp Phe Thr Glu Lys Pro Thr Lys Lys Asn Asn
1505                1510                1515                1520
Pro Ile Ala Lys Lys Glu Pro His Asp Arg Gly Asn Leu Gly Leu Glu
            1525                1530                1535
Gly Ser Cys Thr Val Pro Pro Asn Val Ala Thr Gly Arg Leu Pro Gly
                1540                1545                1550
Ala Ser Leu Leu Leu Glu Pro Ser Ser Leu Thr Ala Asn Met Lys Glu
        1555                1560                1565
Val Pro Leu Phe Arg Leu Arg His Phe Pro Cys Gly Asn Val Asn Tyr
            1570                1575                1580
Gly Tyr Gln Gln Gln Gly Leu Pro Leu Glu Ala Ala Thr Ala Pro Gly
1585                1590                1595                1600
Ala Gly His Tyr Glu Asp Thr Ile Leu Lys Ser Lys Asn Ser Met Asn
            1605                1610                1615
Gln Pro Gly Pro
        1620
```

<210> SEQ ID NO 34
<211> LENGTH: 2391
<212> TYPE: DNA
<213> ORGANISM: Homo sapiens
<220> FEATURE:
<221> NAME/KEY: source
<222> LOCATION: 1..2391
<223> OTHER INFORMATION: /mol_type="unassigned DNA"
    /organism="Homo sapiens"

<400> SEQUENCE: 34

```
atggacggtt tcgccggcag tctcgatgat agtatttctg ctgcaagtac ttctgatgtt    60
caagatcgcc tgtcagctct tgagtcacga gttcagcaac aagaagatga atcactgtg   120
ctaaaggcgg cttttggctga tgttttgagg cgtcttgcaa tctctgaaga tcatgtggcc   180
tcagtgaaaa aatcagtctc aagtaaaggc caaccaagcc ctcgagcagt tattcccatg   240
tcctgtataa ccaatggaag tggtgcaaac agaaaaccaa gtcataccag tgctgtctca   300
attgcaggaa agaaactct ttcatctgct gctaaaagtg gtacagaaaa aaagaaagaa   360
aaaccacaag gacagagaga aaaaaaagag aatctcatt ctaatgatca agtccacaa   420
attcgagcat caccttctcc ccagccctct tcacaacctc tccaaataca cagacaaact   480
ccagaaagca gaatgctac tcccaccaaa agcataaaac gaccatcacc agctgaaaag   540
tcacataatt cttgggaaaa ttcagatgat agccgtaata aattgtcgaa ataccttca    600
acacccaaat taataccaaa agttaccaaa actgcagaca agcataaaga tgtcatcatc   660
aaccaagcaa aaatgtcaac tcgcgaaaaa aacagccaag tgtaccgccg gaagcaccag   720
gagctgcaag ccatgcagat ggagctgcag agccctgagt acaagctgag caagctccgc   780
acctcgacca tcatgaccga ctacaacccc aactactgct tgctggcaa gacctcctcc   840
atcagtgacc tgaaggaggt gccgcggaaa acatcaccc tcattcgggg tctgggccat   900
ggcgcctttg gggaggtgta tgaaggccag gtgtccggaa tgcccaacga cccaagcccc   960
ctgcaagtgg ctgtgaagac gctgcctgaa gtgtgctctg aacaggacga actggatttc  1020
```

| | |
|---|---|
| ctcatggaag ccctgatcat cagcaaattc aaccaccaga acattgttcg ctgcattggg | 1080 |
| gtgagcctgc aatccctgcc ccggttcatc ctgctggagc tcatggcggg gggagacctc | 1140 |
| aagtccttcc tccgagagac ccgccctcgc ccgagccagc cctcctccct ggccatgctg | 1200 |
| gaccttctgc acgtggctcg ggacattgcc tgtggctgtc agtatttgga ggaaaaccac | 1260 |
| ttcatccacc gagacattgc tgccagaaac tgcctcttga cctgtccagg ccctggaaga | 1320 |
| gtggccaaga ttggagactt cgggatggcc cgagacatct acagggcgag ctactataga | 1380 |
| aagggaggct gtgccatgct gccagttaag tggatgcccc cagaggcctt catggaagga | 1440 |
| atattcactt ctaaaacaga cacatggtcc tttggagtgc tgctatggga aatcttttct | 1500 |
| cttggatata tgccataccc cagcaaaagc aaccaggaag ttctggagtt tgtcaccagt | 1560 |
| ggaggccgga tggacccacc caagaactgc cctgggcctg tataccggat aatgactcag | 1620 |
| tgctggcaac atcagcctga agacaggccc aactttgcca tcattttgga gaggattgaa | 1680 |
| tactgcaccc aggacccgga tgtaatcaac accgctttgc cgatagaata tggtccactt | 1740 |
| gtggaagagg aagagaaagt gcctgtgagg cccaaggacc ctgaggtggt tcctcctctc | 1800 |
| ctggtctctc aacaggcaaa acgggaggag gagcgcagcc cagctgcccc accacctctg | 1860 |
| cctaccacct cctctggcaa ggctgcaaag aaacccacag ctgcagagat ctctgttcga | 1920 |
| gtccctagag ggccggccgt ggaaggggga cacgtgaata tggcattctc tcagtccaac | 1980 |
| cctccttcgg agttgcacaa ggtccacgga tccagaaaca gcccaccag cttgtggaac | 2040 |
| ccaacgtacg gctcctggtt tacagagaaa cccaccaaaa agaataatcc tatagcaaag | 2100 |
| aaggagccac acgacagggg taacctgggg ctggagggaa gctgtactgt cccacctaac | 2160 |
| gttgcaactg ggagacttcc gggggcctca ctgctcctag agccctcttc gctgactgcc | 2220 |
| aatatgaagg aggtacctct gttcaggcta cgtcacttcc cttgtgggaa tgtcaattac | 2280 |
| ggctaccagc aacagggctt gcccttagaa gccgctactg cccctggagc tggtcattac | 2340 |
| gaggatacca ttctgaaaag caagaatagc atgaaccagc tgggccctg a | 2391 |

<210> SEQ ID NO 35
<211> LENGTH: 796
<212> TYPE: PRT
<213> ORGANISM: Homo sapiens

<400> SEQUENCE: 35

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
```

```
            130                 135                 140
Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
                180                 185                 190

Asn Lys Leu Ser Lys Ile Pro Ser Thr Pro Lys Leu Ile Pro Lys Val
                195                 200                 205

Thr Lys Thr Ala Asp Lys His Lys Asp Val Ile Ile Asn Gln Ala Lys
210                 215                 220

Met Ser Thr Arg Glu Lys Asn Ser Gln Val Tyr Arg Arg Lys His Gln
225                 230                 235                 240

Glu Leu Gln Ala Met Gln Met Glu Leu Gln Ser Pro Glu Tyr Lys Leu
                245                 250                 255

Ser Lys Leu Arg Thr Ser Thr Ile Met Thr Asp Tyr Asn Pro Asn Tyr
                260                 265                 270

Cys Phe Ala Gly Lys Thr Ser Ser Ile Ser Asp Leu Lys Glu Val Pro
                275                 280                 285

Arg Lys Asn Ile Thr Leu Ile Arg Gly Leu Gly His Gly Ala Phe Gly
                290                 295                 300

Glu Val Tyr Glu Gly Gln Val Ser Gly Met Pro Asn Asp Pro Ser Pro
305                 310                 315                 320

Leu Gln Val Ala Val Lys Thr Leu Pro Glu Val Cys Ser Glu Gln Asp
                325                 330                 335

Glu Leu Asp Phe Leu Met Glu Ala Leu Ile Ile Ser Lys Phe Asn His
                340                 345                 350

Gln Asn Ile Val Arg Cys Ile Gly Val Ser Leu Gln Ser Leu Pro Arg
                355                 360                 365

Phe Ile Leu Leu Glu Leu Met Ala Gly Gly Asp Leu Lys Ser Phe Leu
                370                 375                 380

Arg Glu Thr Arg Pro Arg Pro Ser Gln Pro Ser Ser Leu Ala Met Leu
385                 390                 395                 400

Asp Leu Leu His Val Ala Arg Asp Ile Ala Cys Gly Cys Gln Tyr Leu
                405                 410                 415

Glu Glu Asn His Phe Ile His Arg Asp Ile Ala Ala Arg Asn Cys Leu
                420                 425                 430

Leu Thr Cys Pro Gly Pro Gly Arg Val Ala Lys Ile Gly Asp Phe Gly
                435                 440                 445

Met Ala Arg Asp Ile Tyr Arg Ala Ser Tyr Tyr Arg Lys Gly Gly Cys
450                 455                 460

Ala Met Leu Pro Val Lys Trp Met Pro Pro Glu Ala Phe Met Glu Gly
465                 470                 475                 480

Ile Phe Thr Ser Lys Thr Asp Thr Trp Ser Phe Gly Val Leu Leu Trp
                485                 490                 495

Glu Ile Phe Ser Leu Gly Tyr Met Pro Tyr Pro Ser Lys Ser Asn Gln
                500                 505                 510

Glu Val Leu Glu Phe Val Thr Ser Gly Gly Arg Met Asp Pro Pro Lys
                515                 520                 525

Asn Cys Pro Gly Pro Val Tyr Arg Ile Met Thr Gln Cys Trp Gln His
                530                 535                 540

Gln Pro Glu Asp Arg Pro Asn Phe Ala Ile Ile Leu Glu Arg Ile Glu
545                 550                 555                 560
```

-continued

```
Tyr Cys Thr Gln Asp Pro Asp Val Ile Asn Thr Ala Leu Pro Ile Glu
                565                 570                 575
Tyr Gly Pro Leu Val Glu Glu Glu Lys Val Pro Val Arg Pro Lys
            580                 585                 590
Asp Pro Glu Gly Val Pro Leu Leu Val Ser Gln Gln Ala Lys Arg
            595                 600                 605
Glu Glu Glu Arg Ser Pro Ala Ala Pro Pro Leu Pro Thr Thr Ser
        610                 615                 620
Ser Gly Lys Ala Ala Lys Lys Pro Thr Ala Ala Glu Ile Ser Val Arg
625                 630                 635                 640
Val Pro Arg Gly Pro Ala Val Glu Gly Gly His Val Asn Met Ala Phe
                645                 650                 655
Ser Gln Ser Asn Pro Pro Ser Glu Leu His Lys Val His Gly Ser Arg
                660                 665                 670
Asn Lys Pro Thr Ser Leu Trp Asn Pro Thr Tyr Gly Ser Trp Phe Thr
                675                 680                 685
Glu Lys Pro Thr Lys Lys Asn Asn Pro Ile Ala Lys Lys Glu Pro His
            690                 695                 700
Asp Arg Gly Asn Leu Gly Leu Glu Gly Ser Cys Thr Val Pro Pro Asn
705                 710                 715                 720
Val Ala Thr Gly Arg Leu Pro Gly Ala Ser Leu Leu Leu Glu Pro Ser
                725                 730                 735
Ser Leu Thr Ala Asn Met Lys Glu Val Pro Leu Phe Arg Leu Arg His
                740                 745                 750
Phe Pro Cys Gly Asn Val Asn Tyr Gly Tyr Gln Gln Gln Gly Leu Pro
                755                 760                 765
Leu Glu Ala Ala Thr Ala Pro Gly Ala Gly His Tyr Glu Asp Thr Ile
            770                 775                 780
Leu Lys Ser Lys Asn Ser Met Asn Gln Pro Gly Pro
785                 790                 795
```

<210> SEQ ID NO 36
<211> LENGTH: 3365
<212> TYPE: DNA
<213> ORGANISM: Homo sapiens
<220> FEATURE:
<221> NAME/KEY: source
<222> LOCATION: 1..3365
<223> OTHER INFORMATION: /mol_type="unassigned DNA"
      /organism="Homo sapiens"

<400> SEQUENCE: 36

```
tactctgtcg gtccgctgaa tgaagtgccc gccctctaa gcccggagcc cggcgctttc        60
cccgcaagat ggacggtttc gccggcagtc tcgatgatag tatttctgct gcaagtactt       120
ctgatgttca agatcgcctg tcagctcttg agtcacgagt tcagcaacaa gaagatgaaa       180
tcactgtgct aaaggcggct ttggctgatg ttttgaggcg tcttgcaatc tctgaagatc       240
atgtggcctc agtgaaaaaa tcagtctcaa gtaaaggcca accaagccct cgagcagtta       300
ttcccatgtc ctgtataacc aatggaagtg gtgcaaacag aaaaccaagt cataccagtg       360
ctgtctcaat tgcaggaaaa gaactctttt catctgctgc taaagtggt acagaaaaaa       420 agaaagaaaa accacaagga cagagagaaa aaaagagga atctcattct aatgatcaaa       480
gtccacaaat tcgagcatca ccttctcccc agccctcttc acaacctctc caaatacaca       540
gacaaactcc agaaagcaag aatgctactc ccaccaaaag cataaaacga ccatcaccag       600
```

```
ctgaaaagtc acataattct tgggaaaatt cagatgatag ccgtaataaa ttgtcgaaaa    660
taccttcaac acccaaatta ataccaaaag ttaccaaaac tgcagacaag cataaagatg    720
tcatcatcaa ccaagaagga gaatatatta aaatgtttat gcgcggtcgg ccaattacca    780
tgttcattcc ttccgatgtt gacaactatg atgacatcag aacggaactg cctcctgaga    840
agctcaaact ggagtgggca tatggttatc gaggaaagga ctgtagagct aatgtttacc    900
ttcttccgac cggggaaata gtttatttca ttgcatcagt agtagtacta tttaattatg    960
aggagagaac tcagcgacac tacctgggcc atacagactg tgtgaaatgc cttgctatac   1020
atcctgacaa aattaggatt gcaactggac agatagctgg cgtggataaa gatggaaggc   1080
ctctacaacc ccacgtcaga gtgtgggatt ctgttactct atccacactg cagattattg   1140
gacttggcac ttttgagcgt ggagtaggat gcctggattt ttcaaaagca gattcaggtg   1200
ttcatttatg tgttattgat gactccaatg agcatatgct tactgtatgg gactggcaga   1260
ggaaagcaaa aggagcagaa ataaagacaa caaatgaagt tgttttggct gtggagtttc   1320
acccaacaga tgcaaatacc ataattacat gcggtaaatc tcatattttc ttctggacct   1380
ggagcggcaa ttcactaaca agaaaacagg gaattttttgg gaaatatgaa agcccaaaat   1440
ttgtgcagtg tttagcattc ttggggaatg agatgttct tactgagac tcaggtggag   1500
tcatgcttat atggagcaaa actactgtag agcccacacc tgggaaagga cctaaaggaa   1560
gtggcctgtg tagtgcttca agggccaggc tgccaggcca tgttgcagct gaccacccac   1620
ctgcagtgta ccgccggaag caccaggagc tgcaagccat gcagatggag ctgcagagcc   1680
ctgagtacaa gctgagcaag ctccgcacct cgaccatcat gaccgactac aaccccaact   1740
actgctttgc tggcaagacc tcctccatca gtgacctgaa ggaggtgccg cggaaaaaca   1800
tcaccctcat tcggggtctg ggccatgagc cctttgggga ggtgtatgaa ggccaggtgt   1860
ccggaatgcc caacgaccca agcccctgc aagtggctgt gaagacgctg cctgaagtgt   1920
gctctgaaca ggacgaactg gatttcctca tggaagccct gatcatcagc aaattcaacc   1980
accagaacat tgttcgctgc attggggtga gcctgcaatc cctgccccgg ttcatcctgc   2040
tggagctcat ggcgggggga gacctcaagt ccttcctccg agagacccgc cctcgcccga   2100
gccagccctc ctccctggcc atgctggacc ttctgcacgt ggctcgggac attgcctgtg   2160
gctgtcagta tttggaggaa aaccacttca tccaccgaga cattgctgcc agaaactgcc   2220
tcttgacctg tccaggccct ggaagagtgg ccaagattgg agacttcggg atggcccgag   2280
acatctacag ggcgagctac tatagaaagg gaggctgtgc catgctgcca gttaagtgga   2340
tgcccccaga ggccttcatg gaaggaatat tcacttctaa aacagacaca tggtcctttg   2400
gagtgctgct atgggaaatc ttttctcttg gatatatgcc ataccccagc aaaagcaacc   2460
aggaagttct ggagtttgtc accagtggag gccggatgga cccacccaag aactgccctg   2520
ggcctgtata ccggataatg actcagtgct ggcaacatca gcctgaagac aggcccaact   2580
ttgccatcat ttttgagagg attgaatact gcacccagga cccggatgta atcaacaccg   2640
ctttgccgat agaatatggt ccacttgtgg aagaggaaga gaaagtgcct gtgaggccca   2700
aggaccctga gggggttcct cctctcctgg tctctcaaca ggcaaaacgg gaggaggagc   2760
gcagcccagc tgccccacca cctctgccta ccacctcctc tggcaaggct gcaaagaaac   2820
ccacagctgc agaggtctct gttcgagtcc ctagagggcc ggccgtggaa gggggacacg   2880
tgaatatggc attctctcag tccaacccctc cttcggagtt gcacgggtc cacgatcca   2940
gaaacaagcc caccagcttg tggaacccaa cgtacggctc ctggtttaca gagaaaccca   3000
```

```
ccaaaaagaa taatcctata gcaaagaagg agccacacga gaggggtaac ctggggctgg    3060
agggaagctg tactgtccca cctaacgttg caactgggag acttccgggg gcctcactgc    3120
tcctagagcc ctcttcgctg actgccaata tgaaggaggt acctctgttc aggctacgtc    3180
acttcccttg tgggaatgtc aattacggct accagcaaca gggcttgccc ttagaagccg    3240
ctactgcccc tggagctggt cattacgagg ataccattct gaaaagcaag aatagcatga    3300
accagcctgg gccctgagct cggtcgcaca ctcacttctc ttccttggga tccctaagac    3360
cgtgg                                                               3365
```

<210> SEQ ID NO 37
<211> LENGTH: 1082
<212> TYPE: PRT
<213> ORGANISM: Homo sapiens

<400> SEQUENCE: 37

```
Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Val Leu Phe Asn Tyr Glu Glu Arg Thr Gln Arg His
    290                 295                 300
```

-continued

```
Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
            325                 330                 335

Arg Pro Leu Gln Pro His Val Arg Val Trp Asp Ser Val Thr Leu Ser
        340                 345                 350

Thr Leu Gln Ile Ile Gly Leu Gly Thr Phe Glu Arg Gly Val Gly Cys
    355                 360                 365

Leu Asp Phe Ser Lys Ala Asp Ser Gly Val His Leu Cys Val Ile Asp
370                 375                 380

Asp Ser Asn Glu His Met Leu Thr Val Trp Asp Trp Gln Arg Lys Ala
385                 390                 395                 400

Lys Gly Ala Glu Ile Lys Thr Thr Asn Glu Val Val Leu Ala Val Glu
            405                 410                 415

Phe His Pro Thr Asp Ala Asn Thr Ile Ile Thr Cys Gly Lys Ser His
        420                 425                 430

Ile Phe Phe Trp Thr Trp Ser Gly Asn Ser Leu Thr Arg Lys Gln Gly
    435                 440                 445

Ile Phe Gly Lys Tyr Glu Lys Pro Lys Phe Val Gln Cys Leu Ala Phe
450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
            485                 490                 495

Gly Ser Gly Leu Cys Ser Ala Ser Arg Ala Arg Leu Pro Gly His Val
        500                 505                 510

Ala Ala Asp His Pro Pro Ala Val Tyr Arg Arg Lys His Gln Glu Leu
    515                 520                 525

Gln Ala Met Gln Met Glu Leu Gln Ser Pro Glu Tyr Lys Leu Ser Lys
530                 535                 540

Leu Arg Thr Ser Thr Ile Met Thr Asp Tyr Asn Pro Asn Tyr Cys Phe
545                 550                 555                 560

Ala Gly Lys Thr Ser Ser Ile Ser Asp Leu Lys Glu Val Pro Arg Lys
            565                 570                 575

Asn Ile Thr Leu Ile Arg Gly Leu Gly His Gly Ala Phe Gly Glu Val
        580                 585                 590

Tyr Glu Gly Gln Val Ser Gly Met Pro Asn Asp Pro Ser Pro Leu Gln
    595                 600                 605

Val Ala Val Lys Thr Leu Pro Glu Val Cys Ser Glu Gln Asp Glu Leu
610                 615                 620

Asp Phe Leu Met Glu Ala Leu Ile Ile Ser Lys Phe Asn His Gln Asn
625                 630                 635                 640

Ile Val Arg Cys Ile Gly Val Ser Leu Gln Ser Leu Pro Arg Phe Ile
            645                 650                 655

Leu Leu Glu Leu Met Ala Gly Gly Asp Leu Lys Ser Phe Leu Arg Glu
        660                 665                 670

Thr Arg Pro Arg Pro Ser Gln Pro Ser Ser Leu Ala Met Leu Asp Leu
    675                 680                 685

Leu His Val Ala Arg Asp Ile Ala Cys Gly Cys Gln Tyr Leu Glu Glu
690                 695                 700

Asn His Phe Ile His Arg Asp Ile Ala Ala Arg Asn Cys Leu Leu Thr
705                 710                 715                 720
```

```
Cys Pro Gly Pro Gly Arg Val Ala Lys Ile Gly Asp Phe Gly Met Ala
                725                 730                 735
Arg Asp Ile Tyr Arg Ala Ser Tyr Tyr Arg Lys Gly Gly Cys Ala Met
            740                 745                 750
Leu Pro Val Lys Trp Met Pro Glu Ala Phe Met Glu Gly Ile Phe
        755                 760                 765
Thr Ser Lys Thr Asp Thr Trp Ser Phe Gly Val Leu Leu Trp Glu Ile
770                 775                 780
Phe Ser Leu Gly Tyr Met Pro Tyr Pro Ser Lys Ser Asn Gln Glu Val
785                 790                 795                 800
Leu Glu Phe Val Thr Ser Gly Arg Met Asp Pro Pro Lys Asn Cys
            805                 810                 815
Pro Gly Pro Val Tyr Arg Ile Met Thr Gln Cys Trp Gln His Gln Pro
            820                 825                 830
Glu Asp Arg Pro Asn Phe Ala Ile Ile Leu Glu Arg Ile Glu Tyr Cys
            835                 840                 845
Thr Gln Asp Pro Asp Val Ile Asn Thr Ala Leu Pro Ile Glu Tyr Gly
            850                 855                 860
Pro Leu Val Glu Glu Glu Lys Val Pro Val Arg Pro Lys Asp Pro
865                 870                 875                 880
Glu Gly Val Pro Pro Leu Leu Val Ser Gln Gln Ala Lys Arg Glu Glu
            885                 890                 895
Glu Arg Ser Pro Ala Ala Pro Pro Pro Leu Pro Thr Thr Ser Ser Gly
            900                 905                 910
Lys Ala Ala Lys Lys Pro Thr Ala Ala Glu Val Ser Val Arg Val Pro
        915                 920                 925
Arg Gly Pro Ala Val Glu Gly His Val Asn Met Ala Phe Ser Gln
930                 935                 940
Ser Asn Pro Pro Ser Glu Leu His Arg Val His Gly Ser Arg Asn Lys
945                 950                 955                 960
Pro Thr Ser Leu Trp Asn Pro Thr Tyr Gly Ser Trp Phe Thr Glu Lys
                965                 970                 975
Pro Thr Lys Lys Asn Asn Pro Ile Ala Lys Lys Glu Pro His Glu Arg
            980                 985                 990
Gly Asn Leu Gly Leu Glu Gly Ser Cys Thr Val Pro Asn Val Ala
        995                 1000                1005
Thr Gly Arg Leu Pro Gly Ala Ser Leu Leu Leu Glu Pro Ser Ser Leu
    1010                1015                1020
Thr Ala Asn Met Lys Glu Val Pro Leu Phe Arg Leu Arg His Phe Pro
1025                1030                1035                1040
Cys Gly Asn Val Asn Tyr Gly Tyr Gln Gln Gln Gly Leu Pro Leu Glu
                1045                1050                1055
Ala Ala Thr Ala Pro Gly Ala Gly His Tyr Glu Asp Thr Ile Leu Lys
            1060                1065                1070
Ser Lys Asn Ser Met Asn Gln Pro Gly Pro
        1075                1080
```

<210> SEQ ID NO 38
<211> LENGTH: 3435
<212> TYPE: DNA
<213> ORGANISM: Homo sapiens
<220> FEATURE:
<221> NAME/KEY: source
<222> LOCATION: 1..3435
<223> OTHER INFORMATION: /mol_type="unassigned DNA"
      /organism="Homo sapiens"

<400> SEQUENCE: 38

```
tactctgtcg gtccgctgaa tgaagtgccc gccccctctaa gcccggagcc cggcgctttc      60
cccgcaagat ggacggtttc gccggcagtc tcgatgatag tatttctgct gcaagtactt     120
ctgatgttca agatcgcctg tcagctcttg agtcacgagt tcagcaacaa gaagatgaaa     180
tcactgtgct aaaggcggct ttggctgatg ttttgaggcg tcttgcaatc tctgaagatc     240
atgtggcctc agtgaaaaaa tcagtctcaa gtaaaggcca accaagccct cgagcagtta     300
ttcccatgtc ctgtataacc aatggaagtg gtgcaaacag aaaaccaagt cataccagtg     360
ctgtctcaat tgcaggaaaa gaaactcttt catctgctgc taaaagtggt acagaaaaaa     420
agaaagaaaa accacaagga cagagagaaa aaaagagga atctcattct aatgatcaaa     480
gtccacaaat tcgagcatca ccttctcccc agccctcttc acaacctctc caaatacaca     540
gacaaactcc agaaagcaag aatgctactc ccaccaaaag cataaaacga ccatcaccag     600
ctgaaaagtc acataattct tgggaaaatt cagatgatag ccgtaataaa ttgtcgaaaa     660
taccttcaac acccaaatta ataccaaaag ttaccaaaac tgcagacaag cataaagatg     720
tcatcatcaa ccaagaagga gaatatatta aaatgtttat gcgcggtcgg ccaattacca     780
tgttcattcc ttccgatgtt gacaactatg atgacatcag aacggaactg cctcctgaga     840
agctcaaact ggagtgggca tatggttatc gaggaaagga ctgtagagct aatgtttacc     900
ttcttccgac cggggaaata gtttatttca ttgcatcagt agtagtacta tttaattatg     960
aggagagaac tcagcgacac tacctgggcc atacagactg tgtgaaatgc cttgctatac    1020
atcctgacaa aattaggatt gcaactggac agatagctgg cgtggataaa gatggaaggc    1080
ctctacaacc ccacgtcaga gtgtgggatt ctgttactct atccacactg cagattattg    1140
gacttggcac ttttgagcgt ggagtaggat gcctggattt ttcaaaagca gattcaggtg    1200
ttcatttatg tgttattgat gactccaatg agcatatgct tactgtatgg gactggcaga    1260
ggaaagcaaa aggagcagaa ataaagacaa caaatgaagt tgttttggct gtggagtttc    1320
acccaacaga tgcaaatacc ataattcat gcggtaaatc tcatattttc ttctggacct    1380
ggagcggcaa ttcactaaca agaaaacagg gaattttttgg gaaatatgaa aagccaaaat    1440
tgtgcagtg tttagcattc ttggggaatg gagatgttct tactggagac tcaggtggag    1500
tcatgcttat atggagcaaa actactgtag agcccacacc tggaaaagga cctaaaggtg    1560
tatatcaaat cagcaaacaa atcaaagctc atgatggcag tgtgttcaca ctttgtcaga    1620
tgagaaatgg gatgttatta actggaggag ggaaagacaa aaaaataatt ctgtgggatc    1680
atgatctgaa tcctgaaaga gaaatagagc caggagct gcaagccatg cagatggagc    1740
tgcagagccc tgagtacaag ctgagcaagc tccgcacctc gaccatcatg accgactaca    1800
accccaacta ctgctttgct ggcaagacct cctccatcag tgacctgaag gaggtgccgc    1860
ggaaaaacat caccctcatt cggggtctgg gccatgagc cttttgggag gtgtatgaag    1920
gccaggtgtc cggaatgccc aacgacccaa gcccctgca gtggctgtg aagacgctgc    1980
ctgaagtgtg ctctgaacag gacgaactgg atttcctcat ggaagccctg atcatcagca    2040
aattcaacca ccagaacatt gttcgctgca ttggggtgag cctgcaatcc ctgcccggt    2100
tcatcctgct ggagctcatg gcgggggag acctcaagtc cttcctccga gagacccgcc    2160
ctcgcccgag ccagccctcc tccctggcca tgctggacct tctgcacgtg gctcgggaca    2220
ttgcctgtgg ctgtcagtat ttggaggaaa accacttcat ccaccgagac attgctgcca    2280
```

```
gaaactgcct cttgacctgt ccaggccctg gaagagtggc caagattgga gacttcggga   2340
tggcccgaga catctacagg gcgagctact atagaaaggg aggctgtgcc atgctgccag   2400
ttaagtggat gcccccagag gccttcatgg aaggaatatt cacttctaaa acagacacat   2460
ggtcctttgg agtgctgcta tgggaaatct tttctcttgg atatatgcca taccccagca   2520
aaagcaacca ggaagttctg gagtttgtca ccagtggagg ccggatggac ccacccaaga   2580
actgccctgg gcctgtatac cggataatga ctcagtgctg gcaacatcag cctgaagaca   2640
ggcccaactt tgccatcatt ttggagagga ttgaatactg cacccaggac ccggatgtaa   2700
tcaacaccgc tttgccgata gaatatggtc cacttgtgga agaggaagag aaagtgcctg   2760
tgaggcccaa ggaccctgag ggggttcctc ctctcctggt ctctcaacag gcaaaacggg   2820
aggaggagcg cagcccagct gccccaccac ctctgcctac cacctcctct ggcaaggctg   2880
caaagaaacc cacagctgca gaggtctctg ttcgagtccc tagagggccg gccgtggaag   2940
ggggacacgt gaatatggca ttctctcagt ccaacccctc cttcggagttg cacaaggtcc   3000 acggatccag aaacaagccc accagcttgt ggaacccaac gtacggctcc tggtttacag   3060
agaaacccac caaaaagaat aatcctatag caaagaagga gccacacgac agggtaacc   3120 tggggctgga gggaagctgt actgtcccac ctaacgttgc aactgggaga cttccggggg   3180
cctcactgct cctagagccc tcttcgctga ctgccaatat gaaggaggta cctctgttca   3240
ggctacgtca cttcccttgt gggaatgtca attacggcta ccagcaacag ggcttgccct   3300
tagaagccgc tactgcccct ggagctggtc attacgagga taccattctg aaaagcaaga   3360
atagcatgaa ccagcctggg ccctgagctc ggtcgcacac tcacttctct tccttgggat   3420
ccctaagacc gtgga                                                     3435
```

<210> SEQ ID NO 39
<211> LENGTH: 1105
<212> TYPE: PRT
<213> ORGANISM: Homo sapiens

<400> SEQUENCE: 39

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser

```
                    165                 170                 175
Pro Ala Glu Lys Ser His Asn Ser Trp Glu Asn Ser Asp Asp Ser Arg
                180                 185                 190

Asn Lys Leu Ser Lys Ile Pro Ser Thr Pro Lys Leu Ile Pro Lys Val
            195                 200                 205

Thr Lys Thr Ala Asp Lys His Lys Asp Val Ile Ile Asn Gln Glu Gly
        210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Ile Arg Thr Glu Leu Pro Pro
                245                 250                 255

Glu Lys Leu Lys Leu Glu Trp Ala Tyr Gly Tyr Arg Gly Lys Asp Cys
                260                 265                 270

Arg Ala Asn Val Tyr Leu Leu Pro Thr Gly Glu Ile Val Tyr Phe Ile
                275                 280                 285

Ala Ser Val Val Leu Phe Asn Tyr Glu Glu Arg Thr Gln Arg His
        290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
                340                 345                 350

Thr Leu Gln Ile Ile Gly Leu Gly Thr Phe Glu Arg Gly Val Gly Cys
                355                 360                 365

Leu Asp Phe Ser Lys Ala Asp Ser Gly Val His Leu Cys Val Ile Asp
            370                 375                 380

Asp Ser Asn Glu His Met Leu Thr Val Trp Asp Trp Gln Arg Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
                420                 425                 430

Ile Phe Phe Trp Thr Trp Ser Gly Asn Ser Leu Thr Arg Lys Gln Gly
            435                 440                 445

Ile Phe Gly Lys Tyr Glu Lys Pro Lys Phe Val Gln Cys Leu Ala Phe
450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
                500                 505                 510

Phe Thr Leu Cys Gln Met Arg Asn Gly Met Leu Leu Thr Gly Gly Gly
                515                 520                 525

Lys Asp Arg Lys Ile Ile Leu Trp Asp His Asp Leu Asn Pro Glu Arg
            530                 535                 540

Glu Ile Glu His Gln Glu Leu Gln Ala Met Gln Met Glu Leu Gln Ser
545                 550                 555                 560

Pro Glu Tyr Lys Leu Ser Lys Leu Arg Thr Ser Thr Ile Met Thr Asp
                565                 570                 575

Tyr Asn Pro Asn Tyr Cys Phe Ala Gly Lys Thr Ser Ser Ile Ser Asp
                580                 585                 590
```

```
Leu Lys Glu Val Pro Arg Lys Asn Ile Thr Leu Ile Arg Gly Leu Gly
            595                 600                 605

His Gly Ala Phe Gly Glu Val Tyr Glu Gly Gln Val Ser Gly Met Pro
    610                 615                 620

Asn Asp Pro Ser Pro Leu Gln Val Ala Val Lys Thr Leu Pro Glu Val
625                 630                 635                 640

Cys Ser Glu Gln Asp Glu Leu Asp Phe Leu Met Glu Ala Leu Ile Ile
                645                 650                 655

Ser Lys Phe Asn His Gln Asn Ile Val Arg Cys Ile Gly Val Ser Leu
            660                 665                 670

Gln Ser Leu Pro Arg Phe Ile Leu Leu Glu Leu Met Ala Gly Gly Asp
        675                 680                 685

Leu Lys Ser Phe Leu Arg Glu Thr Arg Pro Arg Pro Ser Gln Pro Ser
    690                 695                 700

Ser Leu Ala Met Leu Asp Leu Leu His Val Ala Arg Asp Ile Ala Cys
705                 710                 715                 720

Gly Cys Gln Tyr Leu Glu Glu Asn His Phe Ile His Arg Asp Ile Ala
                725                 730                 735

Ala Arg Asn Cys Leu Leu Thr Cys Pro Gly Pro Gly Arg Val Ala Lys
            740                 745                 750

Ile Gly Asp Phe Gly Met Ala Arg Asp Ile Tyr Arg Ala Ser Tyr Tyr
        755                 760                 765

Arg Lys Gly Gly Cys Ala Met Leu Pro Val Lys Trp Met Pro Pro Glu
    770                 775                 780

Ala Phe Met Glu Gly Ile Phe Thr Ser Lys Thr Asp Thr Trp Ser Phe
785                 790                 795                 800

Gly Val Leu Leu Trp Glu Ile Phe Ser Leu Gly Tyr Met Pro Tyr Pro
                805                 810                 815

Ser Lys Ser Asn Gln Glu Val Leu Glu Phe Val Thr Ser Gly Gly Arg
            820                 825                 830

Met Asp Pro Pro Lys Asn Cys Pro Gly Pro Val Tyr Arg Ile Met Thr
        835                 840                 845

Gln Cys Trp Gln His Gln Pro Glu Asp Arg Pro Asn Phe Ala Ile Ile
    850                 855                 860

Leu Glu Arg Ile Glu Tyr Cys Thr Gln Asp Pro Asp Val Ile Asn Thr
865                 870                 875                 880

Ala Leu Pro Ile Glu Tyr Gly Pro Leu Val Glu Glu Glu Glu Lys Val
                885                 890                 895

Pro Val Arg Pro Lys Asp Pro Glu Gly Val Pro Pro Leu Leu Val Ser
            900                 905                 910

Gln Gln Ala Lys Arg Glu Glu Arg Ser Pro Ala Ala Pro Pro Pro
        915                 920                 925

Leu Pro Thr Thr Ser Ser Gly Lys Ala Ala Lys Pro Thr Ala Ala
    930                 935                 940

Glu Val Ser Val Arg Val Pro Arg Gly Pro Ala Val Glu Gly Gly His
945                 950                 955                 960

Val Asn Met Ala Phe Ser Gln Ser Asn Pro Pro Ser Glu Leu His Lys
                965                 970                 975

Val His Gly Ser Arg Asn Lys Pro Thr Ser Leu Trp Asn Pro Thr Tyr
            980                 985                 990

Gly Ser Trp Phe Thr Glu Lys Pro Thr Lys Lys Asn Asn Pro Ile Ala
        995                 1000                1005
```

-continued

```
Lys Lys Glu Pro His Asp Arg Gly Asn Leu Gly Leu Glu Gly Ser Cys
    1010                1015                1020

Thr Val Pro Pro Asn Val Ala Thr Gly Arg Leu Pro Gly Ala Ser Leu
1025                1030                1035                1040

Leu Leu Glu Pro Ser Ser Leu Thr Ala Asn Met Lys Glu Val Pro Leu
                1045                1050                1055

Phe Arg Leu Arg His Phe Pro Cys Gly Asn Val Asn Tyr Gly Tyr Gln
    1060                1065                1070

Gln Gln Gly Leu Pro Leu Glu Ala Ala Thr Ala Pro Gly Ala Gly His
        1075                1080                1085

Tyr Glu Asp Thr Ile Leu Lys Ser Lys Asn Ser Met Asn Gln Pro Gly
    1090                1095                1100

Pro
1105

<210> SEQ ID NO 40
<211> LENGTH: 171
<212> TYPE: DNA
<213> ORGANISM: Homo sapiens
<220> FEATURE:
<221> NAME/KEY: source
<222> LOCATION: 1..171
<223> OTHER INFORMATION: /mol_type="unassigned DNA"
      /organism="Homo sapiens"

<400> SEQUENCE: 40
ccaggacact gtgcagattt tcatccaagt ggcacagtgg tggccatagg aacgcactca      60
ggcaggccat gttgcagctg accacccacc tgcagtgtac cgccggaagc accaggagct     120
gcaagccatg cagatggagc tgcagagccc tgagtacaag ctgagcaagc t              171

<210> SEQ ID NO 41
<211> LENGTH: 26
<212> TYPE: PRT
<213> ORGANISM: Homo sapiens

<400> SEQUENCE: 41

Pro Gly His Cys Ala Asp Phe His Pro Ser Gly Thr Val Val Ala Ile
1               5                   10                  15

Gly Thr His Ser Gly Arg Pro Cys Cys Ser
            20                  25

<210> SEQ ID NO 42
<211> LENGTH: 236
<212> TYPE: DNA
<213> ORGANISM: Homo sapiens
<220> FEATURE:
<221> NAME/KEY: source
<222> LOCATION: 1..236
<223> OTHER INFORMATION: /mol_type="unassigned DNA"
      /organism="Homo sapiens"

<400> SEQUENCE: 42
ccaggacact gtgcagattt tcatccaagt ggcacagtgg tggccatagg aacgcactca      60
ggcaggagac aaaaacatga agtcaatttt cccaaaatta aactcattaa aaaatgtgga     120
atgctgccag gccatgttgc agctgaccac ccacctgcag tgtaccgccg gaagcaccag     180
gagctgcaag ccatgcagat ggagctgcag agccctgagt acaagctgag caagct         236

<210> SEQ ID NO 43
<211> LENGTH: 79
<212> TYPE: PRT
```

<213> ORGANISM: Homo sapiens

<400> SEQUENCE: 43

```
Pro Gly His Cys Ala Asp Phe His Pro Ser Gly Thr Val Val Ala Ile
1               5                   10                  15

Gly Thr His Ser Gly Arg Arg Gln Lys His Glu Val Asn Phe Pro Lys
            20                  25                  30

Ile Lys Leu Ile Lys Lys Cys Gly Met Leu Pro Gly His Val Ala Ala
        35                  40                  45

Asp His Pro Pro Ala Val Tyr Arg Arg Lys His Gln Glu Leu Gln Ala
    50                  55                  60

Met Gln Met Glu Leu Gln Ser Pro Glu Tyr Lys Leu Ser Lys Leu
65                  70                  75
```

<210> SEQ ID NO 44
<211> LENGTH: 4173
<212> TYPE: DNA
<213> ORGANISM: Homo sapiens
<220> FEATURE:
<221> NAME/KEY: source
<222> LOCATION: 1..4173
<223> OTHER INFORMATION: /mol_type="unassigned DNA"
      /organism="Homo sapiens"

<400> SEQUENCE: 44

| | |
|---|---|
| atgaaggccc cgctgtgct tgcacctggc atcctcgtgc cctgtttac cttggtgcag | 60 |
| aggagcaatg gggagtgtaa agaggcacta gcaaagtccg agatgaatgt gaatatgaag | 120 |
| tatcagcttc ccaacttcac cgcggaaaca cccatccaga atgtcattct acatgagcat | 180 |
| cacattttcc ttggtgccac taactacatt tatgttttaa atgaggaaga ccttcagaag | 240 |
| gttgctgagt acaagactgg gcctgtgctg gaacacccag attgttccc atgtcaggac | 300 |
| tgcagcagca aagccaattt atcaggaggt gtttggaaag ataacatcaa catggctcta | 360 |
| gttgtcgaca cctactatga tgatcaactc attagctgtg cagcgtcaa cagagggacc | 420 |
| tgccagcgac atgtctttcc ccacaatcat actgctgaca tacagtcgga ggttcactgc | 480 |
| atattctccc cacagataga agagcccagc cagtgtcctg actgtgtggt gagcgccctg | 540 |
| ggagccaaag tcctttcatc tgtaaaggac cggttcatca acttctttgt aggcaatacc | 600 |
| ataaattctt cttatttccc agatcatcca ttgcattcga tatcagtgag aaggctaaag | 660 |
| gaaacgaaag atggtttat gtttttgacg gaccagtcct acattgatgt tttacctgag | 720 |
| ttcagagatt cttaccccat taagtatgtc catgcctttg aaagcaacaa ttttatttac | 780 |
| ttcttgacgg tccaaaggga aactctagat gctcagactt tcacacaag aataatcagg | 840 |
| ttctgttcca taactctgg attgcattcc tacatggaaa tgcctctgga gtgtattctc | 900 |
| acagaaaaga gaaaaagag atccacaaag aaggaagtgt taatatact tcaggctgcg | 960 |
| tatgtcagca agcctggggc ccagcttgct agacaaatag gagccagcct gaatgatgac | 1020 |
| attcttttcg gggtgttcgc acaaagcaag ccagattctg ccgaaccaat ggatcgatct | 1080 |
| gccatgtgtg cattccctat caaatatgtc aacgacttct tcaacaagat cgtcaacaaa | 1140 |
| aacaatgtga atgtctcca gcattttac ggacccaatc atgagcactg ctttaatagg | 1200 |
| acacttctga gaaattcatc aggctgtgaa gcgcgccgtg atgaatatcg aacagagttt | 1260 |
| accacagctt tgcagcgcgt tgacttattc atgggtcaat tcagcgaagt cctcttaaca | 1320 |
| tctatatcca ccttcattaa aggagacctc accatgcta atcttgggac atcagaggt | 1380 |
| cgcttcatgc aggttgtggt ttctcgatca ggaccatcaa cccctcatgt gaattttctc | 1440 |

```
ctggactccc atccagtgtc tccagaagtg attgtggagc atacattaaa ccaaaatggc    1500
tacacactgg ttatcactgg gaagaagatc acgaagatcc cattgaatgg cttgggctgc    1560
agacatttcc agtcctgcag tcaatgcctc tctgccccac cctttgttca gtgtggctgg    1620
tgccacgaca aatgtgtgcg atcggaggaa tgcctgagcg ggacatggac tcaacagatc    1680
tgtctgcctg caatctacaa ggttttccca aatagtgcac cccttgaagg agggacaagg    1740
ctgaccatat gtggctggga ctttggattt cggaggaata taaatttga tttaaagaaa    1800 actagagttc tccttggaaa tgagagctgc accttgactt taagtgagag cacgatgaat    1860
acattgaaat gcacagttgg tcctgccatg aataagcatt tcaatatgtc cataattatt    1920
tcaaatggcc acgggacaac acaatacagt acattctcct atgtggatcc tgtaataaca    1980
agtatttcgc cgaaatacgg tcctatggct ggtggcactt tacttacttt aactggaaat    2040
tacctaaaca gtgggaattc tagacacatt tcaattggtg aaaaacatg tactttaaaa    2100 agtgtgtcaa acagtattct tgaatgttat accccagccc aaaccatttc aactgagttt    2160
gctgttaaat tgaaaattga cttagccaac cgagagacaa gcatcttcag ttaccgtgaa    2220
gatcccattg tctatgaaat tcatccaacc aaatctttta ttagtggtgg agcacaata     2280 acaggtgttg ggaaaaacct gaattcagtt agtgtcccga gaatggtcat aaatgtgcat    2340
gaagcaggaa ggaactttac agtggcatgt caacatcgct ctaattcaga gataatctgt    2400
tgtaccactc cttccctgca acagctgaat ctgcaactcc cctgaaaac  caaagccttt    2460 ttcatgttag atgggatcct ttccaaatac tttgatctca tttatgtaca taatcctgtg    2520
tttaagcctt ttgaaaagcc agtgatgatc tcaatgggca atgaaaatgt actggaaatt    2580
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caattttctt aaccgtcctt    2760
ggaaaagtaa tagttcaacc agatcagaat ttcacaggat tgattgctgg tgttgtctca    2820
atatcaacag cactgttatt actacttggg tttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttt caaatgaatct   3000 gtagactacc gagctacttt tccagaagat cagtttccta attcatctca gaacggttca    3060
tgccgacaag tgcagtatcc tctgacagac atgtcccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca gtagccaaa ggcatgaaat atcttgcaag caaaagtttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
```

```
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140
acacgaccag cctccttctg ggagacatca tag                                 4173
```

<210> SEQ ID NO 45
<211> LENGTH: 1390
<212> TYPE: PRT
<213> ORGANISM: Homo sapiens

<400> SEQUENCE: 45

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300
```

```
Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
```

```
                725                 730                 735
Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu Asn
            755                 760                 765

Ser Val Ser Val Pro Arg Met Val Ile Asn Val His Glu Ala Gly Arg
770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
                900                 905                 910

Gln Ala Ile Ser Ser Thr Val Leu Gly Lys Val Ile Val Gln Pro Asp
            915                 920                 925

Gln Asn Phe Thr Gly Leu Ile Ala Gly Val Val Ser Ile Ser Thr Ala
930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
            980                 985                 990

Thr Glu Met Val Ser Asn Glu Ser Val Asp Tyr Arg Ala Thr Phe Pro
        995                 1000                1005

Glu Asp Gln Phe Pro Asn Ser Ser Gln Asn Gly Ser Cys Arg Gln Val
    1010                1015                1020

Gln Tyr Pro Leu Thr Asp Met Ser Pro Ile Leu Thr Ser Gly Asp Ser
1025                1030                1035                1040

Asp Ile Ser Ser Pro Leu Leu Gln Asn Thr Val His Ile Asp Leu Ser
                1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
            1075                1080                1085

Phe Gly Cys Val Tyr His Gly Thr Leu Leu Asp Asn Asp Gly Lys Lys
        1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
                1125                1130                1135

Pro Asn Val Leu Ser Leu Leu Gly Ile Cys Leu Arg Ser Glu Gly Ser
            1140                1145                1150
```

```
Pro Leu Val Val Leu Pro Tyr Met Lys His Gly Asp Leu Arg Asn Phe
            1155                1160                1165
Ile Arg Asn Glu Thr His Asn Pro Thr Val Lys Asp Leu Ile Gly Phe
        1170                1175                1180
Gly Leu Gln Val Ala Lys Gly Met Lys Tyr Leu Ala Ser Lys Lys Phe
1185                1190                1195                1200
Val His Arg Asp Leu Ala Ala Arg Asn Cys Met Leu Asp Glu Lys Phe
            1205                1210                1215
Thr Val Lys Val Ala Asp Phe Gly Leu Ala Arg Asp Met Tyr Asp Lys
        1220                1225                1230
Glu Tyr Tyr Ser Val His Asn Lys Thr Gly Ala Lys Leu Pro Val Lys
            1235                1240                1245
Trp Met Ala Leu Glu Ser Leu Gln Thr Gln Lys Phe Thr Thr Lys Ser
        1250                1255                1260
Asp Val Trp Ser Phe Gly Val Leu Leu Trp Glu Leu Met Thr Arg Gly
1265                1270                1275                1280
Ala Pro Pro Tyr Pro Asp Val Asn Thr Phe Asp Ile Thr Val Tyr Leu
            1285                1290                1295
Leu Gln Gly Arg Arg Leu Leu Gln Pro Glu Tyr Cys Pro Asp Pro Leu
        1300                1305                1310
Tyr Glu Val Met Leu Lys Cys Trp His Pro Lys Ala Glu Met Arg Pro
            1315                1320                1325
Ser Phe Ser Glu Leu Val Ser Arg Ile Ser Ala Ile Phe Ser Thr Phe
        1330                1335                1340
Ile Gly Glu His Tyr Val His Val Asn Ala Thr Tyr Val Asn Val Lys
1345                1350                1355                1360
Cys Val Ala Pro Tyr Pro Ser Leu Leu Ser Ser Glu Asp Asn Ala Asp
            1365                1370                1375
Asp Glu Val Asp Thr Arg Pro Ala Ser Phe Trp Glu Thr Ser
        1380                1385                1390

<210> SEQ ID NO 46
<211> LENGTH: 4227
<212> TYPE: DNA
<213> ORGANISM: Homo sapiens
<220> FEATURE:
<221> NAME/KEY: source
<222> LOCATION: 1..4227
<223> OTHER INFORMATION: /mol_type="unassigned DNA"
      /organism="Homo sapiens"

<400> SEQUENCE: 46
atgaaggccc cgctgtgct  tgcacctggc atcctcgtgc tcctgtttac cttggtgcag     60
aggagcaatg gggagtgtaa agaggcacta gcaaagtccg agatgaatgt gaatatgaag    120
tatcagcttc ccaacttcac cgcggaaaca cccatccaga atgtcattct acatgagcat    180
cacattttcc ttggtgccac taactacatt tatgttttaa atgaggaaga ccttcagaag    240
gttgctgagt acaagactgg gcctgtgctg aacacccag  attgtttccc atgtcaggac    300
tgcagcagca agccaattt  atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
```

```
ataaattctt cttatttccc agatcatcca ttgcattcga tatcagtgag aaggctaaag    660
gaaacgaaag atggttttat gtttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaagag atccacaaag aaggaagtgt ttaatatact tcaggctgcg     960
tatgtcagca agcctggggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcatttttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca atgtgtgcg atcggaggaa tgcctgagcg ggacatggac tcaacagatc     1680
tgtctgcctg caatctacaa ggttttccca aatagtgcac cccttgaagg agggacaagg   1740
ctgaccatat gtggctggga ctttggattt cggaggaata taaatttga tttaaagaaa     1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tacttttaaaa  2100 agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtacttg gtggaaagaa   2280
cctctcaaca ttgtcagttt tctattttgc tttgccagtg gtgggagcac aataacaggt   2340
gttgggaaaa acctgaattc agttagtgtc ccgagaatgg tcataaatgt gcatgaagca   2400
ggaaggaact ttacagtggc atgtcaacat cgctctaatt cagagataat ctgttgtacc   2460
actccttccc tgcaacagct gaatctgcaa ctcccctga aaaccaaagc cttttttcatg    2520 ttagatggga tcctttccaa atactttgat ctcatttatg tacataatcc tgtgtttaag   2580 cctttttgaaa agccagtgat gatctcaatg ggcaatgaaa atgtactgga aattaaggga   2640
aatgatattg accctgaagc agttaaaggt gaagtgttaa agttggaaa taagagctgt    2700 gagaatatac acttacattc tgaagccgtt ttatgcacgg tccccaatga cctgctgaaa   2760
ttgaacagcg agctaaatat agagtggaag caagcaattt cttcaaccgt ccttggaaaa   2820
gtaatagttc aaccagatca gaatttcaca ggattgattg ctggtgttgt ctcaatatca   2880
acagcactgt tattactact tgggtttttc ctgtggctga aaaagagaaa gcaaattaaa   2940
gatctgggca gtgaattagt tcgctacgat gcaagagtac acactcctca tttggatagg   3000
```

```
cttgtaagtg cccgaagtgt aagcccaact acagaaatgg tttcaaatga atctgtagac    3060
taccgagcta cttttccaga agatcagttt cctaattcat ctcagaacgg ttcatgccga    3120
caagtgcagt atcctctgac agacatgtcc cccatcctaa ctagtgggga ctctgatata    3180
tccagtccat tactgcaaaa tactgtccac attgacctca gtgctctaaa tccagagctg    3240
gtccaggcag tgcagcatgt agtgattggg cccagtagcc tgattgtgca tttcaatgaa    3300
gtcataggaa gagggcattt tggttgtgta tatcatggga ctttgttgga caatgatggc    3360
aagaaaattc actgtgctgt gaaatccttg aacagaatca ctgacatagg agaagtttcc    3420
caatttctga ccgagggaat catcatgaaa gattttagtc atcccaatgt cctctcgctc    3480
ctgggaatct gcctgcgaag tgaagggtct ccgctggtgg tcctaccata catgaaacat    3540
ggagatcttc gaaatttcat tcgaaatgag actcataatc aactgtaaaa agatcttatt    3600
ggctttggtc ttcaagtagc caaaggcatg aaatatcttg caagcaaaaa gtttgtccac    3660
agagacttgg ctgcaagaaa ctgtatgctg atgaaaaat tcacagtcaa ggttgctgat    3720
tttggtcttg ccagagacat gtatgataaa gaatactata gtgtacacaa caaaacaggt    3780
gcaaagctgc cagtgaagtg gatggctttg gaaagtctgc aaactcaaaa gtttaccacc    3840
aagtcagatg tgtggtcctt tggcgtgctc ctctgggagc tgatgacaag aggagcccca    3900
ccttatcctg acgtaaacac ctttgatata actgtttact tgttcaagg gagaagactc    3960 ctacaacccg aatactgccc agaccccttt tatgaagtaa tgctaaaatg ctggcaccct    4020
aaagccgaaa tgcgcccatc cttttctgaa ctggtgtccc ggatatcagc gatcttctct    4080
actttcattg gggagcacta tgtccatgtg aacgctactt atgtgaacgt aaaatgtgtc    4140
gctccgtatc cttctctgtt gtcatcagaa gataacgctg atgatgaggt ggacacacga    4200
ccagcctcct tctgggagac atcatag                                      4227
```

<210> SEQ ID NO 47
<211> LENGTH: 1408
<212> TYPE: PRT
<213> ORGANISM: Homo sapiens

<400> SEQUENCE: 47

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
```

-continued

```
            145                 150                 155                 160
        Ile Phe Ser Pro Gln Ile Glu Glu Pro Ser Gln Cys Pro Asp Cys Val
                            165                 170                 175

Val Ser Ala Leu Gly Ala Lys Val Leu Ser Ser Val Lys Asp Arg Phe
                            180                 185                 190

Ile Asn Phe Phe Val Gly Asn Thr Ile Asn Ser Ser Tyr Phe Pro Asp
                            195                 200                 205

His Pro Leu His Ser Ile Ser Val Arg Arg Leu Lys Glu Thr Lys Asp
                            210                 215                 220

Gly Phe Met Phe Leu Thr Asp Gln Ser Tyr Ile Asp Val Leu Pro Glu
        225                 230                 235                 240

Phe Arg Asp Ser Tyr Pro Ile Lys Tyr Val His Ala Phe Glu Ser Asn
                            245                 250                 255

Asn Phe Ile Tyr Phe Leu Thr Val Gln Arg Glu Thr Leu Asp Ala Gln
                            260                 265                 270

Thr Phe His Thr Arg Ile Ile Arg Phe Cys Ser Ile Asn Ser Gly Leu
                            275                 280                 285

His Ser Tyr Met Glu Met Pro Leu Glu Cys Ile Leu Thr Glu Lys Arg
                            290                 295                 300

Lys Lys Arg Ser Thr Lys Lys Glu Val Phe Asn Ile Leu Gln Ala Ala
        305                 310                 315                 320

Tyr Val Ser Lys Pro Gly Ala Gln Leu Ala Arg Gln Ile Gly Ala Ser
                            325                 330                 335

Leu Asn Asp Asp Ile Leu Phe Gly Val Phe Ala Gln Ser Lys Pro Asp
                            340                 345                 350

Ser Ala Glu Pro Met Asp Arg Ser Ala Met Cys Ala Phe Pro Ile Lys
                            355                 360                 365

Tyr Val Asn Asp Phe Phe Asn Lys Ile Val Asn Lys Asn Asn Val Arg
                            370                 375                 380

Cys Leu Gln His Phe Tyr Gly Pro Asn His Glu His Cys Phe Asn Arg
        385                 390                 395                 400

Thr Leu Leu Arg Asn Ser Ser Gly Cys Glu Ala Arg Arg Asp Glu Tyr
                            405                 410                 415

Arg Thr Glu Phe Thr Thr Ala Leu Gln Arg Val Asp Leu Phe Met Gly
                            420                 425                 430

Gln Phe Ser Glu Val Leu Leu Thr Ser Ile Ser Thr Phe Ile Lys Gly
                            435                 440                 445

Asp Leu Thr Ile Ala Asn Leu Gly Thr Ser Glu Gly Arg Phe Met Gln
        450                 455                 460

Val Val Val Ser Arg Ser Gly Pro Ser Thr Pro His Val Asn Phe Leu
        465                 470                 475                 480

Leu Asp Ser His Pro Val Ser Pro Glu Val Ile Val Glu His Thr Leu
                            485                 490                 495

Asn Gln Asn Gly Tyr Thr Leu Val Ile Thr Gly Lys Lys Ile Thr Lys
                            500                 505                 510

Ile Pro Leu Asn Gly Leu Gly Cys Arg His Phe Gln Ser Cys Ser Gln
                            515                 520                 525

Cys Leu Ser Ala Pro Pro Phe Val Gln Cys Gly Trp Cys His Asp Lys
                            530                 535                 540

Cys Val Arg Ser Glu Glu Cys Leu Ser Gly Thr Trp Thr Gln Gln Ile
        545                 550                 555                 560

Cys Leu Pro Ala Ile Tyr Lys Val Phe Pro Asn Ser Ala Pro Leu Glu
                            565                 570                 575
```

-continued

```
Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
            645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
            690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
            725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
            755                 760                 765

Phe Cys Phe Ala Ser Gly Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
            805                 810                 815

Ile Cys Cys Thr Thr Pro Ser Leu Gln Gln Leu Asn Leu Gln Leu Pro
            820                 825                 830

Leu Lys Thr Lys Ala Phe Phe Met Leu Asp Gly Ile Leu Ser Lys Tyr
            835                 840                 845

Phe Asp Leu Ile Tyr Val His Asn Pro Val Phe Lys Pro Phe Glu Lys
            850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
            885                 890                 895

Asn Lys Ser Cys Glu Asn Ile His Leu His Ser Glu Ala Val Leu Cys
            900                 905                 910

Thr Val Pro Asn Asp Leu Leu Lys Leu Asn Ser Glu Leu Asn Ile Glu
            915                 920                 925

Trp Lys Gln Ala Ile Ser Ser Thr Val Leu Gly Lys Val Ile Val Gln
            930                 935                 940

Pro Asp Gln Asn Phe Thr Gly Leu Ile Ala Gly Val Val Ser Ile Ser
945                 950                 955                 960

Thr Ala Leu Leu Leu Leu Leu Gly Phe Phe Leu Trp Leu Lys Lys Arg
            965                 970                 975

Lys Gln Ile Lys Asp Leu Gly Ser Glu Leu Val Arg Tyr Asp Ala Arg
            980                 985                 990
```

```
Val His Thr Pro His Leu Asp Arg Leu Val Ser Ala Arg Ser Val Ser
            995                 1000                1005

Pro Thr Thr Glu Met Val Ser Asn Glu Ser Val Asp Tyr Arg Ala Thr
    1010                1015                1020

Phe Pro Glu Asp Gln Phe Pro Asn Ser Ser Gln Asn Gly Ser Cys Arg
1025                1030                1035                1040

Gln Val Gln Tyr Pro Leu Thr Asp Met Ser Pro Ile Leu Thr Ser Gly
            1045                1050                1055

Asp Ser Asp Ile Ser Ser Pro Leu Gln Asn Thr Val His Ile Asp
            1060                1065                1070

Leu Ser Ala Leu Asn Pro Glu Leu Val Gln Ala Gln His Val Val
            1075                1080                1085

Ile Gly Pro Ser Ser Leu Ile Val His Phe Asn Glu Val Ile Gly Arg
1090                1095                1100

Gly His Phe Gly Cys Val Tyr His Gly Thr Leu Leu Asp Asn Asp Gly
1105                1110                1115                1120

Lys Lys Ile His Cys Ala Val Lys Ser Leu Asn Arg Ile Thr Asp Ile
            1125                1130                1135

Gly Glu Val Ser Gln Phe Leu Thr Glu Gly Ile Ile Met Lys Asp Phe
            1140                1145                1150

Ser His Pro Asn Val Leu Ser Leu Leu Gly Ile Cys Leu Arg Ser Glu
            1155                1160                1165

Gly Ser Pro Leu Val Val Leu Pro Tyr Met Lys His Gly Asp Leu Arg
            1170                1175                1180

Asn Phe Ile Arg Asn Glu Thr His Asn Pro Thr Val Lys Asp Leu Ile
1185                1190                1195                1200

Gly Phe Gly Leu Gln Val Ala Lys Gly Met Lys Tyr Leu Ala Ser Lys
            1205                1210                1215

Lys Phe Val His Arg Asp Leu Ala Ala Arg Asn Cys Met Leu Asp Glu
            1220                1225                1230

Lys Phe Thr Val Lys Val Ala Asp Phe Gly Leu Ala Arg Asp Met Tyr
            1235                1240                1245

Asp Lys Glu Tyr Tyr Ser Val His Asn Lys Thr Gly Ala Lys Leu Pro
            1250                1255                1260

Val Lys Trp Met Ala Leu Glu Ser Leu Gln Thr Gln Lys Phe Thr Thr
1265                1270                1275                1280

Lys Ser Asp Val Trp Ser Phe Gly Val Leu Leu Trp Glu Leu Met Thr
            1285                1290                1295

Arg Gly Ala Pro Pro Tyr Pro Asp Val Asn Thr Phe Asp Ile Thr Val
            1300                1305                1310

Tyr Leu Leu Gln Gly Arg Arg Leu Leu Gln Pro Glu Tyr Cys Pro Asp
            1315                1320                1325

Pro Leu Tyr Glu Val Met Leu Lys Cys Trp His Pro Lys Ala Glu Met
            1330                1335                1340

Arg Pro Ser Phe Ser Glu Leu Val Ser Arg Ile Ser Ala Ile Phe Ser
1345                1350                1355                1360

Thr Phe Ile Gly Glu His Tyr Val His Val Asn Ala Thr Tyr Val Asn
            1365                1370                1375

Val Lys Cys Val Ala Pro Tyr Pro Ser Leu Leu Ser Ser Glu Asp Asn
            1380                1385                1390

Ala Asp Asp Glu Val Asp Thr Arg Pro Ala Ser Phe Trp Glu Thr Ser
            1395                1400                1405
```

```
<210> SEQ ID NO 48
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="Anti-MTH1 siRNA"
      /organism="Artificial Sequence"

<400> SEQUENCE: 48
cgacgacagc uacugguuu                                                    19

<210> SEQ ID NO 49
<211> LENGTH: 19
<212> TYPE: DNA
<213> ORGANISM: Artificial Sequence
<220> FEATURE:
<221> NAME/KEY: source
<222> LOCATION: 1..19
<223> OTHER INFORMATION: /mol_type="unassigned DNA"
      /note="qPCR-oligonucleotide for detecting p21 "
      /organism="Artificial Sequence"

<400> SEQUENCE: 49
ctgtgatgcg ctaatggcg                                                    19

<210> SEQ ID NO 50
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="pPCR-oligonucleotide for detecting p21"
      /organism="Artificial Sequence"

<400> SEQUENCE: 50
aagtcgaagt tccatcgctc a                                                 21
```